(12) United States Patent
Takahashi et al.

(10) Patent No.: US 9,371,395 B2
(45) Date of Patent: Jun. 21, 2016

(54) ANTI B7-H3 ANTIBODY

(75) Inventors: Shu Takahashi, Chiba (JP); Tatsuji Matsuoka, Tokyo (JP); Kenji Murakami, Chiba (JP); Takeshi Takizawa, Tokyo (JP); Kenji Hirotani, Tokyo (JP); Atsushi Urano, Tokyo (JP); Keisuke Fukuchi, Tokyo (JP); Mitsuhiro Yazawa, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 236 days.

(21) Appl. No.: 13/455,021

(22) Filed: Apr. 24, 2012

(65) Prior Publication Data

US 2013/0078234 A1    Mar. 28, 2013

Related U.S. Application Data

(63) Continuation of application No. PCT/JP2012/060904, filed on Apr. 24, 2012.

(60) Provisional application No. 61/478,878, filed on Apr. 25, 2011.

(30) Foreign Application Priority Data

Apr. 25, 2011 (JP) ................................. 2011-097645

(51) Int. Cl.
| | |
|---|---|
| *C12P 21/08* | (2006.01) |
| *C07K 16/00* | (2006.01) |
| *C07K 16/30* | (2006.01) |
| *C07K 16/28* | (2006.01) |
| *A61K 39/395* | (2006.01) |
| *C07H 21/00* | (2006.01) |
| *C07K 16/42* | (2006.01) |

(52) U.S. Cl.
CPC ............ *C07K 16/42* (2013.01); *A61K 39/39558* (2013.01); *C07K 16/2827* (2013.01); *C07K 16/30* (2013.01); *C07K 2317/24* (2013.01); *C07K 2317/73* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | | |
|---|---|---|---|
| 7,592,429 B2 | 9/2009 | Paszty | |
| 7,875,702 B2 | 1/2011 | Chen | |
| 2002/0168762 A1* | 11/2002 | Chen ............... | C07K 14/70532 435/325 |
| 2003/0105000 A1* | 6/2003 | Pero et al. ....................... | 514/12 |
| 2013/0078234 A1* | 3/2013 | Takahashi et al. ......... | 424/131.1 |

FOREIGN PATENT DOCUMENTS

| | | | | |
|---|---|---|---|---|
| WO | WO 99/54342 | * | 10/1999 | ............. C07H 21/04 |
| WO | WO 2006/016276 A2 | * | 2/2006 | ............. C07K 16/28 |
| WO | 2008/066691 A2 | | 6/2008 | |
| WO | 2008/116219 A2 | | 9/2008 | |

OTHER PUBLICATIONS

Janeway, CA et al. (Immunobiology: The Immune System in Health and Disease, The destruction of antibody-coated pathogens via Fc receptors, 5th ed. New York: Garland Science, NCBI Bookshelf, 2001).*
Kubota et al. (Cancer Sci. Sep. 2009, 100(9): 1566-1572).*
Matsushita et al. (FEBS Letters, 1999, vol. 443, pp. 348-352).*
Singh et al. (Glycobiology, 2001, vol. 11, pp. 587-592).*
Janeway et al. (Immunobiology 5, 2001, p. 100-101).*
Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Burgess et al. (J. of Cell Biol. 111:2129-2138, 1990).*
Human B7-H3 antibody (R&D Systems Tools for Cell Biology Research, Monoclonal Mouse IgG1, Clone #185504, MAB1027, Nov. 8, 2010).*
Crispen et al. (Clin. Cancer Res. Aug. 15, 2008 14(16): 5150-5157).*
Hashiguchi et al. (Proc. Natl. Acad. Sci. Jul. 29, 2008, 105(30): 10,495-10,500).*
Affymetrix eBioscience (Anti-Human/Mouse CD276 (B7-H3) Functional Grade Purified, Cat. No. 16-5937, MIH35, downloaded Aug. 19, 2014).*
Boorjian, S.A., et al., "T-Cell Coregulatory Molecule Expression in Urothelial Cell Carcinoma: Clinicopathologic Correlations and Association With Survival," Clinical Cancer Research 14(15):4800-4808, Aug. 2008.
Castriconi, R., et al., "Identification of 4Ig-B7-H3 as a Neuroblastoma-Associated Molecule That Exerts a Protective Role From an NK Cell-Mediated Lysis," Proceedings of the National Academy of Sciences of the United States of America (PNAS) 101(34):12640-12645, Aug. 2004.
Chapoval, A.I., et al., "B7-H3: A Costimulatory Molecule for T Cell Activation and IFN-γ Production," Nature Immunology 2(3):269-274, Mar. 2001.

(Continued)

*Primary Examiner* — Peter J Reddig

(74) *Attorney, Agent, or Firm* — Christensen O'Connor Johnson Kindness PLLC

(57) ABSTRACT

An antibody exhibiting antitumor activity that binds to B7-H3, a functional fragment of the antibody, a pharmaceutical composition that includes the antibody or the functional fragment, methods for making the antibody or the functional fragment, methods for treating a tumor using the antibody or the functional fragment, and polynucleotides encoding the antibody or the functional fragment.

52 Claims, 47 Drawing Sheets

(56) References Cited

OTHER PUBLICATIONS

Chen, Y.W., et al., "The Immunoregulatory Protein Human B7H3 is a Tumor-Associated Antigen That Regulates Tumor Cell Migration and Invasion," Current Cancer Drug Targets 8(5):404-413, Aug. 2008.

Crispen, P.L., et al., "Tumor Cell and Tumor Vasculature Expression of B7-H3 Predict Survival in Clear Cell Renal Cell Carcinoma," Clinical Cancer Research 14(16):5150-5157, Aug. 2008.

Gregorio, A., et al., "Small Round Blue Cell Tumours: Diagnostic and Prognostic Usefulness of the Expression of B7-H3 Surface Molecule," Histopathology 53(1):73-80, Jul. 2008.

Hashiguchi, M., et al., "Triggering Receptor Expressed on Myeloid Cell-Like Transcript 2 (TLT-2) is a Counter-Receptor for B7-H3 and Enhances T Cell Responses," Proceedings of the National Academy of Sciences of the United States of America (PNAS) 105(30):10495-10500, Jul. 2008.

Leitner, J., "B7-H3 is a Potent Inhibitor of Human T-Cell Activation: No Evidence for B7-H3 and TREML2 Interaction," European Journal of Immunology 39(7):1754-1764, Jul. 2009.

Nagashima, O., et al., "B7-H3 Contributes to the Development of Pathogenic Th2 Cells in a Murine Model of Asthma," Journal of Immunology 181(6):4062-4071, Sep. 2008.

Roth, T.J., et al., "B7-H3 Ligand Expression by Prostate Cancer: A Novel Marker of Prognosis and Potential Target for Therapy," Cancer Research 67(16):7893-7900, Aug. 2007.

Steinberger, P., et al., "Molecular Characterization of Human 4Ig-B7-H3, a Member of the B7 Family With Four Ig-Like Domains," Journal of Immunology 172(4):2352-2359, Feb. 2004.

Sun, J., et al., "Clinical Significance and Regulation of the Costimulatory Molecule B7-H3 in Human Colorectal Carcinoma," Cancer Immunology, Immunotherapy 59(8):1163-1171, Aug. 2010.

Tran, C.N., et al., "Interactions of T Cells With Fibroblast-Like Synoviocytes: Role of the B7 Family Costimulatory Ligand B7-H3," Journal of Immunology 180(5):2989-2998, Mar. 2008.

Yamato, I., et al., "Clinical Importance of B7-H3 Expression in Human Pancreatic Cancer," British Journal of Cancer 101(10):1709-1716, Nov. 2009.

Zang, X., et al., "Tumor Associated Endothelial Expression of B7-H3 Predicts Survival in Ovarian Carcinomas," Modern Pathology 23(8):1104-1112, Aug. 2010.

Zhang, G., et al., "B7-H3 Augments the Inflammatory Response and is Associated With Human Sepsis," Journal of Immunology 185(6):3677-3684, Sep. 2010.

Zhang, G., et al., "Diagnosis Value of Serum B7-H3 Expression in Non-Small Cell Lung Cancer," Lung Cancer 66(2):245-249, Nov. 2009.

Office Action mailed Mar. 16, 2015, issued in corresponding Colombian Application No. 13-275.282, filed Apr. 24, 2012, 26 pages.

Extended European Search Report mailed Jan. 28, 2015, issued in corresponding European Patent Application No. 12 776 528.7, filed Apr. 24, 2012, 10 pages.

Fieger, C.B., et al., "The Anti-B7-H3-4Ig Antibody TES7 Recognizes Cancer Stem Cell Lines, Modulates Angiogenic Factor Secretion, and Exhibits Potent Anti-Tumor Activity In Vivo," Proceedings of the 99th Annual Meeting of the American Association for Cancer Research, San Diego, Apr. 12-16, 2008, Abstract No. 2555.

Office Action mailed Mar. 15, 2016, issued in corresponding Israeli Application No. 229061, filed Apr. 24, 2012, 9 pages.

Hamilton, R.G., "Molecular Engineering: Applications to the Clinical Laboratory," Clinical Chemistry 39(9):1988-1997, Nov. 1993.

Horton, H.M., et al., "Potent In Vitro and In Vivo Activity of an Fc-Engineered Anti-CD19 Monoclonal Antibody Against Lymphoma and Leukemia," Cancer Research 68(19):8049-8057, Oct. 2008.

Nagashima, H., et al., "Enhanced Antibody-Dependent Cellular Phagocytosis by Chimeric Monoclonal Antibodies With Tandemly Repeated Fc Domains," Journal of Bioscience and Bioengineering 111(4):391-396, Jan. 2011.

\* cited by examiner

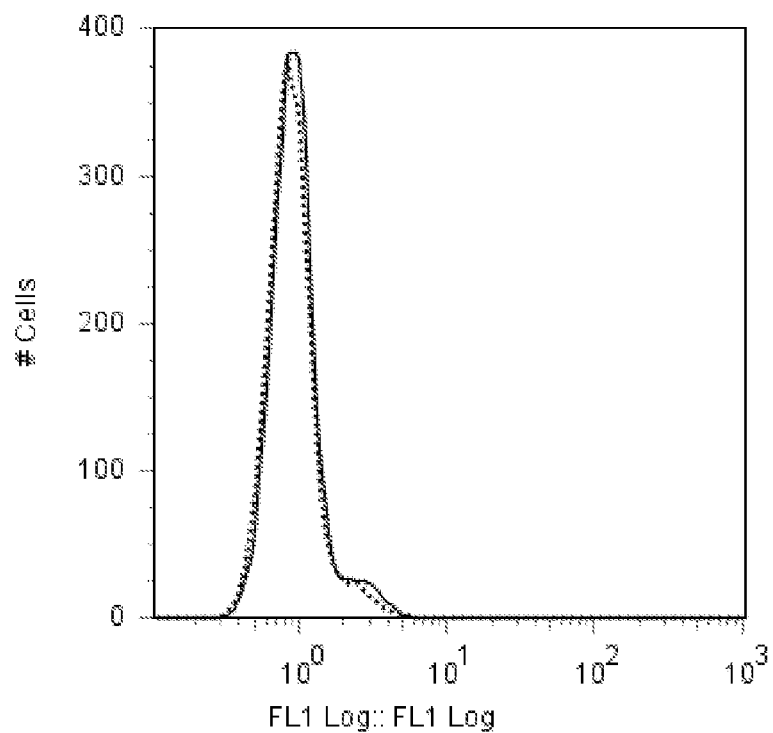
Fig. 5-1  B7-H3 IgV1
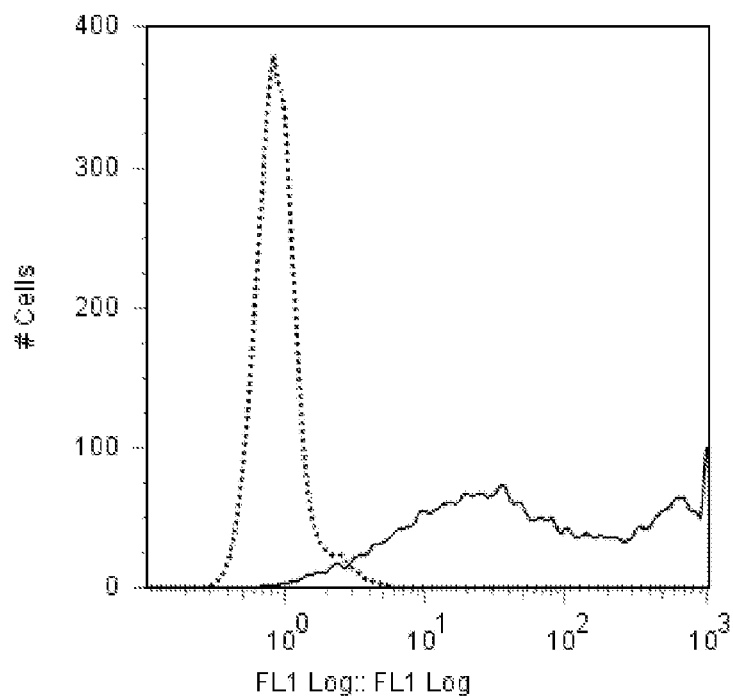
Fig. 5-2  B7-H3 IgC1

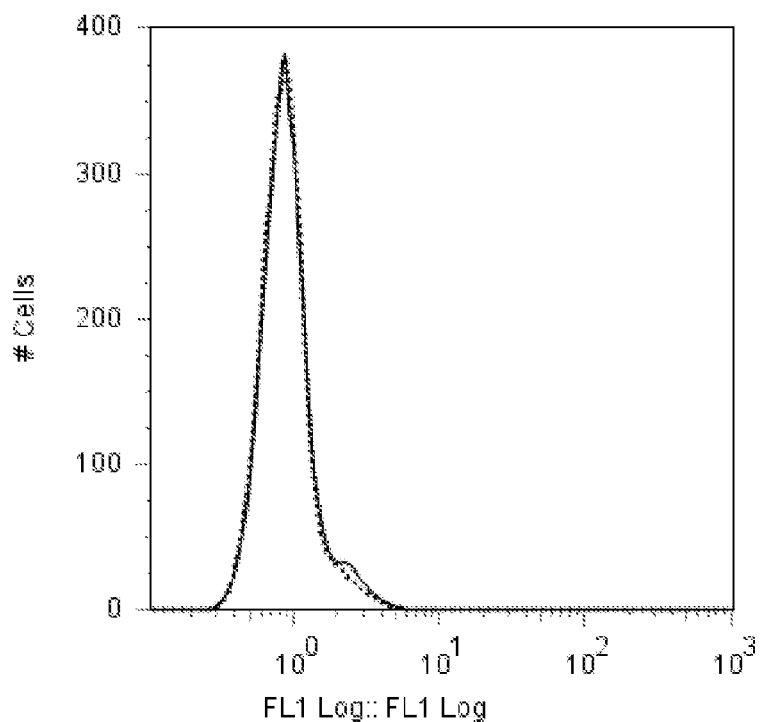
Fig. 5-3  B7-H3 IgV2
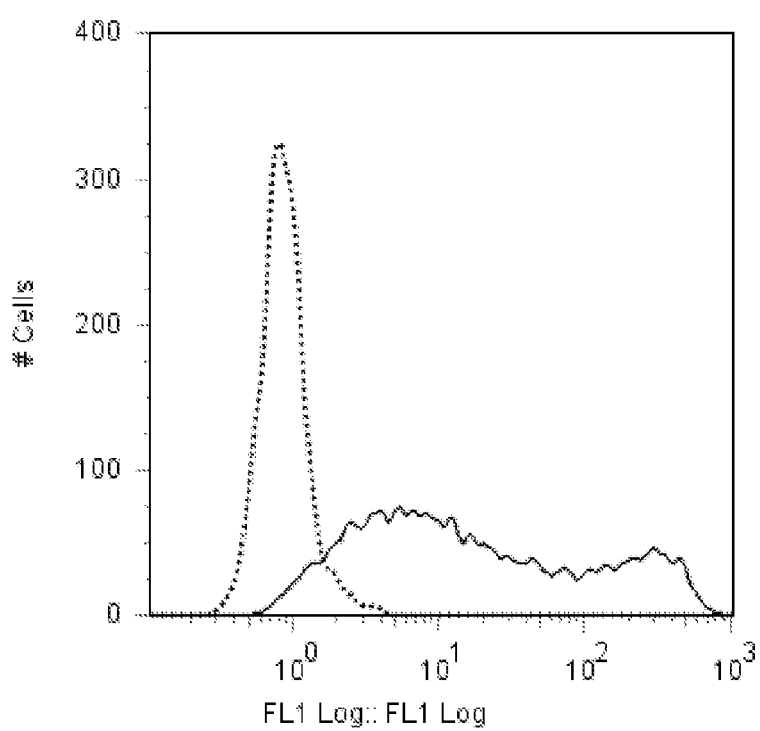
Fig. 5-4  B7-H3 IgC2

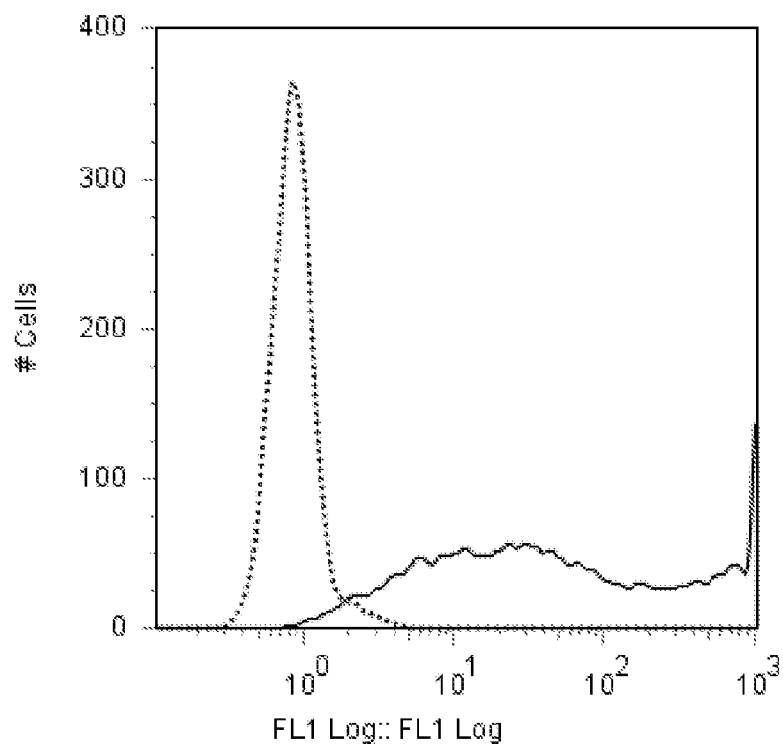
Fig. 5-5  B7-H3 IgC1-V2-C2
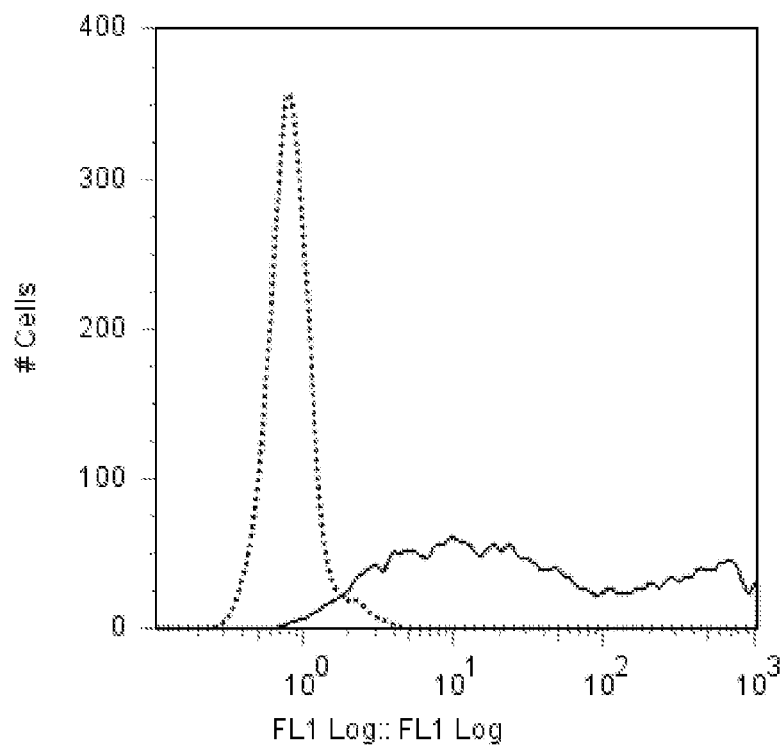
Fig. 5-6  B7-H3 IgV2-C2

B7-H3 variant 1

B7-H3 variant 2

Nucleotide sequence of B7-H3 variant 1 (SEQ ID NO: 5)

atgctgcgtcggcggggcagccctggcatgggtgtgcatgtgggtgcagccctgggagcac
tgtggttctgcctcacaggagccctggaggtccaggtccctgaagacccagtggtggcact
ggtgggcaccgatgccaccctgtgctgctccttctcccctgagcctggcttcagcctggca
cagctcaacctcatctggcagctgacagataccaaacagctggtgcacagctttgctgagg
gccaggaccagggcagcgcctatgccaaccgcacggccctcttcccggacctgctggcaca
gggcaacgcatccctgaggctgcagcgcgtgcgtgtggcggacgagggcagcttcacctgc
ttcgtgagcatccgggatttcggcagcgctgccgtcagcctgcaggtggccgctccctact
cgaagcccagcatgaccctggagcccaacaaggacctgcggccaggggacacggtgaccat
cacgtgctccagctaccagggctaccctgaggctgaggtgttctggcaggatgggcagggt
gtgcccctgactggcaacgtgaccacgtcgcagatggccaacgagcagggcttgtttgatg
tgcacagcatcctgcgggtggtgctgggtgcaaatggcacctacagctgcctggtgcgcaa
ccccgtgctgcagcaggatgcgcacagctctgtcaccatcacaccccagagaagccccaca
ggagccgtggaggtccaggtccctgaggacccggtggtggccctagtgggcaccgatgcca
ccctgcgctgctccttctcccccgagcctggcttcagcctggcacagctcaacctcatctg
gcagctgacagacaccaaacagctggtgcacagtttcaccgaaggccgggaccagggcagc
gcctatgccaaccgcacggccctcttcccggacctgctggcacaaggcaatgcatccctga
ggctgcagcgcgtgcgtgtggcggacgagggcagcttcacctgcttcgtgagcatccggga
tttcggcagcgctgccgtcagcctgcaggtggccgctccctactcgaagcccagcatgacc
ctggagcccaacaaggacctgcggccaggggacacggtgaccatcacgtgctccagctacc
ggggctaccctgaggctgaggtgttctggcaggatgggcagggtgtgcccctgactggcaa
cgtgaccacgtcgcagatggccaacgagcagggcttgtttgatgtgcacagcgtcctgcgg
gtggtgctgggtgcgaatggcacctacagctgcctggtgcgcaaccccgtgctgcagcagg
atgcgcacggctctgtcaccatcacagggcagcctatgacattcccccagaggccctgtg
ggtgaccgtgggctgtctgtctgtctcattgcactgctggtggccctggctttcgtgtgc
tggagaaagatcaaacagagctgtgaggaggagaatgcaggagctgaggaccaggatgggg
agggagaaggctccaagacagccctgcagcctctgaaacactctgacagcaaagaagatga
tggacaagaaatagcctgagcggccgccactgtgctggatatctgcagaattccaccacac
tggactagtggatccgagctcggtaccaagcttaagtttaaaccgctgatcagcctcgact
gtgccttctagttgccagccatctgttgtttgcccctcccccgtgccttccttgaccctgg
aaggtgccactcccactgtcctttcctaataaaatgaggaaattgc

Fig. 13-1

Amino acid sequence of B7-H3 variant 1 (SEQ ID NO: 6)

MLRRRGSPGMGVHVGAALGALWFCLTGALEVQVPEDPVVALVGTDATLCCSFSPEPGFSLA
QLNLIWQLTDTKQLVHSFAEGQDQGSAYANRTALFPDLLAQGNASLRLQRVRVADEGSFTC
FVSIRDFGSAAVSLQVAAPYSKPSMTLEPNKDLRPGDTVTITCSSYQGYPEAEVFWQDGQG
VPLTGNVTTSQMANEQGLFDVHSILRVVLGANGTYSCLVRNPVLQQDAHSSVTITPQRSPT
GAVEVQVPEDPVVALVGTDATLRCSFSPEPGFSLAQLNLIWQLTDTKQLVHSFTEGRDQGS
AYANRTALFPDLLAQGNASLRLQRVRVADEGSFTCFVSIRDFGSAAVSLQVAAPYSKPSMT
LEPNKDLRPGDTVTITCSSYRGYPEAEVFWQDGQGVPLTGNVTTSQMANEQGLFDVHSVLR
VVLGANGTYSCLVRNPVLQQDAHGSVTITGQPMTFPPEALWVTVGLSVCLIALLVALAFVC
WRKIKQSCEEENAGAEDQDGEGEGSKTALQPLKHSDSKEDDGQEIA

Fig. 13-2

Nucleotide sequence of B7-H3 variant 2 (SEQ ID NO: 9)

atgctgcgtcggcggggcagccctggcatgggtgtgcatgtgggtgcagccctgggagcac
tgtggttctgcctcacaggagccctggaggtccaggtccctgaagacccagtggtggcact
ggtgggcaccgatgccaccctgtgctgctccttctcccctgagcctggcttcagcctggca
cagctcaacctcatctggcagctgacagataccaaacagctggtgcacagctttgctgagg
gccaggaccagggcagcgcctatgccaaccgcacggccctcttcccggacctgctggcaca
gggcaacgcatccctgaggctgcagcgcgtgcgtgtggcggacgagggcagcttcacctgc
ttcgtgagcatccgggatttcggcagcgctgccgtcagcctgcaggtggccgctccctact
cgaagcccagcatgaccctggagcccaacaaggacctgcggccaggggacacggtgaccat
cacgtgctccagctaccggggctaccctgaggctgaggtgttctggcaggatgggcagggt
gtgcccctgactggcaacgtgaccacgtcgcagatggccaacgagcagggcttgtttgatg
tgcacagcgtcctgcgggtggtgctgggtgcgaatggcacctacagctgcctggtgcgcaa
ccccgtgctgcagcaggatgcgcacggctctgtcaccatcacagggcagcctatgacattc
cccccagaggccctgtgggtgaccgtggggctgtctgtctgtctcattgcactgctggtgg
ccctggctttcgtgtgctggagaaagatcaaacagagctgtgaggaggagaatgcaggagc
tgaggaccaggatggggagggagaaggctccaagacagccctgcagcctctgaaacactct
gacagcaaagaagatgatggacaagaaatagcc

Fig. 14-1

Amino acid sequence of B7-H3 variant 2 (SEQ ID NO: 10)

MLRRRGSPGMGVHVGAALGALWFCLTGALEVQVPEDPVVALVGTDATLCCSFSPEPGFSLA
QLNLIWQLTDTKQLVHSFAEGQDQGSAYANRTALFPDLLAQGNASLRLQRVRVADEGSFTC
FVSIRDFGSAAVSLQVAAPYSKPSMTLEPNKDLRPGDTVTITCSSYRGYPEAEVFWQDGQG
VPLTGNVTTSQMANEQGLFDVHSVLRVVLGANGTYSCLVRNPVLQQDAHGSVTITGQPMTF
PPEALWVTVGLSVCLIALLVALAFVCWRKIKQSCEEENAGAEDQDGEGEGSKTALQPLKHS
DSKEDDGQEIA

Fig. 14-2

Nucleotide sequence of B7-H3 IgV1 (SEQ ID NO: 20)

GGAGCCCTGGAGGTCCAGGTCCCTGAAGACCCAGTGGTGGCACTGGTGGGCACCGATGCCA
CCCTGTGCTGCTCCTTCTCCCCTGAGCCTGGCTTCAGCCTGGCACAGCTCAACCTCATCTG
GCAGCTGACAGATACCAAACAGCTGGTGCACAGCTTTGCTGAGGGCCAGGACCAGGGCAGC
GCCTATGCCAACCGCACGGCCCTCTTCCCGGACCTGCTGGCACAGGGCAACGCATCCCTGA
GGCTGCAGCGCGTGCGTGTGGCGGACGAGGGCAGCTTCACCTGCTTCGTGAGCATCCGGGA
TTTCGGCAGCGCTGCCGTCAGCCTGCAGGTGGCCGGGCAGCCTATGACATTCCCCCCAGAG
GCCCTGTGGGTGACCGTGGGGCTGTCTGTCTGTCTCATTGCACTGCTGGTGGCCCTGGCTT
TCGTGTGCTGGAGAAAGATCAAACAGAGCTGTGAGGAGGAGAATGCAGGAGCTGAGGACCA
GGATGGGGAGGGAGAAGGCTCCAAGACAGCCCTGCAGCCTCTGAAACACTCTGACAGCAAA
GAAGATGATGGACAAGAAATAGCCTGA

Fig. 15-1

Amino acid sequence of B7-H3 IgV1 (SEQ ID NO: 21)

GALEVQVPEDPVVALVGTDATLCCSFSPEPGFSLAQLNLIWQLTDTKQLVHSFAEGQDQGS
AYANRTALFPDLLAQGNASLRLQRVRVADEGSFTCFVSIRDFGSAAVSLQVAGQPMTFPPE
ALWVTVGLSVCLIALLVALAFVCWRKIKQSCEEENAGAEDQDGEGEGSKTALQPLKHSDSK
EDDGQEIA

Fig. 15-2

Nucleotide sequence of B7-H3 IgC1 (SEQ ID NO: 22)

GCTCCCTACTCGAAGCCCAGCATGACCCTGGAGCCCAACAAGGACCTGCGGCCAGGGGACA
CGGTGACCATCACGTGCTCCAGCTACCAGGGCTACCCTGAGGCTGAGGTGTTCTGGCAGGA
TGGGCAGGGTGTGCCCCTGACTGGCAACGTGACCACGTCGCAGATGGCCAACGAGCAGGGC
TTGTTTGATGTGCACAGCATCCTGCGGGTGGTGCTGGGTGCAAATGGCACCTACAGCTGCC
TGGTGCGCAACCCCGTGCTGCAGCAGGATGCGCACAGCTCTGTCACCATCACACCCCAGAG
AAGCCCCACAGGGCAGCCTATGACATTCCCCCCAGAGGCCCTGTGGGTGACCGTGGGGCTG
TCTGTCTGTCTCATTGCACTGCTGGTGGCCCTGGCTTTCGTGTGCTGGAGAAAGATCAAAC
AGAGCTGTGAGGAGGAGAATGCAGGAGCTGAGGACCAGGATGGGGAGGGAGAAGGCTCCAA
GACAGCCCTGCAGCCTCTGAAACACTCTGACAGCAAAGAAGATGATGGACAAGAAATAGCC
TGA

Fig. 16-1

Amino acid sequence of B7-H3 IgC1 (SEQ ID NO: 23)

APYSKPSMTLEPNKDLRPGDTVTITCSSYQGYPEAEVFWQDGQGVPLTGNVTTSQMANEQG
LFDVHSILRVVLGANGTYSCLVRNPVLQQDAHSSVTITPQRSPTGQPMTFPPEALWVTVGL
SVCLIALLVALAFVCWRKIKQSCEEENAGAEDQDGEGEGSKTALQPLKHSDSKEDDGQEIA

Fig. 16-2

Nucleotide sequence of B7-H3 IgV2 (SEQ ID NO: 24)

GGAGCCGTGGAGGTCCAGGTCCCTGAGGACCCGGTGGTGGCCCTAGTGGGCACCGATGCCA
CCCTGCGCTGCTCCTTCTCCCCGAGCCTGGCTTCAGCCTGGCACAGCTCAACCTCATCTG
GCAGCTGACAGACACCAAACAGCTGGTGCACAGTTTCACCGAAGGCCGGGACCAGGGCAGC
GCCTATGCCAACCGCACGGCCCTCTTCCCGGACCTGCTGGCACAAGGCAATGCATCCCTGA
GGCTGCAGCGCGTGCGTGTGGCGGACGAGGGCAGCTTCACCTGCTTCGTGAGCATCCGGGA
TTTCGGCAGCGCTGCCGTCAGCCTGCAGGTGGCCGGGCAGCCTATGACATTCCCCCCAGAG
GCCCTGTGGGTGACCGTGGGCTGTCTGTCTGTCTCATTGCACTGCTGGTGGCCCTGGCTT
TCGTGTGCTGGAGAAAGATCAAACAGAGCTGTGAGGAGGAGAATGCAGGAGCTGAGGACCA
GGATGGGGAGGGAGAAGGCTCCAAGACAGCCCTGCAGCCTCTGAAACACTCTGACAGCAAA
GAAGATGATGGACAAGAAATAGCCTGA

Fig. 17-1

Amino acid sequence of B7-H3 IgV2 (SEQ ID NO: 25)

GAVEVQVPEDPVVALVGTDATLRCSFSPEPGFSLAQLNLIWQLTDTKQLVHSFTEGRDQGS
AYANRTALFPDLLAQGNASLRLQRVRVADEGSFTCFVSIRDFGSAAVSLQVAGQPMTFPPE
ALWVTVGLSVCLIALLVALAFVCWRKIKQSCEEENAGAEDQDGEGEGSKTALQPLKHSDSK
EDDGQEIA

Fig. 17-2

Nucleotide sequence of B7-H3 IgC2 (SEQ ID NO: 26)

GCTCCCTACTCGAAGCCCAGCATGACCCTGGAGCCCAACAAGGACCTGCGGCCAGGGGACA
CGGTGACCATCACGTGCTCCAGCTACCGGGGCTACCCTGAGGCTGAGGTGTTCTGGCAGGA
TGGGCAGGGTGTGCCCCTGACTGGCAACGTGACCACGTCGCAGATGGCCAACGAGCAGGGC
TTGTTTGATGTGCACAGCGTCCTGCGGGTGGTGCTGGGTGCGAATGGCACCTACAGCTGCC
TGGTGCGCAACCCCGTGCTGCAGCAGGATGCGCACGGCTCTGTCACCATCACAGGGCAGCC
TATGACATTCCCCCAGAGGCCCTGTGGGTGACCGTGGGGCTGTCTGTCTGTCTCATTGCA
CTGCTGGTGGCCCTGGCTTTCGTGTGCTGGAGAAAGATCAAACAGAGCTGTGAGGAGGAGA
ATGCAGGAGCTGAGGACCAGGATGGGGAGGGAGAAGGCTCCAAGACAGCCCTGCAGCCTCT
GAAACACTCTGACAGCAAAGAAGATGATGGACAAGAAATAGCCTGA

Fig. 18-1

Amino acid sequence of B7-H3 IgC2 (SEQ ID NO: 27)

APYSKPSMTLEPNKDLRPGDTVTITCSSYRGYPEAEVFWQDGQGVPLTGNVTTSQMANEQG
LFDVHSVLRVVLGANGTYSCLVRNPVLQQDAHGSVTITGQPMTFPPEALWVTVGLSVCLIA
LLVALAFVCWRKIKQSCEEENAGAEDQDGEGEGSKTALQPLKHSDSKEDDGQEIA

Fig. 18-2

Nucleotide sequence of B7-H3 IgC1-V2-C2 (SEQ ID NO: 28)

```
GCTCCCTACTCGAAGCCCAGCATGACCCTGGAGCCCAACAAGGACCTGCGGCCAGGGGACA
CGGTGACCATCACGTGCTCCAGCTACCAGGGCTACCCTGAGGCTGAGGTGTTCTGGCAGGA
TGGGCAGGGTGTGCCCCTGACTGGCAACGTGACCACGTCGCAGATGGCCAACGAGCAGGGC
TTGTTTGATGTGCACAGCATCCTGCGGGTGGTGCTGGGTGCAAATGGCACCTACAGCTGCC
TGGTGCGCAACCCCGTGCTGCAGCAGGATGCGCACAGCTCTGTCACCATCACACCCCAGAG
AAGCCCCACAGGAGCCGTGGAGGTCCAGGTCCCTGAGGACCCGGTGGTGGCCCTAGTGGGC
ACCGATGCCACCCTGCGCTGCTCCTTCTCCCCCGAGCCTGGCTTCAGCCTGGCACAGCTCA
ACCTCATCTGGCAGCTGACAGACACCAAACAGCTGGTGCACAGTTTCACCGAAGGCCGGGA
CCAGGGCAGCGCCTATGCCAACCGCACGGCCCTCTTCCCGGACCTGCTGGCACAAGGCAAT
GCATCCCTGAGGCTGCAGCGCGTGCGTGTGGCGGACGAGGGCAGCTTCACCTGCTTCGTGA
GCATCCGGGATTTCGGCAGCGCTGCCGTCAGCCTGCAGGTGGCCGCTCCCTACTCGAAGCC
CAGCATGACCCTGGAGCCCAACAAGGACCTGCGGCCAGGGGACACGGTGACCATCACGTGC
TCCAGCTACCGGGGCTACCCTGAGGCTGAGGTGTTCTGGCAGGATGGGCAGGGTGTGCCCC
TGACTGGCAACGTGACCACGTCGCAGATGGCCAACGAGCAGGGCTTGTTTGATGTGCACAG
CGTCCTGCGGGTGGTGCTGGGTGCGAATGGCACCTACAGCTGCCTGGTGCGCAACCCCGTG
CTGCAGCAGGATGCGCACGGCTCTGTCACCATCACAGGGCAGCCTATGACATTCCCCCCAG
AGGCCCTGTGGGTGACCGTGGGGCTGTCTGTCTGTCTCATTGCACTGCTGGTGGCCCTGGC
TTTCGTGTGCTGGAGAAAGATCAAACAGAGCTGTGAGGAGGAGAATGCAGGAGCTGAGGAC
CAGGATGGGGAGGGAGAAGGCTCCAAGACAGCCCTGCAGCCTCTGAAACACTCTGACAGCA
AGGAAGATGATGGACAAGAAATAGCCTGA
```

Fig. 19-1

Amino acid sequence of B7-H3 IgC1-V2-C2 (SEQ ID NO: 29)

```
APYSKPSMTLEPNKDLRPGDTVTITCSSYQGYPEAEVFWQDGQGVPLTGNVTTSQMANEQG
LFDVHSILRVVLGANGTYSCLVRNPVLQQDAHSSVTITPQRSPTGAVEVQVPEDPVVALVG
TDATLRCSFSPEPGFSLAQLNLIWQLTDTKQLVHSFTEGRDQGSAYANRTALFPDLLAQGN
ASLRLQRVRVADEGSFTCFVSIRDFGSAAVSLQVAAPYSKPSMTLEPNKDLRPGDTVTITC
SSYRGYPEAEVFWQDGQGVPLTGNVTTSQMANEQGLFDVHSVLRVVLGANGTYSCLVRNPV
LQQDAHGSVTITGQPMTFPPEALWVTVGLSVCLIALLVALAFVCWRKIKQSCEEENAGAED
QDGEGEGSKTALQPLKHSDSKEDDGQEIA
```

Fig. 19-2

Nucleotide sequence of B7-H3 IgV2-C2 (SEQ ID NO: 30)

GGAGCCGTGGAGGTCCAGGTCCCTGAGGACCCGGTGGTGGCCCTAGTGGGCACCGATGCCA
CCCTGCGCTGCTCCTTCTCCCCCGAGCCTGGCTTCAGCCTGGCACAGCTCAACCTCATCTG
GCAGCTGACAGACACCAAACAGCTGGTGCACAGTTTCACCGAAGGCCGGGACCAGGGCAGC
GCCTATGCCAACCGCACGGCCCTCTTCCCGGACCTGCTGGCACAAGGCAATGCATCCCTGA
GGCTGCAGCGCGTGCGTGTGGCGGACGAGGGCAGCTTCACCTGCTTCGTGAGCATCCGGGA
TTTCGGCAGCGCTGCCGTCAGCCTGCAGGTGGCCGCTCCCTACTCGAAGCCCAGCATGACC
CTGGAGCCCAACAAGGACCTGCGGCCAGGGGACACGGTGACCATCACGTGCTCCAGCTACC
GGGGCTACCCTGAGGCTGAGGTGTTCTGGCAGGATGGGCAGGGTGTGCCCCTGACTGGCAA
CGTGACCACGTCGCAGATGGCCAACGAGCAGGGCTTGTTTGATGTGCACAGCGTCCTGCGG
GTGGTGCTGGGTGCGAATGGCACCTACAGCTGCCTGGTGCGCAACCCCGTGCTGCAGCAGG
ATGCGCACGGCTCTGTCACCATCACAGGGCAGCCTATGACATTCCCCCAGAGGCCCTGTG
GGTGACCGTGGGGCTGTCTGTCTGTCTCATTGCACTGCTGGTGGCCCTGGCTTTCGTGTGC
TGGAGAAAGATCAAACAGAGCTGTGAGGAGGAGAATGCAGGAGCTGAGGACCAGGATGGGG
AGGGAGAAGGCTCCAAGACAGCCCTGCAGCCTCTGAAACACTCTGACAGCAAAGAAGATGA
TGGACAAGAAATAGCCTGA

Fig. 20-1

Amino acid sequence of B7-H3 IgV2-C2 (SEQ ID NO: 31)

GAVEVQVPEDPVVALVGTDATLRCSFSPEPGFSLAQLNLIWQLTDTKQLVHSFTEGRDQGS
AYANRTALFPDLLAQGNASLRLQRVRVADEGSFTCFVSIRDFGSAAVSLQVAAPYSKPSMT
LEPNKDLRPGDTVTITCSSYRGYPEAEVFWQDGQGVPLTGNVTTSQMANEQGLFDVHSVLR
VVLGANGTYSCLVRNPVLQQDAHGSVTITGQPMTFPPEALWVTVGLSVCLIALLVALAFVC
WRKIKQSCEEENAGAEDQDGEGEGSKTALQPLKHSDSKEDDGQEIA

Fig. 20-2

Nucleotide sequence of M30 antibody heavy chain (SEQ ID NO: 50)

```
atggaatggagttggatatttctctttctcctgtcaggaactgcaggtgtccactctgagg
tccagctgcagcagtctggacctgagctggtaaagcctggggcttcagtgaagatgtcctg
caaggcttctggatacacattcactaactatgttatgcactgggtgaagcagaagcctggg
cagggccttgagtggattggatatattaatccttacaatgatgatgttaagtacaatgaga
agttcaaaggcaaggccacacagacttcagacaaatcctccagcacagcctacatggagct
cagcagcctgacctctgaggactctgcggtctattactgtgcaagatgggggtactacggt
agtcccttatactactttgactactggggccaaggcaccactctcacagtctcctcagcca
aaacaacagccccatcggtctatccactggcccctgtgtgtggagatacaactggctcctc
ggtgactctaggatgcctggtcaagggttatttccctgagccagtgaccttgacctggaac
tctggatccctgtccagtggtgtgcacaccttcccagctgtcctgcagtctgacctctaca
ccctcagcagctcagtgactgtaacctcgagcacctggcccagccagtccatcacctgcaa
tgtggcccacccggcaagcagcaccaaggtggacaagaaaattgagcccagagggcccaca
atcaagccctgtcctccatgcaaatgcccagcacctaacctcttgggtggaccatccgtct
tcatcttccctccaaagatcaaggatgtactcatgatctccctgagccccatagtcacatg
tgtggtggtggatgtgagcgaggatgacccagatgtccagatcagctggtttgtgaacaac
gtggaagtacacacagctcagacacaaacccatagagaggattacaacagtactctccggg
tggtcagtgccctccccatccagcaccaggactggatgagtggcaaggagttcaaatgcaa
ggtcaacaacaaagacctcccagcgcccatcgagagaaccatctcaaaacccaaagggtca
gtaagagctccacaggtatatgtcttgcctccaccagaagaagagatgactaagaaacagg
tcactctgacctgcatggtcacagacttcatgcctgaagacatttacgtggagtggaccaa
caacgggaaaacagagctaaactacaagaacactgaaccagtcctggactctgatggttct
tacttcatgtacagcaagctgagagtggaaaagaagaactgggtggaagaaatagctact
cctgttcagtggtccacgagggtctgcacaatcaccacgactaagagcttctcccggac
tccgggtaaa
```

Fig. 21-1

Amino acid sequence of M30 antibody heavy chain (SEQ ID NO: 51)

MEWSWIFLFLLSGTAGVHSEVQLQQSGPELVKPGASVKMSCKASGYTFTNYVMHWVKQKPG
QGLEWIGYINPYNDDVKYNEKFKGKATQTSDKSSSTAYMELSSLTSEDSAVYYCARWGYYG
SPLYYFDYWGQGTTLTVSSAKTTAPSVYPLAPVCGDTTGSSVTLGCLVKGYFPEPVTLTWN
SGSLSSGVHTFPAVLQSDLYTLSSSVTVTSSTWPSQSITCNVAHPASSTKVDKKIEPRGPT
IKPCPPCKCPAPNLLGGPSVFIFPPKIKDVLMISLSPIVTCVVVDVSEDDPDVQISWFVNN
VEVHTAQTQTHREDYNSTLRVVSALPIQHQDWMSGKEFKCKVNNKDLPAPIERTISKPKGS
VRAPQVYVLPPPEEEMTKKQVTLTCMVTDFMPEDIYVEWTNNGKTELNYKNTEPVLDSDGS
YFMYSKLRVEKKNWVERNSYSCSVVHEGLHNHHTTKSFSRTPGK

Fig. 21-2

Nucleotide sequence of M30 antibody light chain (SEQ ID NO: 52)

atggattttctggtgcagattttcagcttcctgctaatcagtgcttcagtcataatgtcca
gaggacaaattgttctctcccagtctccaacaatcctgtctgcatctccaggggagaaggt
cacaatgacttgcagggccagctcaagactaatttacatgcattggtatcagcagaagcca
ggatcctcccccaaaccctggatttatgccacatccaacctggcttctggagtccctgctc
gcttcagtggcagtgggtctgggacctcttactctctcacaatcagcagagtggaggctga
agatgctgccacttattactgccagcagtggaatagtaacccacccacgttcggtactggg
accaagctggagctgaaacgggctgatgctgcaccaactgtatccatcttcccaccatcca
gtgagcagttaacatctggaggtgcctcagtcgtgtgcttcttgaacaacttctaccccaa
agacatcaatgtcaagtggaagattgatggcagtgaacgacaaaatggcgtcctgaacagt
tggactgatcaggacagcaaagacagcacctacagcatgagcagcaccctcacgttgacca
aggacgagtatgaacgacataacagctatacctgtgaggccactcacaagacatcaacttc
acccattgtcaagagcttcaacaggaatgagtgt

Fig. 22-1

Amino acid sequence of M30 antibody light chain (SEQ ID NO: 53)

MDFLVQIFSFLLISASVIMSRGQIVLSQSPTILSASPGEKVTMTCRASSRLIYMHWYQQKP
GSSPKPWIYATSNLASGVPARFSGSGSGTSYSLTISRVEAEDAATYYCQQWNSNPPTFGTG
TKLELKRADAAPTVSIFPPSSEQLTSGGASVVCFLNNFYPKDINVKWKIDGSERQNGVLNS
WTDQDSKDSTYSMSSTLTLTKDEYERHNSYTCEATHKTSTSPIVKSFNRNEC

Fig. 22-2

DNA sequence encoding human κ chain secretory signal, human κ chain constant region, and human poly-A additional signal (SEQ ID NO: 56)

ggtaccacccaagctggctaggtaagcttgctagcgccaccatggtgctgcagacccaggt
gttcatctccctgctgctgtggatctccggcgcatatggcgatatcgtgatgattaaacgt
acggtggccgcccctccgtgttcatcttccccccctccgacgagcagctgaagtccggca
ccgcctccgtggtgtgcctgctgaataacttctaccccagagaggccaaggtgcagtggaa
ggtggacaacgccctgcagtccgggaactcccaggagagcgtgaccgagcaggacagcaag
gacagcacctacagcctgagcagcaccctgaccctgagcaaagccgactacgagaagcaca
aggtgtacgcctgcgaggtgacccaccagggcctgagctcccccgtcaccaagagcttcaa
caggggggagtgttaggggcccgtttaaacgggtggcatccctgtgacccctccccagtgc
ctctcctggccctggaagttgccactccagtgcccaccagccttgtcctaataaaattaag
ttgcatcattttgtctgactaggtgtccttctataatattatggggtggaggggggtggta
tggagcaaggggcaagttgggaagacaacctgtagggcctgcggggtctattgggaaccaa
gctggagtgcagtggcacaatcttggctcactgcaatctccgcctcctggttcaagcgat
tctcctgcctcagcctcccgagttgttgggattccaggcatgcatgaccaggctcacctaa
ttttgtttttttggtagagacggggtttcaccatattggccaggctggtctccaactcct
aatctcaggtgatctacccaccttggcctcccaaattgctgggattacaggcgtgaaccac
tgctccacgcgccctgtagcggcgcattaagcgcggcgggtgtggtggttacgcgcagcgt
gaccgctacacttgccagcgccctagcgcccgctcctttcgctttcttcccttcctttctc
gccacgttcgccggctttccccgtcaagctctaaatcggggggctcccttttagggttccgat
ttagtgctttacggcacctcgaccccaaaaaacttgattagggtgatggttcacgtagtgg
gccatcgccctgatagacggttttttcgccctttgacgttggagtccacgttctttaatagt
ggactcttgttccaaactggaacaacactcaaccctatctcggtctattcttttgatttat
aagggattttgccgatttcggcctattggttaaaaaatgagctgatttaacaaaaatttaa
cgcgaattaattctgtggaatgtgtgtcagttagggtgtggaaagtccccaggctcccag
caggcagaagtatgcaaagcatgcatctcaattagtcagcaaccaggtgtggaaagtcccc
aggctccccagcaggcagaagtatgcaaagcatgcatctcaattagtcagcaaccatagtc
ccgcccctaactccgcccatcccgcccctaactccgcccagttccgccattctccgcccc
atggctgactaatttttttatttatgcagaggccgaggccgcctctgcctctgagctatt
ccagaagtagtgaggaggcttttttggaggcctaggcttttgcaaaaagctcccggg

Fig. 23

DNA fragment comprising DNA sequence encoding amino acids of
signal sequence and constant region of human IgG1 (SEQ ID NO: 57)

tgctagcgccaccatgaaacacctgtggttcttcctcctgctggtggcagctcccagatgg
gtgctgagccaggtgcaattgtgcaggcggttagctcagcctccaccaagggcccaagcgt
cttccccctggcaccctcctccaagagcacctctggcggcacagccgccctgggctgcctg
gtcaaggactacttccccgaacccgtgaccgtgagctggaactcaggcgccctgaccagcg
gcgtgcacaccttccccgctgtcctgcagtcctcaggactctactccctcagcagcgtggt
gaccgtgccctccagcagcttgggcacccagacctacatctgcaacgtgaatcacaagccc
agcaacaccaaggtggacaagagagttgagcccaaatcttgtgacaaaactcacacatgcc
caccctgcccagcacctgaactcctggggggaccctcagtcttcctcttccccccaaaacc
caaggacaccctcatgatctcccggacccctgaggtcacatgcgtggtggtggacgtgagc
cacgaagaccctgaggtcaagttcaactggtacgtggacggcgtggaggtgcataatgcca
agacaaagccccgggaggagcagtacaacagcacgtaccgggtggtcagcgtcctcaccgt
cctgcaccaggactggctgaatggcaaggagtacaagtgcaaggtctccaacaaagccctc
ccagcccccatcgagaaaaccatctccaaagccaaaggccagccccgggaaccacaggtgt
acaccctgcccccatcccgggaggagatgaccaagaaccaggtcagcctgacctgcctggt
caaaggcttctatcccagcgacatcgccgtggagtgggagagcaatggccagcccgagaac
aactacaagaccacccctcccgtgctggactccgacggctccttcttcctctacagcaagc
tcaccgtggacaagagcaggtggcagcagggcaacgtcttctcatgctccgtgatgcatga
ggctctgcacaaccactacacccagaagagcctctccctgtctccggcaaatgagatatc
gggcccgtttaaacgggtggca

Fig. 24

Nucleotide sequence of M30 antibody chimera-type light chain (SEQ ID NO: 58)

atggtgctgcagacccaggtgttcatctccctgctgctgtggatctccggcgcatatggcc
aaattgttctctcccagtctccaacaatcctgtctgcatctccaggggagaaggtcacaat
gacttgcagggccagctcaagactaatttacatgcattggtatcagcagaagccaggatcc
tcccccaaaccctggatttatgccacatccaacctggcttctggagtccctgctcgcttca
gtggcagtgggtctgggacctcttactctctcacaatcagcagagtggaggctgaagatgc
tgccacttattactgccagcagtggaatagtaacccacccacgttcggtactgggaccaag
ctggagctgaaacgtacggtggccgcccctccgtgttcatcttcccccctccgacgagc
agctgaagtccggcaccgcctccgtggtgtgcctgctgaataacttctacccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacaggggggagtgt

Fig. 25-1

Amino acid sequence of M30 antibody chimera-type light chain (SEQ ID NO: 59)

MVLQTQVFISLLLWISGAYGQIVLSQSPTILSASPGEKVTMTCRASSRLIYMHWYQQKPGS
SPKPWIYATSNLASGVPARFSGSGSGTSYSLTISRVEAEDAATYYCQQWNSNPPTFGTGTK
LELKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 25-2

Nucleotide sequence of M30 antibody chimera-type heavy chain (SEQ ID NO: 62)

atgaaacacctgtggttcttcctcctgctggtggcagctcccagatgggtgctgagcgagg
tccagctgcagcagtctggacctgagctggtaaagcctggggcttcagtgaagatgtcctg
caaggcttctggatacacattcactaactatgttatgcactgggtgaagcagaagcctggg
cagggccttgagtggattggatatattaatccttacaatgatgatgttaagtacaatgaga
agttcaaaggcaaggccacacagacttcagacaaatcctccagcacagcctacatggaact
cagcagcctgacctctgaggactctgcggtctattactgtgcaagatgggggtactacggt
agtcccttatactactttgactactggggccaaggcaccactctcacagtcagctcagcct
ccaccaagggcccaagcgtcttccccctggcaccctcctccaagagcacctctggcggcac
agccgccctgggctgcctggtcaaggactacttccccgaacccgtgaccgtgagctggaac
tcaggcgccctgaccagcggcgtgcacaccttccccgctgtcctgcagtcctcaggactct
actccctcagcagcgtggtgaccgtgccctccagcagcttgggcacccagacctacatctg
caacgtgaatcacaagcccagcaacaccaaggtggacaagagagttgagcccaaatcttgt
gacaaaactcacacatgcccaccctgcccagcacctgaactcctggggggaccctcagtct
tcctcttccccccaaaacccaaggacaccctcatgatctcccggacccctgaggtcacatg
cgtggtggtggacgtgagccacgaagaccctgaggtcaagttcaactggtacgtggacggc
gtggaggtgcataatgccaagacaaagccccgggaggagcagtacaacagcacgtaccggg
tggtcagcgtcctcaccgtcctgcaccaggactggctgaatggcaaggagtacaagtgcaa
ggtctccaacaaagccctcccagcccccatcgagaaaaccatctccaaagccaaaggccag
ccccgggaaccacaggtgtacaccctgcccccatcccgggaggagatgaccaagaaccagg
tcagcctgacctgcctggtcaaaggcttctatcccagcgacatcgccgtggagtgggagag
caatggccagcccgagaacaactacaagaccacccctcccgtgctggactccgacggctcc
ttcttcctctacagcaagctcaccgtggacaagagcaggtggcagcagggcaacgtcttct
catgctccgtgatgcatgaggctctgcacaaccactacacccagaagagcctctccctgtc
tcccggcaaa

Fig. 26-1

Amino acid sequence of M30 antibody chimera-type heavy chain (SEQ ID NO: 63)

MKHLWFFLLLVAAPRWVLSEVQLQQSGPELVKPGASVKMSCKASGYTFTNYVMHWVKQKPG
QGLEWIGYINPYNDDVKYNEKFKGKATQTSDKSSSTAYMELSSLTSEDSAVYYCARWGYYG
SPLYYFDYWGQGTTLTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK

Fig. 26-2

Nucleotide sequence of M30-L1-type light chain (SEQ ID NO: 70)

atggtgctgcagacccaggtgttcatctccctgctgctgtggatctccggcgcatatggcg
agatcgtgctgacccagagccccgccaccctgtctctgagccctggcgagagagccaccct
gagctgcagagccagcagccgcctgatctacatgcactggtatcagcagaagcccggccag
gcccccagactgctgatctacgccaccagcaacctggccagcggcatccccgccagatttt
ctggcagcggcagcggcaccgacttcaccctgaccatctctcggctggaacccgaggactt
cgccgtgtactactgccagcagtggaacagcaaccccccaccttcggccagggcaccaag
gtcgaaatcaagcgtacggtggccgccccctccgtgttcatcttccccccctccgacgagc
agctgaagtccggcaccgcctccgtggtgtgcctgctgaataacttctacccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacagggggagtgt

Fig. 27-1

Amino acid sequence of M30-L1-type light chain (SEQ ID NO: 71)

MVLQTQVFISLLLWISGAYGEIVLTQSPATLSLSPGERATLSCRASSRLIYMHWYQQKPGQ
APRLLIYATSNLASGIPARFSGSGSGTDFTLTISRLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 27-2

Nucleotide sequence of M30-L2-type light chain (SEQ ID NO: 72)

atggtgctgcagacccaggtgttcatctccctgctgctgtggatctccggcgcatatggcg
agatcgtgctgacccagagccccgccaccctgtctctgagccctggcgagagagccaccct
gagctgcagagccagcagcaggctgatctacatgcactggtatcagcagaagcccggccag
gcccccagactgtggatctacgccaccagcaacctggccagcggcatccccgccagatttt
ctggcagcggcagcggcaccgactacaccctgaccatcagccgcctggaacccgaggactt
cgccgtgtactactgccagcagtggaacagcaaccccccaccttcggccagggcaccaag
gtcgaaatcaagcgtacggtggccgcccctccgtgttcatcttcccccctccgacgagc
agctgaagtccggcaccgcctccgtggtgtgcctgctgaataacttctaccccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacaggggggagtgt

Fig. 28-1

Amino acid sequence of M30-L2-type light chain (SEQ ID NO: 73)

MVLQTQVFISLLLWISGAYGEIVLTQSPATLSLSPGERATLSCRASSRLIYMHWYQQKPGQ
APRLWIYATSNLASGIPARFSGSGSGTDYTLTISRLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 28-2

Nucleotide sequence of M30-L3-type light chain (SEQ ID NO: 74)

atggtgctgcagacccaggtgttcatctccctgctgctgtggatctccggcgcatatggcc
agatcgtgctgtcccagagccccgccaccctgtctctgagccctggcgagagagccaccct
gacctgcagagccagcagcaggctgatctacatgcactggtatcagcagaagcccggcagc
gcccccaagctgtggatctacgccaccagcaacctggccagcggcatccccgccagatttt
ctggcagcggcagcggcaccagctacaccctgaccatctcccgcctggaacccgaggactt
cgccgtgtactactgccagcagtggaacagcaaccccccaccttcggccagggcaccaag
gtcgaaatcaagcgtacggtggccgcccctccgtgttcatcttccccccctccgacgagc
agctgaagtccggcaccgcctccgtggtgtgcctgctgaataacttctacccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctccccgt
caccaagagcttcaacagggggagtgt

Fig. 29-1

Amino acid sequence of M30-L3-type light chain (SEQ ID NO: 75)

MVLQTQVFISLLLWISGAYGQIVLSQSPATLSLSPGERATLTCRASSRLIYMHWYQQKPGS
APKLWIYATSNLASGIPARFSGSGSGTSYTLTISRLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 29-2

Nucleotide sequence of M30-L4-type light chain (SEQ ID NO: 76)

atggtgctgcagacccaggtgttcatctccctgctgctgtggatctccggcgcatatggcg
agatcgtgctgacccagagccccgccaccctgtctctgagccctggcgagagagccaccct
gagctgcagagccagcagccgcctgatctacatgcactggtatcagcagaagcccggccag
gcccccagacctctgatctacgccaccagcaacctggccagcggcatccccgccagatttt
ctggcagcggcagcggcaccgacttcaccctgaccatcagcagcctggaacccgaggactt
cgccgtgtactactgccagcagtggaacagcaaccccccaccttcggccagggcaccaag
gtcgaaatcaagcgtacggtggccgcccctccgtgttcatcttcccccctccgacgagc
agctgaagtccggcaccgcctccgtggtgtgcctgctgaataacttctacccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacagggggagtgt

Fig. 30-1

Amino acid sequence of M30-L4-type light chain (SEQ ID NO: 77)

MVLQTQVFISLLLWISGAYGEIVLTQSPATLSLSPGERATLSCRASSRLIYMHWYQQKPGQ
APRPLIYATSNLASGIPARFSGSGSGTDFTLTISSLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 30-2

Nucleotide sequence of M30-L5-type light chain (SEQ ID NO: 78)

atggtgctgcagacccaggtgttcatctccctgctgctgtggatctccggcgcatatggcc
agatcgtgctgtcccagagccccgccaccctgtctctgagccctggcgagagagccaccct
gacctgcagagccagcagcaggctgatctacatgcactggtatcagcagaagcccggcagc
gcccccaagccttggatctacgccaccagcaacctggccagcggcatccccgccagatttt
ctggcagcggcagcggcaccagctacaccctgaccatctcccgcctggaacccgaggactt
cgccgtgtactactgccagcagtggaacagcaaccccccaccttcggccagggcaccaag
gtcgaaatcaagcgtacggtggccgcccctcgtgttcatcttccccccctccgacgagc
agctgaagtccggcaccgcctccgtggtgtgcctgctgaataacttctaccccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacagggggagtgt

Fig. 31-1

Amino acid sequence of M30-L5-type light chain (SEQ ID NO: 79)

MVLQTQVFISLLLWISGAYGQIVLSQSPATLSLSPGERATLTCRASSRLIYMHWYQQKPGS
APKPWIYATSNLASGIPARFSGSGSGTSYTLTISRLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 31-2

Nucleotide sequence of M30-L6-type light chain (SEQ ID NO: 80)

atggtgctgcagacccaggtgttcatctccctgctgctgtggatctccggcgcatatggcg
agatcgtgctgacccagagccccgccaccctgtctctgagccctggcgagagagccaccct
gagctgcagagccagcagccgcctgatctacatgcactggtatcagcagaagcccggccag
gcccccagacctctgatctacgccaccagcaacctggccagcggcatccccgccagatttt
ctggcagcggcagcggcaccgacttcaccctgaccatcagccgcctggaacccgaggactt
cgccgtgtactactgccagcagtggaacagcaaccccccaccttcggcagggcaccaag
gtcgaaatcaagcgtacggtggccgcccctccgtgttcatcttcccccctccgacgagc
agctgaagtccggcaccgcctccgtggtgtgcctgctgaataacttctaccccagagaggc
caaggtgcagtggaaggtggacaacgccctgcagtccgggaactccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacagggggagtgt

Fig. 32-1

Amino acid sequence of M30-L6-type light chain (SEQ ID NO: 81)

MVLQTQVFISLLLWISGAYGEIVLTQSPATLSLSPGERATLSCRASSRLIYMHWYQQKPGQ
APRPLIYATSNLASGIPARFSGSGSGTDFTLTISRLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 32-2

Nucleotide sequence of M30-L7-type light chain (SEQ ID NO: 82)

atggtgctgcagacccaggtgttcatctccctgctgctgtggatctccggcgcatatggcg
agatcgtgctgacccagagccccgccaccctgtctctgagccctggcgagagagccaccct
gagctgcagagccagcagccgcctgatctacatgcactggtatcagcagaagcccggccag
gcccccagacctctgatctacgccaccagcaacctggccagcggcatccccgccagatttt
ctggcagcggcagcggcaccgactacaccctgaccatcagccgcctggaacccgaggactt
cgccgtgtactactgccagcagtggaacagcaaccccccaccttcggccagggcaccaag
gtcgaaatcaagcgtacggtggccgccccctccgtgttcatcttccccccctccgacgagc
agctgaagtccggcaccgcctccgtggtgtgcctgctgaataacttctacccagagaggc
caaggtgcagtggaaggtggacaacgccctgcagtccgggaactcccaggagagcgtgacc
gagcaggacagcaaggacagcacctacagcctgagcagcaccctgaccctgagcaaagccg
actacgagaagcacaaggtgtacgcctgcgaggtgacccaccagggcctgagctcccccgt
caccaagagcttcaacagggggagtgt

Fig. 33-1

Amino acid sequence of M30-L7-type light chain (SEQ ID NO: 83)

MVLQTQVFISLLLWISGAYGEIVLTQSPATLSLSPGERATLSCRASSRLIYMHWYQQKPGQ
APRPLIYATSNLASGIPARFSGSGSGTDYTLTISRLEPEDFAVYYCQQWNSNPPTFGQGTK
VEIKRTVAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC

Fig. 33-2

Nucleotide sequence of M30-H1-type heavy chain (SEQ ID NO: 84)

atgaaacacctgtggttcttcctcctgctggtggcagctcccagatgggtgctgagccagg
tgcagctggtgcagtctggcgccgaagtgaagaaacccggcagcagcgtgaaggtgtcctg
caaggccagcggctacaccttcaccaactacgtgatgcactgggtgcgccaggcccctggg
cagggactggaatggatgggctacatcaaccctacaacgacgacgtgaagtacaacgaga
agttcaagggcagagtgaccatcaccgccgacgagagcaccagcaccgcctacatggaact
gagcagcctgcggagcgaggacaccgccgtgtactactgcgccagatggggctactacggc
agcccctgtactacttcgactactggggccagggcaccctggtgacagtcagctcagcct
ccaccaagggcccaagcgtcttccccctggcaccctcctccaagagcacctctggcggcac
agccgccctgggctgcctggtcaaggactacttccccgaacccgtgaccgtgagctggaac
tcaggcgccctgaccagcggcgtgcacaccttccccgctgtcctgcagtcctcaggactct
actccctcagcagcgtggtgaccgtgccctccagcagcttgggcacccagacctacatctg
caacgtgaatcacaagcccagcaacaccaaggtggacaagagagttgagcccaaatcttgt
gacaaaactcacacatgcccaccctgcccagcacctgaactcctggggggaccctcagtct
tcctcttccccccaaaacccaaggacaccctcatgatctcccggacccctgaggtcacatg
cgtggtggtggacgtgagccacgaagaccctgaggtcaagttcaactggtacgtggacggc
gtggaggtgcataatgccaagacaaagcccgggaggagcagtacaacagcacgtaccggg
tggtcagcgtcctcaccgtcctgcaccaggactggctgaatggcaaggagtacaagtgcaa
ggtctccaacaaagccctcccagcccccatcgagaaaaccatctccaaagccaaaggccag
ccccgggaaccacaggtgtacaccctgcccccatcccgggaggagatgaccaagaaccagg
tcagcctgacctgcctggtcaaaggcttctatcccagcgacatcgccgtggagtgggagag
caatggccagcccgagaacaactacaagaccacccctcccgtgctggactccgacggctcc
ttcttcctctacagcaagctcaccgtggacaagagcaggtggcagcagggcaacgtcttct
catgctccgtgatgcatgaggctctgcacaaccactacacccagaagagcctctccctgtc
tcccggcaaa

Fig. 34-1

Amino acid sequence of M30-H1-type heavy chain (SEQ ID NO: 85)

MKHLWFFLLLVAAPRWVLSQVQLVQSGAEVKKPGSSVKVSCKASGYTFTNYVMHWVRQAPG
QGLEWMGYINPYNDDVKYNEKFKGRVTITADESTSTAYMELSSLRSEDTAVYYCARWGYYG
SPLYYFDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK

Fig. 34-2

Nucleotide sequence of M30-H2-type heavy chain (SEQ ID NO: 86)

atgaaacacctgtggttcttcctcctgctggtggcagctcccagatgggtgctgagccagg
tgcagctggtgcagtctggcgccgaagtgaagaaacccggcagcagcgtgaaggtgtcctg
caaggccagcggctacaccttcaccaactacgtgatgcactgggtgcgccaggcccctggg
cagggactggaatggatcggctacatcaacccctacaacgacgacgtgaagtacaacgaga
agttcaagggcagagtgaccatcaccgccgacgagagcaccagcaccgcctacatggaact
gagcagcctgcggagcgaggacaccgccgtgtactactgcgccagatggggctactacggc
agccccctgtactacttcgactactggggccagggcaccctggtgacagtcagctcagcct
ccaccaagggcccaagcgtcttccccctggcaccctcctccaagagcacctctggcggcac
agccgccctgggctgcctggtcaaggactacttccccgaacccgtgaccgtgagctggaac
tcaggcgccctgaccagcggcgtgcacaccttccccgctgtcctgcagtcctcaggactct
actccctcagcagcgtggtgaccgtgcctccagcagcttgggcacccagacctacatctg
caacgtgaatcacaagcccagcaacaccaaggtggacaagagagttgagcccaaatcttgt
gacaaaactcacacatgcccaccctgcccagcacctgaactcctggggggaccctcagtct
tcctcttccccccaaaacccaaggacaccctcatgatctcccggacccctgaggtcacatg
cgtggtggtggacgtgagccacgaagaccctgaggtcaagttcaactggtacgtggacggc
gtggaggtgcataatgccaagacaaagccccgggaggagcagtacaacagcacgtaccggg
tggtcagcgtcctcaccgtcctgcaccaggactggctgaatggcaaggagtacaagtgcaa
ggtctccaacaaagccctcccagcccccatcgagaaaaccatctccaaagccaaaggccag
ccccgggaaccacaggtgtacaccctgcccccatcccgggaggagatgaccaagaaccagg
tcagcctgacctgcctggtcaaaggcttctatcccagcgacatcgccgtggagtgggagag
caatggccagcccgagaacaactacaagaccacccctcccgtgctggactccgacggctcc
ttcttcctctacagcaagctcaccgtggacaagagcaggtggcagcagggcaacgtcttct
catgctccgtgatgcatgaggctctgcacaaccactacacccagaagagcctctccctgtc
tcccggcaaa

Fig. 35-1

Amino acid sequence of M30-H2-type heavy chain (SEQ ID NO: 87)

MKHLWFFLLLVAAPRWVLSQVQLVQSGAEVKKPGSSVKVSCKASGYTFTNYVMHWVRQAPG
QGLEWIGYINPYNDDVKYNEKFKGRVTITADESTSTAYMELSSLRSEDTAVYYCARWGYYG
SPLYYFDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK

Fig. 35-2

Nucleotide sequence of M30-H3-type heavy chain (SEQ ID NO: 88)

atgaaacacctgtggttcttcctcctgctggtggcagctcccagatgggtgctgagcgagg
tgcagctggtgcagtctggcgccgaagtgaagaaacccggcagcagcgtgaaggtgtcctg
caaggccagcggctacaccttcaccaactacgtgatgcactgggtgaaacaggcccctggg
cagggcctggaatggatcggctacatcaaccctacaacgacgacgtgaagtacaacgaga
agttcaagggcaaggccaccatcaccgccgacgagagcaccagcaccgcctacatggaact
gagcagcctgcggagcgaggacaccgccgtgtactactgcgccagatggggctactacggc
agcccctgtactacttcgactactggggccagggcaccctggtgacagtcagctcagcct
ccaccaagggcccaagcgtcttcccctggcaccctcctccaagagcacctctggcggcac
agccgccctgggctgcctggtcaaggactacttccccgaacccgtgaccgtgagctggaac
tcaggcgccctgaccagcggcgtgcacaccttccccgctgtcctgcagtcctcaggactct
actccctcagcagcgtggtgaccgtgcctccagcagcttgggcacccagacctacatctg
caacgtgaatcacaagcccagcaacaccaaggtggacaagagagttgagcccaaatcttgt
gacaaaactcacacatgcccaccctgcccagcacctgaactcctggggggaccctcagtct
tcctcttccccccaaaacccaaggacaccctcatgatctcccggacccctgaggtcacatg
cgtggtggtggacgtgagccacgaagaccctgaggtcaagttcaactggtacgtggacggc
gtggaggtgcataatgccaagacaaagccccgggaggagcagtacaacagcacgtaccggg
tggtcagcgtcctcaccgtcctgcaccaggactggctgaatggcaaggagtacaagtgcaa
ggtctccaacaaagccctcccagcccccatcgagaaaaccatctccaaagccaaaggccag
ccccgggaaccacaggtgtacaccctgcccccatcccgggaggagatgaccaagaaccagg
tcagcctgacctgcctggtcaaaggcttctatcccagcgacatcgccgtggagtgggagag
caatggccagcccgagaacaactacaagaccacccctcccgtgctggactccgacggctcc
ttcttcctctacagcaagctcaccgtggacaagagcaggtggcagcagggcaacgtcttct
catgctccgtgatgcatgaggctctgcacaaccactacacccagaagagcctctccctgtc
tcccggcaaa

Fig. 36-1

Amino acid sequence of M30-H3-type heavy chain (SEQ ID NO: 89)

MKHLWFFLLLVAAPRWVLSEVQLVQSGAEVKKPGSSVKVSCKASGYTFTNYVMHWVKQAPG
QGLEWIGYINPYNDDVKYNEKFKGKATITADESTSTAYMELSSLRSEDTAVYYCARWGYYG
SPLYYFDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK

Fig. 36-2

Nucleotide sequence of M30-H4-type heavy chain (SEQ ID NO: 90)

atgaaacacctgtggttcttcctcctgctggtggcagctcccagatgggtgctgagcgagg
tgcagctggtgcagtctggcgccgaagtgaagaaacccggcagcagcgtgaaggtgtcctg
caaggccagcggctacaccttcaccaactacgtgatgcactgggtcaagcaggcccctggg
cagggcctggaatggatcggctacatcaaccccctacaacgacgacgtgaagtacaacgaga
agttcaagggcaaggccacccagaccagcgacaagagcaccagcaccgcctacatggaact
gagcagcctgcggagcgaggacaccgccgtgtactactgcgccagatggggctactacggc
agcccctgtactacttcgactactggggccagggcaccctggtcaccgtcagctcagcct
ccaccaagggcccaagcgtcttcccctggcaccctcctccaagagcacctctggcggcac
agccgccctgggctgcctggtcaaggactacttccccgaacccgtgaccgtgagctggaac
tcaggcgccctgaccagcggcgtgcacaccttccccgctgtcctgcagtcctcaggactct
actccctcagcagcgtggtgaccgtgccctccagcagcttgggcacccagacctacatctg
caacgtgaatcacaagcccagcaacaccaaggtggacaagagagttgagcccaaatcttgt
gacaaaactcacacatgcccaccctgcccagcacctgaactcctggggggaccctcagtct
tcctcttccccccaaaacccaaggacaccctcatgatctcccggacccctgaggtcacatg
cgtggtggtggacgtgagccacgaagaccctgaggtcaagttcaactggtacgtggacggc
gtggaggtgcataatgccaagacaaagccccgggaggagcagtacaacagcacgtaccggg
tggtcagcgtcctcaccgtcctgcaccaggactggctgaatggcaaggagtacaagtgcaa
ggtctccaacaaagccctcccagcccccatcgagaaaaccatctccaaagccaaaggccag
ccccgggaaccacaggtgtacaccctgcccccatcccgggaggagatgaccaagaaccagg
tcagcctgacctgcctggtcaaaggcttctatcccagcgacatcgccgtggagtgggagag
caatggccagcccgagaacaactacaagaccacccctcccgtgctggactccgacggctcc
ttcttcctctacagcaagctcaccgtggacaagagcaggtggcagcagggcaacgtcttct
catgctccgtgatgcatgaggctctgcacaaccactacacccagaagagcctctccctgtc
tcccggcaaa

Fig. 37-1

Amino acid sequence of M30-H4-type heavy chain (SEQ ID NO: 91)

MKHLWFFLLLVAAPRWVLSEVQLVQSGAEVKKPGSSVKVSCKASGYTFTNYVMHWVKQAPG
QGLEWIGYINPYNDDVKYNEKFKGKATQTSDKSTSTAYMELSSLRSEDTAVYYCARWGYYG
SPLYYFDYWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKRVEPKSC
DKTHTCPPCPAPELLGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGK

Fig. 37-2

ANTI B7-H3 ANTIBODY

STATEMENT REGARDING SEQUENCE LISTING

The sequence listing associated with this application is provided in text format in lieu of a paper copy and is hereby incorporated by reference into the specification. The name of the text file containing the sequence listing is 39233_Sequence_Final_20120424.txt. The text file is 126 KB, was created on Apr. 24, 2012, and is being submitted via EFS-Web with the filing of the specification.

TECHNICAL FIELD

The present invention relates to an antibody which binds to B7-H3 and is useful as a therapeutic and/or preventive agent for a tumor, and also relates to a method of treating and/or preventing a tumor using the antibody.

BACKGROUND ART

B7-H3 is a protein having a single-pass transmembrane structure (Non-patent document 1). The N-terminal extracellular domain of B7-H3 contains two variants. Variant 1 contains a V-like or C-like Ig domain at two sites, respectively, and Variant 2 contains a V-like or C-like Ig domain at one site, respectively. The C-terminal intracellular domain of B7-H3 contains 45 amino acids.

As a receptor for B7-H3, TLT-2 having a single-pass transmembrane structure has been reported (Non-patent document 2). However, there is also a report insisting that TLT-2 is not a receptor for B7-H3 (Non-patent document 3). According to the former report, the activation of CD8-positive T cells is enhanced when the receptor is bound to B7-H3.

It has been clinically reported that B7-H3 is overexpressed in many cancer types, particularly in non-small-cell lung cancer, kidney cancer, urothelial carcinoma, colorectal cancer, prostate cancer, glioblastoma multiforme, ovarian cancer, and pancreatic cancer (Non-patent documents 4 to 11). Further, it has been reported that in prostate cancer, the intensity of expression of B7-H3 positively correlates with clinicopathological malignancy such as tumor volume, extraprostatic invasion, or Gleason score, and also correlates with cancer progression (Non-patent document 8). Similarly, in glioblastoma multiforme, the expression of B7-H3 negatively correlates with event-free survival (Non-patent document 9), and in pancreatic cancer, the expression of B7-H3 correlates with lymph node metastasis and pathological progression (Non-patent document 11). In ovarian cancer, the expression of B7-H3 correlates with lymph node metastasis and pathological progression.

Further, it has been reported that by introducing siRNA against B7-H3 gene into a B7-H3-positive cancer cell line, adhesiveness to fibronectin is reduced to reduce cell migration and matrigel invasion (Non-patent document 12). Further, it has been reported that in glioblastoma multiforme, the expression of B7-H3 allows escape from NK cell-mediated cell death (Non-patent document 13).

On the other hand, B7-H3 has been reported to be expressed not only in cancer cells, but also in tumors or surrounding vessels (Non-patent documents 5 and 14). It has been reported that when B7-H3 is expressed in ovarian cancer blood vessels, the survival rate is decreased.

B7 family molecules have been suggested to be related to the immune system. B7-H3 has been reported to be expressed in monocytes, dendritic cells, and activated T cells (Non-patent document 15). It has been reported that as cytotoxic T cells are activated, B7-H3 co-stimulates the proliferation of CD4-positive or CD8-positive T cells. However, there is also a report that B7-H3 does not play a co-stimulatory role (Non-patent document 1).

B7-H3 molecules have been reported to be related to autoimmune diseases. It has been reported that in rheumatism and other autoimmune diseases, B7-H3 plays an important role in the interaction between fibroblast-like synoviocytes and activated T-cells (Non-patent document 16) and that B7-H3 functions as a co-stimulatory factor when cytokines are released from activated macrophages and therefore is related to the occurrence of sepsis (Non-patent document 17). Further, it has been reported that by administering an anti-B7-H3 antibody to a mouse model of asthma during the induction phase, asthma is improved due to the suppression of Th2 cell-mediated cytokine production in regional lymph nodes through the administration of an anti-mouse B7-H3 antibody (Non-patent document 18).

With respect to B7-H3, it has been reported that an antibody against mouse B7-H3 enhances intratumoral infiltrating CD8-positive T cells and suppresses tumor growth (Non-patent document 14). Further, there is a patent which discloses that an antibody which recognizes B7-H3 variant 1 exhibits an in vivo antitumor effect on adenocarcinoma (Patent document 1).

In spite of these studies, an epitope for an anti-B7-H3 antibody which exhibits an in vivo antitumor effect has not been clarified so far, and there has been no report that a specific amino acid sequence of the extracellular domain of B7-H3 is useful as an epitope for a monoclonal antibody for treating cancer.

Even if antibodies are specific for the same antigen, the properties of the antibodies vary due to a difference of epitopes or sequences of the antibodies. Due to the difference in properties of the antibodies, when being clinically administrated to humans, the antibodies exhibit different reactions in terms of the effectiveness of the medicinal agent, the frequency of therapeutic response, the incidence of side effects or drug resistance, etc.

Also for the antibody against B7-H3, the creation of an antibody having unprecedented properties has been strongly demanded.

RELATED ART DOCUMENTS

Patent Document

Patent Document 1: WO 2008/066691

Non-Patent Documents

Non-patent Document 1: The Journal of Immunology, 2004, vol. 172, pp. 2352-2359
Non-patent Document 2: Proceedings of the National Academy of Sciences of the United States of America, 2008, vol. 105, pp. 10495-10500
Non-patent Document 3: European Journal of Immunology, 2009, vol. 39 pp. 1754-1764
Non-patent Document 4: Lung Cancer, 2009, vol. 66, pp. 245-249
Non-patent Document 5: Clinical Cancer Research, 2008, vol. 14, pp. 5150-5157
Non-patent Document 6: Clinical Cancer Research 2008, vol. 14, pp. 4800-4808
Non-patent Document 7: Cancer Immunology, Immunotherapy, 2010, vol. 59, pp. 1163-1171

Non-patent Document 8: Cancer Research, 2007, vol. 67, pp. 7893-7900

Non-patent Document 9: Histopathology, 2008, vol. 53, pp. 73-80

Non-patent Document 10: Modern Pathology, 2010, vol. 23, pp. 1104-1112

Non-patent Document 11: British Journal of Cancer, 2009, vol. 101, pp. 1709-1716

Non-patent Document 12: Current Cancer Drug Targets, 2008, vol. 8, pp. 404-413

Non-patent Document 13: Proceedings of the National Academy of Sciences of the United States of America, 2004, vol. 101, pp. 12640-12645

Non-patent Document 14: Modern Pathology, 2010, vol. 23, pp. 1104-1112

Non-patent Document 15: Nature Immunology, 2001, vol. 2, pp. 269-274

Non-patent Document 16: The Journal of Immunology, 2008, vol. 180, pp. 2989-2998

Non-patent Document 17: The Journal of Immunology, 2010, vol. 185, pp. 3677-3684

Non-patent Document 18: The Journal of Immunology, 2008, vol. 181, pp. 4062-4071

SUMMARY OF THE INVENTION

Problems to be Solved by the Invention

An object of the invention is to provide an antibody and a functional fragment of the antibody to be used in a pharmaceutical having a therapeutic effect on a tumor, a method of treating a tumor using the antibody or a functional fragment of the antibody, and the like.

Means for Solving the Problems

The present inventors made intensive studies in order to achieve the above object, and as a result, they discovered an antibody which specifically binds to B7-H3 to exhibit an antitumor activity, and thus completed the invention. That is, the invention includes the following inventions.

(1) An antibody characterized by having the following properties:
   (a) specific binding to B7-H3;
   (b) having an antibody-dependent cell-mediated phagocytosis (ADCP) activity; and
   (c) having an in vivo antitumor activity,
   or a functional fragment of the antibody.

(2) The antibody or a functional fragment of the antibody according to the above (1), wherein B7-H3 is a molecule including an amino acid sequence represented by SEQ ID NO: 6 or 10.

(3) The antibody or a functional fragment of the antibody according to the above (1) or (2), which binds to IgC1 and/or IgC2 each of which is a domain of B7-H3.

(4) The antibody or a functional fragment of the antibody according to the above (3), wherein IgC1 is a domain including an amino acid sequence represented by amino acid numbers 140 to 244 in SEQ ID NO: 6, and IgC2 is a domain including an amino acid sequence represented by amino acid numbers 358 to 456 in SEQ ID NO: 6.

(5) The antibody or a functional fragment of the antibody according to any one of the above (1) to (4), which has a competitive inhibitory activity against M30 antibody for the binding to B7-H3.

(6) The antibody or a functional fragment of the antibody according to any one of the above (1) to (5), which has an antibody-dependent cellular cytotoxicity (ADCC) activity and/or a complement-dependent cytotoxicity (CDC) activity.

(7) The antibody or a functional fragment of the antibody according to any one of the above (1) to (6), wherein the tumor is cancer.

(8) The antibody or a functional fragment of the antibody according to the above (7), wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

(9) The antibody or a functional fragment of the antibody according to any one of the above (1) to (8), which comprises CDRH1 consisting of an amino acid sequence represented by SEQ ID NO: 92, CDRH2 consisting of an amino acid sequence represented by SEQ ID NO: 93, and CDRH3 consisting of an amino acid sequence represented by SEQ ID NO: 94 as complementarity determining regions of the heavy chain and comprises CDRL1 consisting of an amino acid sequence represented by SEQ ID NO: 95, CDRL2 consisting of an amino acid sequence represented by SEQ ID NO: 96, and CDRL3 consisting of an amino acid sequence represented by SEQ ID NO: 97 as complementarity determining regions of the light chain.

(10) The antibody or a functional fragment of the antibody according to any one of the above (1) to (9), which comprises a heavy chain variable region consisting of an amino acid sequence represented by amino acid numbers 20 to 141 in SEQ ID NO: 51 and a light chain variable region consisting of an amino acid sequence represented by amino acid numbers 23 to 130 in SEQ ID NO: 53.

(11) The antibody or a functional fragment of the antibody according to any one of the above (1) to (10), wherein a constant region is a human-derived constant region.

(12) The antibody or a functional fragment of the antibody according to the above (11), which comprises a heavy chain consisting of an amino acid sequence represented by SEQ ID NO: 63 and a light chain consisting of an amino acid sequence represented by SEQ ID NO: 59.

(13) The antibody or a functional fragment of the antibody according to any one of the above (1) to (12), which is humanized.

(14) The antibody or a functional fragment of the antibody according to the above (13), which comprises: a heavy chain variable region consisting of an amino acid sequence selected from the group consisting of (a) an amino acid sequence represented by amino acid numbers 20 to 141 in SEQ ID NO: 85, (b) an amino acid sequence represented by amino acid numbers 20 to 141 in SEQ ID NO: 87, (c) an amino acid sequence represented by amino acid numbers 20 to 141 in SEQ ID NO: 89, (d) an amino acid sequence represented by amino acid numbers 20 to 141 in SEQ ID NO: 91, (e) an amino acid sequence having a homology of at least 95% or more with any of the sequences (a) to (d), and (f) an amino acid sequence wherein one or several amino acids are deleted, substituted or added in any of the sequences (a) to (d); and a light chain variable region consisting of an amino acid sequence selected from the group consisting of (g) an amino acid sequence represented by amino acid numbers 21 to 128 in SEQ ID NO: 71, (h) an amino acid sequence represented by amino acid numbers 21 to 128 in SEQ ID NO: 73, (i) an amino acid sequence represented by amino acid numbers 21 to 128 in SEQ ID NO: 75, (j) an amino acid sequence represented by amino acid numbers 21 to 128 in SEQ ID NO: 77, (k) an amino acid sequence represented by amino acid numbers 21 to 128 in SEQ ID NO: 79, (l) an amino acid sequence represented by amino acid numbers 21 to 128 in SEQ ID NO: 81, (m) an amino acid sequence represented by amino acid numbers 21 to 128 in SEQ ID NO: 83, (n) an amino acid sequence having a homology of at least 95% or more with any of the sequences (g) to (m), and (o) an amino acid sequence wherein one or several amino acids are deleted, substituted or added in any of the sequences (g) to (m).

(15) The antibody or a functional fragment of the antibody according to the above (14), which comprises a heavy chain variable region and a light chain variable region selected from the group consisting of: a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 71; a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 73; a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 75; a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 77; a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 79; a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 81; a heavy chain variable region consisting of an amino acid sequence represented by amino acid numbers 20 to 141 in SEQ ID NO: 85 and a light chain variable region consisting of an amino acid sequence represented by amino acid numbers 21 to 128 in SEQ ID NO: 83; a heavy chain variable region consisting of an amino acid sequence represented by amino acid numbers 20 to 141 in SEQ ID NO: 91 and a light chain variable region consisting of an amino acid sequence represented by amino acid numbers 21 to 128 in SEQ ID NO: 71; a heavy chain variable region consisting of an amino acid sequence represented by amino acid numbers 20 to 141 in SEQ ID NO: 91 and a light chain variable region consisting of an amino acid sequence represented by amino acid numbers 21 to 128 in SEQ ID NO: 73; a heavy chain variable region consisting of an amino acid sequence represented by amino acid numbers 20 to 141 in SEQ ID NO: 91 and a light chain variable region consisting of an amino acid sequence represented by amino acid numbers 21 to 128 in SEQ ID NO: 75; and a heavy chain variable region consisting of an amino acid sequence represented by amino acid numbers 20 to 141 in SEQ ID NO: 91 and a light chain variable region consisting of an amino acid sequence represented by amino acid numbers 21 to 128 in SEQ ID NO: 77.

(16) The antibody or a functional fragment of the antibody according to the above (14) or (15), which comprises a heavy chain and a light chain selected from the group consisting of: a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 71; a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 73; a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 75; a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 77; a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 79; a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 81; a heavy chain consisting of an amino acid sequence represented by amino acid numbers 20 to 471 in SEQ ID NO: 85 and a light chain consisting of an amino acid sequence represented by amino acid numbers 21 to 233 in SEQ ID NO: 83; a heavy chain consisting of an amino acid sequence represented by amino acid numbers 20 to 471 in SEQ ID NO: 91 and a light chain consisting of an amino acid sequence represented by amino acid numbers 21 to 233 in SEQ ID NO: 71; a heavy chain consisting of an amino acid sequence represented by amino acid numbers 20 to 471 in SEQ ID NO: 91 and a light chain consisting of an amino acid sequence represented by amino acid numbers 21 to 233 in SEQ ID NO: 73; a heavy chain consisting of an amino acid sequence represented by amino acid numbers 20 to 471 in SEQ ID NO: 91 and a light chain consisting of an amino acid sequence represented by amino acid numbers 21 to 233 in SEQ ID NO: 75; and a heavy chain consisting of an amino acid sequence represented by amino acid numbers 20 to 471 in SEQ ID NO: 91 and a light chain consisting of an amino acid sequence represented by amino acid numbers 21 to 233 in SEQ ID NO: 77.

(17) The antibody or a functional fragment of the antibody according to any one of the above (14) to (16), which comprises a heavy chain and a light chain selected from the group consisting of: a heavy chain consisting of an amino acid sequence represented by SEQ ID NO: 85 and a light chain consisting of an amino acid sequence represented by SEQ ID NO: 71; a heavy chain consisting of an amino acid sequence represented by SEQ ID NO: 85 and a light chain consisting of an amino acid sequence represented by SEQ ID NO: 73; a heavy chain consisting of an amino acid sequence represented by SEQ ID NO:

85 and a light chain consisting of an amino acid sequence represented by SEQ ID NO: 75; a heavy chain consisting of an amino acid sequence represented by SEQ ID NO: 85 and a light chain consisting of an amino acid sequence represented by SEQ ID NO: 77; a heavy chain consisting of an amino acid sequence represented by SEQ ID NO: 85 and a light chain consisting of an amino acid sequence represented by SEQ ID NO: 79; a heavy chain consisting of an amino acid sequence represented by SEQ ID NO: 85 and a light chain consisting of an amino acid sequence represented by SEQ ID NO: 81; a heavy chain consisting of an amino acid sequence represented by SEQ ID NO: 85 and a light chain consisting of g an amino acid sequence represented by SEQ ID NO: 83; a heavy chain consisting of an amino acid sequence represented by SEQ ID NO: 91 and a light chain consisting of an amino acid sequence represented by SEQ ID NO: 71; a heavy chain consisting of an amino acid sequence represented by SEQ ID NO: 91 and a light chain consisting of an amino acid sequence represented by SEQ ID NO: 73; a heavy chain consisting of an amino acid sequence represented by SEQ ID NO: 91 and a light chain consisting of an amino acid sequence represented by SEQ ID NO: 75; and a heavy chain consisting of an amino acid sequence represented by SEQ ID NO: 91 and a light chain consisting of an amino acid sequence represented by SEQ ID NO: 77.

(18) The functional fragment of the antibody according to any one of the above (1) to (17), wherein the functional fragment is selected from the group consisting of Fab, F(ab)$_2$, Fab' and Fv.

(19) A polynucleotide encoding the antibody or a functional fragment of the antibody according to any one of the above (1) to (18).

(20) The polynucleotide according to the above (19), which comprises a nucleotide sequence represented by nucleotide numbers 58 to 423 in SEQ ID NO: 50 and a nucleotide sequence represented by nucleotide numbers 67 to 390 in SEQ ID NO: 52.

(21) The polynucleotide according to the above (19) or (20), which includes a nucleotide sequence represented by SEQ ID NO: 62 and a nucleotide sequence represented by SEQ ID NO: 58.

(22) The polynucleotide according to the above (19) or (20), which comprises: a nucleotide sequence selected from the group consisting of (a) a nucleotide sequence represented by nucleotide numbers 58 to 423 in SEQ ID NO: 84, (b) a nucleotide sequence represented by nucleotide numbers 58 to 423 in SEQ ID NO: 86, (c) a nucleotide sequence represented by nucleotide numbers 58 to 423 in SEQ ID NO: 88, (d) a nucleotide sequence represented by nucleotide numbers 58 to 423 in SEQ ID NO: 90, and (e) a nucleotide sequence comprising a polynucleotide which hybridizes to a polynucleotide consisting of a nucleotide sequence complementary to any of the nucleotide sequences (a) to (d) under stringent conditions; and a nucleotide sequence selected from the group consisting of (f) a nucleotide sequence represented by nucleotide numbers 61 to 384 in SEQ ID NO: 70, (g) a nucleotide sequence represented by nucleotide numbers 61 to 384 in SEQ ID NO: 72, (h) a nucleotide sequence represented by nucleotide numbers 61 to 384 in SEQ ID NO: 74, (i) a nucleotide sequence represented by nucleotide numbers 61 to 384 in SEQ ID NO: 76, (j) a nucleotide sequence represented by nucleotide numbers 61 to 384 in SEQ ID NO: 78, (k) a nucleotide sequence represented by nucleotide numbers 61 to 384 in SEQ ID NO: 80, (1) a nucleotide sequence represented by nucleotide numbers 61 to 384 in SEQ ID NO: 82, and (m) a nucleotide sequence comprising a polynucleotide which hybridizes to a polynucleotide consisting of a nucleotide sequence complementary to any of the nucleotide sequences (f) to (1) under stringent conditions.

(23) The polynucleotide according to the above (22), which comprises nucleotide sequences selected from the group consisting of: a nucleotide sequence represented by nucleotide numbers 58 to 423 in SEQ ID NO: 84 and a nucleotide sequence represented by nucleotide numbers 61 to 384 in SEQ ID NO: 70; a nucleotide sequence represented by nucleotide numbers 58 to 423 in SEQ ID NO: 84 and a nucleotide sequence represented by nucleotide numbers 61 to 384 in SEQ ID NO: 72; a nucleotide sequence represented by nucleotide numbers 58 to 423 in SEQ ID NO: 84 and a nucleotide sequence represented by nucleotide numbers 61 to 384 in SEQ ID NO: 74; a nucleotide sequence represented by nucleotide numbers 58 to 423 in SEQ ID NO: 84 and a nucleotide sequence represented by nucleotide numbers 61 to 384 in SEQ ID NO: 76; a nucleotide sequence represented by nucleotide numbers 58 to 423 in SEQ ID NO: 84 and a nucleotide sequence represented by nucleotide numbers 61 to 384 in SEQ ID NO: 78; a nucleotide sequence represented by nucleotide numbers 58 to 423 in SEQ ID NO: 84 and a nucleotide sequence represented by nucleotide numbers 61 to 384 in SEQ ID NO: 80; a nucleotide sequence represented by nucleotide numbers 58 to 423 in SEQ ID NO: 84 and a nucleotide sequence represented by nucleotide numbers 61 to 384 in SEQ ID NO: 82; a nucleotide sequence represented by nucleotide numbers 58 to 423 in SEQ ID NO: 90 and a nucleotide sequence represented by nucleotide numbers 61 to 384 in SEQ ID NO: 70; a nucleotide sequence represented by nucleotide numbers 58 to 423 in SEQ ID NO: 90 and a nucleotide sequence represented by nucleotide numbers 61 to 384 in SEQ ID NO: 72; a nucleotide sequence represented by nucleotide numbers 58 to 423 in SEQ ID NO: 90 and a nucleotide sequence represented by nucleotide numbers 61 to 384 in SEQ ID NO: 74; and a nucleotide sequence represented by nucleotide numbers 58 to 423 in SEQ ID NO: 90 and a nucleotide sequence represented by nucleotide numbers 61 to 384 in SEQ ID NO: 76.

(24) The polynucleotide according to the above (22) or (23), which comprises nucleotide sequences selected from the group consisting of: a nucleotide sequence represented by nucleotide numbers 58 to 1413 in SEQ ID NO: 84 and a nucleotide sequence represented by nucleotide numbers 61 to 699 in SEQ ID NO: 70; a nucleotide sequence represented by nucleotide numbers 58 to 1413 in SEQ ID NO: 84 and a nucleotide sequence represented by nucleotide numbers 61 to 699 in SEQ ID NO: 72; a nucleotide sequence represented by nucleotide numbers 58 to 1413 in SEQ ID NO: 84 and a nucleotide sequence represented by nucleotide numbers 61 to 699 in SEQ ID NO: 74; a nucleotide sequence represented by nucleotide numbers 58 to 1413 in SEQ ID NO: 84 and a nucleotide sequence represented by nucleotide numbers 61 to 699 in SEQ ID NO: 76; a nucleotide sequence represented by nucleotide numbers 58 to 1413 in SEQ ID NO: 84 and a nucleotide sequence represented by nucleotide numbers 61 to 699 in SEQ ID NO: 78; a nucleotide sequence represented by nucleotide numbers 58 to 1413 in SEQ ID NO: 84 and a nucleotide sequence represented by nucleotide numbers 61 to 699 in SEQ ID NO: 80; a nucleotide sequence represented by nucleotide numbers 58 to 1413 in SEQ ID NO: 84 and a nucleotide sequence represented by nucleotide numbers 61 to 699 in SEQ ID NO: 82; a nucleotide sequence represented by nucleotide numbers 58 to 1413 in SEQ ID NO: 90 and a nucleotide sequence represented by nucleotide numbers 61 to 699 in SEQ ID NO: 70; a nucleotide sequence represented by nucleotide numbers 58 to 1413 in SEQ ID NO: 90 and a nucleotide sequence represented by nucleotide numbers 61 to 699 in SEQ ID NO: 72; a nucleotide sequence represented by nucleotide numbers 58 to 1413 in SEQ ID NO: 90 and a nucleotide sequence represented by nucleotide numbers 61 to 699 in SEQ ID NO: 74; and a nucleotide sequence represented by nucleotide numbers 58 to 1413 in SEQ ID NO: 90 and a nucleotide sequence represented by nucleotide numbers 61 to 699 in SEQ ID NO: 76.

(25) The polynucleotide according to any one of the above (22) to (24), which comprises nucleotide sequences selected from the group consisting of: a nucleotide sequence represented by SEQ ID NO: 84 and a nucleotide sequence represented by SEQ ID NO: 70; a nucleotide sequence represented by SEQ ID NO: 84 and a nucleotide sequence represented by SEQ ID NO: 72; a nucleotide sequence represented by SEQ ID NO: 84 and a nucleotide sequence represented by SEQ ID NO: 74; a nucleotide sequence represented by SEQ ID NO: 84 and a nucleotide sequence represented by SEQ ID NO: 76; a nucleotide sequence represented by SEQ ID NO: 84 and a nucleotide sequence represented by SEQ ID NO: 78; a nucleotide sequence represented by SEQ ID NO: 84 and a nucleotide sequence represented by SEQ ID NO: 80; a nucleotide sequence represented by SEQ ID NO: 84 and a nucleotide sequence represented by SEQ ID NO: 82; a nucleotide sequence represented by SEQ ID NO: 90 and a nucleotide sequence represented by SEQ ID NO: 70; a nucleotide sequence represented by SEQ ID NO: 90 and a nucleotide sequence represented by SEQ ID NO: 72; a nucleotide sequence represented by SEQ ID NO: 90 and a nucleotide sequence represented by SEQ ID NO: 74; and a nucleotide sequence represented by SEQ ID NO: 90 and a nucleotide sequence represented by SEQ ID NO: 76.

(26) An expression vector including a polynucleotide according to any one of the above (19) to (25).

(27) A host cell, which is transformed with the expression vector according to the above (26).

(28) The host cell according to the above (27), wherein the host cell is a eukaryotic cell.

(29) A method of producing an antibody or a functional fragment of the antibody, characterized by including a step of culturing the host cell according to the above (27) or (28) and a step of collecting a desired antibody or a functional fragment of the antibody from a cultured product obtained in the culturing step.

(30) An antibody or a functional fragment of the antibody, characterized by being obtained by the production method according to the above (29).

(31) The functional fragment of the antibody according to the above (30), wherein the functional fragment is selected from the group consisting of Fab, F(ab)$_2$, Fab' and Fv.

(32) The antibody or a functional fragment of the antibody according to any one of the above (1) to (18), (30), and (31), wherein the modification of a glycan is regulated to enhance an antibody-dependent cellular cytotoxic activity.

(33) A pharmaceutical composition characterized by including at least one of the antibodies or functional fragments of the antibodies according to the above (1) to (18), and (30) to (32).

(34) The pharmaceutical composition according to the above (33), which is for treating a tumor.

(35) A pharmaceutical composition for treating a tumor characterized by including at least one of the antibodies or functional fragments of the antibodies according to the above (1) to (18), and (30) to (32) and at least one therapeutic agent for cancer.

(36) The pharmaceutical composition according to the above (34) or (35), wherein the tumor is cancer.

(37) The pharmaceutical composition according to the above (36), wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

(38) A method of treating a tumor, characterized by administering at least one of the antibodies or functional fragments of the antibodies according to the above (1) to (18), and (30) to (32) to an individual.

(39) A method of treating a tumor, characterized by administering at least one of the antibodies or functional fragments of the antibodies according to the above (1) to (18), and (30) to (32) and at least one therapeutic agent for cancer simultaneously, separately, or sequentially to an individual.

(40) The treatment method according to the above (38) or (39), wherein the tumor is cancer.

(41) The treatment method according to the above (40), wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

Advantage of the Invention

According to the invention, a therapeutic agent or the like for cancer comprising an antibody which binds to B7-H3 and has an antitumor activity against cancer cells can be obtained.

BRIEF DESCRIPTION OF THE DRAWINGS

FIG. 5-1 is a graph showing the reactivity of M30 antibody against a B7-H3 deficient mutant (B7-H3 IgV1). The dotted line indicates the binding property of a control antibody, and the solid line indicates the binding property of an M30 antibody.

FIG. 5-2 is a graph showing the reactivity of M30 antibody against a B7-H3 deficient mutant (B7-H3 IgC1). The dotted line indicates the binding property of a control antibody, and the solid line indicates the binding property of an M30 antibody.

FIG. 5-3 is a graph showing the reactivity of M30 antibody against a B7-H3 deficient mutant (B7-H3 IgV2). The dotted line indicates the binding property of a control antibody, and the solid line indicates the binding property of an M30 antibody.

FIG. 5-4 is a graph showing the reactivity of M30 antibody against a B7-H3 deficient mutant (B7-H3 IgC2). The dotted line indicates the binding property of a control antibody, and the solid line indicates the binding property of an M30 antibody.

FIG. 5-5 is a graph showing the reactivity of M30 antibody against a B7-H3 deficient mutant (B7-H3 IgC1-V2-C2). The dotted line indicates the binding property of a control antibody, and the solid line indicates the binding property of an M30 antibody.

FIG. 5-6 is a graph showing the reactivity of M30 antibody against a B7-H3 deficient mutant (B7-H3 IgV2-C2). The dotted line indicates the binding property of a control antibody, and the solid line indicates the binding property of an M30 antibody.

FIG. 6 is a graph showing the antitumor activities of anti-B7-H3 antibodies against mice implanted with NCI-H322 cells. The error bars in the graph represent standard errors (n=10).

FIG. 10-1 is a graph showing the competitive inhibitory activities of cM30 antibody and M30-H1-L4 antibody against M30 for the binding to an extracellular domain polypeptide antigen of a B7-H3 variant 1 antigen. The error bars in the graph represent standard errors (n=3).

FIG. 10-2 is a graph showing the competitive inhibitory activities of cM30 antibody and M30-H1-L4 antibody against M30 for the binding to an extracellular domain polypeptide antigen of a B7-H3 variant 2 antigen. The error bars in the graph represent standard errors (n=3).

FIG. 13-1 shows a nucleotide sequence of B7-H3 variant 1 (SEQ ID NO: 5).

FIG. 13-2 shows an amino acid sequence of the B7-H3 variant 1 (SEQ ID NO: 6).

FIG. 14-1 shows a nucleotide sequence of B7-H3 variant 2 (SEQ ID NO: 9).

FIG. 14-2 shows an amino acid sequence of the B7-H3 variant 2 (SEQ ID NO: 10).

FIG. 15-1 shows a nucleotide sequence of B7-H3 IgV1 (SEQ ID NO: 20).

FIG. 15-2 shows an amino acid sequence of the B7-H3 IgV1 (SEQ ID NO: 21).

FIG. 16-1 shows a nucleotide sequence of B7-H3 IgC1 (SEQ ID NO: 22).

FIG. 16-2 shows an amino acid sequence of the B7-H3 IgC1 (SEQ ID NO: 23).

FIG. 17-1 shows a nucleotide sequence of B7-H3 IgV2 (SEQ ID NO: 24).

FIG. 17-2 shows an amino acid sequence of the B7-H3 IgV2 (SEQ ID NO: 25).

FIG. 18-1 shows a nucleotide sequence of B7-H3 IgC2 (SEQ ID NO: 26).

FIG. 18-2 shows an amino acid sequence of the B7-H3 IgC2 (SEQ ID NO: 27).

FIG. 19-1 shows a nucleotide sequence of B7-H3 IgC1-V2-C2 (SEQ ID NO: 28).

FIG. 19-2 shows an amino acid sequence of the B7-H3 IgC1-V2-C2 (SEQ ID NO: 29).

FIG. 20-1 shows a nucleotide sequence of B7-H3 IgV2-C2 (SEQ ID NO: 30).

FIG. 20-2 shows an amino acid sequence of B7-H3 IgV2-C2 (SEQ ID NO: 31).

FIG. 21-1 shows a nucleotide sequence of an M30 antibody heavy chain (SEQ ID NO: 50).

FIG. 21-2 shows an amino acid sequence of the M30 antibody heavy chain (SEQ ID NO: 51).

FIG. 22-1 shows a nucleotide sequence of an M30 antibody light chain (SEQ ID NO: 52).

FIG. 22-2 shows an amino acid sequence of the M30 antibody light chain (SEQ ID NO: 53).

FIG. 23 shows a nucleotide sequence of a human κ chain secretory signal, a human κ chain constant region, and a human poly-A additional signal (SEQ ID NO: 56).

FIG. 24 shows a nucleotide sequence of a signal sequence and a constant region of human IgG1 (SEQ ID 57).

FIG. 25-1 shows a nucleotide sequence of an M30 antibody chimera-type light chain (SEQ ID NO: 58).

FIG. 25-2 shows an amino acid sequence of the M30 antibody chimera-type light chain (SEQ ID NO: 59).

FIG. 26-1 shows a nucleotide sequence of an M30 antibody chimera-type heavy chain (SEQ ID NO: 62).

FIG. 26-2 shows an amino acid sequence of the M30 antibody chimera-type heavy chain (SEQ ID NO: 63).

FIG. 27-1 shows a nucleotide sequence of an M30-L1-type light chain (SEQ ID NO: 70).

FIG. 27-2 shows an amino acid sequence of the M30-L1-type light chain (SEQ ID NO: 71).

FIG. 28-1 shows a nucleotide sequence of an M30-L2-type light chain (SEQ ID NO: 72).

FIG. 28-2 shows an amino acid sequence of the M30-L2-type light chain (SEQ ID NO: 73).

FIG. 29-1 shows a nucleotide sequence of an M30-L3-type light chain (SEQ ID NO: 74).

FIG. 29-2 shows an amino acid sequence of the M30-L3-type light chain (SEQ ID NO: 75).

FIG. 30-1 shows a nucleotide sequence of an M30-L4-type light chain (SEQ ID NO: 76).

FIG. 30-2 shows an amino acid sequence of the M30-L4-type light chain (SEQ ID NO: 77).

FIG. 31-1 shows a nucleotide sequence of an M30-L5-type light chain (SEQ ID NO: 78).

FIG. 31-2 shows an amino acid sequence of the M30-L5-type light chain (SEQ ID NO: 79).

FIG. 32-1 shows a nucleotide sequence of an M30-L6-type light chain (SEQ ID NO: 80).

FIG. 32-2 shows an amino acid sequence of the M30-L6-type light chain (SEQ ID NO: 81).

FIG. 33-1 shows a nucleotide sequence of an M30-L7-type light chain (SEQ ID NO: 82).

FIG. 33-2 shows an amino acid sequence of the M30-L7-type light chain (SEQ ID NO: 83).

FIG. 34-1 shows a nucleotide sequence of an M30-H1-type heavy chain (SEQ ID NO: 84).

FIG. 34-2 shows an amino acid sequence of the M30-H1-type heavy chain (SEQ ID NO: 85).

FIG. 35-1 shows a nucleotide sequence of an M30-H2-type heavy chain (SEQ ID NO: 86).

FIG. 35-2 shows an amino acid sequence of the M30-H2-type heavy chain (SEQ ID NO: 87).

FIG. 36-1 shows a nucleotide sequence of an M30-H3-type heavy chain (SEQ ID NO: 88).

FIG. 36-2 shows an amino acid sequence of the M30-H3-type heavy chain (SEQ ID NO: 89).

FIG. 37-1 shows a nucleotide sequence of an M30-H4-type heavy chain (SEQ ID NO: 90).

FIG. 37-2 shows an amino acid sequence of the M30-H4-type heavy chain (SEQ ID NO: 91).

MODE FOR CARRYING OUT THE INVENTION

Figure 1:
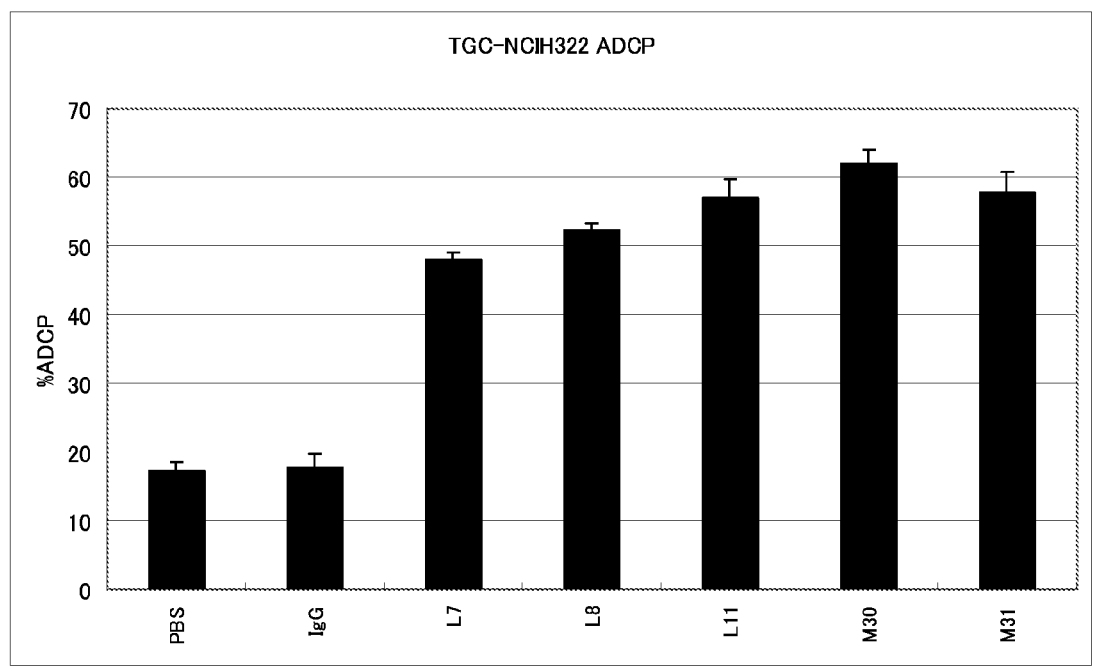
FIG. 1 is a graph showing the presence or absence of an ADCP activity of an anti-B7-H3 antibody against NCI-H322 cells. The error bars in the graph represent standard errors (n=3).

The terms "cancer" and "tumor" as used herein are used with the same meaning.

The term "gene" as used herein includes not only DNA, but also mRNA thereof, cDNA thereof and cRNA thereof.

The term "polynucleotide" as used herein is used with the same meaning as a nucleic acid and also includes DNA, RNA, probes, oligonucleotides, and primers.

The terms "polypeptide" and "protein" as used herein are used without distinction.

The term "cell" as used herein also includes cells in an animal individual and cultured cells.

The term "B7-H3" as used herein is used in the same meaning as B7-H3 protein, and also refers to B7-H3 variant 1 and/or B7-H3 variant 2.

The term "cell injury" as used herein refers to a state in which a pathological change is caused in cells in a form of some kind, and the cell injury is not limited to direct injury and includes all sorts of damages to the structure and function of cells such as DNA cleavage, base-dimer formation, chromosomal cleavage, damage to cell division machinery, and a decrease in various enzymatic activities.

The term "cytotoxic activity" as used herein refers to an activity of causing the above-described cell injury.

The term "antibody-dependent cell-mediated phagocytosis activity" as used herein refers to "antibody-dependent cell phagocytosis (ADCP) activity" and means an activity of phagocytosing target cells such as tumor cells by monocytes or macrophages mediated by an antibody. The term also called "antibody-dependent phagocytosis activity".

The term "antibody-dependent cellular cytotoxicity activity" as used herein refers to "antibody-dependent cellular cytotoxicity (ADCC) activity" and means an activity of damaging target cells such as tumor cells by NK cells mediated by an antibody.

The term "complement-dependent cytotoxicity activity" as used herein refers to "complement-dependent cytotoxicity (CDC) activity" and means an activity of damaging target cells such as tumor cells by a complement mediated by an antibody.

The term "functional fragment of an antibody" as used herein refers to a partial fragment of an antibody having an antigen-binding activity, wherein the fragment has a full or partial function of the antibody, including Fab, F(ab')$_2$, scFv, and the like. The term also includes Fab' which is a monovalent fragment in a variable region of an antibody obtained by treating, F(ab')$_2$ under reducing conditions. However, the term is not limited to these molecules as long as the fragment has a binding affinity for an antigen. Further, these functional fragments include not only a fragment obtained by treating a full-length molecule of an antibody protein with an appropriate enzyme, but also a protein produced in an appropriate host cell using a genetically modified antibody gene.

The term "Fab'" as used herein refers to a monovalent fragment in a variable region of an antibody obtained by treating F(ab')$_2$ under reducing conditions as described above. However, Fab' produced using a genetically modified antibody gene is also included in the Fab' in the invention.

The term "epitope" as used herein refers to a partial peptide or a partial tertiary structure of B7-H3 to which a specific anti-B7-H3 antibody binds. The epitope which is a partial peptide of the above-described B7-H3 can be determined by a method well known to those skilled in the art such as an immunoassay, and for example, the following method can be employed. First, various partial structures of an antigen are produced. In the production of the partial structures, a known oligopeptide synthesis technique can be used. For example, a series of polypeptides having appropriately reduced lengths obtained by sequentially shortening B7-H3 from the C terminus or N terminus are produced using a genetic recombination technique known to those skilled in the art. Thereafter, the reactivity of an antibody against these polypeptides is examined and a recognition site is roughly determined. Then, peptides having shorter lengths are synthesized and the reactivity of the antibody with these peptides is examined, whereby the epitope can be determined. Further, the epitope which is a partial tertiary structure of an antigen to which a specific antibody binds can be determined by specifying the amino acid residues of the antigen which lie adjacent to the antibody by an X-ray structural analysis.

The phrase "antibodies which bind to the same epitope" as used herein refers to different antibodies which bind to a common epitope. If a second antibody binds to a partial peptide or a partial tertiary structure to which a first antibody binds, it can be determined that the first antibody and the second antibody bind to the same epitope.

Further, by confirming that a second antibody competes with a first antibody for the binding to an antigen (that is, the second antibody inhibits the binding between the first antibody and the antigen), it can be determined that the first antibody and the second antibody bind to the same epitope even if the specific epitope sequence or structure has not been determined. Further, when the first antibody and the second antibody bind to the same epitope and also the first antibody has a special activity such as an antitumor activity, it can be expected that also the second antibody has the same activity. Accordingly, when a second anti-B7-H3 antibody binds to a partial peptide to which a first anti-B7-H3 antibody binds, it can be determined that the first antibody and the second antibody bind to the same epitope of B7-H3. Further, by confirming that a second anti-B7-H3 antibody competes with a first anti-B7-H3 antibody for the binding to B7-H3, it can be determined that the first antibody and the second antibody are antibodies which bind to the same epitope of B7-H3.

The term "CDR" as used herein refers to a complementarity determining region (CDR), and it is known that each heavy and light chain of an antibody molecule has three complementarity determining regions (CDRs). The CDR is also called the hypervariable region, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. B7-H3

B7-H3 is a member of the B7 family expressed on antigen-presenting cells as a co-stimulatory molecule, and is considered to act on a receptor on T cells to enhance or suppress immune activity.

B7-H3 is a protein having a single-pass transmembrane structure, and the N-terminal extracellular domain of B7-H3 contains two variants. The B7-H3 variant 1 (4Ig-B7-H3) contains a V-like or C-like Ig domain at two sites, respectively, and the B7-H3 variant 2 (2Ig-B7-H3) contains a V-like or C-like Ig domain at one site, respectively.

As for B7-H3 to be used in the invention, B7-H3 can be directly purified from B7-H3-expressing cells of a human or a non-human mammal (such as a rat or a mouse) and used, or a cell membrane fraction of the above-described cells can be prepared and used. Further, B7-H3 can be obtained by in vitro synthesis thereof or production thereof in a host cell through genetic engineering. In the genetic engineering, specifically, after B7-H3 cDNA is integrated into a vector capable of expressing B7-H3 cDNA, B7-H3 can be obtained by synthesizing it in a solution containing an enzyme, a substrate and an energy substance required for transcription and translation, or by expressing B7-H3 in another prokaryotic or eucaryotic transformed host cell.

The nucleotide sequence of an open reading frame (ORF) of a human B7-H3 variant 1 gene is represented by SEQ ID NO: 5 in the Sequence Listing, and the amino acid sequence thereof is represented by SEQ ID NO: 6 in the Sequence Listing. Further, the sequences of SEQ ID NOS: 5 and 6 are shown in FIG. 13.

The nucleotide sequence of an ORF of a human B7-H3 variant 2 gene is represented by SEQ ID NO: 9 in the Sequence Listing, and the amino acid sequence thereof is represented by SEQ ID NO: 10 in the Sequence Listing. Further, the sequences of SEQ ID NOS: 9 and 10 are shown in FIG. 14.

Further, a protein which consists of an amino acid sequence wherein one or several amino acids are substituted, deleted and/or added in any of the above-described amino acid sequences of B7-H3 and also has a biological activity equivalent to that of the protein is also included in B7-H3.

Mature human B7-H3 variant 1 from which the signal sequence has been removed corresponds to an amino acid sequence consisting of amino acid residues 27 to 534 of the amino acid sequence represented by SEQ ID NO: 6. Further, mature human B7-H3 variant 2 from which the signal sequence has been removed corresponds to an amino acid sequence consisting of amino acid residues 27 to 316 of the amino acid sequence represented by SEQ ID NO: 10.

In the B7-H3 variant 1, the respective domains are present in the order of IgV1, IgC1, IgV2, and IgC2 from the N terminus, and in SEQ ID NO: 6 in the Sequence Listing, IgV1 corresponds to amino acid numbers 27 to 139, IgC1 corresponds to amino acid numbers 140 to 244, IgV2 corresponds to amino acid numbers 245 to 357, and IgC2 corresponds to amino acid numbers 358 to 456. Further, in the B7-H3 variant 2, the respective domains are present in the order of IgV1 and IgC2 from the N terminus, and in SEQ ID NO: 10 in the Sequence Listing, IgV1 corresponds to amino acid numbers 27 to 140 and IgC2 corresponds to amino acid numbers 141 to 243.

B7-H3 cDNA can be obtained by, for example, a so-called PCR method in which a polymerase chain reaction (hereinafter referred to as "PCR") is performed using a cDNA library expressing B7-H3 cDNA as a template and primers which specifically amplify B7-H3 cDNA (Saiki, R. K., et al., Science, (1988) 239, 487-49). A polynucleotide which hybridizes to a polynucleotide consisting of a nucleotide sequence complementary to the nucleotide sequence represented by SEQ ID NO: 5 or 9 in the Sequence Listing under stringent conditions and encodes a protein having a biological activity equivalent to that of B7-H3 is also included in B7-H3 cDNA. Further, a polynucleotide which is a splicing variant transcribed from the human or mouse B7-H3 locus or a polynucleotide which hybridizes thereto under stringent conditions and encodes a protein having a biological activity equivalent to that of B7-H3 is also included in B7-H3 cDNA.

Further, a protein which consists of an amino acid sequence wherein one or several amino acids are substituted, deleted or added in the amino acid sequence represented by SEQ ID NO: 6 or 10 in the Sequence Listing or an amino acid sequence obtained by removing the signal sequence from either of these sequences and has a biological activity equivalent to that of B7-H3 is also included in B7-H3. Further, a protein which consists of an amino acid sequence encoded by a splicing variant transcribed from the human or mouse B7-H3 locus or an amino acid sequence wherein one or several amino acids are substituted, deleted or added in the above amino acid sequence and has a biological activity equivalent to that of B7-H3 is also included in B7-H3.

2. Production of Anti-B7-H3 Antibody

The antibody against B7-H3 of the invention can be obtained by immunizing an animal with B7-H3 or an arbitrary polypeptide selected from the amino acid sequence of B7-H3, and collecting and purifying the antibody produced in vivo according to a common procedure. The biological species of B7-H3 to be used as an antigen is not limited to being human, and an animal can be immunized with B7-H3 derived from an animal other than humans such as a mouse or a rat. In this case, by examining the cross-reactivity between an antibody binding to the obtained heterologous B7-H3 and human B7-H3, an antibody applicable to a human disease can be selected.

Further, a monoclonal antibody can be obtained from a hybridoma established by fusing antibody-producing cells which produce an antibody against B7-H3 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

B7-H3 to be used as an antigen can be obtained by expressing B7-H3 gene in a host cell using genetic engineering.

Specifically, a vector capable of expressing B7-H3 gene is produced, and the resulting vector is transfected into a host cell to express the gene, and then, the expressed B7-H3 is purified. Hereinafter, a method of obtaining an antibody against B7-H3 will be specifically described.

(1) Preparation of Antigen

Examples of the antigen to be used for producing the anti-B7-H3 antibody include B7-H3, a polypeptide consisting of a partial amino acid sequence comprising at least 6 consecutive amino acids of B7-H3, and a derivative obtained by adding a given amino acid sequence or carrier thereto.

B7-H3 can be purified directly from human tumor tissues or tumor cells and used. Further, B7-H3 can be obtained by synthesizing it in vitro or by producing it in a host cell by genetic engineering.

With respect to the genetic engineering, specifically, after B7-H3 cDNA is integrated into a vector capable of expressing B7-H3 cDNA, B7-H3 can be obtained by synthesizing it in a solution containing an enzyme, a substrate and an energy substance required for transcription and translation, or by expressing B7-H3 in another prokaryotic or eucaryotic transformed host cell.

Further, the antigen can also be obtained as a secretory protein by expressing a fusion protein obtained by ligating the extracellular domain of B7-H3, which is a membrane protein, to the constant region of an antibody in an appropriate host-vector system.

B7-H3 cDNA can be obtained by, for example, a so-called PCR method in which a polymerase chain reaction (hereinafter referred to as "PCR") is performed using a cDNA library expressing B7-H3 cDNA as a template and primers which specifically amplify B7-H3 cDNA (see Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a common procedure, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

(2) Production of Anti-B7-H3 Monoclonal Antibody

Examples of the antibody specific binding to B7-H3 include a monoclonal antibody specific binding to B7-H3, and a method of obtaining the antibody is as described below.

The production of a monoclonal antibody generally requires the following operational steps of:

(a) purifying a biopolymer to be used as an antigen;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of a monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, B7-H3 prepared by the method as described above or a partial peptide thereof can be used.

Further, a membrane fraction prepared from recombinant cells expressing B7-H3 or the recombinant cells expressing B7-H3 themselves, and also a partial peptide of the protein of the invention chemically synthesized by a method known to those skilled in the art can also be used as the antigen.

(b) Preparation of Antibody-Producing Cells

The antigen obtained in the step (a) is mixed with an adjuvant such as Freund's complete or incomplete adjuvant or aluminum potassium sulfate and the resulting mixture is used as an immunogen to immunize an experimental animal. As the experimental animal, any animal used in a known hybridoma production method can be used without any trouble. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

Among these, in consideration of compatibility of fusing with myeloma cells described below, in the case of a mouse, BALB/c strain, and in the case of a rat, Wistar and Low strains are particularly preferred as the animal to be immunized.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with B7-H3 or a recombinant thereof, for example, a known method described in detail in, for example, Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Ill. (1964) or the like can be used.

Among these immunization methods, a preferred specific method in the invention is, for example, as follows.

That is, first, a membrane protein fraction serving as the antigen or cells caused to express the antigen is/are intradermally or intraperitoneally administrated to an animal.

However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 2 to 4 weeks, more preferably 2 to 3 weeks after the administration of the antigen as described above.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg.

Spleen cells or lymphocytes including antibody-producing cells are aseptically removed from the immunized animal 1 to 10 days, preferably 2 to 5 days, more preferably 2 to 3 days after the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto.

For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (hereinafter referred to as "BSA"). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to obtain the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1 (P3U1), X63-Ag8.653(X63.653), SP2/0-Ag14(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500•GTG-A12 (GM1500), UC729-6, LICR-LOW-HMy2(HMy2) and 8226AR/NIP4-1(NP41) derived from humans. These HGPRT-deficient strains are available from, for example, the American Type Culture Collection (ATCC) or the like.

These cell strains are subcultured in an appropriate medium such as an 8-azaguanine medium [a medium obtained by adding 8-azaguanine to an RPMI 1640 medium supplemented with glutamine, 2-mercaptoethanol, gentamicin, and fetal bovine serum (hereinafter referred to as "FBS")], Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium [for example, an ASF104 medium (manufactured by Ajinomoto Co., Ltd.) containing 10% FBS] to ensure not less than $2 \times 10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987), Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin.

That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell™-HY Selection Medium D (manufactured by StemCell Technologies, Inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a B7-H3 monoclonal antibody-producing hybridoma strain.

Examples of the thus established hybridoma strain include B7-H3 hybridoma M30. In this specification, an antibody produced by the B7-H3 hybridoma M30 is referred to as "M30 antibody" or simply "M30".

The heavy chain of the M30 antibody has an amino acid sequence represented by SEQ ID NO: 51 in the Sequence Listing. Further, the light chain of the M30 antibody has an amino acid sequence represented by SEQ ID NO: 53 in the Sequence Listing. In the heavy chain amino acid sequence represented by SEQ ID NO: 51 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. Further, in the light chain amino acid sequence represented by SEQ ID NO: 53 in the Sequence Listing, an amino acid sequence consisting of amino acid residues 1 to 22 is a signal sequence, an amino acid sequence consisting of amino acid residues 23 to 130 is a variable region, and an amino acid sequence consisting of amino acid residues 131 to 235 is a constant region.

The heavy chain amino acid sequence represented by SEQ ID NO: 51 in the Sequence Listing is encoded by a nucleotide sequence represented by SEQ ID NO: 50 in the Sequence Listing. In the nucleotide sequence represented by SEQ ID NO: 50 in the Sequence Listing, a nucleotide sequence consisting of nucleotides 1 to 57 encodes the heavy chain signal sequence of the antibody, a nucleotide sequence consisting of nucleotides 58 to 423 encodes the heavy chain variable region of the antibody, and a nucleotide sequence consisting of nucleotides 424 to 1413 encodes the heavy chain constant region of the antibody.

The light chain amino acid sequence represented by SEQ ID NO: 53 in the Sequence Listing is encoded by a nucleotide sequence represented by SEQ ID NO: 52 in the Sequence Listing. In the nucleotide sequence represented by SEQ ID NO: 52 in the Sequence Listing, a nucleotide sequence consisting of nucleotides 1 to 66 encodes the light chain signal sequence of the antibody, a nucleotide sequence consisting of nucleotides 67 to 390 encodes the light chain variable region of the antibody, and a nucleotide sequence consisting of nucleotides 391 to 705 encodes the light chain constant region of the antibody.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administrated in the abdominal cavity, if a mineral oil such as 2,6,10,14-tetramethyl pentadecane (pristane) is administrated 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for B7-H3.

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm [1.4 (OD 280)=Immunoglobulin 1 mg/ml].

Further, even when the monoclonal antibody is separately and independently obtained by performing again the steps of (a) to (h) in (2), it is possible to obtain an antibody having a cytotoxic activity equivalent to that of the M30 antibody. As one example of such an antibody, an antibody which binds to the same epitope as the M30 antibody can be exemplified. The M30 recognizes an epitope in the IgC1 or IgC2 domain, which is a domain in the B7-H3 extracellular domain, and binds to the IgC1 domain or the IgC2 domain or both. Therefore, as the epitope for the M30 antibody, particularly, an epitope present in the IgC1 or IgC2 domain of B7-H3 can be exemplified. If a newly produced monoclonal antibody binds to a partial peptide or a partial tertiary structure to which the M30 antibody binds, it can be determined that the monoclonal antibody binds to the same epitope as the M30 antibody. Further, by confirming that the monoclonal antibody competes with the M30 antibody for the binding to B7-H3 (that is, the monoclonal antibody inhibits the binding between the M30 antibody and B7-H3), it can be determined that the monoclonal antibody binds to the same epitope as the M30 antibody even if the specific epitope sequence or structure has not been determined. When it is confirmed that the monoclonal antibody binds to the same epitope as the M30 antibody, the monoclonal antibody is strongly expected to have a cytotoxic activity equivalent to that of the M30 antibody.

(3) Other Antibodies

The antibody of the invention includes not only the above-described monoclonal antibody against B7-H3 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived constant region can be exemplified (see Proc. Natl. Acad. Sci. USA, 81, 6851-6855, (1984)). A chimeric antibody derived from a mouse anti-human B7-H3 antibody M30 is an antibody consisting of a heavy chain comprising a heavy chain variable region of which an amino acid sequence consists of amino acid residues 20 to 141 of SEQ ID NO: 51 and a light chain comprising a light chain variable region of which an amino acid sequence consists of amino acid residues 23 to 130 of SEQ ID NO: 53, and may have an arbitrary human-derived constant region. As one example of such a chimeric antibody, an antibody consisting of a heavy chain of which an amino acid sequence consists of amino acid residues 1 to 471 of SEQ ID NO: 63 in the Sequence Listing and a light chain of which an amino acid sequence consists of amino acid residues 1 to 233 of SEQ ID NO: 59 in the Sequence Listing can be exemplified. In the heavy chain sequence represented by SEQ ID NO: 63 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region. Further, in the light chain sequence represented by SEQ ID NO: 59 in the Sequence Listing, an amino acid sequence consisting of amino acid residues 1 to 20 is a signal sequence, an amino acid sequence consisting of amino acid residues 21 to 128 is a variable region, and an amino acid sequence consisting of amino acid residues 129 to 233 is a constant region.

The heavy chain amino acid sequence represented by SEQ ID NO: 63 in the Sequence Listing is encoded by a nucleotide sequence represented by SEQ ID NO: 62 in the Sequence Listing. In the nucleotide sequence represented by SEQ ID NO: 62 in the Sequence Listing, a nucleotide sequence consisting of nucleotides 1 to 57 encodes the heavy chain signal sequence of the antibody, a nucleotide sequence consisting of nucleotides 58 to 423 encodes the heavy chain variable region of the antibody, and a nucleotide sequence consisting of nucleotides 424 to 1413 encodes the heavy chain constant region of the antibody.

The light chain amino acid sequence represented by SEQ ID NO: 59 in the Sequence Listing is encoded by a nucleotide sequence represented by SEQ ID NO: 58 in the Sequence Listing. In the nucleotide sequence represented by SEQ ID NO: 58 in the Sequence Listing, a nucleotide sequence consisting of nucleotides 1 to 60 encodes the light chain signal sequence of the antibody, a nucleotide sequence consisting of nucleotides 61 to 384 encodes the light chain variable region of the antibody, and a nucleotide sequence consisting of nucleotides 385 to 699 encodes the light chain constant region of the antibody.

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (WO 90/07861) can be exemplified.

However, the humanized antibody derived from the M30 antibody is not limited to a specific humanized antibody as long as the humanized antibody has all 6 types of CDR sequences of the M30 antibody and has an antitumor activity. The heavy chain variable region of the M30 antibody has CDRH1 (NYVMH) consisting of an amino acid sequence represented by SEQ ID NO: 92 in the Sequence Listing, CDRH2 (YINPYNDDVKYNEKFKG) consisting of an amino acid sequence represented by SEQ ID NO: 93 in the Sequence Listing, and CDRH3 (WGYYGSPLYYFDY) consisting of an amino acid sequence represented by SEQ ID NO: 94 in the Sequence Listing. Further, the light chain variable region of the M30 antibody has CDRL1 (RASSRLIYMH) consisting of an amino acid sequence represented by SEQ ID NO: 95 in the Sequence Listing, CDRL2 (ATSNLAS) consisting of an amino acid sequence represented by SEQ ID NO: 96 in the Sequence Listing, and CDRL3 (QQWNSNPPT) consisting of an amino acid sequence represented by SEQ ID NO: 97 in the Sequence Listing.

As an example of the humanized antibody of a mouse antibody M30, an arbitrary combination of a heavy chain comprising a heavy chain variable region consisting of any one of (1) an amino acid sequence consisting of amino acid residues 20 to 141 of SEQ ID NO: 85, 87, 89, or 91 in the Sequence Listing, (2) an amino acid sequence having a homology of at least 95% or more with the amino acid sequence (1) described above, and (3) an amino acid sequence wherein one or several amino acids in the amino acid sequence (1) described above are deleted, substituted or added and a light chain comprising a light chain variable region consisting of any one of (4) an amino acid sequence consisting of amino acid residues 21 to 128 of SEQ ID NO: 71, 73, 75, 77, 79, 81, or 83 in the Sequence Listing, (5) an amino acid sequence having a homology of at least 95% or more with the amino acid sequence (4) described above, and (6) an amino acid sequence wherein one or several amino acids in the amino acid sequence (4) described above are deleted, substituted or added can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

As an antibody which has a preferred combination of a heavy chain and a light chain described above, an antibody consisting of a heavy chain comprising a heavy chain variable region consisting of an amino acid sequence consisting of amino acid residues 20 to 141 of SEQ ID NO: 85 and a light chain comprising a light chain variable region consisting of an amino acid sequence consisting of amino acid residues 21 to 128 of SEQ ID NO: 71; an antibody consisting of a heavy chain comprising a heavy chain variable region consisting of an amino acid sequence consisting of amino acid residues 20 to 141 of SEQ ID NO: 85 and a light chain comprising a light chain variable region consisting of an amino acid sequence consisting of amino acid residues 21 to 128 of SEQ ID NO: 73; an antibody consisting of a heavy chain comprising a heavy chain variable region consisting of an amino acid sequence consisting of amino acid residues 20 to 141 of SEQ ID NO: 85 and a light chain comprising a light chain variable region consisting of an amino acid sequence consisting of amino acid residues 21 to 128 of SEQ ID NO: 75; an antibody consisting of a heavy chain comprising a heavy chain variable region consisting of an amino acid sequence consisting of amino acid residues 20 to 141 of SEQ ID NO: 85 and a light chain comprising a light chain variable region consisting of an amino acid sequence consisting of amino acid residues 21 to 128 of SEQ ID NO: 77; an antibody consisting of a heavy chain comprising a heavy chain variable region consisting of an amino acid sequence consisting of amino acid residues 20 to 141 of SEQ ID NO: 85 and a light chain comprising a light chain variable region consisting of an amino acid sequence consisting of amino acid residues 21 to 128 of SEQ ID NO: 79; an antibody consisting of a heavy chain comprising a heavy chain variable region consisting of an amino acid sequence consisting of amino acid residues 20 to 141 of SEQ ID NO: 85 and a light chain comprising a light chain variable region consisting of an amino acid sequence consisting of amino acid residues 21 to 128 of SEQ ID NO: 81; an antibody consisting of a heavy chain comprising a heavy chain variable region consisting of an amino acid sequence including amino acid residues 20 to 141 of SEQ ID NO: 85 and a light chain comprising a light chain variable region consisting of an amino acid sequence consisting of amino acid residues 21 to 128 of SEQ ID NO: 83; an antibody consisting of a heavy chain comprising a heavy chain variable region consisting of an amino acid sequence consisting of amino acid residues 20 to 141 of SEQ ID NO: 91 and a light chain comprising a light chain variable region consisting of an amino acid sequence consisting of amino acid residues 21 to 128 of SEQ ID NO: 71; an antibody consisting of a heavy chain comprising a heavy chain variable region consisting of an amino acid sequence consisting of amino acid residues 20 to 141 of SEQ ID NO: 91 and a light chain comprising a light chain variable region consisting of an amino acid sequence consisting of amino acid residues 21 to 128 of SEQ ID NO: 73; an antibody consisting of a heavy chain comprising a heavy chain variable region consisting of an amino acid sequence consisting of amino acid residues 20 to 141 of SEQ ID NO: 91 and a light chain comprising a light chain variable region consisting of an amino acid sequence consisting of amino acid residues 21 to 128 of SEQ ID NO: 75; and an antibody consisting of a heavy chain comprising a heavy chain variable region consisting of an amino acid sequence consisting of amino acid residues 20 to 141 of SEQ ID NO: 91 and a light chain comprising a light chain variable region consisting of an amino acid sequence consisting of amino acid residues 21 to 128 of SEQ ID NO: 77 can be exemplified.

As an antibody which has a more preferred combination of a heavy chain and a light chain described above, an antibody consisting of a heavy chain comprising an amino acid sequence of SEQ ID NO: 85 and a light chain comprising an amino acid sequence of SEQ ID NO: 71; an antibody consisting of a heavy chain comprising an amino acid sequence of SEQ ID NO: 85 and a light chain comprising an amino acid sequence of SEQ ID NO: 73; an antibody consisting of a heavy chain comprising an amino acid sequence of SEQ ID NO: 85 and a light chain comprising an amino acid sequence of SEQ ID NO: 75; an antibody consisting of a heavy chain comprising an amino acid sequence of SEQ ID NO: 85 and a light chain comprising an amino acid sequence of SEQ ID NO: 77; an antibody consisting of a heavy chain comprising an amino acid sequence of SEQ ID NO: 85 and a light chain comprising an amino acid sequence of SEQ ID NO: 79; an antibody consisting of a heavy chain comprising an amino acid sequence of SEQ ID NO: 85 and a light chain comprising an amino acid sequence of SEQ ID NO: 81; an antibody consisting of a heavy chain comprising an amino acid sequence of SEQ ID NO: 85 and a light chain comprising an amino acid sequence of SEQ ID NO: 83; an antibody consisting of a heavy chain comprising an amino acid sequence of SEQ ID NO: 91 and a light chain comprising an amino acid sequence of SEQ ID NO: 71; an antibody consisting of a heavy chain comprising an amino acid sequence of SEQ ID NO: 1 and a light chain comprising an amino acid sequence of SEQ ID NO: 73; an antibody consisting of a heavy chain comprising an amino acid sequence of SEQ ID NO: 91 and a light chain comprising an amino acid sequence of SEQ ID NO: 75; and an antibody consisting of a heavy chain comprising an amino acid sequence of SEQ ID NO: 91 and a light chain comprising an amino acid sequence of SEQ ID NO: 77 can be exemplified.

By combining a sequence having a high homology with the above-described heavy chain amino acid sequence with a sequence having a high homology with the above-described light chain amino acid sequence, it is possible to select an antibody having a cytotoxic activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a cytotoxic activity equivalent to that of each of the above-described antibodies.

The homology between two amino acid sequences can be determined using default parameters of Blast algorithm version 2.2.2 (Altschul, Stephen F., Thomas L. Madden, Alejandro A. Schïffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site 1334907992153_0.

In the heavy chain amino acid sequence represented by SEQ ID NO: 85, 87, 89 or 91 in the Sequence Listing, an amino acid sequence consisting of amino acid residues 1 to 19 is a signal sequence, an amino acid sequence consisting of amino acid residues 20 to 141 is a variable region, and an amino acid sequence consisting of amino acid residues 142 to 471 is a constant region.

Further, in the light chain amino acid sequence represented by SEQ ID NO: 71, 73, 75, 77, 79, 81 or 83 in the Sequence Listing, an amino acid sequence consisting of amino acid residues 1 to 20 is a signal sequence, an amino acid sequence consisting of amino acid residues 21 to 128 is a variable region, and an amino acid sequence consisting of amino acid residues 129 to 233 is a constant region.

The heavy chain amino acid sequences represented by SEQ ID NO: 85, 87, 89 or 91 in the Sequence Listing are encoded by nucleotide sequences represented by SEQ ID NO: 84, 86, 88or 90, respectively, in the Sequence Listing. Further, the sequences represented by SEQ ID NOS: 84 and 85 are shown in FIG. 34, the sequences represented by SEQ ID NOS: 86 and 87 are shown in FIG. 35, the sequences represented by SEQ ID NOS: 88 and 89 are shown in FIG. 36, and the sequences represented by SEQ ID NOS: 90 and 91 are shown in FIG. 37. In each of the above nucleotide sequences, a nucleotide sequence consisting of nucleotides 1 to 57 encodes the heavy chain signal sequence of the antibody, a nucleotide sequence consisting of nucleotides 58 to 423 encodes the heavy chain variable region of the antibody, and a nucleotide sequence consisting of nucleotides 424 to 1413 encodes the heavy chain constant region of the antibody.

The light chain amino acid sequences represented by SEQ ID NO: 71, 73, 75, 77, 79, 81 or 83 in the Sequence Listing are encoded by nucleotide sequences represented by SEQ ID NOS: 70, 72, 74, 76, 78, 80 or 82, respectively, in the Sequence Listing. Further, the sequences represented by SEQ ID NOS: 70 and 71 are shown in FIG. 27, the sequences represented by SEQ ID NOS: 72 and 73 are shown in FIG. 28, the sequences represented by SEQ ID NOS: 74 and 75 are shown in FIG. 29, the sequences represented by SEQ ID NOS: 76 and 77 are shown in FIG. 30, the sequences represented by SEQ ID NOS: 78 and 79 are shown in FIG. 31, the sequences represented by SEQ ID NOS: 80 and 81 are shown in FIG. 32, and the sequences represented by SEQ ID NOS: 82 and 83 are shown in FIG. 33. In each of the above nucleotide sequences, a nucleotide sequence consisting of nucleotides 1 to 60 encodes the light chain signal sequence of the antibody, a nucleotide sequence consisting of nucleotides 61 to 384 encodes the light chain variable region of the antibody, and a nucleotide sequence consisting of nucleotides 385 to 699 encodes the light chain constant region of the antibody.

The homology between any of these nucleotide sequences and a nucleotide sequence of another antibody can be also determined using Blast algorithm.

Further, the antibody of the invention includes a human antibody which binds to the same epitope as the M30 antibody. An anti-B7-H3 human antibody refers to a human antibody having only a gene sequence of an antibody derived from a human chromosome. The anti-B7-H3 human antibody can be obtained by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

Further, a method of obtaining a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (WO 92/01047, WO 92/20791, WO 93/06213, WO 93/11236, WO 93/19172, WO 95/01438, WO 95/15388, Annu Rev. Immunol. (1994) 12, pp. 433-455, Nature Biotechnology (2005) 23 (9), pp. 1105-1116).

If a newly produced human antibody binds to a partial peptide or a partial tertiary structure to which the M30 antibody binds, it can be determined that the human antibody binds to the same epitope as the M30 antibody. Further, by confirming that the human antibody competes with the M30 antibody for the binding to B7-H3 (that is, the human antibody inhibits the binding between the M30 antibody and B7-H3), it can be determined that the human antibody binds to the same epitope as the M30 antibody even if the specific epitope sequence or structure has not been determined. When it is confirmed that the human antibody binds to the same epitope as the M30 antibody, the human antibody is strongly expected to have a cytotoxic activity equivalent to that of the M30 antibody.

The chimeric antibodies, humanized antibodies, or human antibodies obtained by the above-described method are evaluated for the binding property to an antigen by a method shown in Example 3 or the like, and a preferred antibody can be selected.

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

Further, a method in which the full-length heavy and light chain sequences of an antibody are connected using an appropriate linker, whereby a single-chain immunoglobulin is obtained is also known (Lee, H-S, et. al., Molecular Immunology (1999) 36, pp. 61-71; Shirrmann, T. et. al., mAbs (2010), 2, (1) pp. 1-4). By dimerizing such a single-chain immunoglobulin, the resulting dimer can have a structure and an activity similar to those of an antibody which is a tetramer itself. Further, the antibody of the invention may be an antibody which has a single heavy chain variable region and does not have a light chain sequence. Such an antibody is called a single domain antibody (sdAb) or a nanobody, and in fact, such an antibody is observed in a camel or a llama and has been reported to have an antigen-binding affinity (Muyldemans S. et. al., Protein Eng. (1994) 7 (9), 1129-35, Hamers-Casterman C. et. al., Nature (1993) 363 (6428) 446-8). The above-described antibodies can also be construed as a type of functional fragment of the antibody according to the invention.

In the invention, a modified variant of the antibody or a functional fragment of the antibody is also included. The modified variant refers to a variant obtained by subjecting the antibody or a functional fragment of the antibody of the invention to chemical or biological modification. Examples of the chemically modified variant include variants chemically modified by linking a chemical moiety to an amino acid skeleton, variants chemically modified with an N-linked or O-linked carbohydrate chain, etc. Examples of the biologically modified variant include variants obtained by modification after translation (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell.

Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody or a functional fragment of the antibody of the invention is useful for improving the stability and blood retention of the original antibody or a functional fragment of the antibody of the invention, reducing the antigenicity thereof, detecting or isolating such an antibody or an antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, WO 99/54342, WO 00/61739, WO 02/31140, etc. are known. However, the technique is not limited thereto. In the antibody and a functional fragment of the antibody of the invention, an antibody or a functional fragment of the antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody and a gene encoding a light chain sequence thereof described in this specification. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a gene of a desired antibody or a functional fragment of the antibody into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody and a functional fragment of the antibody of the invention, an antibody or a functional fragment of the antibody obtained by a method of producing an antibody or a functional fragment of the antibody, characterized by including a step of culturing the transformed host cell and a step of collecting a desired antibody or a functional fragment of the antibody from a cultured product obtained in the culturing step is also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the invention, an antibody and a functional fragment of the antibody subjected to such modification are also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like can be exemplified. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified. There is no limitation on isotype of the antibody of the invention, and examples thereof include IgG (IgG1, IgG2, IgG3, IgG4), IgM, IgA (IgA1, IgA2), IgD, and IgE, and preferred examples thereof include IgG and IgM, and further more preferred examples thereof include IgG1 and IgG2.

Further, the antibody of the invention may be a functional fragment of the antibody having an antigen-binding site of the antibody or a modified fragment thereof. The fragment of the antibody can be obtained by treating the antibody with a protease such as papain or pepsin, or modifying the antibody gene according to a genetic engineering technique and expressing the modified gene in suitable cultured cells. Among these antibody fragments, a fragment having all or part of the functions of the antibody can be called a functional fragment of the antibody.

As the functions of the antibody, generally an antigen-binding activity, an activity of neutralizing the activity of an antigen, an activity of enhancing the activity of an antigen, an antibody-dependent cellular cytotoxicity (ADCC) activity and a complement-dependent cytotoxicity (CDC) activity can be exemplified. The function of the antibody and a functional fragment of the antibody according to the invention is a binding activity to B7-H3, preferably an antibody-dependent cell-mediated phagocytosis (ADCP) activity, more preferably a cytotoxic activity (antitumor activity) mediated by an ADCP activity against tumor cells. Further, the antibody of the invention may have an ADCC activity and/or a CDC activity in addition to the ADCP activity. In particular, it has been reported that a pharmaceutical containing a currently available antitumor antibody directly acts on tumor cells to block a proliferative signal, directly acts on tumor cells to induce a cell death signal, suppresses angiogenesis, induces an ADCC activity mediated by NK cells, and induces a CDC activity mediated by a complement, thereby suppressing the growth of tumor cells (J Clin Oncol 28: 4390-4399. (2010), Clin Cancer Res; 16 (1); 11-20. (2010)), however, at least the present inventors do not know that the ADCP activity of the anti-B7-H3 antibody according to the invention of this application has been reported as the activity of a pharmaceutical containing a currently available antitumor antibody.

Examples of the fragment of the antibody include Fab, $F(ab')_2$, Fv, single-chain Fv (scFv) in which Fv molecules of the heavy chain and the light chain are connected via an appropriate linker, a diabody (diabodies), a linear antibody, and a polyspecific antibody composed of the antibody fragment. Further, Fab' which is a monovalent fragment in a variable region of an antibody obtained by treating $F(ab')_2$ under reducing conditions is also included in the fragment of the antibody.

Further, the antibody of the invention may be a polyspecific antibody with specificity for at least two different types of antigens. In general, such an antibody binds to two types of antigens (that is, bispecific antibody), however, the "polyspecific antibody" as used herein includes an antibody having specificity for two or more (for example, three) types of antigens.

The polyspecific antibody of the invention may be a full-length antibody or a fragment of such an antibody (for example, a $F(ab')_2$ bispecific antibody). The bispecific antibody can be produced by connecting the heavy and light chains (HL pairs) of two types of antibodies, or can also be produced by fusing hybridomas which produce different monoclonal antibodies to prepare bispecific antibody-producing fused cells (Millstein et al., Nature (1983) 305, pp. 537-539).

The antibody of the invention may be a single-chain antibody (also referred to as scFv). The single-chain antibody can be obtained by connecting the heavy chain variable region and the light chain variable region of the antibody via a polypeptide linker (Pluckthun, The Pharmacology of Monoclonal Antibodies, 113 (edited by Rosenberg and Moore), Springer Verlag, New York, pp. 269-315 (1994), Nature Biotechnology (2005), 23, pp. 1126-1136). Further, a BiscFv fragment produced by connecting two scFv molecules via a polypeptide linker can also be used as the bispecific antibody.

The method of producing a single-chain antibody is known in this technical field (see, for example, U.S. Pat. Nos. 4,946,778, 5,260,203, 5,091,513, 5,455,030, etc.). In this scFv, the heavy chain variable region and the light chain variable region are connected via a linker which does not form a conjugate, preferably via a polypeptide linker (Huston, J. S. et al., Proc. Natl. Acad. Sci. USA (1988), 85, pp. 5879-5883). In the scFv, the heavy chain variable region and the light chain variable region may be derived from the same antibody or different antibodies.

As the polypeptide linker to be used for connecting the variable regions, for example, a given single-chain peptide consisting of 12 to 19 residues is used.

A DNA encoding scFv can be obtained by performing amplification through PCR using a DNA as a template that comprises all or desired part of a DNA selected from a DNA encoding the heavy chain or the heavy chain variable region of the above-described antibody and a DNA encoding the light chain or the light chain variable region thereof and also using a primer pair that defines both ends of the template DNA, and further performing amplification by combining a DNA encoding a polypeptide linker portion and a primer pair that defines both ends of the polypeptide so as to connect the both ends thereof to each of the heavy chain and the light chain.

Further, once DNA encoding scFv is produced, an expression vector comprising the same and a host transformed by the expression vector can be obtained according to a common procedure. Further, by using the resulting host, scFv can be obtained according to a common procedure. An antibody fragment thereof can be produced in a host by obtaining a gene and expressing the gene in the same manner as described above.

The antibody of the invention may be multimerized to increase its affinity for an antigen. The antibody to be multimerized may be one type of antibody or plural antibodies which recognize plural epitopes of the same antigen. As a method of multimerization of the antibody, binding of the IgG CH3 domain to two scFv molecules, binding to streptavidin, introduction of a helix-turn-helix motif, and the like can be exemplified.

The antibody of the invention may be a polyclonal antibody which is a mixture of plural types of anti-B7-H3 antibodies having different amino acid sequences. As one example of the polyclonal antibody, a mixture of plural types of antibodies having different CDR can be exemplified. As such a polyclonal antibody, antibodies obtained by culturing a mixture of cells which produce different antibodies and then purifying the antibodies from the resulting culture can be used (see WO 2004/061104).

As a modified antibody, an antibody bound to any of various types of molecules such as polyethylene glycol (PEG) can also be used.

Further, the antibody of the invention may be in the form of a conjugate formed between any of these antibodies and another medicinal agent (immunoconjugate). Examples of such an antibody include a conjugate in which the antibody is conjugated to a radioactive material or a compound having a pharmacological action (Nature Biotechnology (2005) 23, pp. 1137-1146). Examples thereof include indium ($^{111}$In)-capromab pendetide, technetium ($^{99m}$Tc)-nofetumomab merpentan, indium ($^{111}$In)-ibritumomab, yttrium ($^{90}$Y)-ibritumomab, and iodine ($^{131}$I)-tositumomab.

The obtained antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, HyperD®, POROS®, Sepharose FF (Pharmacia) and the like can be exemplified.

Further, by using a carrier having an antigen immobilized thereon, the antibody can also be purified utilizing the binding property of the antibody to the antigen.

3. Pharmaceutical Comprising Anti-B7-H3 Antibody

The antibodies obtained by the method described in the above item "2. Production of anti-B7-H3 antibody" exhibit a cytotoxic activity against cancer cells, and therefore can be used as a pharmaceutical, particularly a therapeutic agent and/or preventive agent for cancer.

The cytocidal activity exhibited by an antibody in vitro can be determined by measuring the inhibitory activity of cell growth.

For example, a cancer cell line which overexpresses B7-H3 is cultured, an antibody is added to the culture system at different concentrations, and an inhibitory activity against focus formation, colony formation, and spheroid growth can be measured.

The in vivo therapeutic effect of an antibody on cancer using experimental animals can be determined by, for example, administering the antibody to nude mice implanted with a tumor cell line which overexpresses B7-H3 and measuring a change of cancer cells.

Examples of the type of cancer include lung cancer, kidney cancer, urothelial carcinoma, colorectal cancer, prostate cancer, glioblastoma multiforme, ovarian cancer, pancreatic cancer, breast cancer, a melanoma, liver cancer, bladder cancer, stomach cancer, and esophageal cancer, however, the type of cancer is not limited thereto as long as a cancer cell to be treated expresses B7-H3.

An acceptable substance to be used in a preparation of the pharmaceutical composition according to the invention is preferably non-toxic to an individual to whom the pharmaceutical composition is to be administrated in terms of the dose and concentration.

The pharmaceutical composition of the invention can comprise a substance for pharmaceutical use which is capable of changing or maintaining the pH, osmotic pressure, viscosity, transparency, color, isotonicity, aseptic condition, stability, solubility, release rate, absorption rate, and permeability thereof. Examples of such a substance for pharmaceutical use include, but are not limited to, amino acids such as glycine, alanine, glutamine, asparagine, arginine, and lysine; antimicrobial agents; antioxidants such as ascorbic acid, sodium sulfate, and sodium hydrogen sulfite; buffers such as phosphate, citrate, borate buffers, sodium hydrogen carbonate, and Tris-HCl solutions; fillers such as mannitol and glycine; chelating agents such as ethylenediamine tetraacetate (EDTA); complexing agents such as caffeine, polyvinylpyrrolidine, β-cyclodextrin, and hydroxypropyl-β-cyclodextrin; expanders such as glucose, mannose, and dextrin; other carbohydrates such as monosaccharides and disaccharides; coloring agents; flavors; diluents; emulsifying agents; hydrophilic polymers such as polyvinylpyrrolidine; preservatives such as low-molecular weight polypeptides, salt-forming counter ions, benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as sorbitan ester, polysorbates including polysorbate 20 and polysorbate 80, Triton, tromethamine, lecithin, and cholesterol; stability enhancing agents such as sucrose and sorbitol; elasticity enhancing agents such as sodium chloride, potassium chloride, and mannitol and sorbitol; transport agents; excipients; and/or pharmaceutical adjuvants. The amount of these substances for pharmaceutical use is preferably from 0.001 to 100 times, particularly preferably from 0.1 to 10 times the weight of the anti-B7-H3 antibody. Those skilled in the art can appropriately determine a preferred formulation of the pharmaceutical composition in a preparation depending on the disease to which the composition is applied, the route of administration to be applied, or the like.

The excipient or carrier in the pharmaceutical composition may be in the form of a liquid or a solid. An appropriate excipient or carrier may be injectable water, physiological saline, an artificial cerebrospinal fluid, or other substance commonly used for parenteral administration. Further, neutral physiological saline or physiological saline containing serum albumin can also be used as a carrier. The pharmaceutical composition may contain a Tris buffer of pH 7.0 to 8.5, an acetate buffer of pH 4.0 to 5.5, or a citrate buffer of pH 3.0 to 6.2. Further, such a buffer may be supplemented with sorbitol or another compound.

Examples of the pharmaceutical composition of the invention include a pharmaceutical composition comprising the anti-B7-H3 antibody and a pharmaceutical composition comprising the anti-B7-H3 antibody and at least one therapeutic agent for cancer. The pharmaceutical composition of the invention is prepared in the form of a lyophilized product or a liquid as a medicinal agent having a selected composition and a required purity. The pharmaceutical composition comprising the anti-B7-H3 antibody and the pharmaceutical composition comprising the anti-B7-H3 antibody and at least one therapeutic agent for cancer can also be formed into a lyophilized product using an appropriate excipient such as sucrose.

In the above-described pharmaceutical composition, the therapeutic agent for cancer to be incorporated along with the anti-B7-H3 antibody may be administrated simultaneously with, separately from, or sequentially with the anti-B7-H3 antibody, or the therapeutic agent and the anti-B7-H3 antibody may be administrated at different dosage intervals. Examples of such a therapeutic agent for cancer include abraxane, carboplatin, cisplatin, gemcitabine, irinotecan (CPT-11), paclitaxel, pemetrexed, sorafenib, vinblastin, and medicinal agents described in WO 2003/038043, and additional examples thereof include LH-RH analogues (such as leuprorelin and goserelin), estramustine phosphate, estrogen antagonists (such as tamoxifen and raloxifene), and aromatase inhibitors (such as anastrozole, letrozole, and exemestane), however, the agent is not limited thereto as long as the agent is a medicinal agent having an antitumor activity.

An individual to whom the pharmaceutical composition is to be administered is not particularly limited, however, preferred are mammals, and more preferred are humans.

The pharmaceutical composition of the invention can be prepared for parenteral administration or for gastrointestinal absorption through oral administration. The composition and concentration of a preparation can be determined depending on the administration method. The higher the affinity of the anti-B7-H3 antibody comprised in the pharmaceutical composition of the invention is for B7-H3, that is, the lower the dissociation constant (Kd value) thereof is for B7-H3, the more the anti-B7-H3 antibody can exhibit its drug efficacy even when decreasing the dose for humans. Hence, the dose of the pharmaceutical composition of the invention for humans can also be determined based on this result. As for the dose, in the case where a human anti-B7-H3 antibody is administrated to humans, the antibody may be administrated at a dose of from about 0.001 to 100 mg/kg once or several times at intervals of 1 to 180 days. Examples of the dosage form of the pharmaceutical composition of the invention include injections including infusions, suppositories, transnasal agents, sublingual agents, and percutaneous absorbents.

Hereinafter, the invention will be more specifically described with reference to the Examples, however, the invention is not limited thereto.

EXAMPLES

Note that the respective operations regarding gene manipulation in the following Examples were performed according to the methods described in "Molecular Cloning" (written by Sambrook, J., Fritsch, E. F. and Maniatis, T., published by Cold Spring Harbor Laboratory Press in 1989), or in the case of using commercially available reagents or kits, they are used according to the instructions attached thereto unless otherwise stated.

Example 1

Production of Plasmid

1)-1 Production of Human B7-H3 Expression Vector
1)-1-1 Production of Expression Vector for Full-Length Human B7-H3 Variant 1

A PCR reaction was performed using a cDNA synthesized from the total RNA of LNCaP cells (American Type Culture Collection (ATCC)) as a template and also using the following primer set, thereby amplifying a cDNA encoding the human B7-H3 variant 1:

```
Primer 1:
5'-ctatagggagacccaagctggctagcatgctgcgtcggcggg
gcag-3' (SEQ ID NO: 1 in the Sequence Listing);
and Primer 2:
5'-aacgggccctctagactcgagcggccgctcaggctatttcttgt
ccatcatcttctttgctgtcag-3' (SEQ ID NO: 2 in the
Sequence Listing).
```

Subsequently, the thus obtained PCR product was purified using MagExtractor® PCR & Gel cleanup (TOYOBO, Co., Ltd.). Then, the PCR product was digested with restriction enzymes (NheI and NotI), followed by purification using MagExtractor PCR & Gel cleanup (TOYOBO, Co., Ltd.). A pcDNA3.1(+) plasmid DNA was digested with the same restriction enzymes (NheI and NotI), followed by purification using MagExtractor PCR & Gel cleanup (TOYOBO, Co., Ltd.).

The resulting purified DNA solutions were mixed, and further, Ligation high (TOYOBO, Co., Ltd.) was added thereto, and the resulting mixture was incubated at 16° C. for 8 hours to effect ligation. The resulting reaction mixture was added to *E. coli* DH5α competent cells (Invitrogen Corporation) to effect transformation.

Colony direct PCR was performed on the resulting colonies using the PCR primers and the BGH reverse primer, and a candidate clone was selected.

The obtained candidate clone was cultured in a liquid medium (LB/Amp), and a plasmid DNA was extracted using MagExtractor-Plasmid-(TOYOBO, Co., Ltd.).

By using the obtained plasmid DNA as a template, a sequence between the following Primer 3 and Primer 4 was determined by a sequence analysis and the sequences were compared between the obtained clone and the provided CDS sequence:

```
Primer 3 (CMV promoter primer):
5'-cgcaaatgggcggtaggcgtg-3' (SEQ ID NO: 3 in the
Sequence Listing); and Primer 4 (BGH reverse primer):
5'-tagaaggcacagtcgagg-3' (SEQ ID NO: 4 in the
Sequence Listing).
```

After confirming the sequence, the obtained clone was cultured in 200 ml of LB/Amp medium, and a plasmid DNA was extracted using Plasmid Midi V-100 kit (VioGene, Inc.).

The thus obtained vector was named "pcDNA3.1-B7-H3". The sequence of the ORF region of the B7-H3 variant 1 gene cloned in this vector is represented by nucleotide numbers 1 to 1602 in SEQ ID NO: 5 in the Sequence Listing. Further, the amino acid sequence of the B7-H3 variant 1 is represented by SEQ ID NO: 6 in the Sequence Listing.

1)-1-2 Production of Expression Vector for Full-Length Human B7-H3 Variant 2

PCR was performed using a cDNA synthesized from the total RNA of LNCaP cells as a template and also using the following primer set, thereby amplifying a cDNA encoding the human B7-H3 variant 2:

```
Primer 5
5'-ggggacaagtttgtacaaaaaagcaggcttcaccatgctgcgtcg
gcggggcagccctg-3' (SEQ ID NO: 7 in the Sequence
Listing)

Primer 6
5'-ggggaccactttgtacaagaaagctgggtcggctatttcttgt-3'
(SEQ ID NO: 8 in the Sequence Listing).
```

Purification was performed in the same manner as in Example 1)-1-1, and the PCR product after purification was integrated into a pDONR221 vector (Invitrogen Corporation) by a Gateway BP reaction, thereby transforming *E. coli* TOP10 (Invitrogen Corporation).

For the clones obtained after transformation, the size of the insert was confirmed by colony PCR. For 8 clones in which the size of the insert was confirmed, the DNA sequence at the 3' end and the 5' end of the insert was confirmed by performing one sequencing reaction from the vector side to the insert side for both ends. A Gateway LR reaction between the entry clone whose sequence was confirmed and a Gateway destination vector pcDNA-DEST40 (Invitrogen Corporation) was performed. For the clone obtained after transformation of *E. coli* TOP10, the size of the insert was confirmed by colony PCR. For the clone in which the size of the insert was confirmed, the DNA sequence at the 3' end and the 5' end of the insert was analyzed to confirm that the insert of interest was correctly inserted. At least 1 mg of the thus produced plasmid of the clone was purified using PureLink HiPure Plasmid Megaprep Kit (Invitrogen Corporation).

The thus obtained vector was named "pcDNA-DEST40-B7-H3 variant 2". The sequence of the ORF region of the B7-H3 variant 2 gene cloned in this vector is represented by nucleotide numbers 1 to 948 in SEQ ID NO: 9 in the Sequence Listing. Further, the amino acid sequence of the B7-H3 variant 2 is represented by SEQ ID NO: 10 in the Sequence Listing.

1)-2 Production of Expression Vector for B7-H3 Partial Protein

By using the B7-H3 full-length plasmid related to the B7-H3 variant 1 of Example 1)-1-1 as a template, each of the following regions was amplified by PCR. The numbers showing each region of interest correspond to the nucleotide numbers of B7-H3 represented by SEQ ID NO: 5. The primer was designed to contain a stop codon at the 3' end in addition to the Gateway att sequence.

Each of the following regions 1), 2), and 3) was prepared by amplifying two regions and then ligating the regions by PCR to form one fragment. That is, as for the region 1), amplification was performed using Primers 7 and 12, and Primers 15 and 11, and the resulting PCR products were further amplified using Primers 7 and 11. As for the region 2), amplification was performed using Primers 8 and 13, and Primers 15 and 11, and the resulting PCR products were further amplified using Primers 8 and 11. As for the region 3), amplification was performed using Primers 9 and 14, and Primers 15 and 11, and the resulting PCR products were further amplified using Primers 9 and 11. As for the region 4), amplification was performed using Primers 10 and 11. As for the region 5), amplification was performed using Primers 8 and 11. As for the region 6), amplification was performed using Primers 9 and 11.

Regions of Interest
1) B7-H3 variant 1 ORF: 79-417 and 1369-1602 (573 bp)
2) B7-H3 variant 1 ORF: 418-732 and 1369-1602 (549 bp)
3) B7-H3 variant 1 ORF: 733-1071 and 1369-1602 (573 bp)
4) B7-H3 variant 1 ORF: 1072-1602 (531 bp)
5) B7-H3 variant 1 ORF: 418-1602 (1185 bp)
6) B7-H3 variant 1 ORF: 733-1602 (870 bp)

```
Primer number and base sequence
Primer 7
5'-ggggacaagtttgtacaaaaaagcaggcttcggagccctggag
gtccaggtc-3' (SEQ ID NO: 11 in the Sequence
Listing)

Primer 8
5'-ggggacaagtttgtacaaaaaagcaggcttcgctccctactcgaagcc
cagcatg-3' (SEQ ID NO: 12 in the Sequence Listing)

Primer 9
5'-ggggacaagtttgtacaaaaaagcaggcttcggagccgtggaggtcca
ggtc-3' (SEQ ID NO: 13 in the Sequence Listing)
```

-continued

Primer 10
5'-ggggacaagtttgtacaaaaaagcaggcttcgctccctactcgaagcc
cagcatg-3' (SEQ ID NO: 14 in the Sequence Listing)

Primer 11
5'-ggggaccactttgtacaagaaagctgggtctcaggctatttcttgtcc
atcatc-3' (SEQ ID NO: 15 in the Sequence Listing)

Primer 12
5'-gggaatgtcataggctgcccggccacctgcaggctgacggcag-3'
(SEQ ID NO: 16 in the Sequence Listing)

Primer 13
5'-gggaatgtcataggctgccctgtggggcttctctggggtgtg-3'
(SEQ ID NO: 17 in the Sequence Listing)

Primer 14
5'-gggaatgtcataggctgcccggccacctgcaggctgacggcag-3'
(SEQ ID NO: 18 in the Sequence Listing)

Primer 15
5'-gggcagcctatgacattcccccagag-3' (SEQ ID NO: 19 in the Sequence Listing)

Purification was performed in the same manner as in Example 1)-1-1, and each of the amplified products after purification was integrated into a pDONR221 vector by a Gateway BP reaction, thereby transforming E. coli TOP10. For the clones obtained after transformation, the size of the insert was confirmed by colony PCR.

For each of the clones in which the size of the insert was confirmed, the DNA sequence at the 3' end and the 5' end of the insert was confirmed by performing one sequencing reaction from the vector side to the insert side for both ends.

For the clones which were confirmed to have the insert of interest, the total DNA sequence of the insert was also confirmed using the following primers. As a result of sequence analysis, it was confirmed that all of the sequences were completely identical to the information of the sequences of interest.

A Gateway LR reaction between each of the entry clones whose sequence was confirmed and pFLAG-myc-CMV-19-DEST (Invitrogen Corporation) was performed. For the clones obtained after transformation of E. coli DH10B (Invitrogen Corporation), the size of the insert was confirmed by colony PCR.

For each of the clones in which the size of the insert was confirmed, the DNA sequence at the 3' end and the 5' end of the insert was analyzed to confirm that the insert of interest was correctly inserted. Hereinafter, the expression vectors obtained by integrating each of the above regions 1) to 6) were represented by "B7-H3 IgV1", "B7-H3 IgC1", "B7-H3 IgV2", "B7-H3 IgC2", "B7-H3 IgC1-V2-C2", and "B7-H3 IgV2-C2", respectively.

The nucleotide sequences of the ORF regions of the B7-H3 IgV1, B7-H3 IgC1, B7-H3 IgV2, B7-H3 IgC2, B7-H3 IgC1-V2-C2, and B7-H3 IgV2-C2 genes, each of which was cloned in this vector, are represented by SEQ ID NOS: 20, 22, 24, 26, 28, and 30, respectively, in the Sequence Listing. Further, the amino acid sequences of the B7-H3 IgV1, B7-H3 IgC1, B7-H3 IgV2, B7-H3 IgC2, B7-H3 IgC1-V2-C2, and B7-H3 IgV2-C2 are represented by SEQ ID NOS: 21, 23, 25, 27, 29, and 31, respectively, in the Sequence Listing. Further, the sequences represented by SEQ ID NOS: 20 and 21 are shown in FIG. 15, the sequences represented by SEQ ID NOS: 22 and 23 are shown in FIG. 16, the sequences represented by SEQ ID NOS: 24 and 25 are shown in FIG. 17, the sequences represented by SEQ ID NOS: 26 and 27 are shown in FIG. 18, the sequences represented by SEQ ID NOS: 28 and 29 are shown in FIG. 19, and the sequences represented by SEQ ID NOS: 30 and 31 are shown in FIG. 20.

1)-3 Production of Expression Vectors for B7 Family Genes pCMV6-XL-4-B7RP-1, pCMV6-XL-4-B7-H1, and pCMV6-XL-4-B7-DC (which are gene expression vectors obtained by integrating each of B7RP-1, B7-H1, and B7-DC (which are B7 family genes) in an expression vector pCMV6-XL-4) were all purchased from OriGene, Inc.

Vectors expressing each of CD80, CD86, and B7-H4, which are B7 family genes, were produced as follows.

pENTR/221-CD80, pENTR/221-CD86, and pENTR/221-B7-H4, which are clones obtained by integrating each of CD80, CD86, and B7-H4 in an entry vector pENTR/221, were purchased from Invitrogen Corporation A Gateway LR reaction between each of the entry clones whose sequence was confirmed and pcDNA3.1-DEST (Invitrogen Corporation) was performed. For the clones obtained after transformation of E. coli DH10B, the size of the insert was confirmed by colony PCR. For each of the clones in which the size of the insert was confirmed, the DNA sequence at the 3' end and the 5' end of the insert was analyzed to confirm that the insert of interest was correctly inserted.

The nucleotide sequences of the ORF regions of the B7RP-1, B7-H1, B7-DC, CD80, CD86, and B7-H4 genes, each of which was cloned in this vector, are represented by SEQ ID NOS: 32, 34, 36, 38, 40, and 42, respectively, in the Sequence Listing. Further, the amino acid sequences of the B7RP-1, B7-H1, B7-DC, CD80, CD86, and B7-H4 are represented by SEQ ID NOS: 33, 35, 37, 39, 41, and 43, respectively, in the Sequence Listing.

Example 2

Production of Monoclonal Antibody and Screening of Antibody

2)-1 Immunization

BALB/cAnNCrlCrlj mice (Charles River Laboratories Japan, Inc.), FcgRII KO mice (Taconic, Inc., IBL Co., Ltd.), or GANP mice (Transgenic, Inc.) at 4 to 6 weeks of age were used. On days 0, 7, 15, and 24, LNCaP cells, MCF7 cells (ATCC) or AsPC1 cells (ATCC) detached with versene (Invitrogen Corporation) were subcutaneously administrated in the dorsal region of each mouse at a dose of $5 \times 10^6$ cells/mouse. On day 31, the same cells were intravenously administrated to each mouse at a dose of $5 \times 10^6$ cells. On day 34, the spleen was excised from each mouse and used for the production of hybridomas.

2)-2 Production of Hybridomas

Spleen cells and mouse myeloma P3X63Ag8U.1 cells (ATCC) were subjected to cell fusion using PEG 4000 (manufactured by IBL Co., Ltd.), thereby producing hybridomas.

As a result, 9639 clones from the mice immunized with LNCaP cells, 4043 clones from the mice immunized with MCF7 cells, and 3617 clones from the mice immunized with AsPC1 cells were established as hybridomas. By using the obtained culture supernatant of each hybridoma, an antibody-producing hybridoma was screened by a CDC assay.

2)-3 Screening of Antibody by CDC Assay

On day 0, LNCaP cells or MCF7 cells were diluted to 5000 cells per 80 μL and the resulting solution was added to a 96-well plate at 80 μl/well. Then, the cells were cultured overnight. The hybridoma culture supernatant was added at 20 μl/well to the plate in which the cells were seeded, and the plate was left to stand at 4° C. for 1 hour. To a diluted and lyophilized rabbit complement (Cedarlane Laboratories), 1 mL of sterile water was added to each vial on ice, and the vial was left to stand for 1 minute, followed by mixing, and then, the resulting mixture was mixed with 19 mL of 0.1% BSA/RPMI 1640 medium (BSA, Sigma Co., Ltd.). A reaction was allowed to proceed at 37° C. for 1 hour.

The plate was left at room temperature for 30 minutes to return to room temperature. 120 µL of CellTiter-Glo reagent (Promega Corporation) was added to each well, and a reaction was allowed to proceed at room temperature for 10 minutes. The amount of luminescence was measured using a plate reader (ARVO HTS, PerkinElmer, Inc.). In a well exhibiting low luminescence, it was determined that complement-dependent cell death was induced. A hybridoma which produced a culture supernatant that induced such complement-dependent cell death was selected.

As a result, 24 clones from the clones derived from immunization with LNCaP, 36 clones from the clones derived from immunization with MCF7, and 3 clones from the clones derived from immunization with AsPC1 were obtained as positive clones by screening.

Example 3

Identification of Antigen

3)-1 Identification of Immunoprecipitated Substance
3)-1-1 Immunoprecipitation

MCF7 cells were cultured at 5 to $10 \times 10^8$ cells. These cells were detached with a cell scraper and the detached cells were collected and cryopreserved at −80° C. To the cryopreserved cells, 10 ml of a lysis buffer which contained 1% NP-40 (Sigma-Aldrich Co., Ltd.) and a protease inhibitor (F. Hoffmann-La Roche, Ltd.) and was cooled to 4° C. was added and the cell pellet was lysed on ice with a pipette in such a manner that the formation of bubbles was avoided. After being completely lysed, the pellet was left on ice for 30 minutes. The solubilized sample was centrifuged at 4° C. for 20 minutes at 10000 to 15000 rpm, and the resulting supernatant was transferred to a 15 ml falcon tube.

500 µl of protein G-Sepharose 4FF beads (Amersham Pharmacia Biotech Co., Ltd.) were washed three times, and subjected to buffer exchange with a lysis buffer. 500 µl of the protein G-Sepharose 4FF beads were added to the solubilized sample supernatant on ice, and the resulting mixture was subjected to rotary stirring overnight at 4° C.

The sample was passed through Poly-Prep chromatography columns (Bio-Rad Laboratories, Inc.), and a passed-through fraction was used as an immunoprecipitation sample.

3 µg of an antibody solution to be used for immunoprecipitation was added to 50 µl of protein G-Sepharose 4FF beads subjected to buffer exchange with phosphate buffered saline (PBS) (a 1.5 ml tube), and the resulting mixture was subjected to rotary stirring at 4° C. for 1 to 16 hours, whereby the antibody was bound to the beads. To the immunoprecipitation sample, the beads to which the antibody was bound were added, and the resulting mixture was subjected to rotary stirring at 4° C. for 3 hours.

The column was transferred to an empty 15 ml falcon tube, and 6.5 ml of a lysis buffer was added thereto. This procedure was repeated 4 times.

The outlet of the column was capped, and pipetting was performed with 500 µl of a lysis buffer, and the beads were collected in a 1.5 ml tube. This procedure was repeated twice.

After centrifugation at 4° C. for 1 minute at 5000 rpm, the supernatant was carefully removed. Then, 90 µl of an elution buffer (10 mM glycine-HCl, pH 2.0) was added thereto, followed by vortexing and centrifugation. The column of 1.5 ml spin column was detached, and 10 µl of 1 M Tris-HCl (Ph 8.5) was added thereto, and the column was returned to the original place. An elution fraction was transferred thereto, and centrifugation was performed at 10000 rpm for 1 minute, whereby 100 µl of a sample was obtained.

The obtained sample was subjected to MS analysis by a liquid phase digestion technique as shown in the following 3)-1-2.

3)-1-2 Identification of Antigen by Mass Spectrometry Analysis

According to a common procedure, the fraction obtained by the immunoprecipitation method was subjected to a digestion reaction at 37° C. for 16 hours by adding trypsin (modified trypsin, Promega Corporation) through a liquid phase digestion technique. The resulting digested peptides were subjected to a liquid chromatography (LC)/tandem mass spectrometer (MS/MS) (Thermo Fisher Scientific K.K.). The obtained mass spectral data were analyzed using a database search software (Mascot, Matrix Science K.K.). As the database, International Protein Index (IPI) was used. As a result, 34 types of antigens were identified.

From the characteristics of the identified antigens, bibliographic information retrieval was performed in consideration that B7-H3 is a cell membrane protein, and by focusing on B7-H3 (CD276) antigen (B7-H3 variant 1), experiments described in the following 3)-2 and 3)-3 were performed.

3)-2 Preparation of Antigen Gene-Expressing Cells

NIH-3T3 cells (ATCC) were seeded at $5 \times 10^4$ cells/cm$^2$ in a collagen type I-coated flask (manufactured by IWAKI Co., Ltd.) and cultured overnight in DMEM medium (Invitrogen Corporation) containing 10% fetal bovine serum (FBS) under the conditions of 37° C. and 5% $CO_2$.

On the next day, the NIH-3T3 cells were transfected with each of the pcDNA3.1-B7-H3 produced in Example 1)-1-1, pcDNA-DEST40-B7-H3 variant 2 produced in 1)-1-2, and pcDNA-DEST40 which is an empty vector using Lipofectamine 2000 (Invitrogen Corporation), and further cultured overnight under the conditions of 37° C. and 5% $CO_2$.

On the next day, the transfected NIH-3T3 cells were treated with trypsin, and washed with DMEM containing 10% FBS, and thereafter suspended in PBS containing 5% FBS. The thus obtained cell suspension was used in a flow cytometric analysis.

3)-3 Flow Cytometric Analysis

The binding specificity, for B7-H3, of the antibody produced by the hybridoma which immunoprecipitated the B7-H3 variant 1 identified by MS was confirmed by a flow cytometric method. The cell suspension prepared in Example 3)-2 was centrifuged, and the supernatant was removed. Then, the hybridoma culture supernatant was added to the NIH-3T3 cells transfected with each vector to suspend the cells, and the cells were left to stand at 4° C. for 1 hour.

After the cells were washed twice with PBS containing 5% FBS, fluorescein-conjugated goat IgG fraction to mouse IgG (whole molecule) (manufactured by ICN Pharmaceuticals, Inc., #55493) diluted to 1000-fold with PBS containing 5% FBS was added thereto to suspend the cells, and the cells were left to stand at 4° C. for 1 hour.

After the cells were washed twice with PBS containing 5% FBS, the cells were resuspended in PBS containing 5% FBS supplemented with 2 µg/ml 7-aminoactinomycin D (manufactured by Invitrogen Corporation (Molecular Probes)), and the detection was performed using a flow cytometer (FC500, Beckman Coulter, Inc.). The data was analyzed using Flowjo (Tree Star, Inc.).

7-Aminoactinomycin D-positive dead cells were excluded using a gate. Then, the FITC fluorescence intensity histograms of viable cells were created.

A hybridoma which produced a sample that gave a higher fluorescence intensity in the fluorescence intensity histograms of the NIH-3T3 cells expressing the B7-H3 variant 1 and the NIH-3T3 cells expressing the B7-H3 variant 2 than in the fluorescence intensity histogram of the NIH-3T3 cells transfected with the empty vector serving as the control was selected as the anti-B7-H3 antibody-producing hybridoma.

As a result, it was found that the antibodies derived from the anti-B7-H3 antibody-producing hybridomas of 5 clones (L7, L8, L11, M30, and M31) have a cross-reactivity with the B7-H3 variant 1 and the B7-H3 variant 2.

3)-4 Confirmation of Binding Property of Monoclonal Antibody to Cancer Cell Line It was examined as to whether the monoclonal antibodies confirmed to bind to the B7-H3 variant 1 and the B7-H3 variant 2 in Example 3)-3 bind to cancer cells which overexpress the B7-H3 variant 1 and the B7-H3 variant 2 by a flow cytometric method in the same manner as in Example 3)-3.

In place of the transfected NIH-3T3 cells, a human breast cancer cell line (MDA-MB-231) (ATCC) and a human lung cancer cell line (NCI-H322) (ATCC) were used. As a result, it was confirmed that the established monoclonal antibodies all bind to these cancer cell lines.

3)-5 Isotype Determination of Monoclonal Antibody

The isotypes of the monoclonal antibodies were determined using Mouse monoclonal isotyping kit (manufactured by Serotec Co., Ltd.). As a result, the isotypes of the antibodies derived from the anti-B7-H3 antibody-producing hybridomas (L7, L8, L11, M30, and M31) were all IgG2a.

3)-6 Preparation of Monoclonal Antibody

The monoclonal antibody was purified from the ascites of a mouse implanted with a hybridoma or a hybridoma culture supernatant (hereinafter, referred to as a "starting material for antibody purification").

The mouse ascites was prepared as follows. First, BALB/cAJcl-nu/nu (CLEA Japan, Inc.) mice at 7 to 8 weeks of age were treated with pristane (manufactured by Sigma Co., Ltd.), and after about 3 weeks, a hybridoma washed with physiological saline was implanted into the abdominal cavity at $1 \times 10^7$ cells per mouse. After 1 to 2 weeks, the ascites accumulated in the abdominal cavity was collected and sterilized through a 0.22 µm filter, and the resulting material was used as a starting material for antibody purification.

The hybridoma culture supernatant was prepared using CELLine (manufactured by BD Biosciences, Inc.). The culturing was performed according to the manufacturer's protocol except that ClonaCell-HY Growth Medium E (manufactured by StemCell Technologies, Inc., #03805) was used as the medium. The collected culture supernatant was filtered through a 0.45 µm filter, and the resulting material was used as a starting material for antibody purification.

The antibody was purified by an affinity column obtained by immobilizing Recombinant Protein A rPA50 (manufactured by RepliGen Corporation) on Formyl-Cellufine (manufactured by Seikagaku Corporation) (hereinafter abbreviated as "Formyl-Cellufine Protein A") or HiTrap® MabSelect SuRe® (manufactured by GE Healthcare BioSciences Corporation). In the case of the Formyl-Cellufine Protein A, the starting material for antibody purification was diluted to 3-fold with a binding buffer (3 M NaCl, 1.5 M glycine, pH 8.9), and the resulting solution was added to a column, then, the column was washed with the binding buffer, followed by elution with 0.1 M citric acid (pH 4.0). On the other hand, in the case of the HiTrap MabSelect SuRe (GE Healthcare Corporation), the starting material for antibody purification was added to a column, and the column was washed with PBS, followed by elution with 2 M ArginineHCl (pH 4.0).

After the eluted antibody solution was neutralized, the buffer was exchanged with PBS.

The concentration of the antibody was obtained by eluting the antibody bound to POROS® G 20 µm Column PEEK, 4.6 mm×100 mm, 1.7 ml (Applied Biosystems, Inc.) and measuring the absorbance (O.D. 280 nm) of the eluate. Specifically, an antibody sample diluted with PBS was added to POROS G 20 µm equilibrated with an equilibrating buffer (30.6 mM sodium dihydrogen phosphate/12 aq., 19.5 mM monopotassium phosphate, 0.15 M NaCl, pH 7.0). Then, the column was washed with the equilibrating buffer, and the antibody bound to the column was then eluted with an eluent (0.1% (v/v) HCl, 0.15 M NaCl). The peak area of the absorbance (O.D. 280 nm) of the eluate was measured, and the concentration was calculated according to the following equation:

Concentration of antibody sample (mg/ml)=(Peak area of antibody sample)/(Peak area of reference standard (human IgG1))×Concentration of reference standard (mg/ml)×Dilution factor of sample.

Further, the concentration of endotoxin contained in the obtained antibody was measured using Endospecy ES-50M Set (Seikagaku Corporation, #020150) and an endotoxin reference standard CSE-L Set (Seikagaku Corporation, #020055) and was confirmed to be 1 EU/mg or less. The resulting antibody was used in the subsequent experiment.

Example 4

Properties of Anti-B7-H3 Antibody

4)-1 ADCP Activity 1.5 mL of thioglycollate was administrated in the abdominal cavity of a Balb/c-nu/nu mouse (female, at 6 to 10 weeks of age) (Charles River Laboratories Japan, Inc.). 5 Days thereafter, macrophages in the abdominal cavity were collected. The macrophages were added to a 24-well plate at 500 µL/well ($1 \times 10^5$ cells/well) and cultured overnight at 37° C. The thus prepared macrophages were used as effector cells.

The labeling of NCI-H322 cells to be used as target cells was performed using PKH26 dye labeling kit (Sigma Co., Ltd.) The target cells were detached with TrypLE (Invitrogen Corporation) and washed twice with PBS. The cells were suspended in Diluent C at $1 \times 10^7$ cells/ml. PKH26 dye stock (1 mM) was diluted to 8 µM with Diluent C, and immediately thereafter, the diluted dye solution was added thereto in an amount equal to that of the cell suspension. The resulting mixture was left at room temperature for 5 minutes. Then, 1 ml of serum was added thereto, and further, a medium with serum was added thereto, and washing was performed twice. The thus prepared cells were used as the target cells.

The antibody obtained in Example 3)-6 was diluted to 20 µg/ml with a culture solution. Subsequently, the target cells obtained in Example 4)-1-1 were dispensed at $2 \times 10^6$ cells/100 µl/tube and mixed. The resulting mixture was left to stand on ice for 30 minutes. The supernatant was removed, and the cells were washed twice with a culture solution and suspended in 500 µl of a culture solution. The supernatant was removed from the effector cells, and the cells having been treated with the antibody and suspended in the culture solution were added thereto and mixed therewith. Then, the cells were cultured for 3 hours in a $CO_2$ incubator. Thereafter, the cells were detached with Trypsin-EDTA and collected. To the collected cells, an FITC-labeled anti-mouse CD11b antibody (Becton, Dickinson and Company, Ltd.) was added, and the resulting mixture was left to stand on ice for 30 minutes. The supernatant was removed, and the cells were washed twice with a culture solution. The collected cells were suspended in 300 µl of a culture solution and analyzed by FACS Calibur (Becton, Dickinson and Company, Ltd.). In the CD11b-positive macrophages, a PKH26-positive fraction was evaluated as phagocytosis-positive cells (n=3).

As a result, as shown in FIG. 1, the L7, L8, L11, M30, and M31 induced the phagocytosis of the NCI-H322 cells by macrophages to give the percentage of phagocytosis of 48.0±0.9%, 52.3±1.1%, 57.1±2.5%, 61.9±2.1%, and 57.7±3.0%, respectively. Accordingly, it was shown that the L7, L8, L11, M30, and M31 antibodies have an ADCP activity against the NCI-H322 cells.

In the same manner, commercially available anti-B7-H3 antibodies were obtained and the ADCP activity thereof was measured. A rat anti-human B7-H3 antibody MIH35 (eBioscience Company), a mouse anti-human B7-H3 antibody 185504 (R&D Systems, Inc.), MIH42 (Serotec Co., Ltd.), and DCN70 (Biolegend Company) were obtained. It was confirmed that these antibodies bind to B7-H3 in the same manner as in Example 3)-3. By using these antibodies, the ADCP activity was measured by the above method.

Figure 2:
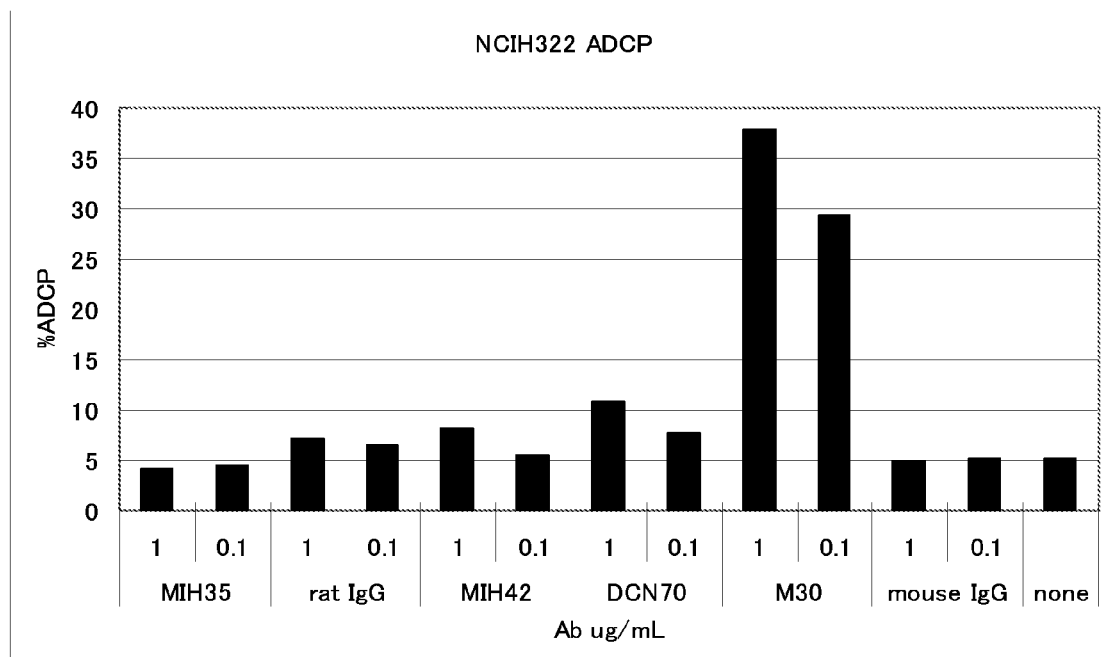
FIG. 2 is a graph showing the presence or absence of an ADCP activity of a commercially available anti-B7-H3 antibody against NCI-H322 cells.

As a result, as shown in FIG. 2, when being added at 1 µg/ml, the MIH35, MIH42, and DCN70 induced the phagocytosis of the NCI-H322 cells by macrophages to 4.2%, 8.2%, and 10.8%, respectively. Accordingly, it was revealed that the MIH35, MIH42, and DCN70 exhibited almost no ADCP activity.

From these results, it was shown that the M30 clones recognizing B7-H3 obtained by screening this time have a particularly higher ADCP activity than the commercially available B7-H3 antibodies.

4)-2 ADCC Activity

4)-2-1 Preparation of Effector Cells

The spleen was aseptically excised from a nude mouse CAnN.Cg-Foxnl$^{nu}$/CrlCrlj (Charles River Laboratories Japan, Inc.). The excised spleen was homogenized with two slide glasses, and subjected to a hemolysis treatment using BD Pharm Lyse (manufactured by BD Biosciences, Ltd. #555899). The thus obtained spleen cells were suspended in phenol red-free RPMI 1640 (manufactured by Invitrogen Corporation) containing 10% Fetal Bovine Serum, Ultra-low IgG (manufactured by Invitrogen Corporation) (hereinafter abbreviated as "ADCC medium"), and the cell suspension was passed through a cell strainer (pore size: 40 µm, manufactured by BD Biosciences, Ltd.). Then, the viable cells were counted by a trypan blue dye exclusion assay. After the spleen cell suspension was centrifuged, the medium was removed, and the cells were resuspended in the ADCC medium at a viable cell density of $1.5 \times 10^7$ cells/ml and used as effector cells.

4)-2-2 Preparation of Target Cells

B7-H3-expressing 293 cells (ATCC) and empty vector-transfected 293 cells prepared in the same manner as in Example 3)-3 were treated with trypsin, and the treated cells of each type were washed with 10% FBS-containing RPMI 1640 (Invitrogen Corporation) and then resuspended in 10% FBS-containing RPMI 1640. The cells ($4 \times 10^6$ cells) of each type were mixed with chromium-51 (5550 kBq) sterilized through a 0.22 µm filter, and labeling was performed for 1 hour under the conditions of 37° C. and 5% $CO_2$. The labeled cells were washed three times with 10% FBS-containing RPMI 1640 (Invitrogen Corporation), and the cells were resuspended at $2 \times 10^5$ cells/ml in the ADCC medium and used as target cells.

4)-2-3 $^{51}$Cr Release Assay

The target cells at a cell density of $2 \times 10^5$ cells/ml were dispensed at 50 µl/well in a 96-well U-shaped bottom microplate. Thereto was added 50 µl of M30 or an isotype control antibody (mIgG2a) (eBioscience Company) diluted with the ADCC medium so that the final concentration of the antibody after adding the effector cells was 2.5 µg/ml. Then, the plate was left to stand at 4° C. for 1 hour. Thereafter, 100 µl of the effector cells at a cell density of $1.5 \times 10^7$ cells/ml were added thereto, and the cells were cultured overnight under the conditions of 37° C. and 5% $CO_2$. On the next day, the supernatant was collected in a LumaPlate (manufactured by PerkinElmer, Inc.), and gamma radiation emitted therefrom was measured using a gamma counter. The percentage of cell lysis caused by the ADCC activity was calculated according to the following equation.

Percentage of cell lysis (%)=$(A-B)/(C-B) \times 100$

A: Radiation count from the sample well
B: Average spontaneous radiation emission count (from wells to which the antibody and the effector cells were not added) (n=3) The same procedure as that for the sample well was performed except that the ADCC medium was added in an amount of 50 µl at the time of adding the antibody and in an amount of 100 µl at the time of adding the effector cells.
C: Average maximum radiation emission count (from wells in which the target cells were dissolved with a surfactant) (n=3) The same procedure as that for the sample well was performed except that 50 µl of the ADCC medium was added at the time of adding the antibody and 100 µl of the ADCC medium containing 2% (v/v) Triton X-100 was added at the time of adding the effector cells.

Figure 3:
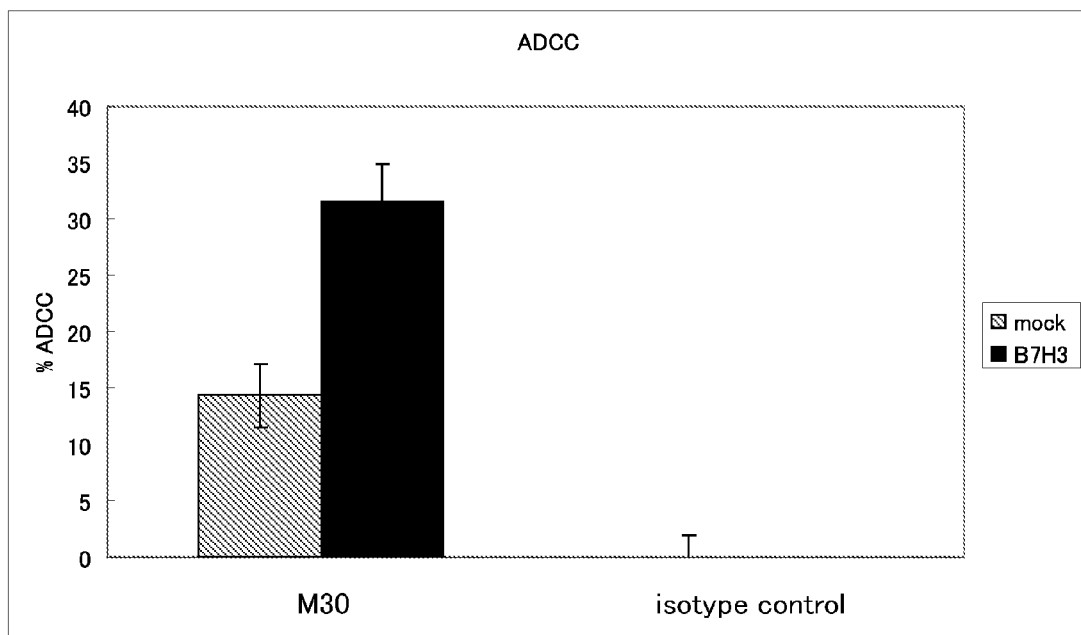
FIG. 3 is a graph showing the presence or absence of an ADCC activity of M30 antibody against empty vector-transfected 293 cells and B7-H3-expressing 293 cells. The error bars in the graph represent standard errors (n=3). In the drawing, the "mock" denotes the ADCC activity of M30 against empty vector-transfected 293 cells, and the "B7H3" denotes the ADCC activity of M30 against B7-H3-expressing 293 cells.

The data shown are an average of triplicate measurements, and the error bars represent standard deviations. The P value was calculated using Student's t-test. The measurement results are shown in FIG. 3.

As a result, the M30 exhibited a cell lysis activity with a percentage of cell lysis of 31.6±3.3% against the B7-H3-expressing 293 cells, and therefore, it was shown that the M30 antibody has an ADCC activity against the B7-H3-expressing 293 cells.

4)-3 CDC Activity

An experiment was performed in the same manner as in Example 2)-3. As the cells for use in the evaluation, NCI-H322 cells were used. Each of the anti-B7-H3 antibodies (L7, L8, L11, M30, and M31) obtained in Example 3)-6 and an isotype control antibody (mIgG2a) diluted with 10% FBS-containing RPMI 1640 (containing antibiotics: penicillin and streptomycin) so that the final concentration of the antibody after adding a complement was 25 µg/ml was added, and the resulting mixture was left to stand at 4° C. for 1 hour. Thereto was added a rabbit complement (manufactured by Cedarlane Laboratories, #CL3051) diluted to 30% with RPMI 1640 so that the final concentration of the complement was 5%, and the resulting mixture was incubated for 1 hour under the conditions of 37° C. and 5% $CO_2$. Then, the mixture was left to stand at room temperature for 30 minutes. In order to measure the cell viability, CellTiter-Glo Luminescent Cell Viability Assay (manufactured by Promega Corporation) was added thereto in an amount equal to that of the culture solution, and the resulting mixture was stirred at room temperature for 10 minutes. Thereafter, the amount of luminescence was measured using a plate reader. The cell viability was calculated according to the following equation.

Cell viability (%)=(a−b)/(c−b)×100 a: Amount of luminescence from the sample well.
b: Average amount of luminescence of background (from wells to which the cells and the antibody were not added) (n=3) The same procedure as that for the sample well was performed except that an equal amount of 10% FBS-containing RPMI 1640 (containing antibiotics: penicillin and streptomycin) was added in place of the cell suspension at the time of cell seeding and 10% FBS-containing RPMI 1640 (containing antibiotics: penicillin and streptomycin) was added in an amount equal to that of the antibody dilution solution at the time of adding the antibody.
c: Average amount of luminescence from wells to which the antibody was not added (n=3) The same procedure as that for the sample well was performed except that 10% FBS-containing RPMI 1640 (containing antibiotics: penicillin and streptomycin) was added in an amount equal to that of the antibody dilution solution at the time of adding the antibody.

Figure 4:
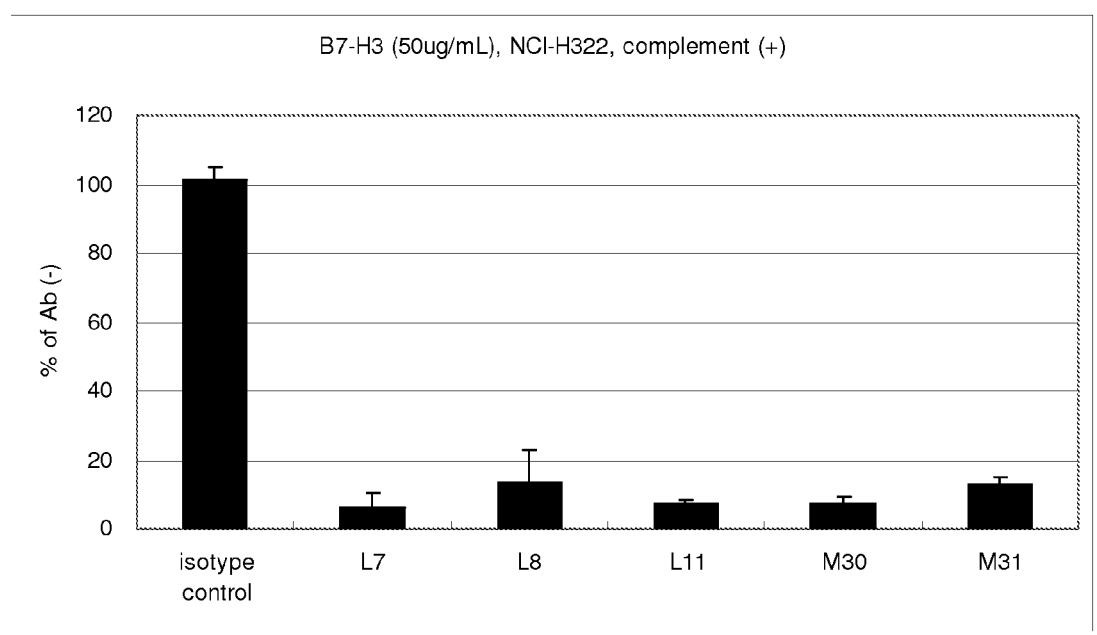
FIG. 4 is a graph showing the presence or absence of a CDC activity of an anti-B7-H3 antibody against NCI-H322 cells. The error bars in the graph represent standard errors (n=3).

The measurement results are shown in FIG. 4. The data shown are an average of triplicate measurements, and the error bars represent standard deviations. As a result, the control antibody, L7, L8, L11, M30, and M31 induced a decrease in cell viability of the NCI-H322 cells to 101.5±3.3%, 6.3±4.2%, 13.6±9.1%, 7.2±1.4%, 7.5±1.8%, and 12.8±2.0%, respectively, in the presence of the complement. Therefore, it was shown that the L7, L8, L11, M30, and M31 antibodies have a CDC activity against the NCI-H322 cells.

4)-4 Determination of Binding Domain

It was examined as to which domain of B7-H3 the M30 binds by a flow cytometric method in the same manner as in Example 3)-3. The NIH-3T3 cells transfected with each of the expression vectors for B7-H3 partial proteins prepared in Example 1)-1-3 were used.

As a result, as shown in FIG. 5, it was confirmed that the M30 binds to B7-H3 IgC1, B7-H3 IgC2, B7-H3 IgC1-V2-C2, and B7-H3 IgV2-C2. The M30 did not bind to B7-H3 IgV1 and B7-H3 IgV2.

From these results, it was shown that the M30 binds to the C1 domain (an amino acid sequence represented by amino acid numbers 140 to 244 in SEQ ID NO: 6) and the C2 domain (an amino acid sequence represented by amino acid numbers 358 to 456 in SEQ ID NO: 6) of B7-H3. In the same manner, it was shown that also the L8, L11, and M31 bind to the C1 domain and the C2 domain, and the L7 binds to the V1 domain (an amino acid sequence represented by amino acid numbers 27 to 139 in SEQ ID NO: 6) and the V2 domain (an amino acid sequence represented by amino acid numbers 245 to 357 in SEQ ID NO: 6).

Accordingly, it was shown that the M30 recognizes an epitope in the IgC1 domain and/or the IgC2 domain, each of which is a domain in the B7-H3 extracellular domain, and binds to the IgC1 domain or the IgC2 domain or both.

4)-5 Antigen Specificity

The antigen specificity of the M30 was examined by a flow cytometric method in the same manner as in Example 3)-3.

293T cells transfected with each of the expression vectors for the CD80, CD86, B7-RP-1, B7-H1, B7-DC, and B7-H4 proteins, which are B7 family proteins, prepared in Example 1)-1-4 were used.

As a result, it was shown that the M30 does not bind to the CD80, CD86, B7-RP-1, B7-H1, B7-DC, and B7-H4, which are B7 family molecules.

Example 5

In Vivo Antitumor Effect

5)-1 In Vivo Antitumor Effect of Anti-B7-H3 Antibody

NCI-H322 cells were detached from a culture flask by a trypsin treatment, and then suspended in 10% FBS-containing RPMI 1640 (Invitrogen Corporation), followed by centrifugation, and the supernatant was removed. The cells were washed twice with the same medium, and then suspended in physiological saline (manufactured by Otsuka Pharmaceutical Co., Ltd.). Then, the cells were implanted subcutaneously in the axillary region of each BALB/cAJcl-nu/nu (CLEA Japan, Inc.) mouse at 6 weeks of age at a dose of $1\times10^7$ cells/mouse. The day of implantation was taken as day 0, and on days 10, 17, 24, 31, and 38, each of the L7, L8, L11, M30, and M31 antibodies was intraperitoneally administrated at a dose of 500 µg/mouse (about 25 mg/kg). To the control, PBS was intraperitoneally administrated in a volume (500 µl) equal to that of the antibody. The tumor volume was measured on days 10, 17, 24, 31, 38, and 45, and the antitumor effect of the administration of the antibody was examined.

Figure 6:
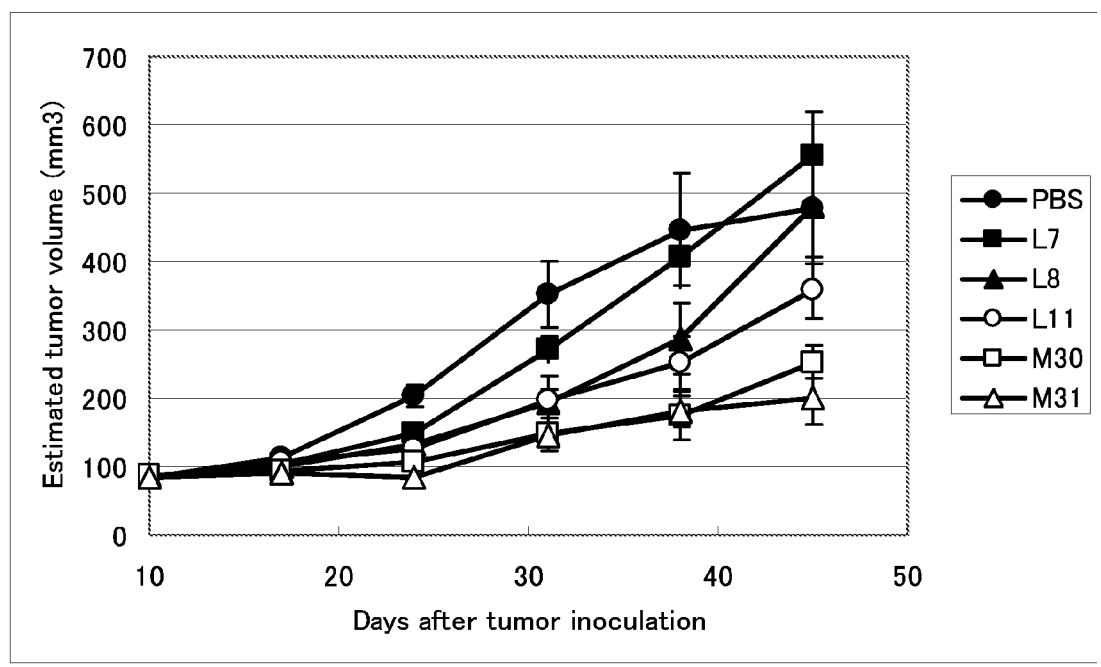

As a result, in the M30 and M31 administration groups, the tumor growth was significantly suppressed as compared with the PBS administration group (The P values for the M30 and M31 compared with the PBS administration group in terms of the tumor volume on day 45 were P<0.05 and P<0.01, respectively. The P values were calculated using Student's t-test.). Further, the tumor growth inhibition ratio (=100−(average tumor volume in antibody administration group)/(average tumor volume in PBS administration group)×100) on day 45 in the case of the L7, L8, L11, M30, and M31 was −16.1%, 0.2%, 25.5%, 47.2%, and 58.2%, respectively. Accordingly, the M30 and M31 antibodies were observed to have a very strong antitumor effect in vivo (FIG. 6).

From the above results, it was revealed that the M30 and M31 antibodies are antibodies which recognize a B7-H3 antigen and exhibit an antitumor effect.

5)-2 In Vivo Antitumor Effect Under Conditions of Depletion of Macrophages

In order to deplete macrophages in vivo, clodronate-encapsulated liposomes were produced. It has been reported that by administrating clodronate-encapsulated liposomes in vivo, macrophages in vivo are depleted (Journal of immunological methods 1994, vol. 174, pp. 83-93). According to the method in this report, clodronate-encapsulated liposomes were produced and used in the following experiment.

NCI-H322 cells were detached from a culture flask by a trypsin treatment, and then suspended in 10% FBS-containing RPMI 1640 (Invitrogen Corporation), followed by centrifugation and the supernatant was removed. The cells were washed twice with the same medium, and then suspended in physiological saline (PBS, manufactured by Otsuka Pharmaceutical Co., Ltd.). Then, the cells were implanted subcutaneously in the axillary region of each BALB/cAJcl-nu/nu (CLEA Japan, Inc.) mouse at 6 weeks of age at a dose of $1\times10^7$ cells/mouse. The day of implantation was taken as day −14, and grouping was performed on day 0.

In a group in which the macrophages in vivo in the mice were depleted, the clodronate-encapsulated liposomes were intravenously injected at a dose of 0.2 mL/mouse on days 0, 4, 7, 11, 14, 18, 21, 25, 28, and 32. Further, in the negative control group, PBS was intravenously injected at a dose of 0.2 mL/mouse on the same days (on days 0, 4, 7, 11, 14, 18, 21, 25, 28, and 32).

Subsequently, the M30 antibody was intraperitoneally administrated to both groups at a dose of 500 µg/mouse (about 25 mg/kg) on days 1, 8, 15, 22, and 29. Further, as the negative control, PBS was intraperitoneally administrated to both groups in a volume (500 µl) equal to that of the M30 antibody on the same days (on days 1, 8, 15, 22, and 29).

The tumor volume was measured on days 0, 8, 15, 22, 29, and 36, and the antitumor effect of the administration of the antibody was examined (n=8).

Figure 7:
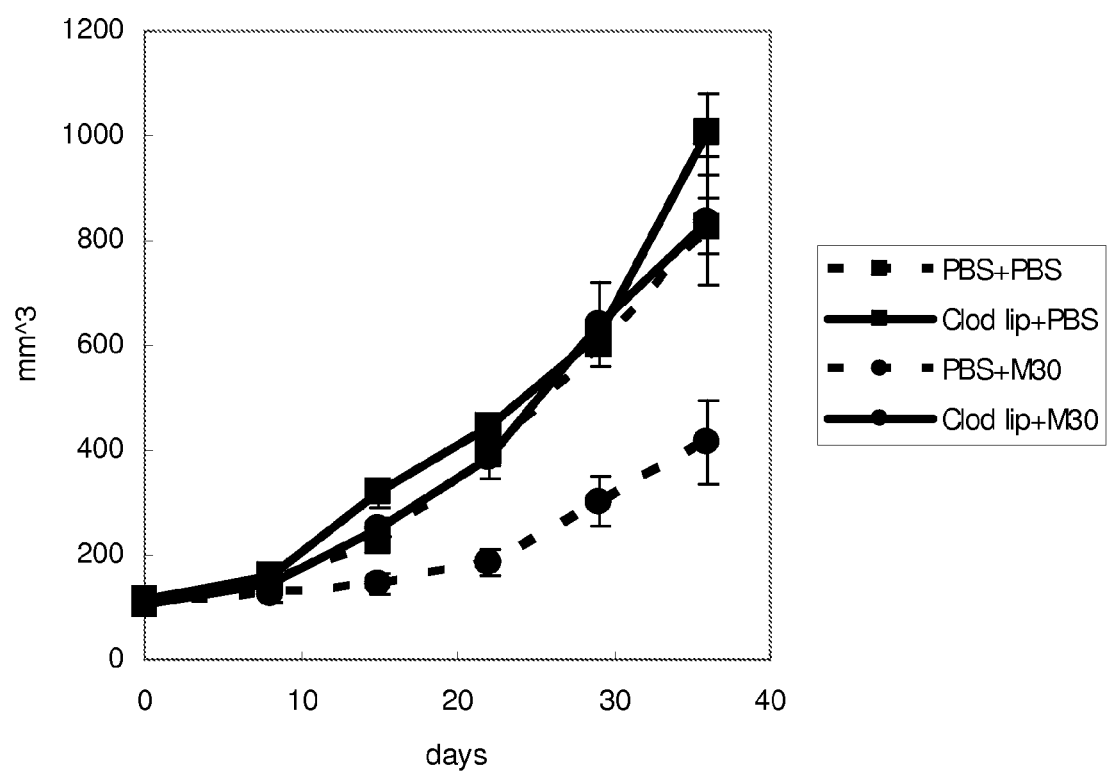
FIG. 7 is a graph showing the antitumor activity of M30 antibody when macrophages were depleted in vivo. The error bars in the graph represent standard errors (n=8). Further, the "mm^3" denotes "$mm^3$".

The results are shown in Tables 1 and 2, and FIG. 7.

TABLE 1

| Tumor volume | On day 0 | | On day 8 | | On day 15 | |
|---|---|---|---|---|---|---|
| | Average ($mm^3$) | Standard deviation | Average ($mm^3$) | Standard deviation | Average ($mm^3$) | Standard deviation |
| PBS + PBS administration group | 104.375 | 6.491581086 | 149 | 10.60828517 | 227.5 | 18.20027472 |
| Clod lip + PBS administration group | 114.625 | 4.862162585 | 159.375 | 7.676349346 | 318.625 | 26.37567704 |
| PBS + M30 administration group | 103.5 | 7.221001118 | 123.625 | 14.89958952 | 145 | 19.58497967 |
| Clod lip + M30 administration group | 104.625 | 5.47049717 | 143.375 | 10.46753058 | 247.75 | 24.44947414 |

| Tumor volume | On day 22 | | On day 29 | | On day 36 | |
|---|---|---|---|---|---|---|
| | Average ($mm^3$) | Standard deviation | Average ($mm^3$) | Standard deviation | Average ($mm^3$) | Standard deviation |
| PBS + PBS administration group | 394.75 | 25.77772433 | 601.25 | 43.17065389 | 827 | 50.82638516 |
| Clod lip + PBS administration group | 443.625 | 23.52653327 | 619.75 | 40.9550058 | 1002.75 | 78.18493415 |
| PBS + M30 administration group | 186.25 | 25.920035 | 301.75 | 47.13610612 | 415.25 | 79.84175197 |
| Clod lip + M30 administration group | 384.25 | 40.10644319 | 641.375 | 80.12176838 | 837.25 | 121.349223 |

In the group of PBS intravenous administration+M30 antibody intraperitoneal administration (PBS+M30 administration group), the tumor growth was significantly suppressed as compared with the group of PBS intravenous administration+PBS intraperitoneal administration (PBS+PBS administration group) serving as the negative control. To be more specific, the P value for the PBS+M30 administration group compared with the PBS+PBS administration group in terms of the tumor volume on day 36 was P<0.05 (The P value was calculated using Student's t-test.). Further, the tumor growth inhibition ratio (=100−(average tumor volume in PBS+M30 administration group)/(average tumor volume in PBS+PBS administration group)×100) on day 36 was 49.8% (Table 2).

On the other hand, in the group of clodronate-encapsulated liposome intravenous administration+PBS intraperitoneal administration (Clod lip+PBS administration group) and the group of clodronate-encapsulated liposome intravenous administration+M30 antibody intraperitoneal administration (Clod lip+M30 administration group), the suppression of tumor growth was not observed. To be more specific, the P values for the Clod lip+PBS administration group and the Clod lip+M30 administration group compared with the PBS+PBS administration group in terms of the tumor volume on day 36 were P=0.52 and P=1, respectively (The P values were calculated using Student's t-test.). Further, the tumor growth inhibition ratio (=100−(average tumor volume in Clod lip+PBS administration group or Clod lip+M30 administration group)/(average tumor volume in PBS+PBS administration group)×100) on day 36 was −21.2% and −1.4%, respectively (Table 2).

TABLE 2

| | Tumor growth inhibition ratio (%) | | | | |
|---|---|---|---|---|---|
| | On day 8 | On day 15 | On day 22 | On day 29 | On day 36 |
| Clod lip + PBS administration group | −6.6 | −39.4 | −12.6 | −3.5 | −21.2 |
| PBS + M30 administration group | 17.5 | 36.4 | 52.8 | 49.7 | 49.8 |
| Clod lip + M30 administration group | 3.2 | −8.6 | 2.6 | −6.6 | −1.4 |

From the above results, it was shown that the antitumor effect of the M30 antibody was suppressed by administering the clodronate-encapsulated liposomes, and therefore, it was revealed that the antitumor effect of the M30 antibody is mainly an effect mediated by macrophages.

Example 6

Cloning of Mouse Antibody M30 cDNA and Determination of Sequence

6)-1 Determination of N-Terminal Amino Acid Sequences of Heavy and Light Chains of Mouse Antibody M30

In order to determine the N-terminal amino acid sequences of the heavy and light chains of the mouse antibody M30, the mouse antibody M30 purified in Example 3)-6 was separated by SDS-PAGE. The protein in the gel was transferred from the gel after separation to a PVDF membrane (pore size: 0.45 μm, manufactured by Invitrogen Corporation). The membrane was washed with a washing buffer (25 mM NaCl, 10 mM sodium borate buffer pH 8.0), and thereafter stained by being immersed in a dye solution (50% methanol, 20% acetic acid, 0.05% Coomassie brilliant blue) for 5 minutes, followed by destaining with 90% methanol. The portions of the band corresponding to the heavy chain (the band with smaller mobility) and the band corresponding to the light chain (the band with larger mobility) visualized on the PVDF membrane were excised.

The portion of the band corresponding to the light chain was incubated at 37° C. for 30 minutes in a small amount of a 0.5% polyvinylpyrrolidone/100 mM acetic acid solution, followed by washing well with water. Subsequently, modified N-terminal residue was removed using Pfu Pyroglutamate Aminopeptidase Kit (TaKaRa Bio, Inc.), followed by washing with water and air drying. Then, an attempt was made to identify their respective N-terminal amino acid sequences by an automatic Edman method (see Edman et al. (1967) Eur. J. Biochem. 1, 80) using Procise (registered trademark) cLC Protein Sequencer Model 492cLC (Applied Biosystems, Inc.).

As a result, the N-terminal amino acid sequence of the band corresponding to the heavy chain of the mouse antibody M30 was EVQLQQSGPE (SEQ ID NO: 44 in the Sequence Listing), and the N-terminal amino acid sequence of the band corresponding to the light chain thereof was IVLSQSPTILSASP (SEQ ID NO: 45 in the Sequence Listing).

6)-2 Preparation of mRNA from Mouse Antibody M30-Producing Hybridoma

In order to clone cDNAs encoding each of the heavy chain and the light chain of the mouse antibody M30, mRNA was prepared from the mouse antibody M30-producing hybridoma using Quick Prep mRNA Purification Kit (GE Healthcare Corporation).

6)-3 Cloning of Mouse Antibody M30 cDNA and Determination of Sequence

With reference to the findings that the isotypes of the heavy and light chains of the mouse antibody M30 are γ2a and κ found in Example 3)-5, and the N-terminal amino acid sequences of the heavy and light chains determined in Example 1-1), and the database of the amino acid sequences of antibodies (see Kabat, E. A. et al., (1991) in Sequences of Proteins of Immunological Interest Vol. I and II, U.S. Department of Health and Human Services), several oligonucleotide primers hybridizing to each of the 5'-terminal region of an antibody gene coding region and the 3'-terminal region thereof comprising a stop codon were synthesized, and a cDNA encoding the heavy chain and a cDNA encoding the light chain were amplified using the mRNA prepared in Example 6-2) and TaKaRa One Step RNA PCR Kit (AMV) (TaKaRa Bio, Inc.). As a result, the cDNA encoding the heavy chain of the antibody and the cDNA encoding the light chain of the antibody could be amplified by the following primer sets.

```
Primer set for the heavy chain
Primer 16
5'-aagaattcatggaatggagttggata-3' (SEQ ID NO: 46
in the Sequence Listing)

Primer 17
5'-aagatatctcatttacccggagtccgggagaa-3' (SEQ ID
NO: 47 in the Sequence Listing)

Primer set for the light chain
Primer 18
5'-aagaattcatggattttctggtgcag-3' (SEQ ID NO:
48 in the Sequence Listing)

Primer 19
5'-aagatatcttaacactcattcctgttgaagct-3' (SEQ ID
NO: 49 in the Sequence Listing)
```

Each of the cDNA encoding the heavy chain and the cDNA encoding the light chain amplified by PCR was cloned using pEF6/V5-His TOPO TA Expression Kit (Invitrogen Corporation), and each of the nucleotide sequences of the heavy chain and the light chain cloned was determined using a gene sequence analyzer ("ABI PRISM 3700 DNA Analyzer; Applied Biosystems" or "Applied Biosystems 3730xl Analyzer; Applied Biosystems"). In the sequencing reaction, GeneAmp 9700 (Applied Biosystems, Inc.) was used.

The determined nucleotide sequence of the cDNA encoding the heavy chain of the mouse antibody M30 is represented by SEQ ID NO: 50 in the Sequence Listing, and the amino acid sequence thereof is represented by SEQ ID NO: 51. Further, the sequences of SEQ ID NOS: 50 and 51 are shown in FIG. 21.

The determined nucleotide sequence of the cDNA encoding the light chain of the mouse antibody M30 is represented by SEQ ID NO: 52 in the Sequence Listing, and the amino acid sequence thereof is represented by SEQ ID NO: 53 in the Sequence Listing. The sequences of SEQ ID NOS: 52 and 53 are shown in FIG. 22.

Further, the amino acid sequences of the heavy chain and the light chain were analyzed by comparison using KabatMan (see PROTEINS: Structure, Function and Genetics, 25 (1996), 130-133), which is the database of the amino acid sequences of antibodies. As a result, it was found that in the heavy chain of the mouse antibody M30, an amino acid sequence represented by amino acid numbers 20 to 141 in SEQ ID NO: 51 in the Sequence Listing is a variable region. It was also found that in the light chain of the mouse antibody M30, an amino acid sequence represented by amino acid numbers 23 to 130 in SEQ ID NO: 53 in the Sequence Listing is a variable region.

Example 7

Production of Chimeric Antibody M30 (cM30 Antibody)

7)-1 Construction of Chimeric and Humanized Light Chain Expression Vector pEF6KCL By performing PCR using a plasmid pEF6/V5-HisB (Invitrogen Corporation) as a template and also using the following primers, a DNA fragment from immediately downstream of BGHpA (Sequence Position: 2174) to SmaI (Sequence Position: 2958) (a DNA fragment comprising f1 origin of replication and SV40 promoter and origin, hereinafter referred to as "fragment A") was obtained.

```
Primer 20
5'-ccacgcgccctgtagcggcgcattaagc-3' (SEQ ID NO:
54 in the Sequence Listing)

Primer 21
5'-aaacccgggagcttttttgcaaaagcctagg-3' (SEQ ID NO:
55 in the Sequence Listing)
```

The obtained fragment A and a DNA fragment (SEQ ID NO: 56, hereinafter referred to as "fragment B", the sequence of SEQ ID NO: 56 is also shown in FIG. 23) comprising a DNA sequence encoding a human κ chain secretory signal, a human κ chain constant region, and a human poly-A additional signal were ligated to each other by overlap extension PCR. The thus obtained DNA fragment in which the fragment A and the fragment B were ligated to each other was digested with the restriction enzymes KpnI and SmaI, which was ligated to a plasmid pEF6/V5-HisB (Invitrogen Corporation) which was digested with the restriction enzymes KpnI and SmaI, whereby a chimeric and humanized light chain expression vector pEF6KCL having a signal sequence, a cloning site, a human κ chain constant region, and a human poly-A additional signal sequence downstream of the EF1 promoter was constructed.

7)-2 Construction of pEF1KCL

A DNA fragment obtained by cleaving the pEF6KCL obtained by the above-described method with the restriction enzymes KpnI and SmaI was ligated to pEF1/myc-HisB (Invitrogen Corporation) which was digested with KpnI and SmaI, whereby a plasmid pEF1KCL was constructed.

7)-3 Construction of Chimeric and Humanized Heavy Chain Expression Vector pEF1FCCU A DNA fragment (SEQ ID NO: 57, the sequence of SEQ ID NO: 57 is also shown in FIG. 24) comprising a DNA sequence encoding amino acids of a signal sequence and a constant region of human IgG1 was digested with the restriction enzymes NheI and PmeI and was ligated to the plasmid pEF1KCL which was digested with NheI and PmeI, whereby a chimeric and humanized heavy chain expression vector pEF1FCCU having a signal sequence, a cloning site, a human heavy chain constant region, and a human poly-A additional signal sequence downstream of the EF1 promoter was constructed.

7)-4 Construction of M30 Chimera-Type Light Chain Expression Vector

By using the cDNA encoding the light chain of the mouse antibody M30 as a template and also using KOD-Plus- (TOYOBO, Co., Ltd.) and the following primer set, a region comprising the cDNA encoding the light chain variable region was amplified. A DNA fragment obtained by cleaving the amplified product with the restriction enzymes NdeI and BsiWI was inserted into the universal chimeric and humanized antibody light chain expression vector (pEF6KCL) at the site cleaved with the restriction enzymes NdeI and BsiWI, whereby an M30 chimera-type light chain expression vector was constructed. The thus obtained expression vector was named "pEF6KCL/M30L". The nucleotide sequence of the M30 chimera-type light chain is represented by SEQ ID NO: 58 in the Sequence Listing, and the amino acid sequence thereof is represented by SEQ ID NO: 59. The sequences of SEQ ID NOS: 58 and 59 are shown in FIG. 25. A threonine residue at position 128 in the amino acid sequence of the cM30 antibody light chain represented by SEQ ID NO: 59 in the Sequence Listing is located in the carboxyl terminus of the light chain variable region and corresponds to an alanine residue at position 130 in the amino acid sequence of the M30 antibody light chain represented by SEQ ID NO: 53 in the Sequence Listing, however, in the amino acid sequence represented by SEQ ID NO: 59, the residue has already been substituted with a threonine residue derived from a human antibody light chain.

```
Primer set for the light chain
Primer 22
5'-aaacatatggcaaattgttctctcccagtctccaacaatcc-3'
(SEQ ID NO: 60 in the Sequence Listing)

Primer 23
5'-aaacgtacgtttcagctccagcttggtcccagtaccg-3' (SEQ
ID NO: 61 in the Sequence Listing)
```

7)-5 Construction of M30 Chimera-Type Heavy Chain Expression Vector

By using the cDNA encoding the heavy chain of the mouse antibody M30 as a template, a DNA fragment obtained by performing PCR using KOD-Plus-(TOYOBO, Co., Ltd.) and the following primer set A was ligated to a DNA fragment obtained by performing PCR using the following primer set B through overlap extension PCR using the following primer set C, whereby the BlpI in the variable region was removed and also a region comprising the cDNA encoding the heavy chain variable region was amplified. A DNA fragment obtained by cleaving the amplified product with the restriction enzyme BlpI was inserted into the universal chimeric and humanized antibody heavy chain expression vector (pEF1FCCU) at the site cleaved with the restriction enzyme BlpI, whereby an M30 chimera-type heavy chain expression vector was constructed. The thus obtained expression vector was named "pEF1FCCU/M30H".

The nucleotide sequence of the M30 chimera-type heavy chain is represented by SEQ ID NO: 62 in the Sequence Listing, and the amino acid sequence thereof is represented by SEQ ID NO: 63. Further, the sequences of SEQ ID NOS: 62 and 63 are shown in FIG. 26.

```
Primer set A
Primer 24
5'-aaagctgagcgaggtccagctgcagcagtctggacctgag-3'
(SEQ ID NO: 64 in the Sequence Listing)

Primer 25
5'-gaggtcaggctgctgagttccatgtaggctgtgctg-3' (SEQ
ID NO: 65 in the Sequence Listing)

Primer set B
Primer 26
5'-cagcacagcctacatggaactcagcagcctgacctc-3' (SEQ
ID NO: 66 in the Sequence Listing)

Primer 27
5'-aaagctgagctgactgtgagagtggtgccttggcccag-3'
(SEQ ID NO: 67 in the Sequence Listing)

Primer set C
Primer 28
5'-aaagctgagcgaggtccagctgcagcagtctggacctgag-3'
(SEQ ID NO: 68 in the Sequence Listing)

Primer 29
5'-aaagctgagctgactgtgagagtggtgccttggcccag-3'
(SEQ ID NO: 69 in the Sequence Listing)
```

7)-6 Preparation of Chimeric Antibody M30

7)-6-1 Production of Chimeric Antibody M30

$1.2 \times 10^9$ cells of FreeStyle 293F cells (Invitrogen Corporation) in the logarithmic growth phase were seeded into 1.2 L of fresh FreeStyle 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro SFM medium (Invitrogen Corporation). Subsequently, pEF1FCCU/M30H (0.4 mg) and pEF6KCL/M30L (0.8 mg) prepared with PureLink HiPure Plasmid Kit (Invitrogen Corporation) were suspended in 20 ml of Opti-Pro SFM medium. Then, 20 ml of the obtained expression vectors/Opti-Pro SFM mixed liquid was added to 20 ml of the obtained polyethyleneimine/Opti-Pro SFM mixed liquid, and the resulting mixture was gently stirred and then left for 5 minutes. Thereafter, the mixture was added to the FreeStyle 293F cells, and shaking culture at 90 rpm was performed for 7 days at 37° C. in an 8% $CO_2$ incubator. The resulting culture supernatant was filtered through a disposable capsule filter (Advantec #CCS-045-E1H).

A chimeric antibody M30 obtained by a combination of pEF1FCCU/M30H and pEF6KCL/M30L was named "cM30" or "cM30 antibody".

7)-6-2 Purification of cM30

The culture supernatant obtained in Example 7)-6-1 was purified by a two-step process including rProtein A affinity chromatography (at 4 to 6° C.) (GE Healthcare Japan Corporation) and ceramic hydroxyapatite (at room temperature). A buffer exchange step after the purification by rProtein A affinity chromatography and after the purification by ceramic hydroxyapatite was performed at room temperature. First, 1100 to 1200 ml of the culture supernatant was applied to MabSelect SuRe (manufactured by GE Healthcare Bio-Sciences Corporation, two HiTrap columns (volume: 1 ml) connected in series) equilibrated with PBS. After all culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Corporation, two HiTrap desalting columns (volume: 5 ml) connected in series), whereby the buffer was exchanged with a buffer containing 5 mM sodium phosphate, 50 mM MES, and 20 mM NaCl at pH 6.5.

Further, the antibody solution subjected to buffer exchange was applied to a ceramic hydroxyapatite column (Japan Bio-Rad Laboratories, Inc., Bio-Scale CHT2-1 hydroxyapatite column (volume: 2 ml)) equilibrated with a buffer containing 5 mM *NaPi*, 50 mM MES, and 20 mM NaCl at pH 6.5. Then, linear concentration gradient elution with sodium chloride was performed, and a fraction containing the antibody was collected. The fraction was applied to a desalting column (manufactured by GE Healthcare Bio-Sciences Corporation, two HiTrap® Desalting columns (volume: 5 ml) connected in series), whereby the liquid was exchanged with CBS (containing 10 mM citrate buffer and 140 mM sodium chloride, pH 6.0).

Finally, the resulting solution was concentrated using Centrifugal UF Filter Device VIVASPIN® 20 (fractional molecular weight: 30 K, Sartorius Co., Ltd., at 4° C.), and the concentration of IgG was adjusted to 1.0 mg/ml or more, and the thus obtained solution was used as a purified sample.

Example 8

Activity of cM30 Antibody

8)-1 Binding Activity of cM30 Antibody to B7-H3

The affinity between the M30 antibody or the cM30 antibody and the B7-H3 antigen was measured by a surface plasmon resonance (SPR) device (GE Healthcare Corporation). According to a common procedure, an anti-mouse IgG or an anti-human IgG antibody was immobilized on a sensor chip, and then, the M30 antibody sample or the cM30 antibody was bound thereto. Thereafter, an extracellular domain polypeptide of a recombinant B7-H3 variant 2 antigen (manufactured by R&D Systems, Inc., #2318-B3-050/CF) was added thereto at different concentrations, and the amount of the antigen bound to the antibody in a running buffer (phosphate buffer, 0.05% SP20) was measured over time. The measured amount was analyzed with a dedicated software (BIAevaluation Version 4.1, GE Healthcare Corporation) and a dissociation constant was calculated.

As a result, the M30 antibody and the cM30 antibody bound to the recombinant B7-H3 antigen with a dissociation constant of 5.89 nM and 3.43 nM, respectively. From these results, it was confirmed that the M30 antibody and the cM30 antibody bind to the B7-H3 antigen and their binding affinities were substantially equal.

8)-2 ADCP Activity of cM30 Antibody

Peripheral blood mononuclear cells (PBMCs) of a healthy subject were isolated according to common procedures and suspended in 10% FBS-containing RPMI 1640 (Invitrogen Corporation) and then seeded in a flask. The cells were cultured overnight in a $CO_2$ incubator. The culture supernatant was removed, and to the cells attached to the flask, 10% FBS-containing RPMI 1640 supplemented with M-CSF and GM-CSF (PeproTech, Inc.) was added, and the cells were cultured for 2 weeks. The cells were detached with TrypLE and collected. Then, the cells were added to a 24-well plate at 500 μl/well ($1×10^5$ cells/well) and cultured overnight at 37° C. The thus prepared cells were used as effector cells.

The labeling of NCI-H322 cells to be used as target cells was performed using PKH26 dye labeling kit (Sigma Co., Ltd.) The target cells were detached with TrypLE and washed twice with PBS. The cells were suspended in Diluent C at $1×10^7$ cells/ml. PKH26 dye stock (1 mM) was diluted to 8 μM with Diluent C, and immediately thereafter, the diluted dye solution was added thereto in an amount equal to that of the cell suspension. The resulting mixture was left at room temperature for 5 minutes. Then, 1 ml of serum was added thereto, and further, a medium with serum was added thereto, and washing was performed twice.

Each of the M30 antibody and the cM30 antibody was diluted to 20 μg/ml with a culture solution. Subsequently, the target cells were dispensed at $2×10^6$ cells/100 μl/tube and mixed. The resulting mixture was left to stand on ice for 30 minutes. The supernatant was removed, and the cells were washed twice with a culture solution and suspended in 500 μl of a culture solution. The supernatant was removed from the effector cells, and the cells having been treated with the antibody and suspended in the culture solution were added thereto and mixed therewith. Then, the cells were cultured for 3 hours in a $CO_2$ incubator. Thereafter, the cells were detached with Trypsin-EDTA and collected. To the collected cells, an FITC-labeled anti-mouse CD11b antibody (Becton, Dickinson and Company, Ltd.) was added, and the resulting mixture was left to stand on ice for 30 minutes. The supernatant was removed, and the cells were washed twice with a culture solution. The collected cells were suspended in 300 μl of a culture medium and analyzed by FACS Calibur (Becton, Dickinson and Company, Ltd.). In the CD11b-positive macrophages, a PKH26-positive fraction was evaluated as phagocytosis-positive cells.

Figure 8:
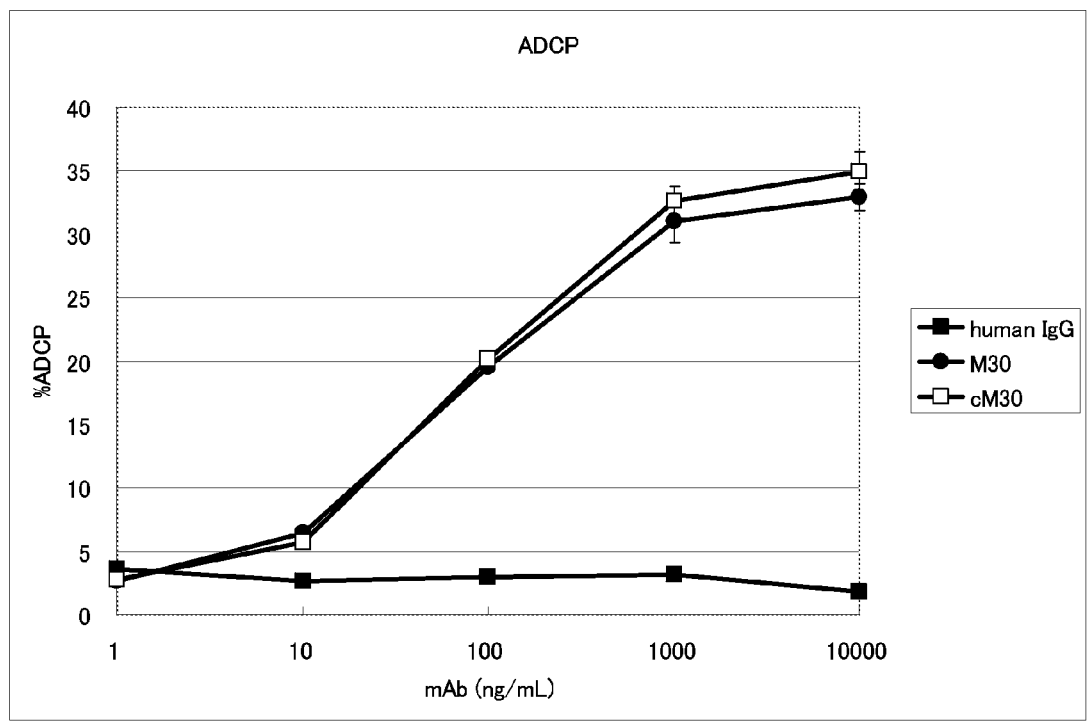
FIG. 8 is a graph showing the ADCP activities of M30 antibody and cM30 antibody against NCI-H322 cells. The error bars in the graph represent standard errors (n=4).

As a result, as shown in FIG. 8, when the M30 antibody and the cM30 antibody were added at 10 μg/ml, the phagocytosis of the NCI-H322 cells by macrophages was induced to 33±1% and 35±2%, respectively. Accordingly, it was shown that the cM30 antibody has an ADCP activity against the NCI-H322 cells in the same manner as the M30 antibody. A similar experimental result was obtained also for an ADCP activity against MDA-MB-231 cells (ATCC).

8)-3 In Vivo Antitumor Effect of cM30 Antibody

MDA-MB-231 cells were detached from a culture flask by a trypsin treatment, and then suspended in 10% FBS-containing RPMI 1640 medium (Invitrogen Corporation), followed by centrifugation and the supernatant was removed. The cells were washed twice with the same medium, and then suspended in BD Matrigel™ Basement Membrane Matrix (manufactured by BD Biosciences, Inc.). Then, the cells were implanted subcutaneously in the axillary region of each mouse (CB17/Icr-Prkdc[scid]/CrlCrlj, Charles River Laboratories Japan, Inc.) at 6 weeks of age at a dose of $5×10^6$ cells/mouse. The day of implantation was taken as day 0, and on days 14, 21, 28, 35, and 42, the M30 antibody or the cM30 antibody was intraperitoneally administered at a dose of 500 μg/mouse (about 25 mg/kg). The tumor volume was measured on days 14, 18, 21, 25, 28, 32, 35, 39, 42, 46, 49, and 52, and the antitumor effect of the administration of the antibody was examined.

As a result, in the M30 and cM30 antibody administration groups, the tumor growth was significantly suppressed as compared with the untreated group in which the antibody was not administered. The P values for the M30 antibody and the cM30 antibody compared with the untreated group in terms of the tumor weight on day 52 were both P<0.001. The P values were calculated using Dunnett's multiple comparison test.

Figure 9:
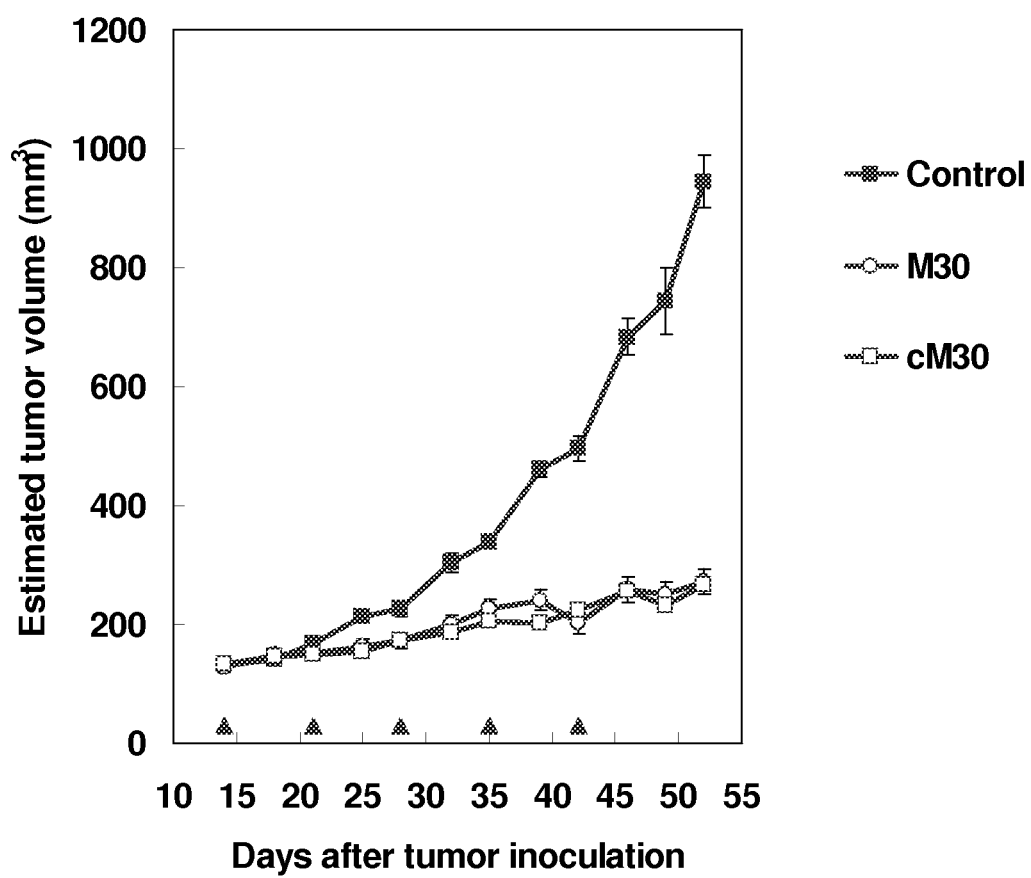
FIG. 9 is a graph showing the antitumor activities of M30 antibody and cM30 antibody against mice implanted with MDA-MB-231 cells. The error bars in the graph represent standard errors (n=9).

Further, the tumor growth inhibition ratio (=100−(average tumor volume in antibody administration group)/(average tumor volume in untreated group)×100) on day 52 was 71.3% in the case of the M30 antibody and 71.7% in the case of the cM30 antibody. Accordingly, the cM30 antibody was observed to have a very strong antitumor effect in vivo in the same manner as the M30 antibody (FIG. 9).

Example 9

Designing of Humanized Antibody of Mouse Anti-Human B7-H3 Antibody #M30

9)-1 Designing of Humanized M30 Antibody
9)-1-1 Molecular Modeling of M30 Variable Regions The molecular modeling of the M30 variable regions was performed according to a method generally known as homology modeling (Methods in Enzymology, 203, 121-153, (1991)). The primary sequences (three-dimensional structures derived from the X-ray crystal structures are available) of the variable regions of human immunoglobulin registered in Protein Data Bank (Nuc. Acid Res. 35, D301-D303 (2007)) were compared with the M30 variable regions determined in Example 6-3).

As a result, 3BKY was selected as a sequence having the highest sequence homology with the M30 light chain variable region among the antibodies which similarly have a deletion in the framework. Further, 3DGG was selected as a sequence having the highest sequence homology with the M30 heavy chain variable region.

The three-dimensional structure of a framework region was prepared based on a "framework model" by combining the coordinates of 3BKY corresponding to the M30 light chain with the coordinates of 3DGG corresponding to the M30 heavy chain. As for the M30 CDRs, as the coordinates defining the conformations most similar to those of CDRH1 (SEQ ID NO: 92), CDRH2 (SEQ ID NO: 93), CDRH3 (SEQ ID NO: 94), CDRL1 (SEQ ID NO: 95), CDRL2 (SEQ ID NO: 96), and CDRL3 (SEQ ID NO: 97) according to the classification of Thornton et al. (J. Mol. Biol., 263, 800-815, (1996)) and the H3 rules (FEBS letters 399, 1-8 (1996)), 2HOJ, 1BBD, 1Q90, 2FBJ, 1LNK, and 1TET were selected, respectively, and incorporated in the framework model.

Finally, in order to obtain a possible molecular model of the M30 variable region in terms of energy, an energy calculation was performed for excluding disadvantageous interatomic contact. The above procedure was carried out using commercially available protein tertiary structure prediction program Prime and coordinate search program MacroModel (Schrodinger, LLC).

9)-1-2 Designing of Amino Acid Sequence of Humanized M30

A humanized M30 antibody was constructed according to a method generally known as CDR grafting (Proc. Natl. Acad. Sci. USA 86, 10029-10033 (1989)).

An acceptor antibody was selected based on the amino acid homology within the framework region. The sequence of the framework region of M30 was compared with all human framework sequences in the Kabat Database (Nuc. Acid Res. 29, 205-206 (2001)) of antibody amino acid sequences. As a result, a mAb49'CL antibody (GenBank in NCBI: D16838.1 and D16837.1) was selected as an acceptor based on a sequence homology of 70% in the framework region.

The amino acid residues in the framework region of mAb49'CL were aligned with the amino acid residues of M30, and the positions where different amino acids were used were identified. The positions of these residues were analyzed using the three-dimensional model of M30 constructed above. Then, donor residues to be grafted onto the acceptor were selected according to the criteria provided by Queen et al. (Proc. Natl. Acad. Sci. USA 86, 10029-10033 (1989)). By transferring some selected donor residues to the acceptor antibody, humanized M30 antibody sequences were constructed as described in the following Example.

9)-2 Humanization of M30 Heavy Chain
9)-2-1 M30-H1-Type Heavy Chain:

A humanized M30 heavy chain designed by substituting amino acid numbers 20 (glutamic acid), 24 (glutamine), 28 (proline), 30 (leucine), 31 (valine), 35 (alanine), 39 (methionine), 57 (lysine), 59 (lysine), 67 (isoleucine), 86 (lysine), 87 (alanine), 89 (glutamine), 91 (serine), 93 (lysine), 95 (serine), 106 (threonine), 110 (serine), 136 (threonine), and 137 (leucine) of the cM30 heavy chain represented by SEQ ID NO: 63 in the Sequence Listing with glutamine, valine, alanine, valine, lysine, serine, valine, arginine, alanine, methionine, arginine, valine, isoleucine, alanine, glutamic acid, threonine, arginine, threonine, leucine, and valine, respectively, was named "M30-H1-type heavy chain".

The amino acid sequence of the M30-H1-type heavy chain is represented by SEQ ID NO: 85.

9)-2-2 M30-H2-Type Heavy Chain:

A humanized M30 heavy chain designed by substituting amino acid numbers 20 (glutamic acid), 24 (glutamine), 28 (proline), 30 (leucine), 31 (valine), 35 (alanine), 39 (methionine), 57 (lysine), 59 (lysine), 86 (lysine), 87 (alanine), 89 (glutamine), 91 (serine), 93 (lysine), 95 (serine), 106 (threonine), 110 (serine), 136 (threonine), and 137 (leucine) of the cM30 heavy chain represented by SEQ ID NO: 63 in the Sequence Listing with glutamine, valine, alanine, valine, lysine, serine, valine, arginine, alanine, arginine, valine, isoleucine, alanine, glutamic acid, threonine, arginine, threonine, leucine, and valine, respectively, was named "M30-H2-type heavy chain".

The amino acid sequence of the M30-H2-type heavy chain is represented by SEQ ID NO: 87.

9)-2-3 M30-H3-Type Heavy Chain:

A humanized M30 heavy chain designed by substituting amino acid numbers 24 (glutamine), 28 (proline), 30 (leucine), 31 (valine), 35 (alanine), 39 (methionine), 59 (lysine), 89 (glutamine), 91 (serine), 93 (lysine), 95 (serine), 106 (threonine), 110 (serine), 136 (threonine), and 137 (leucine) of the cM30 heavy chain represented by SEQ ID NO: 63 in the Sequence Listing with valine, alanine, valine, lysine, serine, valine, alanine, isoleucine, alanine, glutamic acid, threonine, arginine, threonine, leucine, and valine, respectively, was named "M30-H3-type heavy chain".

The amino acid sequence of the M30-H3-type heavy chain is represented by SEQ ID NO: 89.

9)-2-4 M30-H4-Type Heavy Chain:

A humanized M30 heavy chain designed by substituting amino acid numbers 24 (glutamine), 28 (proline), 30 (leucine), 31 (valine), 35 (alanine), 39 (methionine), 59 (lysine), 95 (serine), 106 (threonine), 110 (serine), 136 (threonine), and 137 (leucine) of the cM30 heavy chain represented by SEQ ID NO: 63 in the Sequence Listing with valine, alanine, valine, lysine, serine, valine, alanine, threonine, arginine, threonine, leucine, and valine, respectively, was named "M30-H4-type heavy chain".

The amino acid sequence of the M30-H4-type heavy chain is represented by SEQ ID NO: 91.

9)-3 Humanization of M30 Light Chain

9)-3-1 M30-L1-Type Light Chain:

A humanized M30 light chain designed by substituting amino acid numbers 21 (glutamine), 25 (serine), 29 (threonine), 30 (isoleucine), 33 (alanine), 38 (lysine), 39 (valine), 41 (methionine), 42 (threonine), 61 (serine), 62 (serine), 64 (lysine), 65 (proline), 66 (tryptophan), 77 (valine), 89 (serine), 90 (tyrosine), 91 (serine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with glutamic acid, threonine, alanine, threonine, leucine, arginine, alanine, leucine, serine, glutamine, alanine, arginine, leucine, leucine, isoleucine, aspartic acid, phenylalanine, threonine, leucine, proline, phenylalanine, valine, glutamine, valine, and isoleucine, respectively, was named "M30-L1-type light chain".

The amino acid sequence of the M30-L1-type light chain is represented by SEQ ID NO: 71.

9)-3-2 M30-L2-Type Light Chain:

A humanized M30 light chain designed by substituting amino acid numbers 21 (glutamine), 25 (serine), 29 (threonine), 30 (isoleucine), 33 (alanine), 38 (lysine), 39 (valine), 41 (methionine), 42 (threonine), 61 (serine), 62 (serine), 64 (lysine), 65 (proline), 77 (valine), 89 (serine), 91 (serine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with glutamic acid, threonine, alanine, threonine, leucine, arginine, alanine, leucine, serine, glutamine, alanine, arginine, leucine, isoleucine, aspartic acid, threonine, leucine, proline, phenylalanine, valine, glutamine, valine, and isoleucine, respectively, was named "M30-L2-type light chain".

The amino acid sequence of the M30-L2-type light chain is represented by SEQ ID NO: 73.

9)-3-3 M30-L3-Type Light Chain:

A humanized M30 light chain designed by substituting amino acid numbers 29 (threonine), 30 (isoleucine), 33 (alanine), 38 (lysine), 39 (valine), 41 (methionine), 62 (serine), 65 (proline), 77 (valine), 91 (serine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with alanine, threonine, leucine, arginine, alanine, leucine, alanine, leucine, isoleucine, threonine, leucine, proline, phenylalanine, valine, glutamine, valine, and isoleucine, respectively, was named "M30-L3-type light chain".

The amino acid sequence of the M30-L3-type light chain is represented by SEQ ID NO: 75.

9)-3-4 M30-L4-Type Light Chain:

A humanized M30 light chain designed by substituting amino acid numbers 21 (glutamine), 25 (serine), 29 (threonine), 30 (isoleucine), 33 (alanine), 38 (lysine), 39 (valine), 41 (methionine), 42 (threonine), 61 (serine), 62 (serine), 64 (lysine), 66 (tryptophan), 77 (valine), 89 (serine), 90 (tyrosine), 91 (serine), 96 (arginine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with glutamic acid, threonine, alanine, threonine, leucine, arginine, alanine, leucine, serine, glutamine, alanine, arginine, leucine, isoleucine, aspartic acid, phenylalanine, threonine, serine, leucine, proline, phenylalanine, valine, glutamine, valine, and isoleucine, respectively, was named "M30-L4-type light chain".

The amino acid sequence of the M30-L4-type light chain is represented by SEQ ID NO: 77.

9)-3-5 M30-L5-Type Light Chain:

A humanized M30 light chain designed by substituting amino acid numbers 29 (threonine), 30 (isoleucine), 33 (alanine), 38 (lysine), 39 (valine), 41 (methionine), 62 (serine), 77 (valine), 91 (serine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with alanine, threonine, leucine, arginine, alanine, leucine, alanine, isoleucine, threonine, leucine, proline, phenylalanine, valine, glutamine, valine, and isoleucine, respectively, was named "M30-L5-type light chain". The amino acid sequence of the M30-L5-type light chain is represented by SEQ ID NO: 79.

9)-3-6 M30-L6-Type Light Chain:

A humanized M30 light chain designed by substituting amino acid numbers 21 (glutamine), 25 (serine), 29 (threonine), 30 (isoleucine), 33 (alanine), 38 (lysine), 39 (valine), 41 (methionine), 42 (threonine), 61 (serine), 62 (serine), 64 (lysine), 66 (tryptophan), 77 (valine), 89 (serine), 90 (tyrosine), 91 (serine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with glutamic acid, threonine, alanine, threonine, leucine, arginine, alanine, leucine, serine, glutamine, alanine, arginine, leucine, isoleucine, aspartic acid, phenylalanine, threonine, leucine, proline, phenylalanine, valine, glutamine, valine, and isoleucine, respectively, was named "M30-L6-type light chain".

The amino acid sequence of the M30-L6-type light chain is represented by SEQ ID NO: 81.

9)-3-7 M30-L7-Type Light Chain:

A humanized M30 light chain designed by substituting amino acid numbers 21 (glutamine), 25 (serine), 29 (threonine), 30 (isoleucine), 33 (alanine), 38 (lysine), 39 (valine), 41 (methionine), 42 (threonine), 61 (serine), 62 (serine), 64 (lysine), 66 (tryptophan), 77 (valine), 89 (serine), 91 (serine), 97 (valine), 99 (alanine), 102 (alanine), 104 (threonine), 119 (threonine), 123 (leucine), and 125 (leucine) of the cM30 light chain represented by SEQ ID NO: 59 in the Sequence Listing with glutamic acid, threonine, alanine, threonine, leucine, arginine, alanine, leucine, serine, glutamine, alanine, arginine, leucine, isoleucine, aspartic acid, threonine, leucine, proline, phenylalanine, valine, glutamine, valine, and isoleucine, respectively, was named "M30-L7-type light chain".

The amino acid sequence of the M30-L7-type light chain is represented by SEQ ID NO: 83.

Example 10

Production of Humanized Antibody

10)-1 Construction of M30-L1, M30-L2, M30-L3, M30-L4, M30-L5, M30-L6, and M30-L7-Type Light Chain Expression Vectors DNAs comprising a gene encoding an M30-L1, M30-L2, M30-L3, M30-L4, M30-L5, M30-L6, or M30-L7-type light chain variable region represented by amino acid numbers 21 to 128 in SEQ ID NO: 71, amino acid numbers 21 to 128 in SEQ ID NO: 73, amino acid numbers 21 to 128 in SEQ ID NO: 75, amino acid numbers 21 to 128 in SEQ ID NO: 77, amino acid numbers 21 to 128 in SEQ ID NO: 79, amino acid numbers 21 to 128 in SEQ ID NO: 81, or amino acid numbers 21 to 128 in SEQ ID NO: 83 in the Sequence Listing were synthesized (GENEART, Inc. Artificial Gene Synthesis Service) based on SEQ ID NOS: 70, 72, 74, 76, 78, 80, and 82 according to the nucleotide sequences corresponding to the above SEQ ID NOS according to the amino acid sequences.

Then, each of the DNA fragments obtained by cleaving the synthesized DNAs with the restriction enzymes NdeI and BsiWI was inserted into the universal chimeric and humanized antibody light chain expression vector (pEF6KCL) at the site cleaved with the restriction enzymes NdeI and BsiWI, whereby M30-L1, M30-L2, M30-L3, M30-L4, M30-L5, M30-L6, and M30-L7-type light chain expression vectors were constructed.

The thus obtained expression vectors were named "pEF6KCL/M30-L1", "pEF6KCL/M30-L2", "pEF6KCL/M30-L3", "pEF6KCL/M30-L4", "pEF6KCL/M30-L5", "pEF6KCL/M30-L6", and "pEF6KCL/M30-L7", respectively.

10)-2 Construction of M30-H1, M30-H2, M30-H3, and M30-H4-Type Heavy Chain Expression Vectors DNAs comprising a gene encoding an M30-H1, M30-H2, M30-H3, or M30-H4-type heavy chain variable region represented by amino acid numbers 20 to 141 in SEQ ID NO: 85, amino acid numbers 20 to 141 in SEQ ID NO: 87, amino acid numbers 20 to 141 in SEQ ID NO: 89, or amino acid numbers 20 to 141 in SEQ ID NO: 91 in the Sequence Listing were synthesized (GENEART, Inc. Artificial Gene Synthesis Service) based on SEQ ID NO: 84, 86, 88, and 90 according to the nucleotide sequences corresponding to the above SEQ ID NOS according to the amino acid sequences. Then, each of the DNA fragments obtained by cleaving the synthesized DNAs with the restriction enzyme BlpI was inserted into the universal humanized antibody heavy chain expression vector (pEF1FCCU) at the site cleaved with the restriction enzyme BlpI, whereby M30-H1, M30-H2, M30-H3, and M30-H4-type heavy chain expression vectors were constructed.

The thus obtained expression vectors were named "pEF1FCCU/M30-H1", "pEF1FCCU/M30-H2", "pEF1FCCU/M30-H3", and "pEF1FCCU/M30-H4", respectively.

10)-3 Production of Humanized Antibody $1.2 \times 10^9$ cells of FreeStyle™ 293F cells (Invitrogen Corporation) in the logarithmic growth phase were seeded into 1.2 L of fresh FreeStyle 293 Expression Medium (Invitrogen Corporation) and cultured for 1 hour by shaking at 90 rpm at 37° C. in an 8% $CO_2$ incubator. 3.6 mg of polyethyleneimine (Polyscience #24765) was dissolved in 20 ml of Opti-Pro™ SFM medium (Invitrogen Corporation). Subsequently, a heavy chain expression vector (0.4 mg) and a light chain expression vector (0.8 mg) prepared with PureLink® HiPure Plasmid Kit (Invitrogen Corporation) were suspended in 20 ml of Opti-Pro SFM medium. Then, 20 ml of the obtained expression vectors/Opti-Pro SFM mixed liquid was added to 20 ml of the obtained polyethyleneimine/Opti-Pro SFM mixed liquid, and the resulting mixture was gently stirred and then left for 5 minutes. Thereafter, the mixture was added to the FreeStyle 293F cells, and shaking culture at 90 rpm was performed for 7 days at 37° C. in an 8% $CO_2$ incubator. The resulting culture supernatant was filtered through a disposable capsule filter (Advantec #CCS-045-E1H).

A humanized antibody of M30 obtained by a combination of pEF1FCCU/M30-H1 and pEF6KCL/M30-L1 was named "M30-H1-L1", a humanized antibody of M30 obtained by a combination of pEF1FCCU/M30-H1 and pEF6KCL/M30-L2 was named "M30-H1-L2", a humanized antibody of M30 obtained by a combination of pEF1FCCU/M30-H1 and pEF6KCL/M30-L3 was named "M30-H1-L3", a humanized antibody of M30 obtained by a combination of pEF1FCCU/M30-H1 and pEF6KCL/M30-L4 was named "M30-H1-L4", a humanized antibody of M30 obtained by a combination of pEF1FCCU/M30-H4 and pEF6KCL/M30-L1 was named "M30-H4-L1", a humanized antibody of M30 obtained by a combination of pEF1FCCU/M30-H4 and pEF6KCL/M30-L2 was named "M30-H4-L2", a humanized antibody of M30 obtained by a combination of pEF1FCCU/M30-H4 and pEF6KCL/M30-L3 was named "M30-H4-L3", a humanized antibody of M30 obtained by a combination of pEF1FCCU/M30-H4 and pEF6KCL/M30-L4 was named "M30-H4-L4", a humanized antibody of M30 obtained by a combination of pEF1FCCU/M30-H1 and pEF6KCL/M30-L5 was named "M30-H1-L5", a humanized antibody of M30 obtained by a combination of pEF1FCCU/M30-H1 and pEF6KCL/M30-L6 was named "M30-H1-L6", and a humanized antibody of M30 obtained by a combination of pEF1FCCU/M30-H1 and pEF6KCL/M30-L7 was named "M30-H1-L7".

10)-4 Purification of Humanized Antibody

The culture supernatant obtained in Example 10)-3 was purified by a two-step process including rProtein A affinity chromatography (at 4 to 6° C.) and ceramic hydroxyapatite (at room temperature). A buffer exchange step after the purification by rProtein A affinity chromatography and after the purification by ceramic hydroxyapatite was performed at room temperature.

First, 1100 to 1200 ml of the culture supernatant was applied to MabSelect™ SuRe (manufactured by GE Healthcare Bio-Sciences Co., Ltd., two HiTrap® columns (volume: 1 ml) connected in series) equilibrated with PBS. After all culture solution was poured into the column, the column was washed with 15 to 30 ml of PBS. Subsequently, elution was performed with a 2 M arginine hydrochloride solution (pH 4.0), and a fraction containing the antibody was collected. The fraction was applied to a desalting column (manufactured by GE Healthcare Bio-Sciences Co., Ltd., two HiTrap desalting columns (volume: 5 ml) connected in series), whereby the buffer was exchanged with a buffer containing 5 mM sodium phosphate, 50 mM MES, and 20 mM NaCl at pH 6.5.

Further, the antibody solution subjected to buffer exchange was applied to a ceramic hydroxyapatite column (Japan Bio-Rad Laboratories, Inc., Bio-Scale™ CHT™2-1 hydroxyapatite column (volume: 2 ml)) equilibrated with a buffer containing 5 mM *NaPi,* 50 mM MES, and 20 mM NaCl at pH 6.5. Then, linear concentration gradient elution with sodium chloride was performed, and a fraction containing the antibody was collected.

The fraction was applied to a desalting column (manufactured by GE Healthcare Bio-Sciences Co., Ltd., two HiTrap desalting columns (volume: 5 ml) connected in series), whereby the liquid was exchanged with CBS (containing 10 mM citrate buffer and 140 mM sodium chloride, pH 6.0).

Finally, the resulting solution was concentrated using Centrifugal UF Filter Device VIVASPIN 20 (fractional molecular weight: 30 K, Sartorius Co., Ltd., at 4° C.), and the concentration of IgG was adjusted to 1.0 mg/ml or more, and the thus obtained solution was used as a purified sample.

10)-5 Binding Property of Humanized Antibody to B7-H3 Antigen

The binding property of the humanized M30 antibody to human B7-H3 which is an antigen was measured by a surface plasmon resonance (SPR) device (Biacore, Inc.). According to a common procedure, an anti-human IgG antibody was immobilized on a sensor chip, and then, each of the purified samples of the humanized M30 antibodies obtained in the above 10)-4 was bound thereto. Thereafter, an extracellular domain polypeptide of the B7-H3 variant 2 antigen (manufactured by R&D Systems, Inc., #2318-B3-050/CF) was added thereto at different concentrations, and the amount of the antigen bound to the antibody in a running buffer (phosphate buffer, 0.05% SP20) was measured over time. The measured amount was analyzed with a dedicated software (BIAevaluation) and a dissociation constant (Kd [M]) was calculated. The measurement was performed using the cM30 antibody as a positive control for each measurement operation. The results are as shown in Table 3. All of the humanized M30 antibodies had a binding activity against the B7-H3 antigen.

TABLE 3

|         | Kd [M]  |
|---------|---------|
| M30-H1-L1 | 8.7E-08 |
| M30-H1-L2 | 1.0E-07 |
| M30-H1-L3 | 1.0E-07 |
| M30-H1-L4 | 1.6E-08 |
| M30-H4-L1 | 1.3E-07 |
| M30-H4-L2 | 1.4E-07 |
| M30-H4-L3 | 1.6E-07 |
| M30-H4-L4 | 1.2E-08 |
| M30-H1-L5 | 1.9E-09 |
| M30-H1-L6 | 3.4E-09 |
| M30-H1-L7 | 2.7E-09 |
| cM30    | 7.3E-10 |

Example 11

Measurement of Competitive Inhibitory Activities of cM30 Antibody and Humanized M30 Antibody Against M30 Antibody for the Binding to B7-H3 Antigen The competitive inhibitory activities of the cM30 antibody and the humanized M30 antibody (M30-H1-L4 antibody) against the M30 antibody for the binding to the B7-H3 variant 1 and variant 2 were measured by the following method.

By using EZ-Link® Sulfo-NHS-LC Biotinylation Kit (manufactured by Thermo Scientific Corporation, #21435) and according to the attached protocol, the respective mouse monoclonal antibodies M30 were biotinylated (hereinafter the respective biotinylated M30 antibodies were referred to as "bM30"). Further, as a buffer to be used in the following ELISA method, BD OPTI EIA (BD Biosciences, Inc., #550536) was used in all cases.

Each of the extracellular domain polypeptide of the B7-H3 variant 1 (manufactured by R&D Systems, Inc., #1949-B3-050/CF) and the extracellular domain polypeptide of the B7-H3 variant 2 (manufactured by R&D Systems, Inc., #2318-B3-050/CF) was diluted to 0.5 µg/ml with a coating buffer and the resulting solution was dispensed at 100 µL/well in an immunoplate (manufactured by Nunc, Inc., #442404). Then, the plate was left to stand overnight at 4° C., whereby the protein was adsorbed to the plate. On the next day, an assay diluent was dispensed at 200 µL/well, and the plate was left to stand at room temperature for 4 hours.

After the solution in each well was removed, a mixed solution of the biotinylated antibody at 5 µg/ml and an unlabeled antibody at each concentration (0 µg/ml, 1 µg/ml, 5 µg/ml, 25 µg/ml, 50 µg/ml, or 125 µg/ml) was dispensed at 100 µL/well in an assay diluent, and the plate was left to stand at room temperature for 1 hour.

After each well was washed twice with a wash buffer, a streptavidin-horseradish peroxidase conjugate (manufactured by GE Healthcare Bio-Sciences Corporation, #RPN1231V) diluted to 500-fold with an assay diluent was added at 100 µL/well, and the plate was left to stand at room temperature for 1 hour.

After the solution in each well was removed and each well was washed twice with a wash buffer, a substrate solution was added at 100 µL/well, and a color development reaction was allowed to proceed while stirring the reaction mixture. After completion of the color development, a blocking buffer was added thereto at 100 µl/well to stop the color development reaction. Then, an absorbance at 450 nm was measured using a plate reader.

As a result, the absorbance of the well to which only bM30 was added was 2.36±0.05 (mean±standard deviation (n=12)) in the plate to which the polypeptide of the extracellular domain of the B7-H3 variant 1 was attached, and 1.90±0.20 (mean±standard deviation (n=12)) in the plate to which the polypeptide of the extracellular domain of the B7-H3 variant 2 was attached.

Figures 1, 10:
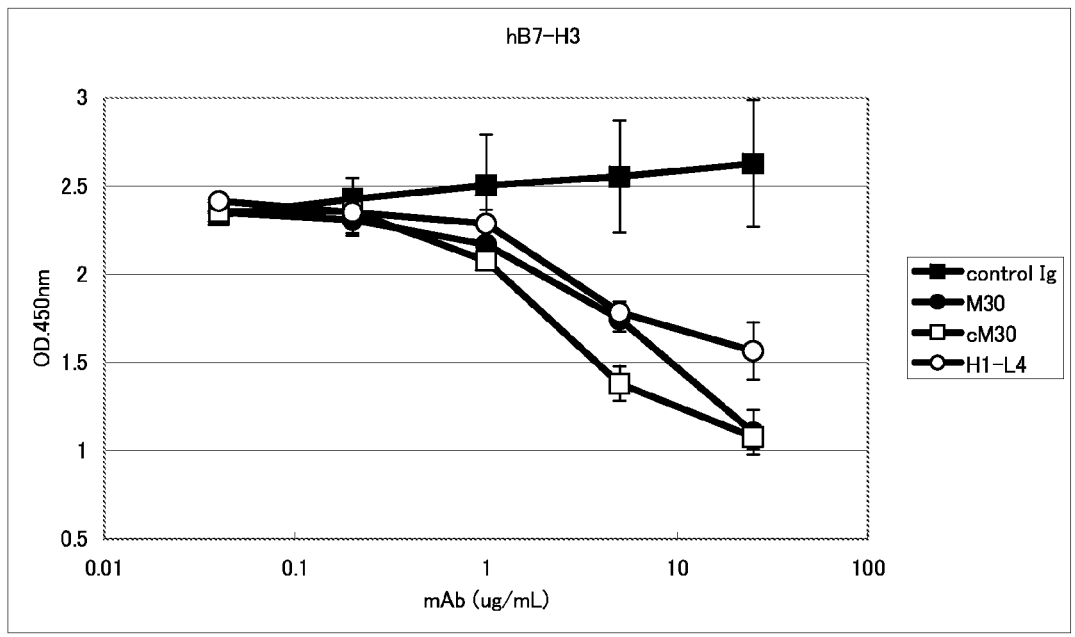
Figures 2, 10:
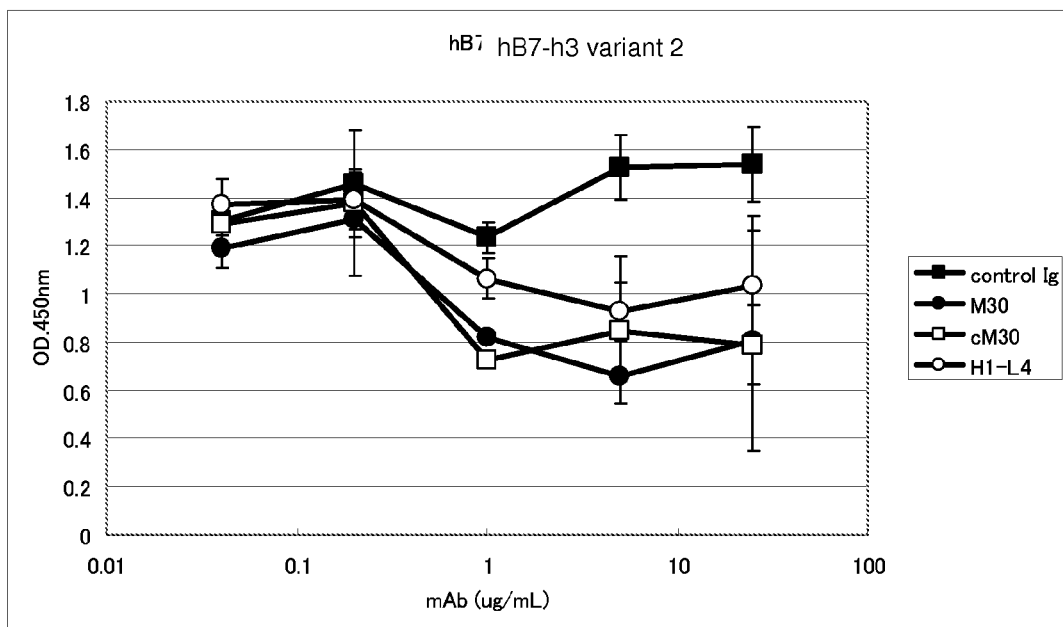

The absorbances in the graphs of FIG. 10 are each expressed as a mean±standard deviation (n=3). The control IgG did not inhibit the binding of bM30 to B7-H3.

On the other hand, it was shown that the binding of bM30 to B7-H3 is inhibited by the M30 antibody itself, the cM30 antibody, which is a chimeric antibody of the M30 antibody, and the M30-H1-L4, which is a humanized antibody, in both of the plate to which the polypeptide of the extracellular domain of the B7-H3 variant 1 was attached and the plate to which the polypeptide of the extracellular domain of the B7-H3 variant 2 was attached.

That is, it was shown that the cM30 antibody and the humanized antibody (M30-H1-L4 antibody) recognize the same epitope of the B7-H3 antigen as the M30 antibody.

Example 12

Activity of Humanized M30 Antibody

12)-1 ADCP Activity of Humanized M30 Antibody

PBMCs of a healthy subject were isolated according to a common procedure and suspended in 10% FBS-containing RPMI 1640 and then seeded in a flask. The cells were cultured overnight in a $CO_2$ incubator. The culture supernatant was removed, and to the cells attached to the flask, 10% FBS-containing RPMI 1640 supplemented with M-CSF and GM-CSF (PeproTech, Inc.) was added, and the cells were cultured for 2 weeks. The cells were detached with TrypLE and collected. Then, the cells were added to a 24-well plate at 500 µl/well ($1 \times 10^5$ cells/well) and cultured overnight at 37° C. The thus prepared cells were used as effector cells.

The labeling of NCI-H322 cells to be used as target cells was performed using PKH26 dye labeling kit (Sigma Co., Ltd.) The target cells were detached with TrypLE and washed twice with PBS. The cells were suspended in Diluent C at $1 \times 10^7$ cells/ml. PKH26 dye stock (1 mM) was diluted to 8 µM with Diluent C, and immediately thereafter, the diluted dye solution was added thereto in an amount equal to that of the cell suspension. The resulting mixture was left at room temperature for 5 minutes. Then, 1 ml of serum was added thereto, and further, a medium with serum was added thereto, and washing was performed twice.

Each of the M30 antibody, the cM30 antibody, and the humanized M30 antibody (M30-H1-L4 antibody) was diluted to 20 µg/ml with 10% FBS-containing RPMI 1640 (Invitrogen Corporation). Subsequently, the target cells (NCI-H322 cells) were dispensed at $2 \times 10^6$ cells/100 µl/tube and mixed. The resulting mixture was left to stand on ice for 30 minutes. The supernatant was removed, and the cells were washed twice with a culture solution and suspended in 500 µl of a culture solution.

The supernatant was removed from the effector cells, and the cells having been treated with the M30 antibody, the cM30 antibody, or the humanized M30 antibody (M30-H1-L4 antibody) and suspended in the culture solution were added thereto and mixed therewith. Then, the cells were cultured for 3 hours in a $CO_2$ incubator.

Thereafter, the cells were detached with Trypsin-EDTA and collected.

To the collected cells, an FITC-labeled anti-mouse CD11b antibody (Becton, Dickinson and Company, Ltd.) was added, and the resulting mixture was left to stand on ice for 30 minutes.

The supernatant was removed, and the cells were washed twice with a culture solution.

Figure 11:
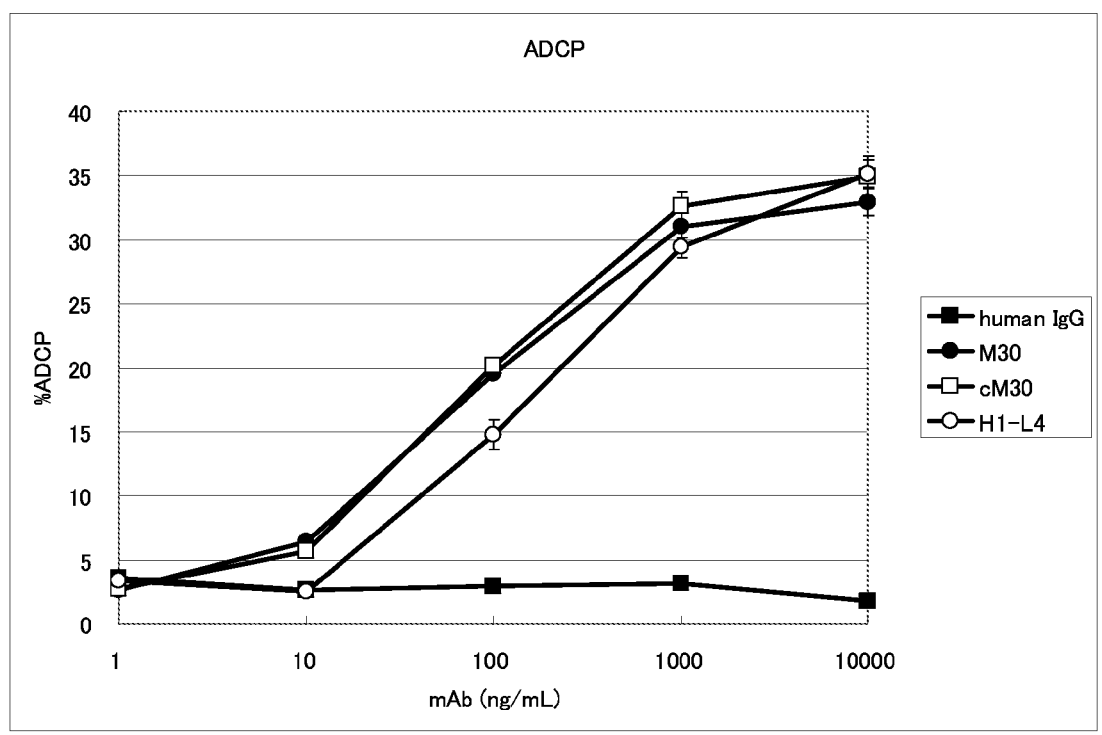
FIG. 11 is a graph showing the ADCP activities of M30 antibody, cM30 antibody, and M30-H1-L4 antibody against NCI-H322 cells. The error bars in the graph represent standard errors (n=4).

The collected cells were suspended in 300 µl of a culture medium and analyzed by FACS Calibur (Becton, Dickinson and Company, Ltd.). In the CD11b-positive macrophages, a PKH26-positive fraction was evaluated as phagocytosis-positive cells. The results are shown in FIG. 11.

In the group with the addition of the humanized M30 antibody (M30-H1-L4 antibody), an ADCP activity against the NCI-H322 cells was observed in the same manner as in the groups with the addition of the M30 antibody or the cM30 antibody.

12)-2 ADCC Activity of Humanized M30 Antibody

PBMCs of a healthy subject were isolated according to a common procedure and suspended in 10% FBS-containing RPMI 1640 and then seeded in a flask. The cells were cultured overnight in a $CO_2$ incubator.

The floating cells were collected, followed by a washing procedure, and the resulting cells were used as peripheral blood lymphocytes (PBLs). The obtained PBLs were suspended in phenol red-free RPMI 1640 (manufactured by Invitrogen Corporation) containing 10% Fetal Bovine Serum (manufactured by Invitrogen Corporation) (hereinafter abbreviated as "ADCC medium"), and the cell suspension was passed through a cell strainer (pore size: 40 µm, manufactured by BD Biosciences, Ltd.). Then, the viable cells were counted by a trypan blue dye exclusion assay. After the PBLs suspension was centrifuged, the medium was removed, and the cells were resuspended in the ADCC medium at a viable cell density of $2.5 \times 10^6$ cells/ml and used as effector cells.

NCI-H322 cells were treated with trypsin, and the treated cells were washed with 10% FBS-containing RPMI 1640 and then resuspended in 10% FBS-containing RPMI 1640. The cells ($4 \times 10^6$ cells) were mixed with chromium-51 (5550 kBq) sterilized through a 0.22 µm filter, and labeling was performed for 1 hour under the conditions of 37° C. and 5% $CO_2$. The labeled cells were washed three times with the ADCC medium, and the cells were resuspended at $2 \times 10^5$ cells/ml in the ADCC medium and used as target cells.

The target cells at a cell density of $2 \times 10^5$ cells/ml were dispensed at 50 µl/well in a 96-well U-shaped bottom microplate. Thereto was added 50 µl of each of the cM30 antibody and the humanized M30 antibodies (M30-H1-L4, M30-H4-L4, M30-H1-L5, M30-H1-L6, and M30-H1-L7) diluted with the ADCC medium so that the final concentration of the antibody after adding the effector cells was 1, 10, 100, or 1000 ng/ml. Then, 100 µl of the effector cells at a cell density of $2.5 \times 10^6$ cells/ml were added thereto, and the cells were cultured for 4 hours under the conditions of 37° C. and 5% $CO_2$. The supernatant was collected in a LumaPlate (manufactured by PerkinElmer, Inc.), and gamma radiation emitted therefrom was measured using a gamma counter. The percentage of cell lysis caused by the ADCC activity was calculated according to the following equation.

Percentage of cell lysis (%)=$(A-B)/(C-B) \times 100$

A: Radiation count from the sample well

B: Average spontaneous radiation emission count (from wells to which the antibody and the effector cells were not added) (n=3) The same procedure as that for the sample well was performed except that the ADCC medium was added in an amount of 50 µl at the time of adding the antibody and in an amount of 100 µl at the time of adding the effector cells.

C: Average maximum radiation emission count (from wells in which the target cells were dissolved with a surfactant) (n=3) The same procedure as that for the sample well was performed except that 50 µl of the ADCC medium was added at the time of adding the antibody and 100 µl of the ADCC medium containing 2% (v/v) Triton X-100 was added at the time of adding the effector cells.

Figure 12:
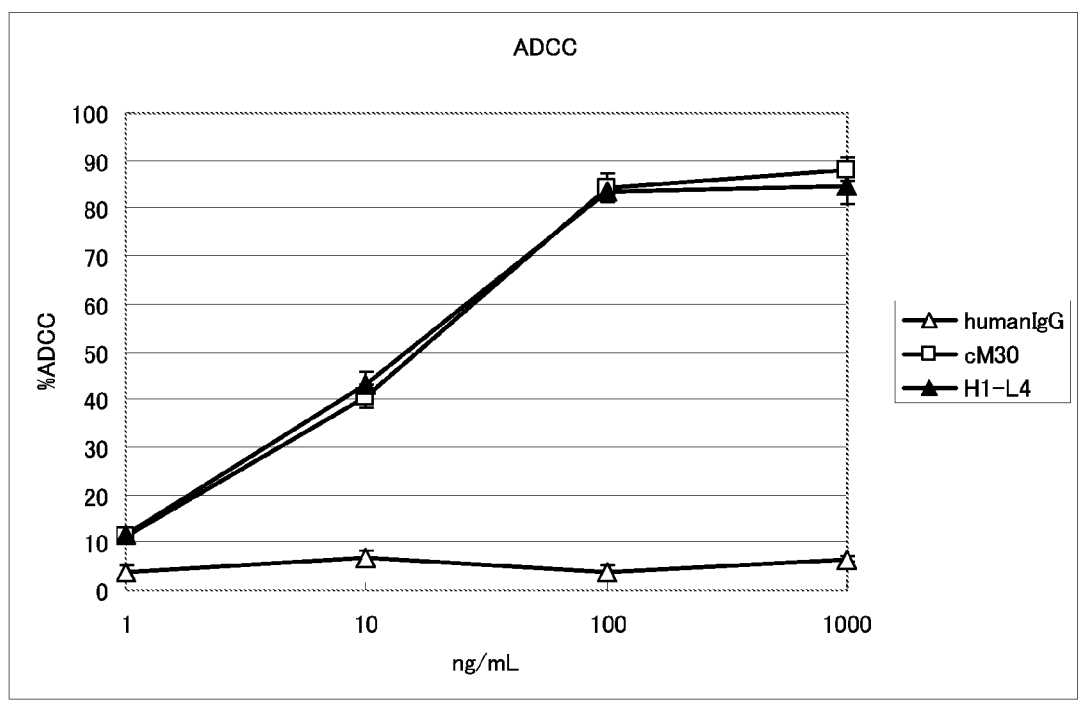
FIG. 12 is a graph showing the ADCC activities of cM30 antibody and M30-H1-L4 antibody against NCI-H322 cells. The error bars in the graph represent standard errors (n=3).

The results are shown in Table 4 and FIG. 12.

The data shown are an average of triplicate measurements, and the error bars represent standard deviations. The P value was calculated using Student's t-test.

In the group with the addition of the M30-H1-L4 antibody, an ADCC activity was observed in the same manner as in the group with the addition of the cM30 antibody. Also other humanized M30 antibodies (M30-H4-L4, M30-H1-L5, M30-H1-L6, and M30-H1-L7) were observed to have an ADCC activity in the same manner.

TABLE 4

|  | 1 ng/mL | | 10 ng/mL | | 100 ng/mL | | 1000 ng/mL | |
| --- | --- | --- | --- | --- | --- | --- | --- | --- |
|  | Average (%) | Standard deviation | Average (%) | Standard deviation | Average (%) | Standard deviation | Average (%) | Standard deviation |
| human IgG | 3.8 | 1.6 | 6.8 | 1.5 | 3.9 | 1.4 | 6.5 | 0.5 |
| cM30 | 11.1 | 1.2 | 40.5 | 2.7 | 84.3 | 2.3 | 88.2 | 4.0 |
| M30-H1-L4 | 11.5 | 1.0 | 43.1 | 0.1 | 83.6 | 0.7 | 84.7 | 1.0 |
| M30-H4-L4 | 7.6 | 1.1 | 26.6 | 1.6 | 68.9 | 2.6 | 81.7 | 1.5 |
| M30-H1-L5 | 9.6 | 1.1 | 30.5 | 2.0 | 67.8 | 5.0 | 78.8 | 3.0 |
| M30-H1-L6 | 9.8 | 1.6 | 32.0 | 2.2 | 74.7 | 4.0 | 81.3 | 2.0 |
| M30-H1-L7 | 8.3 | 0.7 | 29.4 | 0.7 | 71.7 | 2.0 | 80.7 | 0.7 |

12)-3 In Vivo Antitumor Effect of Humanized M30 Antibody

MDA-MB-231 cells were detached from a culture flask by a trypsin treatment, and then suspended in 10% FBS-containing RPMI 1640 medium (Life Technologies Corporation), followed by centrifugation and the supernatant was removed. The cells were washed twice with the same medium, and then suspended in BD Matrigel Basement Membrane Matrix (manufactured by BD Biosciences, Inc.). Then, the cells were implanted subcutaneously in the axillary region of each mouse (FOX CHASE SCID C.B.17/Icr-scid/scidJcl, CLEA Japan, Inc.) at 6 weeks of age at a dose of $5 \times 10^6$ cells/mouse. The day of implantation was taken as day 0, and on days 14, 21, 28, 35, and 42, the humanized M30 antibody (M30-H1-

L4 antibody) was intraperitoneally administered at a dose of 10, 1, 0.1, or 0.01 mg/kg (about 200, 20, 2, or 0.2 μg/mouse, respectively). The tumor volume was measured on days 14, 18, 21, 25, 28, 31, 35, 39, 42, 45, and 49, and the antitumor effect of the administration of the antibody was examined.

As a result, in the groups of administration of the humanized M30 antibody (M30-H1-L4 antibody) at 10, 1, and 0.1 mg/kg, the tumor growth was significantly suppressed as compared with the untreated group in which the antibody was not administered. In the groups of administration of the humanized M30 antibody (M30-H1-L4 antibody) at 10, 1, and 0.1 mg/kg, the tumor growth inhibition ratio (=100−(average tumor weight in antibody administration group)/(average tumor weight in untreated group)×100) compared with the untreated group in terms of the tumor weight on day 49 was 67, 54, and 51%, respectively, and the P values were all $P<0.0001$. The P values were calculated using Dunnett's multiple comparison test.

Figure 38:
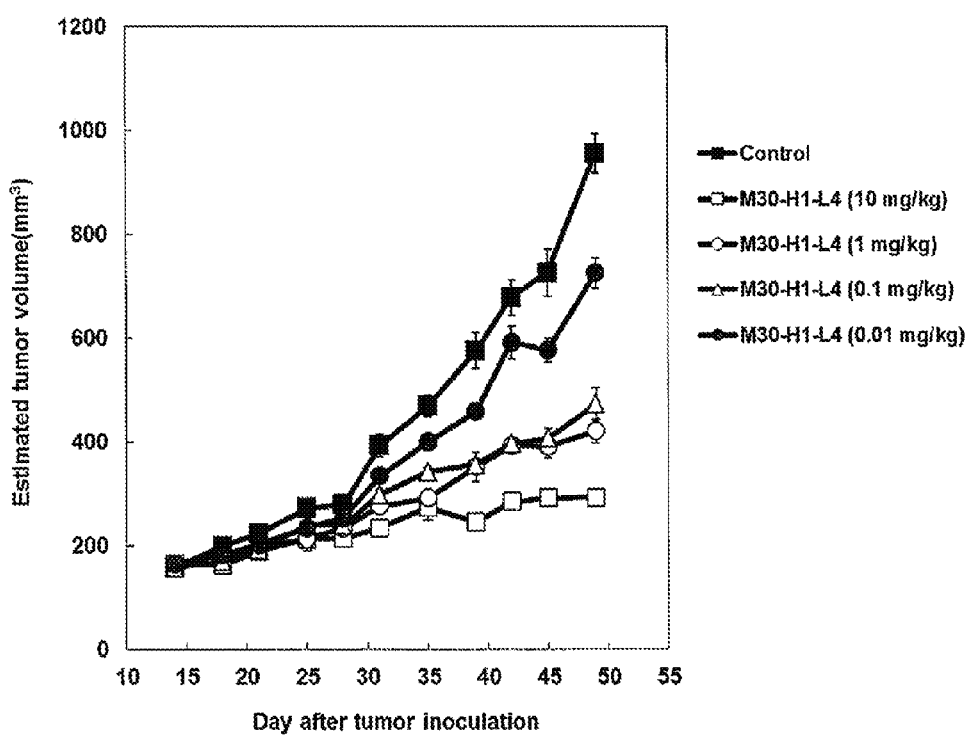
FIG. 38 is a graph showing the antitumor activity of a humanized M30 (M30-H1-L4) antibody against mice implanted with MDA-MB-231 cells. The error bars in the graph represent standard errors (n=6).

Further, the tumor growth inhibition ratio (%) (=100−(average tumor volume in antibody administration group)/(average tumor volume in untreated group)×100) of the M30-H1-L4 antibody on day 49 in the 10, 1, 0.1, and 0.01 mg/kg administration groups was 84, 68, 61, and 30%, respectively. Accordingly, the humanized M30 antibody (M30-H1-L4 antibody) was observed to have a very strong antitumor effect in vivo in the same manner as the M30 antibody and the cM30 antibody, and it was confirmed that the effect was exhibited in a dose-response manner (FIG. 38).

INDUSTRIAL APPLICABILITY

The anti-B7-H3 antibody of the invention has an antitumor activity, and a pharmaceutical composition comprising the anti-B7-H3 antibody can become an anticancer agent.

SEQUENCE LISTING FREE TEXT

SEQ ID NO: 1: PCR primer 1
SEQ ID NO: 2: PCR primer 2
SEQ ID NO: 3: CMV promoter primer: primer 3
SEQ ID NO: 4: BGH reverse primer: primer 4
SEQ ID NO: 5: nucleotide sequence of B7-H3 variant 1
SEQ ID NO: 6: amino acid sequence of B7-H3 variant 1
SEQ ID NO: 7: PCR primer 5
SEQ ID NO: 8: PCR primer 6
SEQ ID NO: 9: nucleotide sequence of B7-H3 variant 2
SEQ ID NO: 10: amino acid sequence of B7-H3 variant 2
SEQ ID NO: 11: PCR primer 7
SEQ ID NO: 12: PCR primer 8
SEQ ID NO: 13: PCR primer 9
SEQ ID NO: 14: PCR primer 10
SEQ ID NO: 15: PCR primer 11
SEQ ID NO: 16: PCR primer 12
SEQ ID NO: 17: PCR primer 13
SEQ ID NO: 18: PCR primer 14
SEQ ID NO: 19: PCR primer 15
SEQ ID NO: 20: nucleotide sequence of B7-H3 IgV1
SEQ ID NO: 21: amino acid sequence of B7-H3 IgV1
SEQ ID NO: 22: nucleotide sequence of B7-H3 IgC1
SEQ ID NO: 23: amino acid sequence of B7-H3 IgC1
SEQ ID NO: 24: nucleotide sequence of B7-H3 IgV2
SEQ ID NO: 25: amino acid sequence of B7-H3 IgV2
SEQ ID NO: 26: nucleotide sequence of B7-H3 IgC2
SEQ ID NO: 27: amino acid sequence of B7-H3 IgC2
SEQ ID NO: 28: nucleotide sequence of B7-H3 IgC1-V2-C2
SEQ ID NO: 29: amino acid sequence of B7-H3 IgC1-V2-C2
SEQ ID NO: 30: nucleotide sequence of B7-H3 IgV2-C2
SEQ ID NO: 31: amino acid sequence of B7-H3 IgV2-C2
SEQ ID NO: 32: nucleotide sequence of B7RP-1
SEQ ID NO: 33: amino acid sequence of B7RP-1
SEQ ID NO: 34: nucleotide sequence of B7-H1
SEQ ID NO: 35: amino acid sequence of B7-H1
SEQ ID NO: 36: nucleotide sequence of B7-DC
SEQ ID NO: 37: amino acid sequence of B7-DC
SEQ ID NO: 38: nucleotide sequence of CD80
SEQ ID NO: 39: amino acid sequence of CD80
SEQ ID NO: 40: nucleotide sequence of CD86
SEQ ID NO: 41: amino acid sequence of CD86
SEQ ID NO: 42: nucleotide sequence of B7-H4
SEQ ID NO: 43: amino acid sequence of B7-H4
SEQ ID NO: 44: N-terminal amino acid sequence of mouse antibody M30 heavy chain
SEQ ID NO: 45: N-terminal amino acid sequence of mouse antibody M30 light chain
SEQ ID NO: 46: PCR primer 16
SEQ ID NO: 47: PCR primer 17
SEQ ID NO: 48: PCR primer 18
SEQ ID NO: 49: PCR primer 19
SEQ ID NO: 50: nucleotide sequence of cDNA encoding M30 antibody heavy chain
SEQ ID NO: 51: amino acid sequence of M30 antibody heavy chain
SEQ ID NO: 52: nucleotide sequence of cDNA encoding M30 antibody light chain
SEQ ID NO: 53: amino acid sequence of M30 antibody light chain
SEQ ID NO: 54: PCR primer 20
SEQ ID NO: 55: PCR primer 21
SEQ ID NO: 56: DNA sequence encoding human κ chain secretory signal, human κ chain constant region, and human poly-A additional signal
SEQ ID NO: 57: DNA fragment comprising DNA sequence encoding amino acids of signal sequence and constant region of human IgG1
SEQ ID NO: 58: nucleotide sequence of cDNA encoding M30 antibody chimera-type light chain
SEQ ID NO: 59: amino acid sequence of M30 antibody chimera-type light chain
SEQ ID NO: 60: PCR primer 22
SEQ ID NO: 61: PCR primer 23
SEQ ID NO: 62: nucleotide sequence of cDNA encoding M30 antibody chimera-type heavy chain
SEQ ID NO: 63: amino acid sequence of M30 antibody chimera-type heavy chain
SEQ ID NO: 64: PCR primer 24
SEQ ID NO: 65: PCR primer 25
SEQ ID NO: 66: PCR primer 26
SEQ ID NO: 67: PCR primer 27
SEQ ID NO: 68: PCR primer 28
SEQ ID NO: 69: PCR primer 29
SEQ ID NO: 70: nucleotide sequence of M30-L1-type light chain
SEQ ID NO: 71: amino acid sequence of M30-L1-type light chain
SEQ ID NO: 72: nucleotide sequence of M30-L2-type light chain
SEQ ID NO: 73: amino acid sequence of M30-L2-type light chain
SEQ ID NO: 74: nucleotide sequence of M30-L3-type light chain
SEQ ID NO: 75: amino acid sequence of M30-L3-type light chain
SEQ ID NO: 76: nucleotide sequence of M30-L4-type light chain SEQ ID NO: 77: amino acid sequence of M30-L4-type light chain
SEQ ID NO: 78: nucleotide sequence of M30-L5-type light chain
SEQ ID NO: 79: amino acid sequence of M30-L5-type light chain
SEQ ID NO: 80: nucleotide sequence of M30-L6-type light chain
SEQ ID NO: 81: amino acid sequence of M30-L6-type light chain
SEQ ID NO: 82: nucleotide sequence of M30-L7-type light chain
SEQ ID NO: 83: amino acid sequence of M30-L7-type light chain
SEQ ID NO: 84: nucleotide sequence of M30-H1-type heavy chain
SEQ ID NO: 85: amino acid sequence of M30-H1-type heavy chain
SEQ ID NO: 86: nucleotide sequence of M30-H2-type heavy chain
SEQ ID NO: 87: amino acid sequence of M30-H2-type heavy chain
SEQ ID NO: 88: nucleotide sequence of M30-H3-type heavy chain
SEQ ID NO: 89: amino acid sequence of M30-H3-type heavy chain
SEQ ID NO: 90: nucleotide sequence of M30-H4-type heavy chain
SEQ ID NO: 91: amino acid sequence of M30-H4-type heavy chain
SEQ ID NO: 92: amino acid sequence of M30 antibody CDRH1
SEQ ID NO: 93: amino acid sequence of M30 antibody CDRH2
SEQ ID NO: 94: amino acid sequence of M30 antibody CDRH3
SEQ ID NO: 95: amino acid sequence of M30 antibody CDRL1
SEQ ID NO: 96: amino acid sequence of M30 antibody CDRL2
SEQ ID NO: 97: amino acid sequence of M30 antibody CD

The invention claimed is:

1. An antibody characterized by having the following properties:
   (a) specific binding to an IgC1 and/or IgC2 domain of B7-H3,
   (b) having a constant region that is a human constant region;
   (c) comprising CDRH1 consisting of an amino acid sequence comprising SEQ ID NO: 92, CDRH2 consisting of an amino acid sequence comprising SEQ ID NO: 93, and CDRH3 consisting of an amino acid sequence comprising SEQ ID NO: 94 as complementarity determining regions of the heavy chain and comprising CDRL1 consisting of an amino acid sequence comprising SEQ ID NO: 95, CDRL2 consisting of an amino acid sequence comprising SEQ ID NO: 96, and CDRL3 consisting of an amino acid sequence comprising SEQ ID NO: 97 as complementarity determining regions of the light chain;
   (d) having an antibody-dependent cell-mediated phagocytosis (ADCP) activity; and
   (e) having an in vivo antitumor activity against tumors expressing B7-H3 comprising SEQ ID NO: 6 or SEQ ID NO:10.

2. The antibody according to claim 1, which has a competitive inhibitory activity against M30 antibody for the binding to B7-H3.

3. The antibody according to claim 1, which has an antibody-dependent cellular cytotoxicity (ADCC) activity and/or a complement-dependent cytotoxicity (CDC) activity.

4. The antibody according to any one of claims 1, 2 and 3, wherein the tumor is cancer.

5. The antibody according to claim 4, wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

6. The antibody according to claim 1, which comprises a heavy chain variable region consisting of an amino acid sequence comprising amino acid numbers 20 to 141 in SEQ ID NO: 51 and a light chain variable region consisting of an amino acid sequence comprising amino acid numbers 23 to 130 in SEQ ID NO: 53.

7. The antibody according to claim 1, which comprises a heavy chain consisting of an amino acid sequence comprising SEQ ID NO: 63 and a light chain consisting of an amino acid sequence comprising SEQ ID NO: 59.

8. The antibody according to claim 1, which is humanized.

9. The antibody according to claim 8, which comprises a heavy chain variable region consisting of an amino acid sequence selected from the group consisting of (a) an amino acid sequence comprising amino acid numbers 20 to 141 in SEQ ID NO: 85, (b) an amino acid sequence comprising amino acid numbers 20 to 141 in SEQ ID NO: 87, (c) an amino acid sequence comprising amino acid numbers 20 to 141 in SEQ ID NO: 89, (d) an amino acid sequence comprising amino acid numbers 20 to 141 in SEQ ID NO: 91, (e) an amino acid sequence having a homology of at least 95% or more with any of the framework amino acid residues of the sequences (a) to (d), and (f) an amino acid sequence wherein one or several amino acids are deleted, substituted or added within any of the framework region sequences of (a) to (d); and a light chain variable region consisting of an amino acid sequence selected from the group consisting of (g) an amino acid sequence comprising amino acid numbers 21 to 128 in SEQ ID NO: 71, (h) an amino acid sequence comprising amino acid numbers 21 to 128 in SEQ ID NO: 73, (i) an amino acid sequence comprising amino acid numbers 21 to 128 in SEQ ID NO: 75, (j) an amino acid sequence comprising amino acid numbers 21 to 128 in SEQ ID NO: 77, (k) an amino acid sequence comprising amino acid numbers 21 to 128 in SEQ ID NO: 79, (l) an amino acid sequence comprising amino acid numbers 21 to 128 in SEQ ID NO: 81, (m) an amino acid sequence comprising amino acid numbers 21 to 128 in SEQ ID NO: 83, (n) an amino acid sequence having a homology of at least 95% or more with any of the framework amino acids of the sequences (g) to (m), and (o) an amino acid sequence wherein one or several amino acids are deleted, substituted or added within any of the framework region sequences of (g) to (m).

10. The antibody according to claim 9, which comprises a heavy chain variable region and a light chain variable region selected from the group consisting of a heavy chain variable region consisting of an amino acid sequence comprising amino acid numbers 20 to 141 in SEQ ID NO: 85 and a light chain variable region consisting of an amino acid sequence comprising amino acid numbers 21 to 128 in SEQ ID NO: 71; a heavy chain variable region consisting of an amino acid sequence comprising amino acid numbers 20 to 141 in SEQ ID NO: 85 and a light chain variable region consisting of an amino acid sequence comprising amino acid numbers 21 to 128 in SEQ ID NO: 73; a heavy chain variable region consisting of an amino acid sequence comprising amino acid numbers 20 to 141 in SEQ ID NO: 85 and a light chain variable region consisting of an amino acid sequence comprising amino acid numbers 21 to 128 in SEQ ID NO: 75; a heavy chain variable region consisting of an amino acid sequence comprising amino acid numbers 20 to 141 in SEQ ID NO: 85 and a light chain variable region consisting of an amino acid sequence comprising amino acid numbers 21 to 128 in SEQ ID NO: 77; a heavy chain variable region consisting of an amino acid sequence comprising amino acid numbers 20 to 141 in SEQ ID NO:85 and a light chain variable region consisting of an amino acid sequence comprising amino acid numbers 21 to 128 in SEQ ID NO: 79; a heavy chain variable region consisting of an amino acid sequence comprising amino acid numbers 20 to 141 in SEQ ID NO: 85 and a light chain variable region consisting of an amino acid sequence comprising amino acid numbers 21 to 128 in SEQ ID NO: 81; a heavy chain variable region consisting of an amino acid sequence comprising amino acid numbers 20 to 141 in SEQ ID NO: 85 and a light chain variable region consisting of an amino acid sequence comprising amino acid numbers 21 to 128 in SEQ ID NO:83; a heavy chain variable region consisting of an amino acid sequence comprising amino acid numbers 20 to 141 in SEQ ID NO: 91 and a light chain variable region consisting of an amino acid sequence comprising amino acid numbers 21 to 128 in SEQ ID NO: 71; a heavy chain variable region consisting of an amino acid sequence comprising amino acid numbers 20 to 141 in SEQ ID NO: 91 and a light chain variable region consisting of an amino acid sequence comprising amino acid numbers 21 to 128 in SEQ ID NO: 73; a heavy chain variable region consisting of an amino acid sequence comprising amino acid numbers 20 to 141 in SEQ ID NO:91 and a light chain variable region consisting of an amino acid sequence comprising amino acid numbers 21 to 128 in SEQ ID NO: 75; and a heavy chain variable region consisting of an amino acid sequence comprising amino acid numbers 20 to 141 in SEQ ID NO: 91 and a light chain variable region consisting of an amino acid sequence comprising amino acid numbers 21 to 128 in SEQ ID NO: 77.

11. The antibody according to claim 9, which comprises a heavy chain and a light chain selected from the group consisting of a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 71; a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 73; a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 75; a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 77; a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 79; a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 81; a heavy chain consisting of an amino acid sequence comprising amino acid numbers 20 to 471 in SEQ ID NO: 85 and a light chain consisting of an amino acid sequence comprising amino acid numbers 21 to 233 in SEQ ID NO: 83; a heavy chain consisting of an amino acid sequence comprising amino acid numbers 20 to 471 in SEQ ID NO: 91 and a light chain consisting of an amino acid sequence comprising amino acid numbers 21 to 233 in SEQ ID NO: 71; a heavy chain consisting of an amino acid sequence comprising amino acid numbers 20 to 471 in SEQ ID NO: 91 and a light chain consisting of an amino acid sequence comprising amino acid numbers 21 to 233 in SEQ ID NO: 73; a heavy chain consisting of an amino acid sequence comprising amino acid numbers 20 to 471 in SEQ ID NO: 91 and a light chain consisting of an amino acid sequence comprising amino acid numbers 21 to 233 in SEQ ID NO: 75; and a heavy chain consisting of an amino acid sequence comprising amino acid numbers 20 to 471 in SEQ ID NO: 91 and a light chain consisting of an amino acid sequence comprising amino acid numbers 21 to 233 in SEQ ID NO: 77.

12. The antibody according to claim 9, which comprises a heavy chain and a light chain selected from the group consisting of: a heavy chain consisting of an amino acid sequence comprising SEQ ID NO: 85 and a light chain consisting of an amino acid sequence comprising SEQ ID NO: 71; a heavy chain consisting of an amino acid sequence comprising SEQ ID NO: 85 and a light chain consisting of an amino acid sequence comprising SEQ ID NO: 73; a heavy chain consisting of an amino acid sequence comprising SEQ ID NO: 85 and a light chain consisting of an amino acid sequence comprising SEQ ID NO: 75; a heavy chain consisting of an amino acid sequence comprising SEQ ID NO: 85 and a light chain consisting of an amino acid sequence comprising SEQ ID NO: 77; a heavy chain consisting of an amino acid sequence comprising SEQ ID NO:85 and a light chain consisting of an amino acid sequence comprising SEQ ID NO: 79; a heavy chain consisting of an amino acid sequence comprising SEQ ID NO: 85 and a light chain consisting of an amino acid sequence comprising SEQ ID NO: 81; a heavy chain consisting of an amino acid sequence comprising SEQ ID NO: 85 and a light chain consisting of an amino acid sequence SEQ ID NO: 83; a heavy chain consisting of an amino acid sequence comprising SEQ ID NO: 91 and a light chain consisting of an amino acid sequence comprising SEQ ID NO:71; a heavy chain consisting of an amino acid sequence comprising SEQ ID NO: 91 and a light chain consisting of an amino acid sequence comprising SEQ ID NO: 73; a heavy chain consisting of an amino acid sequence comprising SEQ ID NO: 91 and a light chain consisting of an amino acid sequence comprising SEQ ID NO: 75; and a heavy chain consisting of an amino acid sequence comprising SEQ ID NO: 91 and a light chain consisting of an amino acid sequence comprising SEQ ID NO: 77.

13. A polynucleotide encoding the antibody according to claim 1.

14. The polynucleotide according to claim 13, which comprises a nucleotide sequence comprising nucleotide numbers 58 to 423 in SEQ ID NO: 50 and a nucleotide sequence comprising nucleotide numbers 67 to 390 in SEQ ID NO:52.

15. The polynucleotide according to claim 13, which comprises a nucleotide sequence comprising SEQ ID NO: 62 and a nucleotide sequence comprising SEQ ID NO: 58.

16. The polynucleotide according to claim 13, which comprises: a nucleotide sequence selected from the group consisting of (a) a nucleotide sequence comprising nucleotide numbers 58 to 423 in SEQ ID NO: 84, (b) a nucleotide sequence comprising nucleotide numbers 58 to 423 in SEQ ID NO: 86, (c) a nucleotide sequence comprising nucleotide numbers 58 to 423 in SEQ ID NO: 88, (d) a nucleotide sequence comprising nucleotide numbers 58 to 423 in SEQ ID NO: 90, and (e) a nucleotide sequence comprising a polynucleotide which hybridizes to a polynucleotide consisting of a nucleotide sequence complementary to any of the nucleotide sequences (a) to (d) under stringent conditions; and a nucleotide sequence selected from the group consisting of (f) a nucleotide sequence comprising nucleotide numbers 61 to 384 in SEQ ID NO: 70, (g) a nucleotide sequence comprising nucleotide numbers 61 to 384 in SEQ ID NO: 72, (h) a nucleotide sequence comprising nucleotide numbers 61 to 384 in SEQ ID NO: 74, (i) a nucleotide sequence comprising nucleotide numbers 61 to 384 in SEQ ID NO: 76, (j) a nucleotide sequence comprising nucleotide numbers 61 to 384 in SEQ ID NO: 78, (k) a nucleotide sequence comprising nucleotide numbers 61 to 384 in SEQ ID NO: 80, (l) a nucleotide sequence comprising nucleotide numbers 61 to 384 in SEQ ID NO: 82, and (m) a nucleotide sequence comprising a polynucleotide which hybridizes to a polynucleotide consisting of a nucleotide sequence complementary to any of the nucleotide sequences (f) to (l) under stringent conditions.

17. The polynucleotide according to claim 16, which comprises nucleotide sequences selected from the group consisting of: a nucleotide sequence comprising nucleotide numbers 58 to 423 in SEQ ID NO: 84 and a nucleotide sequence comprising nucleotide numbers 61 to 384 in SEQ ID NO: 70; a nucleotide sequence comprising nucleotide numbers 58 to 423 in SEQ ID NO: 84 and a nucleotide sequence comprising nucleotide numbers 61 to 384 in SEQ ID NO: 72; a nucleotide sequence comprising nucleotide numbers 58 to 423 in SEQ ID NO: 84 and a nucleotide sequence comprising nucleotide numbers 61 to 384 in SEQ ID NO: 74; a nucleotide sequence comprising nucleotide numbers 58 to 423 in SEQ ID NO: 84 and a nucleotide sequence comprising nucleotide numbers 61 to 384 in SEQ ID NO: 76; a nucleotide sequence comprising nucleotide numbers 58 to 423 in SEQ ID NO: 84 and a nucleotide sequence comprising nucleotide numbers 61 to 384 in SEQ ID NO: 78; a nucleotide sequence comprising nucleotide numbers 58 to 423 in SEQ ID NO: 84 and a nucleotide sequence comprising nucleotide numbers 61 to 384 in SEQ ID NO: 80; a nucleotide sequence comprising nucleotide numbers 58 to 423 in SEQ ID NO: 84 and a nucleotide sequence comprising nucleotide numbers 61 to 384 in SEQ ID NO: 82; a nucleotide sequence comprising nucleotide numbers 58 to 423 in SEQ ID NO: 90 and a nucleotide sequence comprising nucleotide numbers 61 to 384 in SEQ ID NO: 70; a nucleotide sequence comprising nucleotide numbers 58 to 423 in SEQ ID NO: 90 and a nucleotide sequence comprising nucleotide numbers 61 to 384 in SEQ ID NO: 72; a nucleotide sequence comprising nucleotide numbers 58 to 423 in SEQ ID NO: 90 and a nucleotide sequence comprising nucleotide numbers 61 to 384 in SEQ ID NO: 74; and a nucleotide sequence comprising nucleotide numbers 58 to 423 in SEQ ID NO: 90 and a nucleotide sequence comprising nucleotide numbers 61 to 384 in SEQ ID NO: 76.

18. The polynucleotide according to claim 16, which comprises nucleotide sequences selected from the group consisting of: a nucleotide sequence comprising nucleotide numbers 58 to 1413 in SEQ ID NO: 84 and a nucleotide sequence comprising nucleotide numbers 61 to 699 in SEQ ID NO: 70; a nucleotide sequence comprising nucleotide numbers 58 to 1413 in SEQ ID NO: 84 and a nucleotide sequence comprising nucleotide numbers 61 to 699 in SEQ ID NO: 72; a nucleotide sequence comprising nucleotide numbers 58 to 1413 in SEQ ID NO: 84 and a nucleotide sequence comprising nucleotide numbers 61 to 699 in SEQ ID NO: 74; a nucleotide sequence comprising nucleotide numbers 58 to 1413 in SEQ ID NO: 84 and a nucleotide sequence comprising nucleotide numbers 61 to 699 in SEQ ID NO: 76; a nucleotide sequence comprising nucleotide numbers 58 to 1413 in SEQ ID NO: 84 and a nucleotide sequence comprising nucleotide numbers 61 to 699 in SEQ ID NO: 78; a nucleotide sequence comprising nucleotide numbers 58 to 1413 in SEQ ID NO: 84 and a nucleotide sequence comprising nucleotide numbers 61 to 699 in SEQ ID NO: 80; a nucleotide sequence comprising nucleotide numbers 58 to 1413 in SEQ ID NO: 84 and a nucleotide sequence comprising nucleotide numbers 61 to 699 in SEQ ID NO: 82; a nucleotide sequence comprising nucleotide numbers 58 to 1413 in SEQ ID NO: 90 and a nucleotide sequence comprising nucleotide numbers 61 to 699 in SEQ ID NO: 70; a nucleotide sequence comprising nucleotide numbers 58 to 1413 in SEQ ID NO: 90 and a nucleotide sequence comprising nucleotide numbers 61 to 699 in SEQ ID NO: 72; a nucleotide sequence comprising nucleotide numbers 58 to 1413 in SEQ ID NO: 90 and a nucleotide sequence comprising nucleotide numbers 61 to 699 in SEQ ID NO: 74; and a nucleotide sequence comprising nucleotide numbers 58 to 1413 in SEQ ID NO: 90 and a nucleotide sequence comprising nucleotide numbers 61 to 699 in SEQ ID NO: 76.

19. The polynucleotide according to claim 13, which comprises nucleotide sequences selected from the group consisting of: a nucleotide sequence comprising SEQ ID NO: 84 and a nucleotide sequence comprising SEQ ID NO: 70; a nucleotide sequence comprising SEQ ID NO: 84 and a nucleotide sequence comprising SEQ ID NO: 72; a nucleotide sequence comprising SEQ ID NO: 84 and a nucleotide sequence comprising SEQ ID NO: 74; a nucleotide sequence comprising SEQ ID NO: 84 and a nucleotide sequence comprising SEQ ID NO: 76; a nucleotide sequence comprising SEQ ID NO: 84 and a nucleotide sequence comprising SEQ ID NO: 78; a nucleotide sequence comprising SEQ ID NO:84 and a nucleotide sequence comprising SEQ ID NO: 80; a nucleotide sequence comprising SEQ ID NO: 84 and a nucleotide sequence comprising SEQ ID NO: 82; a nucleotide sequence comprising SEQ ID NO: 90 and a nucleotide sequence comprising SEQ ID NO: 70; a nucleotide sequence comprising SEQ ID NO: 90 and a nucleotide sequence comprising SEQ ID NO: 72; a nucleotide sequence comprising SEQ ID NO: 90 and a nucleotide sequence comprising SEQ ID NO: 74; and a nucleotide sequence comprising SEQ ID NO: 90 and a nucleotide sequence comprising SEQ ID NO: 76.

20. An expression vector comprising a polynucleotide according to any one of claims 13-19.

21. A host cell, which is transformed in vitro with the expression vector according to claim 20.

22. The host cell according to claim 21, wherein the host cell is a eukaryotic cell.

23. A method of producing an antibody, comprising a step of culturing a host cell according to claim 21 and a step of collecting the antibody from a cultured product obtained in the culturing step.

24. An antibody obtained by a production method comprising a step of culturing a host cell according to claim 21 and a step of collecting the antibody from a cultured product obtained in the culturing step.

25. The antibody according to any one of claims 1, 2, 3, 6 and 7-12, wherein the modification of a glycan, when present, is regulated to enhance an antibody-dependent cellular cytotoxic activity as compared with an unmodified antibody or functional fragment of the antibody.

26. A pharmaceutical composition, comprising at least one of the antibodies according to any one of claims 1, 2, 3, 10 and 7-12.

27. A method of treating a tumor expressing B7-H3, comprising administering at least one of the antibodies according to any one of claims, 1, 2, 3, 6 and 7-12 to an individual.

28. A method of treating a tumor expressing B7-H3, comprising administering at least one of the antibodies according to any one of claims, 1, 2, 3, 6 and 7-12 and at least one therapeutic agent for cancer simultaneously, separately, or sequentially to an individual.

29. The method according to claim 27, wherein the tumor is cancer.

30. The method according to claim 29, wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

31. The method according to claim 28, wherein the tumor is cancer.

32. The method according to claim 31, wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

33. An antibody obtained by a production method comprising a step of culturing a host cell transformed with an expression vector comprising a polynucleotide encoding the antibody according to claim 4 and a step of collecting the antibody from a cultured product obtained in the culturing step.

34. The antibody according to claim 33, wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

35. The antibody of claim 24, wherein the modification of a glycan, when present, is regulated to enhance an antibody-dependent cellular cytotoxic activity as compared with an unmodified antibody.

36. The antibody according to claim 4, wherein the modification of a glycan, when present, is regulated to enhance an antibody dependent cellular cytotoxicity as compared with an unmodified antibody.

37. The antibody according to claim 36, wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

38. An antibody according to claim 33, wherein the modification of a glycan, when present, is regulated to enhance an antibody dependent cellular cytotoxicity as compared with an unmodified antibody.

39. An antibody according to claim 34, wherein the modification of a glycan, when present, is regulated to enhance an antibody dependent cellular cytotoxicity as compared with an unmodified antibody.

40. A pharmaceutical composition, comprising at least one antibody according to claim 24.

41. A pharmaceutical composition, comprising at least one antibody according to claim 25.

42. A pharmaceutical composition, comprising at least one antibody according to claim 33.

43. A pharmaceutical composition, comprising at least one antibody according to claim 4.

44. The pharmaceutical composition according to claim 43, wherein the cancer is lung cancer, breast cancer, prostate cancer, pancreatic cancer, colorectal cancer, a melanoma, liver cancer, ovarian cancer, bladder cancer, stomach cancer, esophageal cancer, or kidney cancer.

45. A pharmaceutical composition, comprising at least one antibody according to claim 34.

46. A pharmaceutical composition, comprising at least one antibody according to claim 35.

47. A pharmaceutical composition, comprising at least one antibody according to claim 36.

48. A pharmaceutical composition, comprising at least one antibody according to claim 37.

49. A pharmaceutical composition, comprising at least one antibody according to claim 38.

50. A pharmaceutical composition, comprising at least one antibody according to claim 39.

51. A method of treating a tumor expressing B7-H3, comprising administering at least one of the antibodies according to claim 24 to an individual.

52. A method of treating a tumor expressing B7-H3, comprising administering at least one of the antibodies according to claim 24 and at least one therapeutic agent for cancer simultaneously, separately, or sequentially to an individual.

\* \* \* \* \*

```
                             SEQUENCE LISTING

<160> NUMBER OF SEQ ID NOS: 97

<210> SEQ ID NO 1
<211> LENGTH: 46
<212> TYPE: DNA
<213> ORGANISM: Artificial Sequence
<220> FEATURE:
<223> OTHER INFORMATION: PCR primer

<400> SEQUENCE: 1
ctatagggag acccaagctg gctagcatgc tgcgtcggcg gggcag                    46

<210> SEQ ID NO 2
<211> LENGTH: 66
<212> TYPE: DNA
<213> ORGANISM: Artificial Sequence
<220> FEATURE:
<223> OTHER INFORMATION: PCR primer

<400> SEQUENCE: 2
aacgggccct ctagactcga gcggccgctc aggctatttc ttgtccatca tcttctttgc    60
tgtcag                                                               66

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
cgcaaatggg cggtaggcgt g                                              21

<210> SEQ ID NO 4
<211> LENGTH: 18
<212> TYPE: DNA
<213> ORGANISM: Artificial Sequence
<220> FEATURE:
<223> OTHER INFORMATION: PCR primer

<400> SEQUENCE: 4
tagaaggcac agtcgagg                                                  18
```

<210> SEQ ID NO 5
<211> LENGTH: 1815
<212> TYPE: DNA
<213> ORGANISM: Homo sapiens

<400> SEQUENCE: 5

```
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca cgcatccct gaggctgcag cgcgtgcgtg tggcggacga ggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccagggc taccctgagg ctgaggtgtt ctggcaggat     540
ggcagggtg tgcccctgac tggcaacgtg accacgtcgc agatggccaa cgagcagggc     600
ttgtttgatg tgcacagcat cctgcgggtg gtgctgggtg caaatggcac ctacagctgc     660
ctggtgcgca ccccgtgct gcagcaggat gcgcacagct ctgtcaccat cacccccag     720
agaagcccca caggagccgt ggaggtccag gtccctgagg accggtggt ggccctagtg     780
ggcaccgatg ccaccctgcg ctgctccttc tcccccgagc ctggcttcag cctggcacag     840
ctcaacctca tctggcagct gacagacacc aaacagctgg tgcacagttt caccgaaggc     900
cgggaccagg gcagcgccta tgccaaccgc acggccctct cccggacct gctggcacaa     960
ggcaatgcat ccctgaggct gcagcgcgtg cgtgtggcgg acgagggcag cttcacctgc    1020
ttcgtgagca tccgggattt cggcagcgct gccgtcagcc tgcaggtggc cgctccctac    1080
tcgaagccca gcatgaccct ggagcccaac aaggacctgc ggccagggga cacggtgacc    1140
atcacgtgct ccagctaccg ggctaccct gaggctgagg tgttctggca ggatgggcag    1200
ggtgtgcccc tgactggcaa cgtgaccacg tcgcagatgg ccaacgagca gggcttgttt    1260
gatgtgcaca gcgtcctgcg ggtggtgctg ggtgcgaatg gcacctacag ctgcctggtg    1320
cgcaaccccg tgctgcagca ggatgcgcac ggctctgtca ccatcacagg gcagcctatg    1380
acattccccc cagaggccct gtgggtgacc gtggggctgt ctgtctgtct cattgcactg    1440
ctggtggccc tggctttcgt gtgctggaga aagatcaaac agagctgtga ggaggagaat    1500
gcaggagctg aggaccagga tggggaggga aaggctcca agacagccct gcagcctctg    1560
aaacactctg acagcaaaga agatgatgga caagaaatag cctgagcggc cgccactgtg    1620
ctggatatct gcagaattcc accacactgg actagtggat ccgagctcgg taccaagctt    1680
aagtttaaac cgctgatcag cctcgactgt gccttctagt tgccagccat ctgttgtttg    1740
ccctcccccc gtgccttcct tgaccctgga aggtgccact cccactgtcc tttcctaata    1800
aaatgaggaa attgc                                                     1815
```

<210> SEQ ID NO 6
<211> LENGTH: 534
<212> TYPE: PRT
<213> ORGANISM: Homo sapiens

<400> SEQUENCE: 6

Met Leu Arg Arg Arg Gly Ser Pro Gly Met Gly Val His Val Gly Ala

-continued

```
  1               5                   10                  15
Ala Leu Gly Ala Leu Trp Phe Cys Leu Thr Gly Ala Leu Glu Val Gln
                 20                  25                  30
Val Pro Glu Asp Pro Val Val Ala Leu Val Gly Thr Asp Ala Thr Leu
                 35                  40                  45
Cys Cys Ser Phe Ser Pro Glu Pro Gly Phe Ser Leu Ala Gln Leu Asn
                 50                  55                  60
Leu Ile Trp Gln Leu Thr Asp Thr Lys Gln Leu Val His Ser Phe Ala
 65                  70                  75                  80
Glu Gly Gln Asp Gln Gly Ser Ala Tyr Ala Asn Arg Thr Ala Leu Phe
                     85                  90                  95
Pro Asp Leu Leu Ala Gln Gly Asn Ala Ser Leu Arg Leu Gln Arg Val
                100                 105                 110
Arg Val Ala Asp Glu Gly Ser Phe Thr Cys Phe Val Ser Ile Arg Asp
                115                 120                 125
Phe Gly Ser Ala Ala Val Ser Leu Gln Val Ala Ala Pro Tyr Ser Lys
                130                 135                 140
Pro Ser Met Thr Leu Glu Pro Asn Lys Asp Leu Arg Pro Gly Asp Thr
145                 150                 155                 160
Val Thr Ile Thr Cys Ser Ser Tyr Gln Gly Tyr Pro Glu Ala Glu Val
                165                 170                 175
Phe Trp Gln Asp Gly Gln Gly Val Pro Leu Thr Gly Asn Val Thr Thr
                180                 185                 190
Ser Gln Met Ala Asn Glu Gln Gly Leu Phe Asp Val His Ser Ile Leu
                195                 200                 205
Arg Val Val Leu Gly Ala Asn Gly Thr Tyr Ser Cys Leu Val Arg Asn
                210                 215                 220
Pro Val Leu Gln Gln Asp Ala His Ser Ser Val Thr Ile Thr Pro Gln
225                 230                 235                 240
Arg Ser Pro Thr Gly Ala Val Glu Val Gln Val Pro Glu Asp Pro Val
                245                 250                 255
Val Ala Leu Val Gly Thr Asp Ala Thr Leu Arg Cys Ser Phe Ser Pro
                260                 265                 270
Glu Pro Gly Phe Ser Leu Ala Gln Leu Asn Leu Ile Trp Gln Leu Thr
                275                 280                 285
Asp Thr Lys Gln Leu Val His Ser Phe Thr Glu Gly Arg Asp Gln Gly
                290                 295                 300
Ser Ala Tyr Ala Asn Arg Thr Ala Leu Phe Pro Asp Leu Leu Ala Gln
305                 310                 315                 320
Gly Asn Ala Ser Leu Arg Leu Gln Arg Val Arg Val Ala Asp Glu Gly
                325                 330                 335
Ser Phe Thr Cys Phe Val Ser Ile Arg Asp Phe Gly Ser Ala Ala Val
                340                 345                 350
Ser Leu Gln Val Ala Ala Pro Tyr Ser Lys Pro Ser Met Thr Leu Glu
                355                 360                 365
Pro Asn Lys Asp Leu Arg Pro Gly Asp Thr Val Thr Ile Thr Cys Ser
                370                 375                 380
Ser Tyr Arg Gly Tyr Pro Glu Ala Glu Val Phe Trp Gln Asp Gly Gln
385                 390                 395                 400
Gly Val Pro Leu Thr Gly Asn Val Thr Thr Ser Gln Met Ala Asn Glu
                405                 410                 415
Gln Gly Leu Phe Asp Val His Ser Val Leu Arg Val Val Leu Gly Ala
                420                 425                 430
```

```
Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
            515                 520                 525

Asp Gly Gln Glu Ile Ala
            530

<210> SEQ ID NO 7
<211> LENGTH: 59
<212> TYPE: DNA
<213> ORGANISM: Artificial Sequence
<220> FEATURE:
<223> OTHER INFORMATION: PCR primer

<400> SEQUENCE: 7
ggggacaagt ttgtacaaaa aagcaggctt caccatgctg cgtcggcggg gcagccctg      59

<210> SEQ ID NO 8
<211> LENGTH: 43
<212> TYPE: DNA
<213> ORGANISM: Artificial Sequence
<220> FEATURE:
<223> OTHER INFORMATION: PCR primer

<400> SEQUENCE: 8
ggggaccact ttgtacaaga aagctgggtc ggctatttct tgt                       43

<210> SEQ ID NO 9
<211> LENGTH: 948
<212> TYPE: DNA
<213> ORGANISM: Homo sapiens

<400> SEQUENCE: 9
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca cgcatccct gaggctgcag cgcgtgcgtg tggcggacga gggcagcttc     360
acctgcttcg tgagcatccg ggatttcggc agcgctgccg tcagcctgca ggtggccgct     420
ccctactcga agcccagcat gaccctggag cccaacaagg acctgcggcc aggggacacg     480
gtgaccatca cgtgctccag ctaccggggc taccctgagg ctgaggtgtt ctggcaggat     540
gggcagggtg tgcccctgac tggcaacgtg accacgtcgc agatggccaa cgagcagggc     600
ttgtttgatg tgcacagcgt cctgcgggtg gtgctgggtg cgaatggcac ctacagctgc     660
ctggtgcgca accccgtgct gcagcaggat gcgcacggct ctgtcaccat cacgggcag     720 cctatgacat tcccccaga ggccctgtgg gtgaccgtgg ggctgtctgt ctgtctcatt     780
```

```
gcactgctgg tggccctggc tttcgtgtgc tggagaaaga tcaaacagag ctgtgaggag      840
gagaatgcag gagctgagga ccaggatggg gagggagaag gctccaagac agccctgcag      900
cctctgaaac actctgacag caaagaagat gatggacaag aaatagcc                  948
```

<210> SEQ ID NO 10
<211> LENGTH: 316
<212> TYPE: PRT
<213> ORGANISM: Homo sapiens

<400> SEQUENCE: 10

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315
```

<210> SEQ ID NO 11
<211> LENGTH: 52
<212> TYPE: DNA

```
<213> ORGANISM: Artificial Sequence
<220> FEATURE:
<223> OTHER INFORMATION: PCR primer

<400> SEQUENCE: 11
ggggacaagt ttgtacaaaa aagcaggctt cggagccctg gaggtccagg tc            52

<210> SEQ ID NO 12
<211> LENGTH: 55
<212> TYPE: DNA
<213> ORGANISM: Artificial Sequence
<220> FEATURE:
<223> OTHER INFORMATION: PCR primer

<400> SEQUENCE: 12
ggggacaagt ttgtacaaaa aagcaggctt cgctccctac tcgaagccca gcatg         55

<210> SEQ ID NO 13
<211> LENGTH: 52
<212> TYPE: DNA
<213> ORGANISM: Artificial Sequence
<220> FEATURE:
<223> OTHER INFORMATION: PCR primer

<400> SEQUENCE: 13
ggggacaagt ttgtacaaaa aagcaggctt cggagccgtg gaggtccagg tc            52

<210> SEQ ID NO 14
<211> LENGTH: 55
<212> TYPE: DNA
<213> ORGANISM: Artificial Sequence
<220> FEATURE:
<223> OTHER INFORMATION: PCR primer

<400> SEQUENCE: 14
ggggacaagt ttgtacaaaa aagcaggctt cgctccctac tcgaagccca gcatg         55

<210> SEQ ID NO 15
<211> LENGTH: 54
<212> TYPE: DNA
<213> ORGANISM: Artificial Sequence
<220> FEATURE:
<223> OTHER INFORMATION: PCR primer

<400> SEQUENCE: 15
ggggaccact ttgtacaaga aagctgggtc tcaggctatt tcttgtccat catc          54

<210> SEQ ID NO 16
<211> LENGTH: 43
<212> TYPE: DNA
<213> ORGANISM: Artificial Sequence
<220> FEATURE:
<223> OTHER INFORMATION: PCR primer

<400> SEQUENCE: 16
gggaatgtca taggctgccc ggccacctgc aggctgacgg cag                      43

<210> SEQ ID NO 17
<211> LENGTH: 42
<212> TYPE: DNA
<213> ORGANISM: Artificial Sequence
<220> FEATURE:
<223> OTHER INFORMATION: PCR primer

<400> SEQUENCE: 17
gggaatgtca taggctgccc tgtggggctt ctctggggtg tg                       42
```

```
<210> SEQ ID NO 18
<211> LENGTH: 43
<212> TYPE: DNA
<213> ORGANISM: Artificial Sequence
<220> FEATURE:
<223> OTHER INFORMATION: PCR primer

<400> SEQUENCE: 18
gggaatgtca taggctgccc ggccacctgc aggctgacgg cag          43

<210> SEQ ID NO 19
<211> LENGTH: 27
<212> TYPE: DNA
<213> ORGANISM: Artificial Sequence
<220> FEATURE:
<223> OTHER INFORMATION: PCR primer

<400> SEQUENCE: 19
gggcagccta tgacattccc cccagag                            27

<210> SEQ ID NO 20
<211> LENGTH: 576
<212> TYPE: DNA
<213> ORGANISM: Homo sapiens

<400> SEQUENCE: 20
ggagccctgg aggtccaggt ccctgaagac ccagtggtgg cactggtggg caccgatgcc    60
accctgtgct gctccttctc ccctgagcct ggcttcagcc tggcacagct caacctcatc   120
tggcagctga cagataccaa acagctggtg cacagctttg ctgagggcca ggaccagggc   180
agcgcctatg ccaaccgcac ggccctcttc ccggacctgc tggcacaggg caacgcatcc   240
ctgaggctgc agcgcgtgcg tgtggcggac gagggcagct tcacctgctt cgtgagcatc   300
cgggatttcg gcagcgctgc cgtcagcctg caggtggccg ggcagccgat gacattcccc   360
ccagaggccc tgtgggtgac cgtggggctg tctgtctgtc tcattgcact gctggtggcc   420
ctggctttcg tgtgctggag aaagatcaaa cagagctgtg aggaggagaa tgcaggagct   480
gaggaccagg atggggaggg agaaggctcc aagacagccc tgcagcctct gaaacactct   540
gacagcaaag aagatgatgg acaagaaata gcctga                            576

<210> SEQ ID NO 21
<211> LENGTH: 191
<212> TYPE: PRT
<213> ORGANISM: Homo sapiens

<400> SEQUENCE: 21

Gly Ala Leu Glu Val Gln Val Pro Glu Asp Pro Val Val Ala Leu Val
1               5                   10                  15

Gly Thr Asp Ala Thr Leu Cys Cys Ser Phe Ser Pro Glu Pro Gly Phe
            20                  25                  30

Ser Leu Ala Gln Leu Asn Leu Ile Trp Gln Leu Thr Asp Thr Lys Gln
        35                  40                  45

Leu Val His Ser Phe Ala Glu Gly Gln Asp Gln Gly Ser Ala Tyr Ala
    50                  55                  60

Asn Arg Thr Ala Leu Phe Pro Asp Leu Leu Ala Gln Gly Asn Ala Ser
65                  70                  75                  80

Leu Arg Leu Gln Arg Val Arg Val Ala Asp Glu Gly Ser Phe Thr Cys
                85                  90                  95
```

```
Phe Val Ser Ile Arg Asp Phe Gly Ser Ala Ala Val Ser Leu Gln Val
                100                 105                 110
Ala Gly Gln Pro Met Thr Phe Pro Pro Glu Ala Leu Trp Val Thr Val
            115                 120                 125
Gly Leu Ser Val Cys Leu Ile Ala Leu Leu Val Ala Leu Ala Phe Val
        130                 135                 140
Cys Trp Arg Lys Ile Lys Gln Ser Cys Glu Glu Asn Ala Gly Ala
145                 150                 155                 160
Glu Asp Gln Asp Gly Glu Gly Glu Gly Ser Lys Thr Ala Leu Gln Pro
                165                 170                 175
Leu Lys His Ser Asp Ser Lys Glu Asp Asp Gly Gln Glu Ile Ala
            180                 185                 190
```

<210> SEQ ID NO 22
<211> LENGTH: 552
<212> TYPE: DNA
<213> ORGANISM: Homo sapiens

<400> SEQUENCE: 22

```
gctccctact cgaagcccag catgaccctg agcccaaca aggacctgcg gccaggggac        60
acggtgacca tcacgtgctc cagctaccag ggctaccctg aggctgaggt gttctggcag       120
gatgggcagg gtgtgcccct gactggcaac gtgaccacgt cgcagatggc caacgagcag       180
ggcttgtttg atgtgcacag catcctgcgg gtggtgctgg gtgcaaatgg cacctacagc       240
tgcctggtgc gcaaccccgt gctgcagcag gatgcgcaca gctctgtcac catcacaccc       300
cagagaagcc ccacagggca gcctatgaca ttccccccag aggccctgtg ggtgaccgtg       360
gggctgtctg tctgtctcat tgcactgctg gtggccctgg ctttcgtgtg ctggagaaag       420
atcaaacaga gctgtgagga ggagaatgca ggagctgagg accaggatgg ggagggagaa       480
ggctccaaga cagccctgca gcctctgaaa cactctgaca gcaaagaaga tgatggacaa       540
gaaatagcct ga                                                           552
```

<210> SEQ ID NO 23
<211> LENGTH: 183
<212> TYPE: PRT
<213> ORGANISM: Homo sapiens

<400> SEQUENCE: 23

```
Ala Pro Tyr Ser Lys Pro Ser Met Thr Leu Glu Pro Asn Lys Asp Leu
1               5                   10                  15
Arg Pro Gly Asp Thr Val Thr Ile Thr Cys Ser Ser Tyr Gln Gly Tyr
            20                  25                  30
Pro Glu Ala Glu Val Phe Trp Gln Asp Gly Gln Gly Val Pro Leu Thr
        35                  40                  45
Gly Asn Val Thr Thr Ser Gln Met Ala Asn Glu Gln Gly Leu Phe Asp
    50                  55                  60
Val His Ser Ile Leu Arg Val Val Leu Gly Ala Asn Gly Thr Tyr Ser
65                  70                  75                  80
Cys Leu Val Arg Asn Pro Val Leu Gln Gln Asp Ala His Ser Ser Val
                85                  90                  95
Thr Ile Thr Pro Gln Arg Ser Pro Thr Gly Gln Pro Met Thr Phe Pro
            100                 105                 110
Pro Glu Ala Leu Trp Val Thr Val Gly Leu Ser Val Cys Leu Ile Ala
        115                 120                 125
Leu Leu Val Ala Leu Ala Phe Val Cys Trp Arg Lys Ile Lys Gln Ser
```

```
                130                 135                 140
Cys Glu Glu Glu Asn Ala Gly Ala Glu Asp Gln Asp Gly Gly Glu
145                 150                 155                 160

Gly Ser Lys Thr Ala Leu Gln Pro Leu Lys His Ser Asp Ser Lys Glu
                165                 170                 175

Asp Asp Gly Gln Glu Ile Ala
            180

<210> SEQ ID NO 24
<211> LENGTH: 576
<212> TYPE: DNA
<213> ORGANISM: Homo sapiens

<400> SEQUENCE: 24
ggagccgtgg aggtccaggt ccctgaggac ccggtggtgg ccctagtggg caccgatgcc    60
accctgcgct gctccttctc ccccgagcct ggcttcagcc tggcacagct caacctcatc   120
tggcagctga cagacaccaa acagctggtg cacagtttca ccgaaggccg ggaccagggc   180
agcgcctatg ccaaccgcac ggccctcttc ccggacctgc tgcacaagg caatgcatcc    240 ctgaggctgc agcgcgtgcg tgtggcggac gagggcagct tcacctgctt cgtgagcatc   300
cgggatttcg gcagcgctgc cgtcagcctg caggtggccg gcagccta t gacattcccc    360 ccagaggccc tgtgggtgac cgtggggctg tctgtctgtc tcattgcact gctggtggcc   420
ctggctttcg tgtgctggag aaagatcaaa cagagctgtg aggaggagaa tgcaggagct   480
gaggaccagg atgggagggg agaaggctcc aagacagccc tgcagcctct gaaacactct   540
gacagcaaag aagatgatgg acaagaaata gcctga                             576

<210> SEQ ID NO 25
<211> LENGTH: 191
<212> TYPE: PRT
<213> ORGANISM: Homo sapiens

<400> SEQUENCE: 25

Gly Ala Val Glu Val Gln Val Pro Glu Asp Pro Val Val Ala Leu Val
1               5                   10                  15

Gly Thr Asp Ala Thr Leu Arg Cys Ser Phe Ser Pro Glu Pro Gly Phe
                20                  25                  30

Ser Leu Ala Gln Leu Asn Leu Ile Trp Gln Leu Thr Asp Thr Lys Gln
            35                  40                  45

Leu Val His Ser Phe Thr Glu Gly Arg Asp Gln Gly Ser Ala Tyr Ala
        50                  55                  60

Asn Arg Thr Ala Leu Phe Pro Asp Leu Leu Ala Gln Gly Asn Ala Ser
65                  70                  75                  80

Leu Arg Leu Gln Arg Val Arg Val Ala Asp Glu Gly Ser Phe Thr Cys
                85                  90                  95

Phe Val Ser Ile Arg Asp Phe Gly Ser Ala Ala Val Ser Leu Gln Val
                100                 105                 110

Ala Gly Gln Pro Met Thr Phe Pro Pro Glu Ala Leu Trp Val Thr Val
            115                 120                 125

Gly Leu Ser Val Cys Leu Ile Ala Leu Leu Val Ala Leu Ala Phe Val
        130                 135                 140

Cys Trp Arg Lys Ile Lys Gln Ser Cys Glu Glu Glu Asn Ala Gly Ala
145                 150                 155                 160

Glu Asp Gln Asp Gly Glu Gly Glu Gly Ser Lys Thr Ala Leu Gln Pro
                165                 170                 175
```

Leu Lys His Ser Asp Ser Lys Glu Asp Asp Gly Gln Glu Ile Ala
            180                 185                 190

<210> SEQ ID NO 26
<211> LENGTH: 534
<212> TYPE: DNA
<213> ORGANISM: Homo sapiens

<400> SEQUENCE: 26

```
gctccctact cgaagcccag catgaccctg agcccaaca aggacctgcg gccaggggac      60
acggtgacca tcacgtgctc cagctaccgg ggctaccctg aggctgaggt gttctggcag     120
gatgggcagg gtgtgcccct gactggcaac gtgaccacgt cgcagatggc caacgagcag     180
ggcttgtttg atgtgcacag cgtcctgcgg gtggtgctgg gtgcgaatgg cacctacagc     240
tgcctggtgc gcaaccccgt gctgcagcag gatgcgcacg gctctgtcac catcacaggg     300
cagcctatga cattcccccc agaggccctg tgggtgaccg tggggctgtc tgtctgtctc     360
attgcactgc tggtggccct ggctttcgtg tgctggagaa agatcaaaca gagctgtgag     420
gaggagaatg caggagctga ggaccaggat ggggagggag aaggctccaa gacagccctg     480
cagcctctga acactctga cagcaaagaa gatgatggac aagaaatagc ctga            534
```

<210> SEQ ID NO 27
<211> LENGTH: 177
<212> TYPE: PRT
<213> ORGANISM: Homo sapiens

<400> SEQUENCE: 27

Ala Pro Tyr Ser Lys Pro Ser Met Thr Leu Glu Pro Asn Lys Asp Leu
1               5                   10                  15

Arg Pro Gly Asp Thr Val Thr Ile Thr Cys Ser Ser Tyr Arg Gly Tyr
            20                  25                  30

Pro Glu Ala Glu Val Phe Trp Gln Asp Gly Gln Gly Val Pro Leu Thr
        35                  40                  45

Gly Asn Val Thr Thr Ser Gln Met Ala Asn Glu Gln Gly Leu Phe Asp
    50                  55                  60

Val His Ser Val Leu Arg Val Val Leu Gly Ala Asn Gly Thr Tyr Ser
65                  70                  75                  80

Cys Leu Val Arg Asn Pro Val Leu Gln Gln Asp Ala His Gly Ser Val
                85                  90                  95

Thr Ile Thr Gly Gln Pro Met Thr Phe Pro Pro Glu Ala Leu Trp Val
            100                 105                 110

Thr Val Gly Leu Ser Val Cys Leu Ile Ala Leu Leu Val Ala Leu Ala
        115                 120                 125

Phe Val Cys Trp Arg Lys Ile Lys Gln Ser Cys Glu Glu Glu Asn Ala
    130                 135                 140

Gly Ala Glu Asp Gln Asp Gly Glu Gly Glu Gly Ser Lys Thr Ala Leu
145                 150                 155                 160

Gln Pro Leu Lys His Ser Asp Ser Lys Glu Asp Asp Gly Gln Glu Ile
                165                 170                 175

Ala

<210> SEQ ID NO 28
<211> LENGTH: 1188
<212> TYPE: DNA
<213> ORGANISM: Homo sapiens

<400> SEQUENCE: 28

```
gctccctact cgaagcccag catgaccctg gagcccaaca aggacctgcg gccaggggac        60
acggtgacca tcacgtgctc cagctaccag ggctaccctg aggctgaggt gttctggcag       120
gatgggcagg gtgtgcccct gactggcaac gtgaccacgt cgcagatggc caacgagcag       180
ggcttgtttg atgtgcacag catcctgcgg gtggtgctgg gtgcaaatgg cacctacagc       240
tgcctggtgc gcaaccccgt gctgcagcag gatgcgcaca gctctgtcac catcacaccc       300
cagagaagcc ccacaggagc cgtggaggtc caggtccctg aggacccggt ggtggcccta       360
gtgggcaccg atgccaccct cgctgctcc ttctcccccg agcctggctt cagcctggca       420
cagctcaacc tcatctggca gctgacagac accaaacagc tggtgcacag tttcaccgaa       480
ggccgggacc agggcagcgc ctatgccaac cgcacggccc tcttcccgga cctgctggca       540
caaggcaatg catccctgag gctgcagcgc gtgcgtgtgg cggacgaggg cagcttcacc       600
tgcttcgtga gcatccggga tttcggcagc gctgccgtca gcctgcaggt ggccgctccc       660
tactcgaagc ccagcatgac cctggagccc aacaaggacc tgcggccagg ggacacggtg       720
accatcacgt gctccagcta ccggggctac cctgaggctg aggtgttctg gcaggatggg       780
cagggtgtgc ccctgactgg caacgtgacc acgtcgcaga tggccaacga gcagggcttg       840
tttgatgtgc acagcgtcct gcgggtggtg ctgggtgcga atggcaccta cagctgcctg       900
gtgcgcaacc ccgtgctgca gcaggatgcg cacggctctg tcaccatcac agggcagcct       960
atgacattcc cccagaggc cctgtgggtg accgtggggc tgtctgtctg tctcattgca      1020
ctgctggtgg ccctggcttt cgtgtgctgg agaaagatca acagagctg tgaggaggag      1080
aatgcaggag ctgaggacca ggatggggag ggagaaggct ccaagacagc cctgcagcct      1140
ctgaaacact ctgacagcaa agaagatgat ggacaagaaa tagcctga                  1188
```

<210> SEQ ID NO 29
<211> LENGTH: 395
<212> TYPE: PRT
<213> ORGANISM: Homo sapiens

<400> SEQUENCE: 29

```
Ala Pro Tyr Ser Lys Pro Ser Met Thr Leu Glu Pro Asn Lys Asp Leu
1               5                   10                  15

Arg Pro Gly Asp Thr Val Thr Ile Thr Cys Ser Ser Tyr Gln Gly Tyr
            20                  25                  30

Pro Glu Ala Glu Val Phe Trp Gln Asp Gly Gln Gly Val Pro Leu Thr
        35                  40                  45

Gly Asn Val Thr Thr Ser Gln Met Ala Asn Glu Gln Gly Leu Phe Asp
    50                  55                  60

Val His Ser Ile Leu Arg Val Val Leu Gly Ala Asn Gly Thr Tyr Ser
65                  70                  75                  80

Cys Leu Val Arg Asn Pro Val Leu Gln Gln Asp Ala His Ser Ser Val
                85                  90                  95

Thr Ile Thr Pro Gln Arg Ser Pro Thr Gly Ala Val Glu Val Gln Val
            100                 105                 110

Pro Glu Asp Pro Val Val Ala Leu Val Gly Thr Asp Ala Thr Leu Arg
        115                 120                 125

Cys Ser Phe Ser Pro Glu Pro Gly Phe Ser Leu Ala Gln Leu Asn Leu
    130                 135                 140

Ile Trp Gln Leu Thr Asp Thr Lys Gln Leu Val His Ser Phe Thr Glu
145                 150                 155                 160
```

```
Gly Arg Asp Gln Gly Ser Ala Tyr Ala Asn Arg Thr Ala Leu Phe Pro
            165                 170                 175

Asp Leu Leu Ala Gln Gly Asn Ala Ser Leu Arg Leu Gln Arg Val Arg
        180                 185                 190

Val Ala Asp Glu Gly Ser Phe Thr Cys Phe Val Ser Ile Arg Asp Phe
    195                 200                 205

Gly Ser Ala Ala Val Ser Leu Gln Val Ala Pro Tyr Ser Lys Pro
210                 215                 220

Ser Met Thr Leu Glu Pro Asn Lys Asp Leu Arg Pro Gly Asp Thr Val
225                 230                 235                 240

Thr Ile Thr Cys Ser Ser Tyr Arg Gly Tyr Pro Glu Ala Glu Val Phe
                245                 250                 255

Trp Gln Asp Gly Gln Gly Val Pro Leu Thr Gly Asn Val Thr Thr Ser
            260                 265                 270

Gln Met Ala Asn Glu Gln Gly Leu Phe Asp Val His Ser Val Leu Arg
        275                 280                 285

Val Val Leu Gly Ala Asn Gly Thr Tyr Ser Cys Leu Val Arg Asn Pro
    290                 295                 300

Val Leu Gln Gln Asp Ala His Gly Ser Val Thr Ile Thr Gly Gln Pro
305                 310                 315                 320

Met Thr Phe Pro Pro Glu Ala Leu Trp Val Thr Val Gly Leu Ser Val
                325                 330                 335

Cys Leu Ile Ala Leu Leu Val Ala Leu Ala Phe Val Cys Trp Arg Lys
            340                 345                 350

Ile Lys Gln Ser Cys Glu Glu Glu Asn Ala Gly Ala Glu Asp Gln Asp
        355                 360                 365

Gly Glu Gly Glu Gly Ser Lys Thr Ala Leu Gln Pro Leu Lys His Ser
    370                 375                 380

Asp Ser Lys Glu Asp Asp Gly Gln Glu Ile Ala
385                 390                 395

<210> SEQ ID NO 30
<211> LENGTH: 873
<212> TYPE: DNA
<213> ORGANISM: Homo sapiens

<400> SEQUENCE: 30
ggagccgtgg aggtccaggt ccctgaggac ccggtggtgg ccctagtggg caccgatgcc      60
accctgcgct gctccttctc ccccgagcct ggcttcagcc tggcacagct caacctcatc     120
tggcagctga cagacaccaa acagctggtg cacagtttca ccgaaggccg ggaccagggc     180
agcgcctatg ccaaccgcac ggccctcttc ccggacctgc tggcacaagg caatgcatcc     240
ctgaggctgc agcgcgtgcg tgtggcggac gagggcagct tcacctgctt cgtgagcatc     300
cgggatttcg gcagcgctgc cgtcagcctg caggtggccg ctccctactc gaagcccagc     360
atgaccctgg agcccaacaa ggacctgcgg ccagggggaca cggtgaccat cacgtgctcc     420
agctaccggg gctaccctga ggctgaggtg ttctggcagg atgggcaggg tgtgcccctg     480
actggcaacg tgaccacgtc gcagatggcc aacgagcagg gcttgtttga tgtgcacagc     540
gtcctgcggg tggtgctggg tgcgaatggc acctacagct gcctggtgcg caaccccgtg     600
ctgcagcagg atgcgcacgg ctctgtcacc atcacagggc agcctatgac attcccccca     660
gaggccctgt gggtgaccgt ggggctgtct gtctgtctca ttgcactgct ggtggccctg     720
gctttcgtgt gctggagaaa gatcaaacag agctgtgagg aggagaatgc aggagctgag     780
```

```
gaccaggatg gggagggaga aggctccaag acagccctgc agcctctgaa acactctgac      840
agcaaagaag atgatggaca agaaatagcc tga                                   873
```

<210> SEQ ID NO 31
<211> LENGTH: 290
<212> TYPE: PRT
<213> ORGANISM: Homo sapiens

<400> SEQUENCE: 31

```
Gly Ala Val Glu Val Gln Val Pro Glu Asp Pro Val Val Ala Leu Val
1               5                   10                  15

Gly Thr Asp Ala Thr Leu Arg Cys Ser Phe Ser Pro Glu Pro Gly Phe
            20                  25                  30

Ser Leu Ala Gln Leu Asn Leu Ile Trp Gln Leu Thr Asp Thr Lys Gln
        35                  40                  45

Leu Val His Ser Phe Thr Glu Gly Arg Asp Gln Gly Ser Ala Tyr Ala
    50                  55                  60

Asn Arg Thr Ala Leu Phe Pro Asp Leu Leu Ala Gln Gly Asn Ala Ser
65                  70                  75                  80

Leu Arg Leu Gln Arg Val Arg Val Ala Asp Glu Gly Ser Phe Thr Cys
                85                  90                  95

Phe Val Ser Ile Arg Asp Phe Gly Ser Ala Ala Val Ser Leu Gln Val
            100                 105                 110

Ala Ala Pro Tyr Ser Lys Pro Ser Met Thr Leu Glu Pro Asn Lys Asp
        115                 120                 125

Leu Arg Pro Gly Asp Thr Val Thr Ile Thr Cys Ser Ser Tyr Arg Gly
    130                 135                 140

Tyr Pro Glu Ala Glu Val Phe Trp Gln Asp Gly Gln Gly Val Pro Leu
145                 150                 155                 160

Thr Gly Asn Val Thr Thr Ser Gln Met Ala Asn Glu Gln Gly Leu Phe
                165                 170                 175

Asp Val His Ser Val Leu Arg Val Val Leu Gly Ala Asn Gly Thr Tyr
            180                 185                 190

Ser Cys Leu Val Arg Asn Pro Val Leu Gln Gln Asp Ala His Gly Ser
        195                 200                 205

Val Thr Ile Thr Gly Gln Pro Met Thr Phe Pro Pro Glu Ala Leu Trp
    210                 215                 220

Val Thr Val Gly Leu Ser Val Cys Leu Ile Ala Leu Leu Val Ala Leu
225                 230                 235                 240

Ala Phe Val Cys Trp Arg Lys Ile Lys Gln Ser Cys Glu Glu Glu Asn
                245                 250                 255

Ala Gly Ala Glu Asp Gln Asp Gly Glu Gly Glu Gly Ser Lys Thr Ala
            260                 265                 270

Leu Gln Pro Leu Lys His Ser Asp Ser Lys Glu Asp Asp Gly Gln Glu
        275                 280                 285

Ile Ala
    290
```

<210> SEQ ID NO 32
<211> LENGTH: 909
<212> TYPE: DNA
<213> ORGANISM: Homo sapiens

<400> SEQUENCE: 32

```
atgcggctgg gcagtcctgg actgctcttc ctgctcttca gcagccttcg agctgatact      60
```

```
caggagaagg aagtcagagc gatggtaggc agcgacgtgg agctcagctg cgcttgccct    120
gaaggaagcc gttttgattt aaatgatgtt tacgtatatt ggcaaaccag tgagtcgaaa    180
accgtggtga cctaccacat cccacagaac agctccttgg aaaacgtgga cagccgctac    240
cggaaccgag ccctgatgtc accggccggc atgctgcggg cgacttctc cctgcgcttg     300 ttcaacgtca ccccccagga cgagcagaag tttcactgcc tggtgttgag ccaatccctg    360
ggattccagg aggttttgag cgttgaggtt acactgcatg tggcagcaaa cttcagcgtg    420
cccgtcgtca gcgccccca gcccctcc caggatgagc tcaccttcac gtgtacatcc       480
ataaacggct accccaggcc caacgtgtac tggatcaata agacggacaa cagcctgctg    540
gaccaggctc tgcagaatga caccgtcttc ttgaacatgc ggggcttgta tgacgtggtc    600
agcgtgctga ggatcgcacg gaccccagc gtgaacattg gctgctgcat agagaacgtg     660
cttctgcagc agaacctgac tgtcggcagc agacaggaa atgacatcgg agagagagac     720
aagatcacag agaatccagt cagtaccggc gagaaaaacg cggccacgtg gagcatcctg    780
gctgtcctgt gcctgcttgt ggtcgtggcg gtggccatag gctgggtgtg cagggaccga    840
tgcctccaac acagctatgc aggtgcctgg gctgtgagtc cggagacaga gctcactggc    900
cacgtttga                                                            909

<210> SEQ ID NO 33
<211> LENGTH: 302
<212> TYPE: PRT
<213> ORGANISM: Homo sapiens

<400> SEQUENCE: 33

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
                20                  25                  30

Val Glu Leu Ser Cys Ala Cys Pro Glu Gly Ser Arg Phe Asp Leu Asn
            35                  40                  45

Asp Val Tyr Val Tyr Trp Gln Thr Ser Glu Ser Lys Thr Val Val Thr
        50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
```

```
                210                 215                 220
Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Ala Val Ala
                260                 265                 270

Ile Gly Trp Val Cys Arg Asp Arg Cys Leu Gln His Ser Tyr Ala Gly
            275                 280                 285

Ala Trp Ala Val Ser Pro Glu Thr Glu Leu Thr Gly His Val
            290                 295                 300

<210> SEQ ID NO 34
<211> LENGTH: 873
<212> TYPE: DNA
<213> ORGANISM: Homo sapiens

<400> SEQUENCE: 34
atgaggatat ttgctgtctt tatattcatg acctactggc atttgctgaa cgcatttact     60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg acaagcagtg accatcaag tcctgagtgg taagaccacc    540
accaccaatt ccaagagaga ggagaagctt ttcaatgtga ccagcacact gagaatcaac    600
acaacaacta tgagattttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aaatgtggca tccaagatac aaactcaaag    840
aagcaaagtg atacacattt ggaggagacg taa                                 873

<210> SEQ ID NO 35
<211> LENGTH: 290
<212> TYPE: PRT
<213> ORGANISM: Homo sapiens

<400> SEQUENCE: 35

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
```

```
                           85                  90                  95
Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
        130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
        210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 36
<211> LENGTH: 909
<212> TYPE: DNA
<213> ORGANISM: Homo sapiens

<400> SEQUENCE: 36
atgcggctgg gcagtcctgg actgctcttc ctgctcttca gcagccttcg agctgatact    60
caggagaagg aagtcagagc gatggtaggc agcgacgtgg agctcagctg cgcttgccct   120
gaaggaagcc gttttgattt aaatgatgtt tacgtatatt ggcaaaccag tgagtcgaaa   180
accgtggtga cctaccacat cccacagaac agctccttgg aaaacgtgga cagccgctac   240
cggaaccgag ccctgatgtc accggccggc atgctgcggg cgacttctc cctgcgcttg    300 ttcaacgtca cccccaggga cgagcagaag tttcactgcc tggtgttgag ccaatccctg   360
ggattccagg aggttttgag cgttgaggtt acactgcatg tggcagcaaa cttcagcgtg   420
cccgtcgtca gcgcccccca gccccctcc caggatgagc tcaccttcac gtgtacatcc    480
ataaacggct accccaggcc caacgtgtac tggatcaata agacggacaa cagcctgctg   540
gaccaggctc tgcagaatga caccgtcttc ttgaacatgc ggggcttgta tgacgtggtc   600
agcgtgctga ggatcgcacg gacccccagc gtgaacattg ctgctgcat agagaacgtg    660 cttctgcagc agaacctgac tgtcggcagc agacaggaa tgacatcgg agagagagac     720 aagatcacag agaatccagt cagtaccggc gagaaaaacg cggccacgtg gagcatcctg   780 gctgtccctgt gcctgcttgt ggtcgtggcg gtggccatag ctgggtgtg cagggaccga   840 tgcctccaac acagctatgc aggtgcctgg gctgtgagtc cggagacaga gctcactggc   900
``` cacgtttga                                                                909

<210> SEQ ID NO 37
<211> LENGTH: 302
<212> TYPE: PRT
<213> ORGANISM: Homo sapiens

<400> SEQUENCE: 37

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300

<210> SEQ ID NO 38
<211> LENGTH: 867
<212> TYPE: DNA
<213> ORGANISM: Homo sapiens

<400> SEQUENCE: 38
atgggccaca cacggaggca gggaacatca ccatccaagt gtccataacct caatttcttt      60 cagctcttgg tgctggctgg tctttctcac ttctgttcag gtgttatcca cgtgaccaag     120

```
gaagtgaaag aagtggcaac gctgtcctgt ggtcacaatg tttctgttga agagctggca      180
caaactcgca tctactggca aaaggagaag aaaatggtgc tgactatgat gtctggggac      240
atgaatatat ggcccgagta caagaaccgg accatctttg atatcactaa taacctctcc      300
attgtgatcc tggctctgcg cccatctgac gagggcacat acgagtgtgt tgttctgaag      360
tatgaaaaag acgctttcaa gcgggaacac ctggctgaag tgacgttatc agtcaaagct      420
gacttcccta cacctagtat atctgacttt gaaattccaa cttctaatat tagaaggata      480
atttgctcaa cctctggagg ttttccagag cctcacctct cctggttgga aaatggagaa      540
gaattaaatg ccatcaacac aacagtttcc caagatcctg aaactgagct ctatgctgtt      600
agcagcaaac tggatttcaa tatgacaacc aaccacagct tcatgtgtct catcaagtat      660
ggacatttaa gagtgaatca gaccttcaac tggaatacaa ccaagcaaga gcattttcct      720
gataacctgc tcccatcctg gccattacc  ttaatctcag taaatggaat ttttgtgata      780
tgctgcctga cctactgctt tgccccaaga tgcagagaga aaggaggaa tgagagattg      840 agaagggaaa gtgtacgccc tgtatag                                          867
```

<210> SEQ ID NO 39
<211> LENGTH: 288
<212> TYPE: PRT
<213> ORGANISM: Homo sapiens

<400> SEQUENCE: 39

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240
```

```
Asp Asn Leu Leu Pro Ser Trp Ala Ile Thr Leu Ile Ser Val Asn Gly
            245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
            275                 280                 285

<210> SEQ ID NO 40
<211> LENGTH: 990
<212> TYPE: DNA
<213> ORGANISM: Homo sapiens

<400> SEQUENCE: 40
atggatcccc agtgcactat gggactgagt aacattctct tgtgatggc cttcctgctc      60 tctggtgctg ctcctctgaa gattcaagct tatttcaatg agactgcaga cctgccatgc    120
caatttgcaa actctcaaaa ccaaagcctg agtgagctag tagtattttg gcaggaccag    180
gaaaacttgg ttctgaatga ggtatactta ggcaaagaga aatttgacag tgttcattcc    240
aagtatatgg gccgcacaag ttttgattcg gacagttgga ccctgagact tcacaatctt    300
cagatcaagg acaagggctt gtatcaatgt atcatccatc acaaaaagcc cacaggaatg    360
attcgcatcc accagatgaa ttctgaactg tcagtgcttg ctaacttcag tcaacctgaa    420
atagtaccaa tttctaatat aacagaaaat gtgtacataa atttgacctg ctcatctata    480
cacggttacc cagaacctaa agatgagt gttttgctaa gaaccaagaa ttcaactatc     540
gagtatgatg gtattatgca gaaatctcaa gataatgtca cagaactgta cgacgtttcc    600
atcagcttgt ctgtttcatt ccctgatgtt acgagcaata tgaccatctt ctgtattctg    660
gaaactgaca gacgcggct tttatcttca cctttctcta tagagcttga ggaccctcag    720
cctcccccag accacattcc ttggattaca gctgtacttc aacagttat tatatgtgtg     780 atggttttct gtctaattct atggaaatgg aagaagaaga agcggcctcg caactcttat    840
aaatgtggaa ccaacacaat ggagagggaa gagagtgaac agaccaagaa aagagaaaaa    900
atccatatac ctgaaagatc tgatgaagcc cagcgtgttt ttaaaagttc gaagacatct    960
tcatgcgaca aaagtgatac atgttttag                                     990

<210> SEQ ID NO 41
<211> LENGTH: 329
<212> TYPE: PRT
<213> ORGANISM: Homo sapiens

<400> SEQUENCE: 41

Met Asp Pro Gln Cys Thr Met Gly Leu Ser Asn Ile Leu Phe Val Met
1               5                   10                  15

Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Gln Glu Asn Leu Val
    50                  55                  60

Leu Asn Glu Val Tyr Leu Gly Lys Glu Lys Phe Asp Ser Val His Ser
65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
            100                 105                 110
```

```
His His Lys Lys Pro Thr Gly Met Ile Arg Ile His Gln Met Asn Ser
            115                 120                 125

Glu Leu Ser Val Leu Ala Asn Phe Ser Gln Pro Glu Ile Val Pro Ile
130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325

<210> SEQ ID NO 42
<211> LENGTH: 849
<212> TYPE: DNA
<213> ORGANISM: Homo sapiens

<400> SEQUENCE: 42
atggcttccc tggggcagat cctcttctgg agcataatta gcatcatcat tattctggct    60
ggagcaattg cactcatcat tggctttggt atttcaggga cactccat cacagtcact    120 actgtcgcct cagctgggaa cattgggag atggaatcc tgagctgcac ttttgaacct    180
gacatcaaac tttctgatat cgtgatacaa tggctgaagg aaggtgtttt aggcttggtc    240
catgagttca agaaggcaa agatgagctg tcggagcagg atgaaatgtt cagaggccgg    300
acagcagtgt ttgctgatca agtgatagtt ggcaatgcct ctttgcggct gaaaaacgtg    360
caactcacag atgctggcac ctacaaatgt tatatcatca cttctaaagg caaggggaat    420
gctaaccttg agtataaaac tggagccttc agcatgccgg aagtgaatgt ggactataat    480
gccagctcag agaccttgcg tgtgaggct ccccgatggt tcccccagcc cacagtggtc    540
tgggcatccc aagttgacca gggagccaac ttctcggaag tctccaatac cagctttgag    600
ctgaactctg agaatgtgac catgaaggtt gtgtctgtgc tctacaatgt tacgatcaac    660
aacacatact cctgtatgat tgaaaatgac attgccaaag caacagggga tatcaaagtg    720
acagaatcgg agatcaaaag gcggagtcac ctacagctgc taaactcaaa ggcttctctg    780
tgtgtctctt ctttctttgc catcagctgg gcacttctgc ctctcagccc ttacctgatg    840
```

<210> SEQ ID NO 43
<211> LENGTH: 282
<212> TYPE: PRT
<213> ORGANISM: Homo sapiens

<400> SEQUENCE: 43

```
Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280
```

<210> SEQ ID NO 44
<211> LENGTH: 10
<212> TYPE: PRT
<213> ORGANISM: Mus musculus

<400> SEQUENCE: 44

```
Glu Val Gln Leu Gln Gln Ser Gly Pro Glu
1               5                   10
```

<210> SEQ ID NO 45
<211> LENGTH: 14
<212> TYPE: PRT

<213> ORGANISM: Mus musculus

<400> SEQUENCE: 45

Ile Val Leu Ser Gln Ser Pro Thr Ile Leu Ser Ala Ser Pro
1               5                   10

<210> SEQ ID NO 46
<211> LENGTH: 26
<212> TYPE: DNA
<213> ORGANISM: Artificial Sequence
<220> FEATURE:
<223> OTHER INFORMATION: PCR primer

<400> SEQUENCE: 46
aagaattcat ggaatggagt tggata                                    26

<210> SEQ ID NO 47
<211> LENGTH: 32
<212> TYPE: DNA
<213> ORGANISM: Artificial Sequence
<220> FEATURE:
<223> OTHER INFORMATION: PCR primer

<400> SEQUENCE: 47
aagatatctc atttacccgg agtccgggag aa                             32

<210> SEQ ID NO 48
<211> LENGTH: 26
<212> TYPE: DNA
<213> ORGANISM: Artificial Sequence
<220> FEATURE:
<223> OTHER INFORMATION: PCR primer

<400> SEQUENCE: 48
aagaattcat ggattttctg gtgcag                                    26

<210> SEQ ID NO 49
<211> LENGTH: 32
<212> TYPE: DNA
<213> ORGANISM: Artificial Sequence
<220> FEATURE:
<223> OTHER INFORMATION: PCR primer

<400> SEQUENCE: 49
aagatatctt aacactcatt cctgttgaag ct                             32

<210> SEQ ID NO 50
<211> LENGTH: 1413
<212> TYPE: DNA
<213> ORGANISM: Mus musculus

<400> SEQUENCE: 50
atggaatgga gttggatatt tctctttctc ctgtcaggaa ctgcaggtgt ccactctgag    60
gtccagctgc agcagtctgg acctgagctg gtaaagcctg ggcttcagt gaagatgtcc   120 tgcaaggctt ctggatacac attcactaac tatgttatgc actgggtgaa gcagaagcct   180
gggcagggcc ttgagtggat tggatatatt aatccttaca atgatgatgt taagtacaat   240
gagaagttca aggcaaggc cacacagact tcagacaaat cctccagcac agcctacatg   300
gagctcagca gcctgacctc tgaggactct gcggtctatt actgtgcaag atgggggtac   360
tacggtagtc cctttatacta ctttgactac tggggccaag gcaccactct cacagtctcc   420
tcagccaaaa caacagcccc atcggtctat ccactggccc ctgtgtgtgg agatacaact   480

```
ggctcctcgg tgactctagg atgcctggtc aagggttatt tccctgagcc agtgaccttg    540
acctggaact ctggatccct gtccagtggt gtgcacacct tcccagctgt cctgcagtct    600
gacctctaca ccctcagcag ctcagtgact gtaacctcga gcacctggcc cagccagtcc    660
atcacctgca atgtgcccca cccggcaagc agcaccaagg tggacaagaa aattgagccc    720
agagggccca caatcaagcc ctgtcctcca tgcaaatgcc cagcacctaa cctcttgggt    780
ggaccatccg tcttcatctt ccctccaaag atcaaggatg tactcatgat ctccctgagc    840
cccatagtca catgtgtggt ggtggatgtg agcgaggatg acccagatgt ccagatcagc    900
tggtttgtga caacgtgga agtacacaca gctcagacac aaaccccatag agaggattac    960 aacagtactc tccgggtggt cagtgccctc cccatccagc accaggactg gatgagtggc   1020
aaggagttca atgcaaggt caacaacaaa gacctcccag cgcccatcga gagaaccatc   1080
tcaaacccca agggtcagt aagagctcca caggtatatg tcttgcctcc accagaagaa   1140
gagatgacta agaaacaggt cactctgacc tgcatggtca cagacttcat gcctgaagac   1200
atttacgtgg agtggaccaa caacgggaaa acagagctaa actacaagaa cactgaacca   1260
gtcctggact ctgatggttc ttacttcatg tacagcaagc tgagagtgga aaagaagaac   1320
tgggtggaaa gaaatagcta ctcctgttca gtggtccacg agggtctgca caatcaccac   1380
acgactaaga gcttctcccg gactccgggt aaa                                1413

<210> SEQ ID NO 51
<211> LENGTH: 471
<212> TYPE: PRT
<213> ORGANISM: Mus musculus

<400> SEQUENCE: 51

Met Glu Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asn Tyr Val Met His Trp Val Lys Gln Lys Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Lys Ala Thr Gln Thr Ser Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Thr Leu Thr Val Ser Ser Ala Lys Thr
    130                 135                 140

Thr Ala Pro Ser Val Tyr Pro Leu Ala Pro Val Cys Gly Asp Thr Thr
145                 150                 155                 160

Gly Ser Ser Val Thr Leu Gly Cys Leu Val Lys Gly Tyr Phe Pro Glu
                165                 170                 175

Pro Val Thr Leu Thr Trp Asn Ser Gly Ser Leu Ser Ser Gly Val His
            180                 185                 190

Thr Phe Pro Ala Val Leu Gln Ser Asp Leu Tyr Thr Leu Ser Ser Ser
        195                 200                 205
```

```
Val Thr Val Thr Ser Ser Thr Trp Pro Ser Gln Ser Ile Thr Cys Asn
            210                 215                 220

Val Ala His Pro Ala Ser Ser Thr Lys Val Asp Lys Lys Ile Glu Pro
225                 230                 235                 240

Arg Gly Pro Thr Ile Lys Pro Cys Pro Pro Cys Lys Cys Pro Ala Pro
                245                 250                 255

Asn Leu Leu Gly Gly Pro Ser Val Phe Ile Phe Pro Pro Lys Ile Lys
                260                 265                 270

Asp Val Leu Met Ile Ser Leu Ser Pro Ile Val Thr Cys Val Val Val
            275                 280                 285

Asp Val Ser Glu Asp Asp Pro Asp Val Gln Ile Ser Trp Phe Val Asn
290                 295                 300

Asn Val Glu Val His Thr Ala Gln Thr Gln Thr His Arg Glu Asp Tyr
305                 310                 315                 320

Asn Ser Thr Leu Arg Val Val Ser Ala Leu Pro Ile Gln His Gln Asp
                325                 330                 335

Trp Met Ser Gly Lys Glu Phe Lys Cys Lys Val Asn Asn Lys Asp Leu
            340                 345                 350

Pro Ala Pro Ile Glu Arg Thr Ile Ser Lys Pro Lys Gly Ser Val Arg
                355                 360                 365

Ala Pro Gln Val Tyr Val Leu Pro Pro Pro Glu Glu Glu Met Thr Lys
            370                 375                 380

Lys Gln Val Thr Leu Thr Cys Met Val Thr Asp Phe Met Pro Glu Asp
385                 390                 395                 400

Ile Tyr Val Glu Trp Thr Asn Asn Gly Lys Thr Glu Leu Asn Tyr Lys
                405                 410                 415

Asn Thr Glu Pro Val Leu Asp Ser Asp Gly Ser Tyr Phe Met Tyr Ser
                420                 425                 430

Lys Leu Arg Val Glu Lys Lys Asn Trp Val Glu Arg Asn Ser Tyr Ser
            435                 440                 445

Cys Ser Val Val His Glu Gly Leu His Asn His Thr Thr Lys Ser
        450                 455                 460

Phe Ser Arg Thr Pro Gly Lys
465                 470

<210> SEQ ID NO 52
<211> LENGTH: 705
<212> TYPE: DNA
<213> ORGANISM: Mus musculus

<400> SEQUENCE: 52
atggattttc tggtgcagat tttcagcttc ctgctaatca gtgcttcagt cataatgtcc      60
agaggacaaa ttgttctctc ccagtctcca acaatcctgt ctgcatctcc aggggagaag     120
gtcacaatga cttgcagggc cagctcaaga ctaatttaca tgcattggta tcagcagaag     180
ccaggatcct cccccaaacc ctggatttat gccacatcca acctggcttc tggagtccct     240
gctcgcttca gtggcagtgg gtctgggacc tcttactctc tcacaatcag cagagtggag     300
gctgaagatg ctgccactta ttactgccag cagtggaata gtaacccacc cacgttcggt     360
actgggacca agctggagct gaaacgggct gatgctgcac caactgtatc catcttccca     420
ccatccagtg agcagttaac atctggaggt gcctcagtcg tgtgcttctt gaacaacttc     480
taccccaaag acatcaatgt caagtggaag attgatggca gtgaacgaca aaatggcgtc     540
ctgaacagtt ggactgatca ggacagcaaa gacagcacct acagcatgag cagcacccte     600
```

```
acgttgacca aggacgagta tgaacgacat aacagctata cctgtgaggc cactcacaag    660
acatcaactt cacccattgt caagagcttc aacaggaatg agtgt                    705
```

<210> SEQ ID NO 53
<211> LENGTH: 235
<212> TYPE: PRT
<213> ORGANISM: Mus musculus

<400> SEQUENCE: 53

```
Met Asp Phe Leu Val Gln Ile Phe Ser Phe Leu Leu Ile Ser Ala Ser
1               5                   10                  15

Val Ile Met Ser Arg Gly Gln Ile Val Leu Ser Gln Ser Pro Thr Ile
            20                  25                  30

Leu Ser Ala Ser Pro Gly Glu Lys Val Thr Met Thr Cys Arg Ala Ser
        35                  40                  45

Ser Arg Leu Ile Tyr Met His Trp Tyr Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Asn Ser Asn Pro Pro Thr Phe Gly Thr Gly Thr Lys Leu Glu Leu Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235
```

<210> SEQ ID NO 54
<211> LENGTH: 28
<212> TYPE: DNA
<213> ORGANISM: Artificial Sequence
<220> FEATURE:
<223> OTHER INFORMATION: PCR primer

<400> SEQUENCE: 54

```
ccacgcgccc tgtagcggcg cattaagc                                       28
```

<210> SEQ ID NO 55
<211> LENGTH: 30
<212> TYPE: DNA
<213> ORGANISM: Artificial Sequence
<220> FEATURE:
<223> OTHER INFORMATION: PCR primer

<400> SEQUENCE: 55

```
aaacccggga gcttttttgca aaagcctagg                                      30
```

<210> SEQ ID NO 56
<211> LENGTH: 1704
<212> TYPE: DNA
<213> ORGANISM: Artificial Sequence
<220> FEATURE:
<223> OTHER INFORMATION: human kappa chain secretion signal, human kappa
      chain constant region and human poly A additional signal

<400> SEQUENCE: 56

```
ggtaccaccc aagctggcta ggtaagcttg ctagcgccac catggtgctg cagacccagg      60
tgttcatctc cctgctgctg tggatctccg gcgcatatgg cgatatcgtg atgattaaac     120
gtacggtggc cgcccccctcc gtgttcatct ccccccctc cgacgagcag ctgaagtccg     180
gcaccgcctc cgtggtgtgc ctgctgaata acttctaccc cagagaggcc aaggtgcagt     240
ggaaggtgga caacgccctg cagtccggga actcccagga gagcgtgacc gagcaggaca     300
gcaaggacag cacctacagc ctgagcagca ccctgaccct gagcaaagcc gactacgaga     360
agcacaaggt gtacgcctgc gaggtgaccc accagggcct gagctccccc gtcaccaaga     420
gcttcaacag ggggagtgt aggggcccg tttaaacggg tggcatccct gtgacccctc     480
cccagtgcct ctcctggccc tggaagttgc cactccagtg cccaccagcc ttgtcctaat     540
aaaattaagt tgcatcattt tgtctgacta ggtgtccttc tataatatta tggggtggag     600
ggggtggta tggagcaagg ggcaagttgg aagacaacc tgtagggcct gcggggtcta     660
ttgggaacca agctggagtg cagtggcaca atcttggctc actgcaatct ccgcctcctg     720
ggttcaagcg attctcctgc ctcagcctcc cgagttgttg ggattccagg catgcatgac     780
caggctcacc taatttttgt tttttggta gagacgggt ttcaccatat tggccaggct     840
ggtctccaac tcctaatctc aggtgatcta cccaccttgg cctcccaaat tgctgggatt     900
acaggcgtga accactgctc cacgcgcccc gtagcgcgc attaagcgcg gcgggtgtgg     960
tggttacgcg cagcgtgacc gctacacttg ccagcgccct agcgcccgct cctttcgctt    1020
tcttccctc ctttctcgcc acgttcgccg gctttcccg tcaagctcta atcggggc       1080
tccctttagg gttccgatt agtgcttac ggcacctcga cccaaaaaaa cttgattagg    1140
gtgatggttc acgtagtggg ccatcgcccct gatagacggt tttcgccct ttgacgttgg    1200
agtccacgtt ctttaatagt ggactcttgt tccaaactgg aacaacactc aaccctatct    1260
cggtctattc ttttgattta agggattt tgccgattc ggcctattgg ttaaaaatg     1320
agctgattta acaaaaattt aacgcgaatt aattctgtgg aatgtgtgtc agttagggtg    1380
tggaaagtcc ccaggctccc cagcaggcag aagtatgcaa agcatgcatc tcaattagtc    1440
agcaaccagg tgtggaaagt ccccaggctc cccagcaggc agaagtatgc aaagcatgca    1500
tctcaattag tcagcaacca tagtcccgcc cctaactccg cccatcccgc ccctaactcc    1560
gcccagttcc gcccattctc cgccccatgg ctgactaatt ttttttattt atgcagaggc    1620
cgaggccgcc tctgcctctg agctattcca gaagtagtga ggaggctttt ttggaggcct    1680
aggcttttgc aaaaagctcc cggg                                          1704
```

<210> SEQ ID NO 57
<211> LENGTH: 1120
<212> TYPE: DNA
<213> ORGANISM: Artificial Sequence
<220> FEATURE:
<223> OTHER INFORMATION: human IgG1 signal sequence and constant region

<400> SEQUENCE: 57

```
tgctagcgcc accatgaaac acctgtggtt cttcctcctg ctggtggcag ctcccagatg    60
ggtgctgagc caggtgcaat gtgcaggcg gttagctcag cctccaccaa gggcccaagc   120
gtcttccccc tggcaccctc ctccaagagc acctctggcg cacagccgc cctgggctgc   180
ctggtcaagg actacttccc cgaacccgtg accgtgagct ggaactcagg cgccctgacc   240
agcggcgtgc acaccttccc cgctgtcctg cagtcctcag gactctactc cctcagcagc   300
gtggtgaccg tgccctccag cagcttgggc acccagacct acatctgcaa cgtgaatcac   360
aagcccagca caccaaggt ggacaagaga gttgagccca atcttgtga caaaactcac   420
acatgcccac cctgcccagc acctgaactc ctgggggac cctcagtctt cctcttcccc   480
ccaaaaccca aggacaccct catgatctcc cggacccctg aggtcacatg cgtggtggtg   540
gacgtgagcc acgaagaccc tgaggtcaag ttcaactggt acgtggacgg cgtggaggtg   600
cataatgcca agacaaagcc ccgggaggag cagtacaaca gcacgtaccg ggtggtcagc   660
gtcctcaccg tcctgcacca ggactggctg aatggcaagg agtacaagtg caaggtctcc   720
aacaaagccc tcccagcccc catcgagaaa accatctcca aagccaaagg ccagccccgg   780
gaaccacagg tgtacaccct gcccccatcc cgggaggaga tgaccaagaa ccaggtcagc   840
ctgacctgcc tggtcaaagg cttctatccc agcgacatcg ccgtggagtg ggagagcaat   900
ggccagcccg agaacaacta caagaccacc cctcccgtgc tggactccga cggctccttc   960
ttcctctaca gcaagctcac cgtggacaag agcaggtggc agcagggcaa cgtcttctca  1020
tgctccgtga tgcatgaggc tctgcacaac cactacaccc agaagagcct ctccctgtct  1080
cccggcaaat gagatatcgg gcccgtttaa acgggtggca                        1120
```

<210> SEQ ID NO 58
<211> LENGTH: 699
<212> TYPE: DNA
<213> ORGANISM: Artificial Sequence
<220> FEATURE:
<223> OTHER INFORMATION: Light chain of chimeric M30

<400> SEQUENCE: 58

```
atggtgctgc agacccaggt gttcatctcc ctgctgctgt ggatctccgg cgcatatggc    60
caaattgttc tctcccagtc tccaacaatc ctgtctgcat ctccagggga gaaggtcaca   120
atgacttgca gggccagctc aagactaatt tacatgcatt ggtatcagca gaagccagga   180
tcctccccca aaccctggat ttatgccaca tccaacctgg cttctggagt ccctgctcgc   240
ttcagtggca gtgggtctgg gacctcttac tctctcacaa tcagcagagt ggaggctgaa   300
gatgctgcca cttattactg ccagcagtgg aatagtaacc cacccacgtt cggtactggg   360
accaagctgg agctgaaacg tacggtggcc gccccctccg tgttcatctt ccccccctcc   420
gacgagcagc tgaagtccgg caccgcctcc gtggtgtgcc tgctgaataa cttctacccc   480
agagaggcca aggtgcagtg gaaggtggac aacgccctgc agtccgggaa ctcccaggag   540
agcgtgaccg agcaggacag caaggacagc acctacagcc tgagcagcac cctgaccctg   600
agcaaagccg actacgagaa gcacaaggtg tacgcctgcg aggtgaccca ccagggcctg   660
agctccccg tcaccaagag cttcaacagg ggggagtgt                           699
```

<210> SEQ ID NO 59
<211> LENGTH: 233
<212> TYPE: PRT
<213> ORGANISM: Artificial Sequence
<220> FEATURE:
<223> OTHER INFORMATION: Light chain of chimeric M30

<400> SEQUENCE: 59

```
Met Val Leu Gln Thr Gln Val Phe Ile Ser Leu Leu Trp Ile Ser
1               5                   10                  15

Gly Ala Tyr Gly Gln Ile Val Leu Ser Gln Ser Pro Thr Ile Leu Ser
                20                  25                  30

Ala Ser Pro Gly Glu Lys Val Thr Met Thr Cys Arg Ala Ser Ser Arg
            35                  40                  45

Leu Ile Tyr Met His Trp Tyr Gln Gln Lys Pro Gly Ser Ser Pro Lys
        50                  55                  60

Pro Trp Ile Tyr Ala Thr Ser Asn Leu Ala Ser Gly Val Pro Ala Arg
65                  70                  75                  80

Phe Ser Gly Ser Gly Ser Gly Thr Ser Tyr Ser Leu Thr Ile Ser Arg
                85                  90                  95

Val Glu Ala Glu Asp Ala Ala Thr Tyr Tyr Cys Gln Gln Trp Asn Ser
            100                 105                 110

Asn Pro Pro Thr Phe Gly Thr Gly Thr Lys Leu Glu Leu Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 60
<211> LENGTH: 42
<212> TYPE: DNA
<213> ORGANISM: Artificial Sequence
<220> FEATURE:
<223> OTHER INFORMATION: PCR primer

<400> SEQUENCE: 60
aaacatatgg ccaaattgtt ctctcccagt ctccaacaat cc                42

<210> SEQ ID NO 61
<211> LENGTH: 37
<212> TYPE: DNA
<213> ORGANISM: Artificial Sequence
<220> FEATURE:
<223> OTHER INFORMATION: PCR primer

<400> SEQUENCE: 61
aaacgtacgt ttcagctcca gcttggtccc agtaccg                     37

<210> SEQ ID NO 62
<211> LENGTH: 1413
<212> TYPE: DNA
<213> ORGANISM: Artificial Sequence
<220> FEATURE:
<223> OTHER INFORMATION: Heavy chain of chimeric M30

<400> SEQUENCE: 62

```
atgaaacacc tgtggttctt cctcctgctg gtggcagctc ccagatgggt gctgagcgag      60
gtccagctgc agcagtctgg acctgagctg gtaaagcctg gggcttcagt gaagatgtcc     120
tgcaaggctt ctggatacac attcactaac tatgttatgc actgggtgaa gcagaagcct     180
gggcagggcc ttgagtggat tggatatatt aatccttaca atgatgatgt taagtacaat     240
gagaagttca aggcaaggc cacacagact tcagacaaat cctccagcac agcctacatg     300
gaactcagca gcctgacctc tgaggactct gcggtctatt actgtgcaag atggggtac     360
tacggtagtc ccttatacta ctttgactac tggggccaag gcaccactct cacagtcagc     420
tcagcctcca ccaagggccc aagcgtcttc cccctggcac cctcctccaa gagcacctct     480
ggcggcacag ccgccctggg ctgcctggtc aaggactact ccccgaacc cgtgaccgtg     540
agctggaact caggcgccct gaccagcggc gtgcacacct tcccgctgt cctgcagtcc     600
tcaggactct actccctcag cagcgtggtg accgtgccct ccagcagctt gggcacccag     660
acctacatct gcaacgtgaa tcacaagccc agcaacacca aggtggacaa gagagttgag     720
cccaaatctt gtgacaaaac tcacacatgc ccaccctgcc cagcacctga actcctgggg     780
ggaccctcag tcttcctctt ccccccaaaa cccaaggaca ccctcatgat ctcccggacc     840
cctgaggtca catgcgtggt ggtggacgtg agccacgaag accctgaggt caagttcaac     900
tggtacgtgg acggcgtgga ggtgcataat gccaagacaa agcccgggga ggagcagtac     960
aacagcacgt accgggtggt cagcgtcctc accgtcctgc accaggactg gctgaatggc    1020
aaggagtaca agtgcaaggt ctccaacaaa gccctcccag cccccatcga aaaaccatc     1080
tccaaagcca aggccagcc ccgggaacca caggtgtaca ccctgccccc atcccgggag    1140
gagatgacca agaaccaggt cagcctgacc tgcctggtca aaggcttcta tcccagcgac    1200
atcgccgtgg agtgggagag caatggccag ccggagaaca actacaagac cacccctccc    1260
gtgctggact ccgacggctc cttcttcctc tacagcaagc tcaccgtgga caagagcagg    1320
tggcagcagg gcaacgtctt ctcatgctcc gtgatgcatg aggctctgca caaccactac    1380
acccagaaga gcctctccct gtctccggc aaa                                   1413
```

<210> SEQ ID NO 63
<211> LENGTH: 471
<212> TYPE: PRT
<213> ORGANISM: Artificial Sequence
<220> FEATURE:
<223> OTHER INFORMATION: Heavy chain of chimeric M30

<400> SEQUENCE: 63

```
Met Lys His Leu Trp Phe Phe Leu Leu Leu Val Ala Ala Pro Arg Trp
1               5                   10                  15

Val Leu Ser Glu Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
        35                  40                  45

Thr Asn Tyr Val Met His Trp Val Lys Gln Lys Pro Gly Gln Gly Leu
    50                  55                  60

Glu Trp Ile Gly Tyr Ile Asn Pro Tyr Asn Asp Asp Val Lys Tyr Asn
65                  70                  75                  80

Glu Lys Phe Lys Gly Lys Ala Thr Gln Thr Ser Asp Lys Ser Ser Ser
```

```
                85                  90                  95
Thr Ala Tyr Met Glu Leu Ser Ser Leu Thr Ser Glu Asp Ser Ala Val
            100                 105                 110

Tyr Tyr Cys Ala Arg Trp Gly Tyr Tyr Gly Ser Pro Leu Tyr Tyr Phe
            115                 120                 125

Asp Tyr Trp Gly Gln Gly Thr Thr Leu Thr Val Ser Ser Ala Ser Thr
            130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
            290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 64
<211> LENGTH: 40
<212> TYPE: DNA
<213> ORGANISM: Artificial Sequence
```

<220> FEATURE:
<223> OTHER INFORMATION: PCR primer

<400> SEQUENCE: 64
aaagctgagc gaggtccagc tgcagcagtc tggacctgag                40

<210> SEQ ID NO 65
<211> LENGTH: 36
<212> TYPE: DNA
<213> ORGANISM: Artificial Sequence
<220> FEATURE:
<223> OTHER INFORMATION: PCR primer

<400> SEQUENCE: 65
gaggtcaggc tgctgagttc catgtaggct gtgctg                36

<210> SEQ ID NO 66
<211> LENGTH: 36
<212> TYPE: DNA
<213> ORGANISM: Artificial Sequence
<220> FEATURE:
<223> OTHER INFORMATION: PCR primer

<400> SEQUENCE: 66
cagcacagcc tacatggaac tcagcagcct gacctc                36

<210> SEQ ID NO 67
<211> LENGTH: 39
<212> TYPE: DNA
<213> ORGANISM: Artificial Sequence
<220> FEATURE:
<223> OTHER INFORMATION: PCR primer

<400> SEQUENCE: 67
aaagctgagc tgactgtgag agtggtgcct tggccccag                39

<210> SEQ ID NO 68
<211> LENGTH: 40
<212> TYPE: DNA
<213> ORGANISM: Artificial Sequence
<220> FEATURE:
<223> OTHER INFORMATION: PCR primer

<400> SEQUENCE: 68
aaagctgagc gaggtccagc tgcagcagtc tggacctgag                40

<210> SEQ ID NO 69
<211> LENGTH: 39
<212> TYPE: DNA
<213> ORGANISM: Artificial Sequence
<220> FEATURE:
<223> OTHER INFORMATION: PCR primer

<400> SEQUENCE: 69
aaagctgagc tgactgtgag agtggtgcct tggccccag                39

<210> SEQ ID NO 70
<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 70
atggtgctgc agacccaggt gttcatctcc ctgctgctgt ggatctccgg cgcatatggc                60

```
gagatcgtgc tgacccagag ccccgccacc ctgtctctga gccctggcga gagagccacc    120
ctgagctgca gagccagcag ccgcctgatc tacatgcact ggtatcagca gaagcccggc    180
caggccccca gactgctgat ctacgccacc agcaacctgg ccagcggcat ccccgccaga    240 tttctggca gcggcagcgg caccgacttc accctgacca tctctcggct ggaacccgag    300
gacttcgccg tgtactactg ccagcagtgg aacagcaacc cccccacctt cggccagggc    360
accaaggtcg aaatcaagcg tacggtggcc gcccctccg tgttcatctt ccccccctcc     420
gacgagcagc tgaagtccgg caccgcctcc gtggtgtgcc tgctgaataa cttctacccc    480
agagaggcca aggtgcagtg gaaggtggac aacgccctgc agtccgggaa ctcccaggag    540
agcgtgaccg agcaggacag caaggacagc acctacagcc tgagcagcac cctgaccctg    600
agcaaagccg actacgagaa gcacaaggtg tacgcctgcg aggtgaccca ccagggcctg    660
agctcccccg tcaccaagag cttcaacagg ggggagtgt                           699
```

<210> SEQ ID NO 71
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 71

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Leu Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 72

<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 72

```
atggtgctgc agacccaggt gttcatctcc ctgctgctgt ggatctccgg cgcatatggc    60
gagatcgtgc tgacccagag ccccgccacc ctgtctctga gccctggcga gagagccacc   120
ctgagctgca gccagcag caggctgatc tacatgcact ggtatcagca aaagcccggc   180
caggccccca gactgtggat ctacgccacc agcaacctgg ccagcggcat ccccgccaga   240
ttttctggca gcggcagcgg caccgactac accctgacca tcagccgcct ggaacccgag   300
gacttcgccg tgtactactg ccagcagtgg aacagcaacc cccccacctt cggccagggc   360
accaaggtcg aaatcaagcg tacggtggcc gccccctccg tgttcatctt cccccccctcc   420
gacgagcagc tgaagtccgg cacccgcctcc gtggtgtgcc tgctgaataa cttctacccc   480
agagaggcca aggtgcagtg gaaggtggac aacgccctgc agtccgggaa ctcccaggag   540
agcgtgaccg agcaggacag caaggacagc acctacagcc tgagcagcac cctgaccctg   600
agcaaagccc actacgagaa gcacaaggtg tacgcctgcg aggtgaccca ccagggcctg   660
agctccccccg tcaccaagag cttcaacagg ggggagtgt                         699
```

<210> SEQ ID NO 73
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 73

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Leu Trp Ile Tyr Ala Thr Ser Asn Leu Ala Ser Gly Ile Pro Ala Arg
65                  70                  75                  80

Phe Ser Gly Ser Gly Ser Gly Thr Asp Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
```

```
            195                 200                 205
Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 74
<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 74

```
atggtgctgc agacccaggt gttcatctcc ctgctgctgt ggatctccgg cgcatatggc    60
cagatcgtgc tgtcccagag ccccgccacc ctgtctctga gccctggcga gagagccacc   120
ctgacctgca gagccagcag caggctgatc tacatgcact ggtatcagca gaagcccggc   180
agcgccccca agctgtggat ctacgccacc agcaacctgg ccagcggcat ccccgccaga   240 tttctggca gcggcagcgg caccagctac accctgacca tctcccgcct ggaacccgag   300
gacttcgccg tgtactactg ccagcagtgg aacagcaacc cccccacctt cggccagggc   360
accaaggtcg aaatcaagcg tacggtggcc gcccccctccg tgttcatctt cccccccctcc   420 gacgagcagc tgaagtccgg caccgcctcc gtggtgtgcc tgctgaataa cttctacccc   480
agagaggcca aggtgcagtg gaaggtggac aacgccctgc agtccgggaa ctcccaggag   540
agcgtgaccg agcaggacag caaggacagc acctacagcc tgagcagcac cctgaccctg   600
agcaaagccg actacgagaa gcacaaggtg tacgcctgcg aggtgaccca ccagggcctg   660
agctcccccg tcaccaagag cttcaacagg ggggagtgt                          699
```

<210> SEQ ID NO 75
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 75

```
Met Val Leu Gln Thr Gln Val Phe Ile Ser Leu Leu Trp Ile Ser
1               5                   10                  15

Gly Ala Tyr Gly Gln Ile Val Leu Ser Gln Ser Pro Ala Thr Leu Ser
                20                  25                  30

Leu Ser Pro Gly Glu Arg Ala Thr Leu Thr Cys Arg Ala Ser Ser Arg
            35                  40                  45

Leu Ile Tyr Met His Trp Tyr Gln Gln Lys Pro Gly Ser Ala Pro Lys
        50                  55                  60

Leu Trp Ile Tyr Ala Thr Ser Asn Leu Ala Ser Gly Ile Pro Ala Arg
65                  70                  75                  80

Phe Ser Gly Ser Gly Ser Gly Thr Ser Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140
```

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 76
<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 76

```
atggtgctgc agacccaggt gttcatctcc ctgctgctgt ggatctccgg cgcatatggc    60
gagatcgtgc tgacccagag ccccgccacc ctgtctctga gccctggcga gagagccacc   120
ctgagctgca gagccagcag ccgcctgatc tacatgcact ggtatcagca gaagcccggc   180
caggcccccc gacctctgat ctacgccacc agcaacctgg ccagcggcat cccgccaga    240
tttctggca gcggcagcgg caccgacttc accctgacca tcagcagcct ggaacccgag    300
gacttcgccg tgtactactg ccagcagtgg aacagcaacc cccccacctt cggccagggc    360
accaaggtcg aaatcaagcg tacggtggcc gccccctccg tgttcatctt cccccctcc    420
gacgagcagc tgaagtccgg caccgcctcc gtggtgtgcc tgctgaataa cttctacccc   480
agagaggcca aggtgcagtg gaaggtggac aacgccctgc agtccgggaa ctcccaggag   540
agcgtgaccg agcaggacag caaggacagc acctacagcc tgagcagcac cctgaccctg   600
agcaaagccg actacgagaa gcacaaggtg tacgcctgcg aggtgaccca ccagggcctg   660
agctcccccg tcaccaagag cttcaacagg ggggagtgt                           699
```

<210> SEQ ID NO 77
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 77

```
Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95
```

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 78
<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 78
atggtgctgc agacccaggt gttcatctcc ctgctgctgt ggatctccgg cgcatatggc      60
cagatcgtgc tgtcccagag ccccgccacc ctgtctctga gccctggcga gagagccacc     120
ctgacctgca gagccagcag caggctgatc tacatgcact ggtatcagca gaagcccggc     180
agcgccccca gccttggat ctacgccacc agcaacctgg ccagcggcat ccccgccaga     240
ttttctggca gcggcagcgg caccagctac accctgacca tctcccgcct ggaacccgag     300
gacttcgccg tgtactactg ccagcagtgg aacagcaacc cccccacctt cggccagggc     360
accaaggtcg aaatcaagcg tacggtggcc gccccctccg tgttcatctt ccccccctcc     420
gacgagcagc tgaagtccgg caccgcctcc gtggtgtgcc tgctgaataa cttctacccc     480
agagaggcca aggtgcagtg gaaggtggac aacgccctgc agtccgggaa ctcccaggag     540
agcgtgaccg agcaggacag caaggacagc acctacagcc tgagcagcac cctgaccctg     600
agcaaagccg actacgagaa gcacaaggtg tacgcctgcg aggtgaccca ccagggcctg     660
agctcccccg tcaccaagag cttcaacagg ggggagtgt                            699

<210> SEQ ID NO 79
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 79

Met Val Leu Gln Thr Gln Val Phe Ile Ser Leu Leu Leu Trp Ile Ser
1               5                   10                  15

Gly Ala Tyr Gly Gln Ile Val Leu Ser Gln Ser Pro Ala Thr Leu Ser
            20                  25                  30

Leu Ser Pro Gly Glu Arg Ala Thr Leu Thr Cys Arg Ala Ser Ser Arg

```
                35                  40                  45
Leu Ile Tyr Met His Trp Tyr Gln Gln Lys Pro Gly Ser Ala Pro Lys
 50                  55                  60
Pro Trp Ile Tyr Ala Thr Ser Asn Leu Ala Ser Gly Ile Pro Ala Arg
 65                  70                  75                  80
Phe Ser Gly Ser Gly Ser Gly Thr Ser Tyr Thr Leu Thr Ile Ser Arg
                 85                  90                  95
Leu Glu Pro Glu Asp Phe Ala Val Tyr Tyr Cys Gln Gln Trp Asn Ser
            100                 105                 110
Asn Pro Pro Thr Phe Gly Gln Gly Thr Lys Val Glu Ile Lys Arg Thr
        115                 120                 125
Val Ala Ala Pro Ser Val Phe Ile Phe Pro Pro Ser Asp Glu Gln Leu
130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
210                 215                 220
Thr Lys Ser Phe Asn Arg Gly Glu Cys
225                 230

<210> SEQ ID NO 80
<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 80
atggtgctgc agacccaggt gttcatctcc ctgctgctgt ggatctccgg cgcatatggc      60
gagatcgtgc tgacccagag ccccgccacc ctgtctctga gccctggcga gagagccacc     120
ctgagctgca gagccagcag ccgcctgatc tacatgcact ggtatcagca gaagcccggc     180
caggccccca gacctctgat ctacgccacc agcaacctgg ccagcggcat ccccgccaga     240 tttttctggca gcggcagcgg caccgacttc accctgacca tcagccgcct ggaacccgag     300
gacttcgccg tgtactactg ccagcagtgg aacagcaacc cccccacctt cggccagggc     360
accaaggtcg aaatcaagcg tacggtggcc gcccctccg tgttcatctt cccccctcc     420 gacgagcagc tgaagtccgg caccgcctcc gtggtgtgcc tgctgaataa cttctacccc     480
agagaggcca aggtgcagtg gaaggtggac aacgccctgc agtccgggaa ctcccaggag     540
agcgtgaccg agcaggacag caaggacagc acctacagcc tgagcagcac cctgaccctg     600
agcaaagccg actacgagaa gcacaaggtg tacgcctgcg aggtgaccca ccagggcctg     660
agctccccgg tcaccaagag cttcaacagg ggggagtgt                            699

<210> SEQ ID NO 81
<211> LENGTH: 233
<212> TYPE: PRT
<213> ORGANISM: Artificial Sequence
<220> FEATURE:
<223> OTHER INFORMATION: Humanized light chain of M30
```

<400> SEQUENCE: 81

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 82
<211> LENGTH: 699
<212> TYPE: DNA
<213> ORGANISM: Artificial Sequence
<220> FEATURE:
<223> OTHER INFORMATION: Humanized light chain of M30

<400> SEQUENCE: 82

```
atggtgctgc agacccaggt gttcatctcc ctgctgctgt ggatctccgg cgcatatggc    60
gagatcgtgc tgacccagag ccccgccacc ctgtctctga gcctggcga gagagccacc   120 ctgagctgca gagccagcag ccgcctgatc tacatgcact ggtatcagca aaagcccggc   180
caggccccca gacctctgat ctacgccacc agcaacctgg ccagcggcat ccccgccaga   240 tttttctggca gcggcagcgg caccgactac accctgacca tcagccgcct ggaacccgag   300
gacttcgccg tgtactactg ccagcagtgg aacagcaacc cccccacctt cggccagggc   360
accaaggtcg aaatcaagcg tacggtggcc gcccctccg tgttcatctt ccccccctcc   420
gacgagcagc tgaagtccgg caccgcctcc gtggtgtgcc tgctgaataa cttctacccc   480
agagaggcca aggtgcagtg gaaggtggac aacgccctgc agtccggaa ctcccaggag   540 agcgtgacca gcaggacag caaggacagc acctacagcc tgagcagcac cctgaccctg   600
agcaaagccg actacgagaa gcacaaggtg tacgcctgcg aggtgaccca ccagggcctg   660
```

```
agctcccccg tcaccaagag cttcaacagg ggggagtgt                              699
```

<210> SEQ ID NO 83
<211> LENGTH: 233
<212> TYPE: PRT
<213> ORGANISM: Artificial Sequence
<220> FEATURE:
<223> OTHER INFORMATION: Humanized light chain of M30

<400> SEQUENCE: 83

```
Met Val Leu Gln Thr Gln Val Phe Ile Ser Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Tyr Thr Leu Thr Ile Ser Arg
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 84
<211> LENGTH: 1413
<212> TYPE: DNA
<213> ORGANISM: Artificial Sequence
<220> FEATURE:
<223> OTHER INFORMATION: Humanized heavy chain of M30

<400> SEQUENCE: 84

```
atgaaacacc tgtggttctt cctcctgctg gtggcagctc ccagatgggt gctgagccag      60
gtgcagctgg tgcagtctgg cgccgaagtg aagaaaccg gcagcagcgt gaaggtgtcc      120
tgcaaggcca gcggctacac cttcaccaac tacgtgatgc actgggtgcg ccaggcccct     180
gggcagggac tggaatggat gggctacatc aaccctaca acgacgacgt gaagtacaac      240
gagaagttca agggcagagt gaccatcacc gccgacgaga gcaccagcac cgcctacatg     300
gaactgagca gcctgcggag cgaggacacc gccgtgtact actgcgccag atggggctac     360
```

```
tacggcagcc ccctgtacta cttcgactac tggggccagg gcaccctggt gacagtcagc    420
tcagcctcca ccaagggccc aagcgtcttc ccctggcac cctcctccaa gagcacctct    480
ggcggcacag ccgccctggg ctgcctggtc aaggactact ccccgaacc cgtgaccgtg    540 agctggaact caggcgccct gaccagcggc gtgcacacct ccccgctgt cctgcagtcc    600 tcaggactct actccctcag cagcgtggtg accgtgccct ccagcagctt gggcacccag    660
acctacatct gcaacgtgaa tcacaagccc agcaacacca aggtggacaa gagagttgag    720
cccaaatctt gtgacaaaac tcacacatgc ccaccctgcc cagcacctga actcctgggg    780
ggaccctcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agcccgggga ggagcagtac    960
aacagcacgt accgggtggt cagcgtcctc accgtcctgc accaggactg gctgaatggc   1020
aaggagtaca agtgcaaggt ctccaacaaa gccctcccag cccccatcga aaaaccatc   1080 tccaaagcca aggccagcc cgggaaccca caggtgtaca ccctgccccc atcccgggag   1140
gagatgacca gaaccaggt cagcctgacc tgcctggtca aaggcttcta tcccagcgac   1200
atcgccgtgg agtgggagag caatggccag ccgagaaca actacaagac cacccctccc   1260
gtgctggact ccgacggctc cttcttcctc tacagcaagc tcaccgtgga caagagcagg   1320
tggcagcagg gcaacgtctt ctcatgctcc gtgatgcatg aggctctgca caaccactac   1380
acccagaaga gcctctccct gtctccggc aaa                                 1413

<210> SEQ ID NO 85
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 85

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ser Ser Val Lys Val Ser Cys Lys Ala Ser Gly Tyr Thr Phe
            35                  40                  45

Thr Asn Tyr Val Met His Trp Val Arg Gln Ala Pro Gly Gln Gly Leu
        50                  55                  60

Glu Trp Met Gly Tyr Ile Asn Pro Tyr Asn Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
            245                 250                 255

Glu Leu Leu Gly Gly Pro Ser Val Phe Leu Phe Pro Pro Lys Pro Lys
        260                 265                 270

Asp Thr Leu Met Ile Ser Arg Thr Pro Glu Val Thr Cys Val Val Val
    275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
            325                 330                 335

Trp Leu Asn Gly Lys Glu Tyr Lys Cys Lys Val Ser Asn Lys Ala Leu
        340                 345                 350

Pro Ala Pro Ile Glu Lys Thr Ile Ser Lys Ala Lys Gly Gln Pro Arg
    355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Val Leu Asp Ser Asp Gly Ser Phe Phe Leu Tyr Ser
        420                 425                 430

Lys Leu Thr Val Asp Lys Ser Arg Trp Gln Gln Gly Asn Val Phe Ser
    435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 86
<211> LENGTH: 1413
<212> TYPE: DNA
<213> ORGANISM: Artificial Sequence
<220> FEATURE:
<223> OTHER INFORMATION: Humanized heavy chain of M30

<400> SEQUENCE: 86
atgaaacacc tgtggttctt cctcctgctg gtggcagctc ccagatgggt gctgagccag      60
gtgcagctgg tgcagtctgg cgccgaagtg aagaaaccg gcagcagcgt gaaggtgtcc     120
tgcaaggcca gcggctacac cttcaccaac tacgtgatgc actgggtgcg ccaggcccct     180
gggcagggac tggaatggat cggctacatc aaccctaca cgacgacgt gaagtacaac      240 gagaagttca gggcagagt gaccatcacc gccgacgaga gcaccagcac cgcctacatg     300
gaactgagca gcctgcggag cgaggacacc gccgtgtact actgcgccag atggggctac     360
```

```
tacggcagcc ccctgtacta cttcgactac tggggccagg gcaccctggt gacagtcagc      420
tcagcctcca ccaagggccc aagcgtcttc ccctggcac cctcctccaa gagcacctct      480
ggcggcacag ccgccctggg ctgcctggtc aaggactact ccccgaacc cgtgaccgtg      540 agctggaact caggcgccct gaccagcggc gtgcacacct tccccgctgt cctgcagtcc      600
tcaggactct actccctcag cagcgtggtg accgtgccct ccagcagctt gggcacccag      660
acctacatct gcaacgtgaa tcacaagccc agcaacacca aggtggacaa gagagttgag      720
cccaaatctt gtgacaaaac tcacacatgc ccaccctgcc cagcacctga actcctgggg      780
ggaccctcag tcttcctctt ccccccaaaa cccaaggaca ccctcatgat ctcccggacc      840
cctgaggtca catgcgtggt ggtggacgtg agccacgaag accctgaggt caagttcaac      900
tggtacgtgg acggcgtgga ggtgcataat gccaagacaa agcccgggga ggagcagtac      960
aacagcacgt accgggtggt cagcgtcctc accgtcctgc accaggactg gctgaatggc     1020
aaggagtaca agtgcaaggt ctccaacaaa gccctcccag cccccatcga gaaaaccatc     1080
tccaaagcca aggccagcc ccgggaacca caggtgtaca ccctgccccc atcccgggag     1140
gagatgacca gaaccaggt cagcctgacc tgcctggtca aaggcttcta tcccagcgac     1200
atcgccgtgg agtgggagag caatggccag cccgagaaca actacaagac caccccctcc     1260
gtgctggact ccgacggctc cttcttcctc tacagcaagc tcaccgtgga caagagcagg     1320
tggcagcagg gcaacgtctt ctcatgctcc gtgatgcatg aggctctgca caaccactac     1380
acccagaaga gcctctccct gtctccggc aaa                                  1413

<210> SEQ ID NO 87
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 87

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Arg Gln Ala Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

Pro Val Thr Val Ser Trp Asn Ser Gly Ala Leu Thr Ser Gly Val His
         180                 185                 190

Thr Phe Pro Ala Val Leu Gln Ser Ser Gly Leu Tyr Ser Leu Ser Ser
         195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                 245                 250                 255

Glu Leu Leu Gly Gly Pro Ser Val Phe Leu Phe Pro Pro Lys Pro Lys
         260                 265                 270

Asp Thr Leu Met Ile Ser Arg Thr Pro Glu Val Thr Cys Val Val Val
         275                 280                 285

Asp Val Ser His Glu Asp Pro Glu Val Lys Phe Asn Trp Tyr Val Asp
         290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                 325                 330                 335

Trp Leu Asn Gly Lys Glu Tyr Lys Cys Lys Val Ser Asn Lys Ala Leu
         340                 345                 350

Pro Ala Pro Ile Glu Lys Thr Ile Ser Lys Ala Lys Gly Gln Pro Arg
         355                 360                 365

Glu Pro Gln Val Tyr Thr Leu Pro Pro Ser Arg Glu Glu Met Thr Lys
         370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                 405                 410                 415

Thr Thr Pro Pro Val Leu Asp Ser Asp Gly Ser Phe Phe Leu Tyr Ser
         420                 425                 430

Lys Leu Thr Val Asp Lys Ser Arg Trp Gln Gln Gly Asn Val Phe Ser
         435                 440                 445

Cys Ser Val Met His Glu Ala Leu His Asn His Tyr Thr Gln Lys Ser
         450                 455                 460

Leu Ser Leu Ser Pro Gly Lys
465                 470

<210> SEQ ID NO 88
<211> LENGTH: 1413
<212> TYPE: DNA
<213> ORGANISM: Artificial Sequence
<220> FEATURE:
<223> OTHER INFORMATION: Humanized heavy chain of M30

<400> SEQUENCE: 88
atgaaacacc tgtggttctt cctcctgctg gtggcagctc ccagatgggt gctgagcgag      60
gtgcagctgg tgcagtctgg cgccgaagtg aagaaacccg gcagcagcgt gaaggtgtcc     120
tgcaaggcca gcggctacac cttcaccaac tacgtgatgc actgggtgaa acaggcccct     180
gggcagggcc tggaatggat cggctacatc aaccctaca cgacgacgt gaagtacaac       240 gagaagttca aggcaaggc caccatcacc gccgacgaga gcaccagcac cgcctacatg      300
gaactgagca gcctgcggag cgaggacacc gccgtgtact actgcgccag atggggctac    360

```
tacggcagcc ccctgtacta cttcgactac tggggccagg gcaccctggt gacagtcagc    420
tcagcctcca ccaagggccc aagcgtcttc cccctggcac cctcctccaa gagcacctct    480
ggcggcacag ccgccctggg ctgcctggtc aaggactact tccccgaacc cgtgaccgtg    540
agctggaact caggcgccct gaccagcggc gtgcacacct tcccgctgt cctgcagtcc     600 tcaggactct actccctcag cagcgtggtg accgtgccct ccagcagctt gggcacccag    660
acctacatct gcaacgtgaa tcacaagccc agcaacacca aggtggacaa gagagttgag    720
cccaaatctt gtgacaaaac tcacacatgc ccaccctgcc cagcacctga actcctgggg    780
ggaccctcag tcttcctctt ccccccaaaa cccaaggaca cctcatgat ctccccggacc    840 cctgaggtca catgcgtggt ggtggacgtg agccacgaag accctgaggt caagttcaac    900
tggtacgtgg acggcgtgga ggtgcataat gccaagacaa agccccggga ggagcagtac    960
aacagcacgt accgggtggt cagcgtcctc accgtcctgc accaggactg gctgaatggc   1020
aaggagtaca agtgcaaggt ctccaacaaa gccctcccag cccccatcga gaaaaccatc   1080
tccaaagcca aaggccagcc ccgggaacca caggtgtaca ccctgccccc atcccgggag   1140
gagatgacca gaaccaggt cagcctgacc tgcctggtca aaggcttcta tcccagcgac    1200
atcgccgtgg agtgggagag caatggccag ccgagaaca actacaagac cacccctccc    1260
gtgctggact ccgacggctc cttcttcctc tacagcaagc tcaccgtgga caagagcagg   1320
tggcagcagg gcaacgtctt ctcatgctcc gtgatgcatg aggctctgca caaccactac   1380
acccagaaga gcctctccct gtctccggc aaa                                  1413
```

<210> SEQ ID NO 89
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 89

```
Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Lys Gln Ala Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Lys Ala Thr Ile Thr Ala Asp Glu Ser Thr Ser
            85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
            165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
            195                 200                 205

Val Val Thr Val Pro Ser Ser Ser Leu Gly Thr Gln Thr Tyr Ile Cys
210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 90
<211> LENGTH: 1413
<212> TYPE: DNA
<213> ORGANISM: Artificial Sequence
<220> FEATURE:
<223> OTHER INFORMATION: Humanized heavy chain of M30

<400> SEQUENCE: 90
atgaaacacc tgtggttctt cctcctgctg gtggcagctc ccagatgggt gctgagcgag      60
gtgcagctgg tgcagtctgg cgccgaagtg aagaaacccg gcagcagcgt gaaggtgtcc     120
tgcaaggcca gcggctacac cttcaccaac tacgtgatgc actgggtcaa gcaggcccct     180
gggcagggcc tggaatggat cggctacatc aaccccctaca cgacgacgt gaagtacaac     240 gagaagttca aggcaaggc cacccagacc agcgacaaga gcaccagcac cgcctacatg     300
gaactgagca gcctgcggag cgaggacacc gccgtgtact actgcgccag atggggctac     360
```

-continued

```
tacggcagcc ccctgtacta cttcgactac tggggccagg gcaccctggt caccgtcagc      420
tcagcctcca ccaagggccc aagcgtcttc cccctggcac cctcctccaa gagcacctct      480
ggcggcacag ccgccctggg ctgcctggtc aaggactact tccccgaacc cgtgaccgtg      540
agctggaact caggcgccct gaccagcggc gtgcacacct tcccgctgt cctgcagtcc       600 tcaggactct actccctcag cagcgtggtg accgtgccct ccagcagctt gggcacccag      660
acctacatct gcaacgtgaa tcacaagccc agcaacacca aggtggacaa gagagttgag      720
cccaaatctt gtgacaaaac tcacacatgc ccaccctgcc cagcacctga actcctgggg      780
ggaccctcag tcttcctctt ccccccaaaa cccaaggaca cctcatgat ctcccggacc       840 cctgaggtca catgcgtggt ggtggacgtg agccacgaag accctgaggt caagttcaac      900
tggtacgtgg acggcgtgga ggtgcataat gccaagacaa agccccggga ggagcagtac      960
aacagcacgt accgggtggt cagcgtcctc accgtcctgc accaggactg gctgaatggc      1020
aaggagtaca agtgcaaggt ctccaacaaa gccctcccag cccccatcga gaaaaccatc      1080
tccaaagcca aaggccagcc ccgggaacca caggtgtaca ccctgccccc atcccgggag      1140
gagatgacca agaaccaggt cagcctgacc tgcctggtca aaggcttcta tcccagcgac      1200
atcgccgtgg agtgggagag caatggccag cccgagaaca actacaagac caccctcccc     1260
gtgctggact ccgacggctc cttcttcctc tacagcaagc tcaccgtgga caagagcagg     1320
tggcagcagg gcaacgtctt ctcatgctcc gtgatgcatg aggctctgca caaccactac     1380
acccagaaga gcctctccct gtctccggc aaa                                    1413
```

<210> SEQ ID NO 91
<211> LENGTH: 471
<212> TYPE: PRT
<213> ORGANISM: Artificial Sequence
<220> FEATURE:
<223> OTHER INFORMATION: Humanized heavy chain of M30

<400> SEQUENCE: 91

```
Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Thr Asn Tyr Val Met His Trp Val Lys Gln Ala Pro Gly Gln Gly Leu
    50                  55                  60

Glu Trp Ile Gly Tyr Ile Asn Pro Tyr Asn Asp Val Lys Tyr Asn
65                  70                  75                  80

Glu Lys Phe Lys Gly Lys Ala Thr Gln Thr Ser Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
        115                 120                 125

Asp Tyr Trp Gly Gln Gly Thr Leu Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175
```

```
Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 92
<211> LENGTH: 5
<212> TYPE: PRT
<213> ORGANISM: Mus musculus

<400> SEQUENCE: 92

Asn Tyr Val Met His
1               5

<210> SEQ ID NO 93
<211> LENGTH: 17
<212> TYPE: PRT
<213> ORGANISM: Mus musculus

<400> SEQUENCE: 93

Tyr Ile Asn Pro Tyr Asn Asp Asp Val Lys Tyr Asn Glu Lys Phe Lys
1               5                   10                  15
```

```
Gly

<210> SEQ ID NO 94
<211> LENGTH: 13
<212> TYPE: PRT
<213> ORGANISM: Mus musculus

<400> SEQUENCE: 94

Trp Gly Tyr Tyr Gly Ser Pro Leu Tyr Tyr Phe Asp Tyr
1               5                   10

<210> SEQ ID NO 95
<211> LENGTH: 10
<212> TYPE: PRT
<213> ORGANISM: Mus musculus

<400> SEQUENCE: 95

Arg Ala Ser Ser Arg Leu Ile Tyr Met His
1               5                   10

<210> SEQ ID NO 96
<211> LENGTH: 7
<212> TYPE: PRT
<213> ORGANISM: Mus musculus

<400> SEQUENCE: 96

Ala Thr Ser Asn Leu Ala Ser
1               5

<210> SEQ ID NO 97
<211> LENGTH: 9
<212> TYPE: PRT
<213> ORGANISM: Mus musculus

<400> SEQUENCE: 97

Gln Gln Trp Asn Ser Asn Pro Pro Thr
1               5
```